(12) United States Patent
Beight et al.

(10) Patent No.: US 7,129,245 B2
(45) Date of Patent: Oct. 31, 2006

(54) AROMATIC AMIDES

(75) Inventors: Douglas Wade Beight, Frankfort, IN (US); Trelia Joyce Craft, Indianapolis, IN (US); Carl Penman Denny, Zionsville, IN (US); Jeffry Bernard Franciskovich, Zionsville, IN (US); Theodore Goodson, Jr., Indianapolis, IN (US); Steven Edward Hall, Chapel Hill, NC (US); David Kent Herron, Indianapolis, IN (US); Sajan Joseph, Indianapolis, IN (US); Valentine Joseph Klimkowski, Carmel, IN (US); Jeffrey Alan Kyle, Fishers, IN (US); John Joseph Masters, Fishers, IN (US); David Mendel, Indianapolis, IN (US); Guy Milot, Chapel Hill, NC (US); Marta Maria Piñelro-Núñez, Brownsburg, IN (US); Jason Scott Sawyer, Indianapolis, IN (US); Robert Theodore Shuman, Sedona, AZ (US); Gerald Floyd Smith, Greenwood, IN (US); Anne Louise Tebbe, Hamburg (DE); Jennifer Marie Tinsley, Ypsilanti, MI (US); Leonard Crayton Weir, Westfield, IN (US); James Howard Wikel, Greenwood, IN (US); Michael Robert Wiley, Indianapolis, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 548 days.

(21) Appl. No.: 10/629,817

(22) Filed: Jul. 29, 2003

(65) Prior Publication Data

US 2005/0282862 A1    Dec. 22, 2005

Related U.S. Application Data

(62) Division of application No. 09/857,751, filed as application No. PCT/US99/29946 on Dec. 15, 1999, now Pat. No. 6,635,657.

(60) Provisional application No. 60/113,556, filed on Dec. 23, 1998.

(51) Int. Cl.
*A61K 31/506* (2006.01)
*C07D 239/04* (2006.01)

(52) U.S. Cl. ..................................... 514/275; 544/231
(58) Field of Classification Search ................ 544/231; 514/275
See application file for complete search history.

(56) References Cited

U.S. PATENT DOCUMENTS

| 6,140,351 | A | 10/2000 | Arnaiz et al. |
| 6,380,221 | B1 | 4/2002 | Arnaiz et al. |
| 6,635,657 | B1 * | 10/2003 | Beight et al. ................ 514/318 |

FOREIGN PATENT DOCUMENTS

| WO | WO 96/28427 | | 9/1996 | |
| WO | WO 99/00121 | | 1/1999 | |
| WO | WO 99/00126 | | 1/1999 | |
| WO | WO 99/00127 | | 1/1999 | |
| WO | WO 99/00128 | | 1/1999 | |
| WO | WO 99/32477 | | 7/1999 | |
| WO | WO2000027819 | * | 5/2000 | |
| WO | WO 00/39092 | | 7/2000 | |
| WO | WO 00/39111 | | 7/2000 | |
| WO | WO 00/39117 | | 7/2000 | |
| WO | 9929946 | * | 10/2003 | .................. 514/318 |

OTHER PUBLICATIONS

El-Zanfally, Condensation of Acetanthranil and Phenylanthranil with Certain Aminoheterocycles. Attempted Preparation of Some 2,3-Disubstituted 4 (3H)-Quinazolinones, Egypt. J. Pharm. Sci., 12(1):29-34 (1976).*
Jensen & Ingvorsen, Tuberculostatic Derivatives of p-aminobenzoic acid, III. Heterocyclic Derivatives of 4-aminosalicyclic acid, Acta Chemica Scandinavica 6: 161-5 (1952).*
U.S. Appl. No. 08/994,284, filed Dec. 1997, Chou et al.
U.S. Appl. No. 09/187,459, filed Nov. 1998, Arnaiz et al.
Vacca, Joseph P. (Annette M. Doherty Section Editor), Annual Reports in Medicinal Chemistry, (1998), 33, 81-90.
Current Pharmaceutical Design, 1996, 2., "Factor Xa Inhibitors," Kunitada, Satoshi, et al., pp. 531-542.
Katakura, S., et al., Eur. J. Med. Chem., (1995), 30, 387-394.

* cited by examiner

*Primary Examiner*—Cecilia Tsang
*Assistant Examiner*—R. James Balls
(74) *Attorney, Agent, or Firm*—Thomas E. Jackson

(57) ABSTRACT

This application relates to a compound of formula I (or a pharmaceutically acceptable salt thereof) as defined herein, pharmaceutical compositions thereof, and its use as an inhibitor of factor Xa, as well as a process for its preparation and intermediates therefor.

24 Claims, No Drawings

AROMATIC AMIDES

This application is a divisional of U.S. application Ser. No. 09/857,751, filed Jun. 8, 2001, now U.S. Pat. No. 6,635,657, which is the National Stage of International Application No. PCT/US99/29946, filed 15 Dec. 1999, which claims the benefit of U.S. Provisional Application No. 60/113,556, filed 23 Dec. 1998, all of which are incorporated herein by reference.

This invention relates to antithrombotic aromatic amides which demonstrate activity as inhibitors of factor Xa and, accordingly, which are useful anticoagulants in mammals. In particular it relates to aromatic amides having high anticoagulant activity, and antithrombotic activity. Thus, this invention relates to new amides which are inhibitors of factor Xa, pharmaceutical compositions containing the amides as active ingredients, and the use of the amides as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Joseph P. Vacca (Annette M. Doherty Section Editor), *Annual Reports in Medicinal Chemistry*, (1998), 33, 81–90.

Although the heparins and coumarins are effective anticoagulants, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the amides of the present invention, as defined below, are potent inhibitors of factor Xa which may have high bioavailability following oral administration.

According to the invention there is provided a compound of formula I

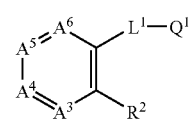

(or a pharmaceutically acceptable salt thereof) wherein:

$A^3, A^4, A^5$ and $A^6$, together with the two carbons to which they are attached, complete a substituted benzene in which $A^3$ is $CR^3$, $A^4$ is $CR^4$, $A^6$ is $CR^5$, and $A^6$ is $CR^6$; wherein $R^3$ is hydrogen, methyl, methoxy, fluoro, chloro or carboxy;

one of $R^4$ and $R^5$ is hydrogen, (1–4C)alkyl, halo, trifluoromethyl, trifluoromethoxy, $R^fO$—, $R^fO_2CCH_2O$—, $HO(CH_2)_aO$— (in which a is 2, 3 or 4), $R^fO_2C$—, $R^fO_2CCH_2$—, $R^gNH$—, $R^hSO_2$—, hydroxymethyl, formyl, cyano, acetyl, 1-hydroxyethyl, 1-(hydroxyimino)ethyl, 1-(methoxyimino)ethyl, methylthio or $R^fO_2C(CH_2)_2$—;

the other of $R^4$ and $R^5$ is hydrogen; and $R^6$ is hydrogen, methyl, fluoro, chloro or methoxy;

in which $R^f$ is hydrogen, (1–4C)alkyl or benzyl; $R^g$ is hydrogen or $R^hSO_2$—; and $R^h$ is (1–4C)alkyl or dimethylamino;

or each of $R^3$, $R^4$ and $R^6$ is hydrogen; and $R^5$ is vinyl, 2-cyanovinyl, 2-({(1–2C)alkoxy}carbonyl)vinyl or $R^a$ in which $R^a$ is phenyl (which is unsubstituted or bears one or more substituents independently selected from halo, methyl, methoxy and hydroxy) or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen);

$L^1$ is —CO—NH— such that $-L^1-Q^1$ is —CO—NH-$Q^1$;

$Q^1$ is 2-pyridinyl (which bears a methyl, methoxy, methylthio, fluoro or chloro substituent at the 5-position), 3-pyridinyl (which bears a methyl, fluoro or chloro substituent at the 6-position), 2-pyrimidinyl (which may bear a methyl, fluoro or chloro substituent at the 5-position) or 3-pyridazinyl (which may bear a methyl, fluoro or chloro substituent at the 6-position);

$R^2$ is $-L^2-Q^2$ in which $-L^2-$ is —NH—CO—, —NH—CO—X—, —NH—CO—O—X—, —NH—CO—NH—X—, —NH—CH_2—, —NH—C(CH_3)H—, —N(CH_3)—CH_2— or —O—CH_2—; and $Q^2$ is $Q^{2A}$, $Q^{2B}$, $Q^{2C}$, $Q^{2D}$, $Q^{2E}$ or $Q^{2F}$ wherein X is a single bond or methylene and the values of $L^2$ and $Q^2$ are together selected from —NH—CO—X-$Q^{2A}$, —NHCO—O—X-$Q^{2A}$, —NH—CO—NH—X-$Q^{2A}$, —NH—CH_2-$Q^{2A}$, —NH—C(CH_3)H-$Q^{2A}$, —N(CH_3)—CH_2-$Q^{2A}$, —O—CH_2-$Q^{2A}$, —NH—CO—X-$Q^{2B}$, NH—CO-$Q^{2C}$, —NH—CO-$Q^{2D}$, —NH—CO-$Q^{2E}$ and —NH—CO-$Q^{2F}$ in which:

$Q^{2A}$ (showing the $L^2$ to which it is attached) is

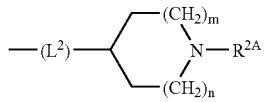

in which
each of m and n independently is 0 or 1, or m is 2 and n is 1, and
$R^{2A}$ is hydrogen, t-butyl, methylsulfonyl, —$CHR^yR^z$, —$CHR^wR^x$, or 4-pyridinyl (which is unsubstituted or bears a substituent $R^v$ at the 2- or 3-position) wherein
$R^v$ is methyl, hydroxymethyl, {(1–2C) alkoxy}carbonyl; cyano, carbamoyl, thiocarbamoyl, or N-hydroxyamidino;
each of $R^w$ and $R^x$ independently is hydrogen or (1–3C) normal alkyl; or —$CHR^wR^x$ is 2-indanyl or (showing the nitrogen to which it is attached) is

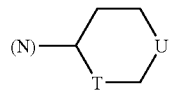

in which T is a single bond or methylene and U is methylene, ethylene, oxy, —$S(O)_q$— (wherein q is 0, 1 or 2) or imino (which may bear a methyl substituent), or T is ethan-1,1-diyl and U is a single bond or methylene;
$R^y$ is hydrogen or methyl; and
$R^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen);
or $R^{2A}$ is -$L^b$-$CH_2$—$R^b$ in which -$L^b$- is a direct bond, —$CH_2$—, —$C(CH_3)H$— or —$CH_2$—$CH_2$—; and $R^b$ is carboxy, {(1–2C)alkoxy}carbonyl, cyano, carbamoyl or trifluoromethyl;
or $R^{2A}$ is —CO—$R^c$ in which $R^c$ is hydrogen, (1–3C) alkyl, {(1–2C)alkoxy}carbonyl-$(CH_2)_c$— (in which c is 1 or 2), phenyl (which is unsubstituted or bears one or more substituents independently selected from halo, methyl, methoxy and hydroxy), heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen) or —$NR^dR^e$ in which each of $R^d$ and $R^e$ is independently hydrogen, methyl or ethyl, or —$NR^dR^e$ is pyrrolidino, piperidino, morpholino or thiomorpholino;
$Q^{2B}$ is 1-piperazinyl which bears at the 4-position the group $R^{2A}$ (defined as above);
$Q^{2C}$ is 3,4-didehydropiperidin-4-yl which bears at the 1-position the group $R^{2A}$ (defined as above);
$Q^{2D}$ is cyclohexyl which bears at the 4-position the group —$NR^sR^t$ in which each of $R^s$ and $R^t$ independently is hydrogen or methyl or $R^s$ and $R^t$ together are trimethylene or tetramethylene;

$Q^{2E}$ is 1-piperidinyl which bears at the 4-position the group —$NR^sR^t$ (defined as above); and
$Q^{2F}$ (showing the $L^2$ to which it is attached) is

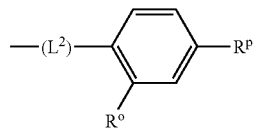

in which $R^o$ is hydrogen, halo, (1–6C)alkyl, hydroxy, (1–4C) alkoxy, benzyloxy or (1–4C)alkylthio; and $R^p$ is acetylamino, 1-hydroxyethyl, 1-hydroxy-1-methylethyl, 1-methoxy-1-methylethyl, 4-piperidinyl, 4-pyridinyl, dimethylaminosulfonyl or -J-$R^q$ in which J is a single bond, methylene, carbonyl, oxy, —$S(O)_q$— (wherein q is 0, 1 or 2), or —$NR^r$— (wherein $R^r$ is hydrogen or methyl); and $R^q$ is (1–6C)alkyl, phenyl, 3-pyridyl or 4-pyridyl; or —$NR^qR^r$ is pyrrolidino.
A particular compound of formula I is on wherein:
$A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein
$R^3$ is hydrogen, methyl, fluoro, chloro or carboxy;
one of $R^4$ and $R^5$ is hydrogen, (1–4C)alkyl, halo, trifluoromethyl, trifluoromethoxy, $R^fO$—, $R^fO_2CCH_2O$—, $HO(CH_2)_aO$— (in which a is 2, 3 or 4), $R^fO_2C$—, $R^fO_2CCH_2$—, $R^gNH$— or $R^hSO_2$—;
the other of $R^4$ and $R^5$ is hydrogen; and
$R^6$ is hydrogen, methyl, fluoro, chloro or methoxy;
in which $R^f$ is hydrogen, (1–4C)alkyl or benzyl; $R^g$ is hydrogen or $R^hSO_2$—; and $R^h$ is (1–4C)alkyl or dimethylamino;
$L^1$ is —CO—NH— such that -$L^1$-$Q^1$ is —CO—NH-$Q^1$;
$Q^1$ is 2-pyridinyl (which bears a methyl, methoxy, methylthio, fluoro or chloro substituent at the 5-position), 3-pyridinyl (which bears a methyl, fluoro or chloro substituent at the 6-position), 2-pyrimidinyl (which may bear a methyl, fluoro or chloro substituent at the 5-position) or 3-pyridazinyl (which may bear a methyl, fluoro or chloro substituent at the 6-position);
$R^2$ is -$L^2$-$Q^2$ in which -$L^2$- is —NH—CO—, —NH—CO—X—, —NH—CO—O—X—, —NH—CO—NH—X—, —NH—$CH_2$— or —O—$CH_2$—; and $Q^2$ is $Q^{2A}$, $Q^{2B}$, $Q^{2C}$, $Q^{2D}$, $Q^{2E}$ or $Q^{2F}$ wherein X is a single bond or methylene and the values of $L^2$ and $Q^2$ are together selected from —NH—CO—X-$Q^{2A}$, —NH—CO—O—X-$Q^{2A}$, —NH—CO—NH—X-$Q^{2A}$, —NH—$CH_2$-$Q^{2A}$, —O—$CH_2$-$Q^{2A}$, —NH—CO—X-$Q^{2B}$, —NH—CO-$Q^{2C}$, —NH—CO-$Q^{2D}$, —NH—CO-$Q^{2E}$ and —NH—CO-$Q^{2F}$ in which:
$Q^{2A}$ (showing the $L^2$ to which it is attached) is

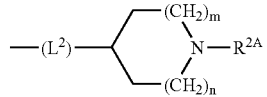

in which
each of m and n independently is 0 or 1, and
$R^{2A}$ is hydrogen, t-butyl, methylsulfonyl, —$CHR^yR^z$, —$CHR^wR^x$, or 4-pyridinyl (which is unsubstituted or bears a substituent $R^v$ at the 2- or 3-position) wherein
$R^v$ is methyl, hydroxymethyl, {(1–2C)alkoxy}carbonyl; cyano, carbamoyl, thiocarbamoyl, or N-hydroxyamidino;

each of R$^w$ and R$^x$ independently is hydrogen or (1–3C) normal alkyl; or —CHR$^w$R$^x$ is 2-indanyl or (showing the nitrogen to which it is attached) is

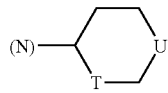

in which T is a single bond or methylene and U is methylene ethylene, oxy, —S(O)$_q$— (wherein q is 0, 1 or 2) or imino (which may bear a methyl substituent), or T is ethan-1,1-diyl and U is a single bond or methylene;

R$^y$ is hydrogen or methyl; and

R$^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen);

Q$^{2B}$ is 1-piperazinyl which bears at the 4-position the group R$^{2A}$ (defined as above);

Q$^{2C}$ is 3,4-didehydropiperidin-4-yl which bears at the 1-position the group R$^{2A}$ (defined as above);

Q$^{2D}$ is cyclohexyl which bears at the 4-position the group —NR$^s$R$^t$ in which each of R$^s$ and R$^t$ independently is hydrogen or methyl or R$^s$ and R$^t$ together are trimethylene or tetramethylene;

Q$^{2E}$ is 1-piperidinyl which bears at the 4-position the group —NR$^s$R$^t$ (defined as above); and Q$^{2F}$ (showing the L$^2$ to which it is attached) is

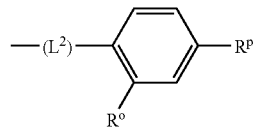

in which R$^o$ is hydrogen, halo, (1–6C)alkyl, hydroxy, (1–4C)alkoxy, benzyloxy or (1–4C)alkylthio; and R$^p$ is acetylamino, 1-hydroxyethyl, 1-hydroxy-1-methylethyl, 1-methoxy-1-methylethyl, 4-piperidinyl, 4-pyridinyl, dimethylaminosulfonyl or -J-R$^q$ in which J is a single bond, methylene, carbonyl, oxy, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl.

As used herein, the expression a compound of formula I or the expression a compound of the invention includes the compound and any conventional prodrug thereof, as well as a pharmaceutically acceptable salt of said compound or prodrug.

A more particular compound of formula I is one wherein A$^3$, A$^4$, A$^5$ and A$^6$, together with the two carbons to which they are attached, complete a substituted benzene in which A$^3$ is CR$^3$, A$^4$ is CR$^4$, A$^5$ is CR$^5$, and A$^6$ is CR$^6$; wherein R$^3$ is hydrogen;

one of R$^4$ and R$^5$ is hydrogen, methyl, fluoro, chloro, trifluoromethyl, trifluoromethoxy, R$^f$O$_2$C— or R$^g$NH—;

the other of R$^4$ and R$^5$ is hydrogen; and

R$^6$ is hydrogen;

in which R$^f$ is hydrogen, (1–4C)alkyl or benzyl; R$^g$ is hydrogen or R$^h$SO$_2$—; and R$^h$ is (1–4C)alkyl or dimethylamino;

L$^1$ is —CO—NH— such that -L$^1$-Q$^1$ is —CO—NH-Q$^1$;

Q$^1$ is 2-pyridinyl (which bears a methyl, fluoro or chloro substituent at the 5-position), 3-pyridinyl (which bears a methyl, fluoro or chloro substituent at the 6-position), 2-pyrimidinyl (which may bear a methyl, fluoro or chloro substituent at the 5-position) or 3-pyridazinyl (which may bear a methyl, fluoro or chloro substituent at the 6-position);

R$^2$ is -L$^2$-Q$^2$ in which -L$^2$- is —NH—CO—, —NH—CO—X—, —NH—CO—O—X—, —NH—CO—NH—X—, —NH—CH$_2$— or —O—CH$_2$—; and Q$^2$ is Q$^{2A}$, Q$^{2B}$, Q$^{2C}$, Q$^{2D}$, Q$^{2E}$ or Q$^{2F}$ wherein X is a single bond or methylene and the values of L$^2$ and Q$^2$ are together selected from —NH—CO—X-Q$^{2A}$, —NH—CO—O—X-Q$^{2A}$, —NH—CO—NH—X-Q$^{2A}$, —NH—CH$_2$-Q$^{2A}$, —O—CH$_2$-Q$^{2A}$, —NH—CO—X-Q$^{2B}$, —NH—CO-Q$^{2C}$, —NH—CO-Q$^{2D}$, —NH—CO-Q$^{2E}$ and —NH—CO-Q$^{2F}$ in which:

Q$^{2A}$ (showing the L$^2$ to which it is attached) is

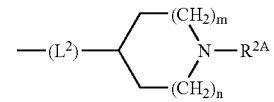

in which each of m and n independently is 0 or 1, and

R$^{2A}$ is hydrogen, —CHR$^y$R$^z$, —CHR$^w$R$^x$, or 4-pyridinyl (which is unsubstituted or bears a substituent R$^v$ at the 2- or 3-position) wherein R$^v$ is methyl, hydroxymethyl, {(1–2C)alkoxy}carbonyl; cyano, carbamoyl, thiocarbamoyl, or N-hydroxyamidino;

each of R$^w$ and R$^x$ independently is hydrogen or (1–3C) normal alkyl; or —CHR$^w$R$^x$ is 2-indanyl or (showing the nitrogen to which it is attached) is

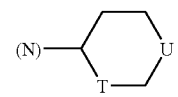

in which T is a single bond or methylene and U is methylene, oxy, thioxy or imino (which may bear a methyl substituent), or T is ethan-1,1-diyl and U is a single bond or methylene;

R$^y$ is hydrogen or methyl; and

R$^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen);

Q$^{2B}$ is 1-piperazinyl which bears at the 4-position the group R$^{2A}$ (defined as above);

Q$^{2C}$ is 3,4-didehydropiperidin-4-yl which bears at the 1-position the group R$^{2A}$ (defined as above);

Q$^{2D}$ is cyclohexyl which bears at the 4-position the group —NR$^s$R$^t$ in which each of R$^s$ and R$^t$ independently is hydrogen or methyl or R$^s$ and R$^t$ together are trimethylene or tetramethylene;

Q$^{2E}$ is 1-piperidinyl which bears at the 4-position the group —NR$^s$R$^t$ (defined as above); and $Q^{2F}$ (showing the $L^2$ to which it is attached) is

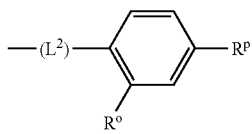

in which $R^o$ is hydrogen and $R^p$ is acetylamino, 1-hydroxyethyl, 1-hydroxy-1-methylethyl, 1-methoxy-1-methylethyl, 4-piperidinyl, 4-pyridinyl, dimethylaminosulfonyl or -J-$R^q$ in which J is a single bond, methylene, carbonyl, oxy, —S(O)$_q$— (wherein q is 0, 1 or 2), or —NR$^r$— (wherein R$^r$ is hydrogen or methyl); and $R^q$ is (1–6C)alkyl, phenyl, 3-pyridyl or 4-pyridyl.

A pharmaceutically acceptable salt of an antithrombotic agent of the instant invention includes one which is an acid-addition salt made from a basic compound of formula I and an acid which provides a pharmaceutically acceptable anion, as well as a salt which is made from an acidic compound of formula I and a base which provides a pharmaceutically acceptable cation. Thus, a salt of a novel compound of formula I as provided herein made with an acid or base which affords a pharmaceutically acceptable counterion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as isopropyl being specifically denoted.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–2C)alkyl is methyl or ethyl, and more particularly is methyl; for (1–3C)normal alkyl is methyl, ethyl or propyl; for (1–4C)alkyl is methyl, ethyl, propyl, isopropyl, butyl, isobutyl, or t-butyl, and more particularly is methyl, isopropyl, butyl or t-butyl; for (1–6C)alkyl is methyl, ethyl, propyl, butyl, pentyl or hexyl, and more particularly is methyl, butyl, or hexyl. A particular value for (3–6C)cycloalkyl is cyclopropyl, cyclobutyl, cyclopenytyl or cyclohexyl. A particular value for halo is bromo or chloro, and more particularly is chloro.

A particular value for $Q^1$ is 5-chloropyridin-2-yl, 5-fluoropyridin-2-yl, or 6-chloropyridazin-3-yl. A particular value for $R^2$ is (1-isopropylpiperidin-4-ylcarbonyl)amino, (1-cyclohexylpiperidin-4-ylcarbonyl)amino, (4-isopropylpiperazin-1-ylcarbonyl)amino, [1-(tetrahydropyran-4-yl)piperidin-4-ylcarbonyl]amino, [4-(1-pyrrolidinyl)piperidin-1-ylcarbonyl]amino, [1-(4-pyridinyl)piperidin-4-ylmethyl]amino, [1-(2-carboxypyridin-4-yl)piperidin-4-ylmethyl]amino, or [1-(2-methoxycarbonylpyridin-4-yl)piperidin-4-ylmethyl]amino. A particular set of values for $R^3$–$R^6$ is that each of $R^3$–$R^6$ is hydrogen. Another particular set of values for $R^3$–$R^6$ is that each of $R^3$, $R^4$ and $R^6$ is hydrogen and $R^5$ is chloro or fluoro. A further particular set of values for $R^3$–$R^6$ is that each of $R^3$, $R^4$ and $R^6$ is hydrogen and $R^5$ is $R^a$ wherein $R^a$ is phenyl, furanyl, thienyl, 2-isothiazolyl or pyridyl.

A particular species is one those listed below as example 44, 51, 69, 70, 75, 80, 84, 96 or 97.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

A compound of formula I may be prepared by processes which include processes known in the chemical art for the production of structurally analogous compounds or by a novel process described herein. A process for the preparation of a compound of formula I (or a pharmaceutically acceptable salt thereof) and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I (or a pharmaceutically acceptable salt thereof) as provided in any of the above descriptions which is selected from any of those described in the examples, including the following.

(A) For a compound of formula I in which $-L^2-Q^2$, is $-NH-CO-Q^2$, $-NH-CO-X-Q^2$, $-NH-CO-O-X-Q^2$ or $-NH-CO-NH-X-Q^2$, acylating an amine of formula II,

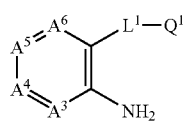

II using a corresponding acid of formula $HO-CO-Q^2$, $HO-CO-X-Q^2$, $HO-CO-O-X-Q^2$, or $HO-CO-NH-X-Q^2$, or an activated derivative thereof. Typical activated derivatives include the acid halides, activated esters, including 4-nitrophenyl esters and those derived from coupling reagents, as well as (when the product is a urea) isocyanates. Typical procedures include those described at example 1-D, example 4-B and example 9-A.

(B) For a compound of formula I in which $-L^2-Q^2$ is $-O-CH_2-Q^{2A}$, akylating a phenol of formula III

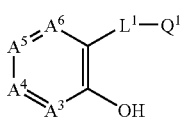

III using a reagent of formula $Y-CH_2-Q^{2A}$ in which Y is a conventional leaving group. As used herein, a leaving group "Y" is a moiety which is displaced in a nucleophilic substitution reaction, for example a halo group (such as chloro, bromo or iodo), a sulfonate ester group (such as methylsulfonyloxy, p-toluylsulfonyloxy or trifluoromethylsulfonyloxy), or the reactive species derived from treating an alcohol with triphenylphospine, diethyl azodicarboxylate and triethyl amine (in a Mitsunobu reaction), for example as described at example 8-B.

(C) Acylating an amine of formula $H_2N-Q^1$, or a deprotonated derivative thereof, using an acid of formula IV, or an activated derivative thereof.

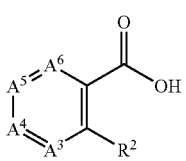

IV

Typical deprotonated derivatives of the amine $H_2N-Q^1$ include, for example, that derived from treatment of the amine with an organomagnesium reagent, for example, with allylmagnesium bromide or methylmagnesium bromide. Typical activated derivatives include the acid halides, activated esters, including 4-nitrophenyl esters and those derived from coupling reagents.

For a compound of formula I in which $R^2$ is of the form $-NH-CO-Q^2$, the activated acid may be a [1,3]oxazine of formula IVa,

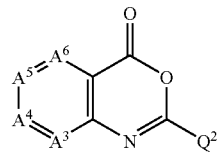

IVa wherein $Q^2$ represents, for example, $Q^{2A}$, $Q^{2B}$, $Q^{2C}$, $Q^{2D}$, $Q^{2E}$ or $Q^{2F}$. A typical procedure is one such as described at example 46-D (using potassium cyanide to promote the reaction) or at example 51-D.

For a compound of formula I in which $R^2$ is of the form $-NH-CH_2-Q^2$, the activated acid may be an anhydride of formula IVb,

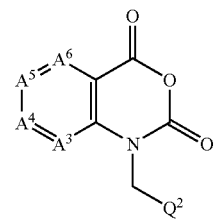

IVb wherein $Q^2$ represents $Q^{2A}$. A typical procedure is similar to that described at example 51-D for use with the activated acid of formula IVa.

(D) For a compound of formula I in which $R^2$ is $-NH-CH_2-Q^{2A}$, alkylating an amine of formula II directly, using a compound of formula $Y-CH_2-Q^{2A}$, or (preferably) indirectly by reductive alkylation using an aldehyde of formula $Q^{2A}$-CHO. In the reductive alkylation the intermediate imine of formula V or acid addition salt thereof (which provide a further aspect of the invention),

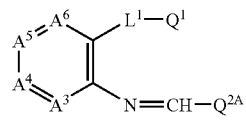

V may be formed in situ and reduced directly, or may be isolated prior to reduction, for example as described at examples 47-D and 59-B where the reduction is carried out using borane trimethylamine complex in glacial acetic acid.

(E) For a compound of formula I in which $R^2$ is $-NH-CO-O-X-Q^{2A}$, or $-NH-CO-NH-X-Q^{2A}$, acylating an alcohol of formula HO—X-Q$^{2A}$ or an amine of formula NH$_2$—X-Q$^{2A}$, using an activated derivative of an acid of formula VI,

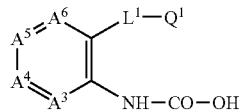

particularly, the corresponding isocyanate or 4-nitrophenyl ester. The procedure may be carried out analogously to the starting material preparation of example 51-A.

(F) For a compound of formula I in which R$^2$ is —NH—CO—X-Q$^{2B}$ in which X is a single bond, acylating at the 1-position a piperazine of formula H-Q$^{2B}$, using an activated derivative of an acid of formula VI, particularly, the corresponding isocyanate or 4-nitrophenyl ester. The procedure may be carried out analogously to the starting material preparation of example 51-A or of example 95-A.

(G) For a compound of formula I in which R$^2$ is —NH—CO—X-Q$^{2B}$ in which X is methylene, alkylating at the 1-position a piperazine of formula H-Q$^{2B}$, using an alkylating agent of formula VII

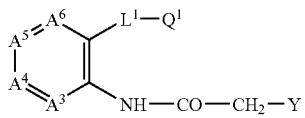

in which Y is a leaving group, for example as described at example 45-B.

(H) For a compound of formula I in which R$^{2A}$ is methylsulfonyl, substituting the amino nitrogen of a corresponding compound of formula I in which R$^{2A}$ is hydrogen using an activated derivative of methanesulfonic acid, for example using methanesulfonyl chloride in the presence of added base.

(I) For a compound of formula I in which R$^{2A}$ is —CHR$^y$R$^z$ or —CHR$^w$R$^x$, alkylating the amino nitrogen of a corresponding compound of formula I in which R$^{2A}$ is hydrogen using an alkylating agent of formula Y—CHR$^y$R$^z$ or Y—CHR$^w$R$^x$ or, preferably, reductively alkylating the amine using a compound of formula R$^y$—CO—R$^z$ or R$^w$—CO—R$^x$. The direct alkylation may be completed in a polar solvent in the presence of a base, for example as described at example 102. The reductive alkylation conveniently is carried out, for example, using sodium cyanoborohydride in methanol/acetic acid as described at example 9-C and at examples 48 and 112 or using sodium triacetoxyborohydride in an inert solvent such as 1,2-dichloroethane along with an excess of the carbonyl compound and glacial acetic acid as described at example 27.

(J) For a compound of formula I in which R$^{2A}$ is 4-pyridinyl (which is unsubstituted or bears a substituent R$^v$ at the 2- or 3-position), substituting the amino nitrogen of a corresponding compound of formula I in which R$^{2A}$ is hydrogen using a corresponding pyridin reagent bearing a leaving group Y at the 4-position, for example with a 4-chloropyridine in ethanol as described at example 52 or at example 85.

(K) For a compound of formula I in which R$^{2A}$ is 4-pyridinyl in which R$^v$ is alkoxycarbonyl, esterifying a corresponding compound of formula I in which R$^v$ is carboxy, for example as described at example 97.

(L) For a compound of formula I in which R$^{2A}$ is 4-pyridinyl in which R$^v$ is hydroxymethyl, reducing the ester of a corresponding compound of formula I in which R$^v$ is alkoxycarbonyl.

(M) For a compound of formula I in which R$^{2A}$ is 4-pyridinyl in which R$^v$ is carbamoyl, amidating the ester of a corresponding compound of formula I in which R$^v$ is alkoxycarbonyl.

(N) For a compound of formula I in which R$^{2A}$ is 4-pyridinyl in which R$^v$ is thiocarbamoyl, adding H$_2$S to the nitrile of a corresponding compound of formula I in which R$^v$ is cyano.

(O) For a compound of formula I in which R$^{2A}$ is 4-pyridinyl in which R$^v$ is N-hydroxyamidino, adding H$_2$NOH to the nitrile of a corresponding compound of formula I in which R$^v$ is cyano. The addition may be direct or indirect, such as via an imidate ester or by treating a compound in which R$^v$ is thiocarbamoyl with methyl iodide to form a thioimidate ester, then treatment with hydroxylamine.

(P) For a compound of formula I in which R$^{2A}$ is 4-pyridinyl in which R$^v$ is carboxy, decomposing the ester of a corresponding compound of formula I in which R$^v$ is alkoxycarbonyl.

(Q) For a compound of formula I in which —NR$^s$R$^t$ is other than amino, alkylating a corresponding compound of formula I in which —NR$^s$R$^t$ is amino using a conventional method. When R$^s$ and R$^t$ together are trimethylene or tetramethylene, a difunctional alkylating agent, such as 1,3-dibromopropane or 1,4-dibromobutane is preferred.

(R) For a compound of formula I which bears —NR$^s$R$^t$, reductively alkylating H—NR$^s$R$^t$ using a corresponding compound but in which the carbon to bear the —NR$^s$R$^t$ group bears an oxo group, for example, using a procedure similar to one of procedure (I) above, as described at example 98.

(S) For a compound of formula I in which R$^p$ is 1-hydroxy-1-methylethyl, adding a methyl group to the carbonyl group of a corresponding compound of formula I in which R$^p$ is acetyl using an organometallic reagent such as, for example, methylmagnesium bromide.

(T) For a compound of formula I in which R$^p$ is 1-methoxy-1-methylethyl, treating a corresponding compound of formula I in which R$^p$ is 1-hydroxy-1-methylethyl with methanol and an acid catalyst.

(U) For a compound of formula I in which R$^4$ or R$^5$ is amino, reducing the nitro group of a compound corresponding to a compound of formula I but in which R$^4$ or R$^5$ is nitro.

(V) For a compound of formula I in which R$^4$ or R$^5$ is R$^g$NH— and R$^g$ is R$^h$SO$_2$—, substituting the amino group of a corresponding compound of formula I in which R$^4$ or R$^5$ is amino using an activated derivative of the sulfonic acid R$^h$SO$_2$—OH.

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

A novel intermediate or starting material compound such as, for example, a novel compound of formula II, III, IV or VI, etc., provides a further aspect of the invention. The various starting materials may be made by processes which include processes known in the chemical art for the production of structurally analogous compounds or by a novel process described herein or one analogous thereto.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which $R^4$ is hydroxy, but in which the corresponding substituent is —$OP^p$ in place of hydroxy, wherein $P^p$ is a phenol protecting group other than (1–4C)alkyl or benzyl. Phenol protecting groups are well known in the art, for example as described in T. W. Greene and P. G. M. Wuts, "Protecting Groups in Organic Synthesis" (1991). Further, $P^p$ may denote a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of formula I which bears an acidic moiety, such as a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II, III, IV or VI discussed above.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
| --- | --- |
| Isotonic saline | 1,000 mL |

The solution of the above ingredients generally is administered intravenously to a subject at a rate of 1 mL per minute.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

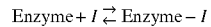

$$Enzyme + I \rightleftarrows Enzyme - I$$

$$Kass = \frac{[Enzyme - I]}{[(Enzyme) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 µL buffer (0.03 M Tris, 0.15 M NaCl pH 7) in each well, followed by 25 µL of inhibitor solution (in 100% methanol, or in 50% v:v aqueous methanol) and 25 µL enzyme solution; within two minutes, 150 µL aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA; 5.9 nM human thrombin or 1.4 nM bovine trypsin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.81 mM HD-Ile-Pro-Arg-pNA; and 0.37 nM urokinase is used with 0.30 mM pyro-gfsGlu-Gly-Arg-pNA.

Kass is calculated for a range of concentrations of test compounds and the mean value reported in units of liter per mole. In general, a factor Xa inhibiting compound of formula I of the instant invention, as exemplified herein, exhibits a Kass of 0.1 to $0.5 \times 10^6$ L/mole or much greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1–11 (1980; and Smith, et al., *Biochemistry*, 11, 2958–2967, (1972). Human fibrinogen (98 percent pure/ plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 µL thrombin (73 NIH unit/mL) to 100 µL human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 µg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M.). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

FeCl$_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varion) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{AUC\ po}{AUC\ iv} \times \frac{Dose\ iv}{Dose\ po} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means+/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-µA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-µL sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time d vice (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of p<0.05. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
aq=aqueous
Bn or Bzl=benzyl
Boc=t-butyloxycarbonyl
Bu=butyl
n-BuLi=butyllithium
Calcd=calculated
conc=concentrated
DMF=dimethylformamide
DMSO=dimethylsulfoxide
eq=(molar) equivalent
Et=ethyl
EtOAc=ethyl acetate
$Et_3N$=triethylamine
$Et_2O$=diethyl ether
EtOH=ethanol
FTIR=Fourier transform IR
Hex=hexanes
HPLC=High Performance Liquid Chromatography
HRMS=high resolution mass spectrum
i-PrOH=isopropanol
IR=Infrared Spectrum
LC-MS=liquid chromatography-mass spectrum (using HPLC)
Me=methyl
MeOH=methanol
MS-ES (or ES-MS)=electrospray mass spectrum
MS-FAB (or FAB-MS)=fast atom bombardment mass spectrum
MS-FIA (or FIA-MS)=flow injection analysis mass spectrum
MS-FD (or FD-MS)=field desorption mass spectrum
MS-IS (or IS-MS)=ion spray mass spectrum
NMR=Nuclear Magnetic Resonance
Ph=phenyl
i-Pr=isopropyl
RPHPLC=Reversed Phase High Performance Liquid Chromatography
RT (or $R_t$)=retention time
satd=saturated
$SiO_2$=silica gel
SCX=strong cation exchange (resin)
TBS=tert-butyldimethylsilyl
TFA=trifluoroacetic acid
THF=tetrahydrofuran
TIPS=triisopropylsilyl
TLC=thin layer chromatography
tosyl=p-toluenesulfonyl
triflic acid=trifluoromethanesulfonic acid Unless otherwise stated, pH adjustments and work up are with aqueous acid or base solutions. $^1$H-NMR indicates a satisfactory NMR spectrum was obtained for the compound described. IR (or FTIR) indicates a satisfactory infra red spectrum was obtained for the compound described.

For consistency and clarity, a number of compounds are named as substituted benzamide derivatives.

Analytical HPLC method was a linear gradient of 90/10 to 50/50 (0.1% TFA in water/0.1% TFA in acetonitrile) over 40 minutes with a flow rate of 1 mL/min.

LC-MS Method A: gradient from 50% acetonitrile-40% water-10% water with 0.1% trifluoroacetic acid to 90% acetonitrile-10% water with 0.1% trifluoroacetic acid over 5 min; hold 5 min; 0.5 mL/min; Zorbax SB-$C_{18}$ column, 4.6 by 75 mm; 25° C. LC-MS Method B: gradient from 20% acetonitrile-70% water-10% water with 0.1% trifluoroacetic acid to 70% acetonitrile-20% water-10% water with 0.1% trifluoroacetic acid over 5 min; hold 5 min; 0.5 mL/min; Zorbax SB-$C_{18}$ column, 4.6 by 75 mm; 25° C.

EXAMPLE 1

Preparation of N-(5-Methylpyridin-2-yl)-2-[[1-(4-pyridinyl)piperidin-4-ylcarbonyl]amino]benzamide Hydrochloride

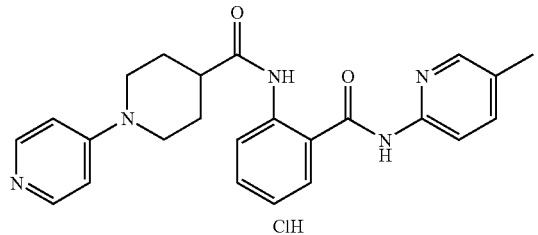

A. N-(5-Methylpyridin-2-yl)-2-nitrobenzamide

To a stirring solution of 2-amino-5-methylpyridine (3.1 g, 29 mmol) and pyridine (7.3 mL, 90 mmol) in dichloromethane (200 mL) was added 2-nitrobenzoyl chloride (5.7 g, 30 mmol). After 4 h, the solvent was removed in vacuo and the residue was partitioned between ethyl acetate (500 mL) and water (250 mL). The organic phase was separated and washed again with water (250 mL) followed by brine (250 mL) and then dried with $MgSO_4$, filtered and partially concentrated in vacuo, which resulted in the formation of a precipitate. After standing overnight, the solid was filtered and dried in vacuo to give 3.9 g (52%) of white solid.

$^1$H-NMR

FD-MS, m/e 256.9 (m)

Analysis for $C_{13}H_{11}N_3O_3$: Calcd: C, 60.70; H, 4.31; N, 16.33; Found: C, 61.21; H, 4.32; N, 16.63.

B. N-(5-Methylpyridin-2-yl)-2-aminobenzamide

To a stirring solution of N-(5-methylpyridin-2-yl)-2-nitrobenzamide (1.5 g, 5.8 mmol) and $Ni(OAc)_2.4H_2O$ (2.9 g, 11.7 mmol) in THF (20 mL) and methanol (40 mL) at 0° C. was added, in small portions, sodium borohydride (0.88 g, 23.2 mol). After complete addition and an additional 5 min, the solvent was evaporated in vacuo and the residue was partitioned between ethyl acetate (200 mL) and 50% conc $NH_4OH$ (200 mL). The organic phase was separated and washed again with 50% conc $NH_4OH$, followed by brine, then dried with $MgSO_4$, filtered and concentrated in vacuo to give 1.25 g (95%) of a light yellow solid.

$^1$H-NMR

FD-MS, m/e 227.1 (m)

C. 1-(4-Pyridinyl)piperidin-4-ylcarbonyl Chloride

To a stirring suspension of 1-(4-pyridinyl)piperidin-4-ylcarboxylic acid (0.8 g, 3.88 mmol) in dichloromethane (75 mL) at reflux was added thionyl chloride (0.45 mL, 5.82 mmol). After 3 h, the solvent was removed in vacuo and the residue was dissolved in dichloromethane (75 mL), giving a solution of the title compound, approximately 0.05 M.

D. N-(5-Methylpyridin-2-yl)-2-[[1-(4-pyridinyl)piperidin-4-ylcarbonyl]amino]benzamide Hydrochloride To a stirring solution of N-(5-methylpyridin-2-yl)-2-aminobenzamide (0.28 g, 1.2 mmol) in pyridine (5 mL) and dichloromethane (40 mL) was added a solution of 1-(4-pyridinyl)piperidin-4-ylcarbonyl chloride (0.55 g, 2.5 mmol) in dichloromethane (40 mL). After stirring overnight, the solvent was removed in vacuo and the residue was partitioned between ethyl acetate (300 mL) and 1 N NaOH (150 mL). The organic phase was separated and washed again with 1 N NaOH, followed by water and brine, then dried with $MgSO_4$, filtered and concentrated in vacuo. The residue was then purified by preparative RPHPLC (C18), eluting with a linear gradient of 90/10 to 50/50 (0.01% HCl/acetonitrile) over 180 min. The pure product containing fractions were combined and lypholized to give 222 mg (40%) of a white powder.

$^1$H-NMR

FD-MS, m/e 416 (m)

Analysis for $C_{24}H_{25}N_5O_2.2.1HCl.1.5H_2O$: Calcd: C, 55.53; H, 5.84; N, 13.49; Cl, 14.34; Found: C, 55.54; H, 5.79; N, 13.44; Cl, 14.17.

EXAMPLE 2

Preparation of N-(5-Chloropyridin-2-yl)-2-[[1-(4-pyridinyl)piperidin-4-ylcarbonyl]amino]benzamide Hydrochloride

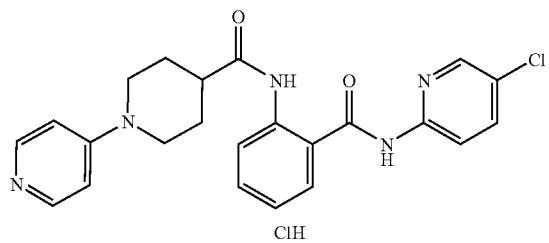

A. N-(5-Chloropyridin-2-yl)-2-nitrobenzamide

Using methods substantially equivalent to those described in example 1-A, N-(5-chloropyridin-2-yl)-2-nitrobenzamide (6.5 g, 79%) was prepared from 2-amino-5-chloropyridine and 2-nitrobenzoyl chloride.

$^1$H-NMP,

FD-MS, m/e 276.9 (m)

Analysis for $C_{12}H_8N_3O_3Cl$: Calcd: C, 51.91; H, 2.90; N, 15.13; Found: C, 52.61; H, 2.89; N, 15.29.

B. N-(5-Chloropyridin-2-yl)-2-aminobenzamide

To a solution of N-(5-chloropyridin-2-yl)-2-nitrobenzamide (2 g, 7.2 mmol) in THF (50 mL) and ethyl acetate (50 mL) was added Raney Ni (0.2 g) and the mixture was placed under hydrogen (4.1 bar) in a high pressure apparatus. After shaking overnight, the mixture was filtered and concentrated in vacuo and purified by flash chromatography to give 1.5 g (83%) of an off-white solid.

$^1$H-NMR

C. N-(5-Chloropyridin-2-yl)-2-[(1-(4-pyridinyl)piperidin-4-ylcarbonyl)amino]benzamide Hydrochloride Using methods substantially equivalent to those described in example 1-D, N-(5-chloropyridin-2-yl)-2-[[1-(4-pyridinyl)piperidin-4-ylcarbonyl]amino]benzamide hydrochloride (2.07 g, 69%) was prepared from N-(5-chloropyridin-2-yl)-2-aminobenzamide and 1-(4-pyridinyl)piperidin-4-ylcarbonyl chloride.

$^1$H-NMR

IS-MS, m/e 436 (m+1)

Analysis for $C_{23}H_{22}N_5O_2Cl\cdot0.9HCl\cdot0.9H_2O$: Calcd: C, 56.96; H, 5.13; N, 14.44; Cl, 13.89; Found: C, 57.16; H, 4.75; N, 14.29; Cl, 14.03.

EXAMPLE 3

Preparation of N-(6-Chloropyridin-3-yl)-2-[[1-(4-pyridinyl)piperidin-4-ylcarbonyl]amino]benzamide Hydrochloride

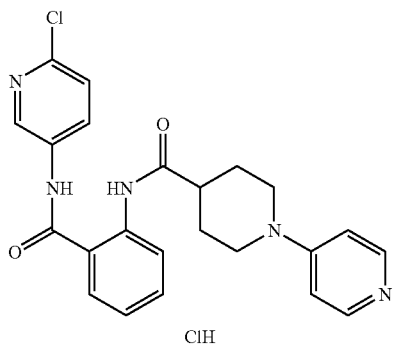

A. N-(6-Chloropyridin-3-yl)-2-nitrobenzamide

Using methods substantially equivalent to those described in example 1-A, N-(6-chloropyridin-3-yl)-2-nitrobenzamide (1.24 g, 73%) was prepared from 2-nitrobenzoyl chloride and 3-amino-6-chloropyridine.

$^1$H-NMR

IS-MS, m/e 278 (m+1)

Analysis for $C_{12}H_8N_3O_3Cl$: Calcd: C, 51.91; H, 2.90; N, 15.13; Found: C, 51.80; H, 3.09; N, 14.98.

B. N-(6-Chloropyridin-3-yl)-2-aminobenzamide

To a stirred solution of N-(6-chloropyridin-3-yl)-2-nitrobenzamide (0.6 g, 2.15 mmol) in methanol (150 mL) and tetrahydrofuran (75 mL) was added nickel acetate tetrahydrate (1.07 g, 4.3 mmol). Sodium borohydride (0.326 g, 8.61 mmol) was then added in small portions. After gas evolution had ceased, the solvent was removed in vacuo. The residue was partitioned between ethyl acetate and concentrated ammonium hydroxide, and the layers separated. The organic phase was washed with concentrated ammonium hydroxide and saturated aqueous sodium chloride solution, dried (magnesium sulfate), filtered, and concentrated in vacuo. The solid was suspended in ether, sonicated, and filtered to give 0.243 g (46%) of a pink solid.

$^1$H-NMR

IS-MS, m/e 248.3 (m+1)

Analysis for $C_{12}H_{10}N_3OCl$: Calcd: C, 58.19; H, 4.07; N, 16.96; Found: C, 59.63; H, 4.13; N, 17.27.

C. N-(6-Chloropyridin-3-yl)-2-[[1-(4-pyridinyl)piperidin-4-ylcarbonyl]amino]benzamide Hydrochloride Using methods substantially equivalent to those described in example 1-D, N-(6-chloropyridin-3-yl)-2-[[1-(4-pyridinyl)piperidin-4-ylcarbonyl]amino]benzamide hydrochloride (0.12 g, 26%) was prepared from N-(6-chloropyridin-3-yl)-2-aminobenzamide and 1-(4-pyridyl)piperidin-4-ylcarbonyl chloride.

$^1$H-NMR

IS-MS, m/e 436.2 (m+1)

Analysis for $C_{23}H_{22}N_5O_2Cl\cdot1.9HCl\cdot2.4H_2O$: Calcd: C, 53.96; H, 5.45; N, 13.68; Cl, 13.16; Found: C, 53.97; H, 5.06; N, 13.28; Cl, 13.32.

EXAMPLE 4

Preparation of N-(5-Chloropyridin-2-yl)-2-[[1-(4-pyridinyl)pyrrolidin-3-yloxycarbonyl]amino]benzamide Hydrochloride

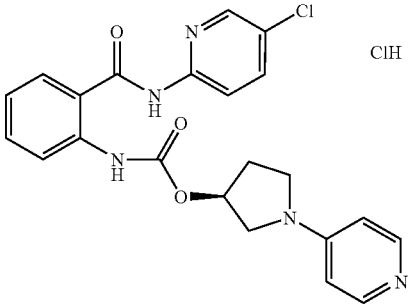

A. 1-(4-Pyridinyl)-3-hydroxypyrrolidine

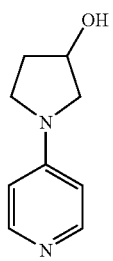

A mixture of 3-hydroxypyrrolidine (9.9 g, 113.64 mmol), 4-bromopyridinium hydrochloride (22.098 g, 113.64 mmol), triethylamine (47.5 mL, 341.0 mmol) and 3:1 ethanol:water (150 mL), in a pressure tube reaction vessel, was purged with nitrogen and sealed. The mixture was heated to 150° C. for 96 hours and cooled. The solvent was evaporated and ethyl acetate (50 mL) was added. After trituration, the organic solvent was decanted off and saved. Methylene chloride (80 mL) and 2 N sodium hydroxide (60 mL) were added to the solid. The mixture was shaken vigorously and was filtered with water and methylene chloride wash to give the title compound as an off-white solid. The organic supernatant and the methylene chloride and water washes were combined. This mixture was extracted with methylene chloride. The organic layer was sodium sulfate dried and concentrated. The residue was triturated with methylene chloride and the solid was filtered. This solid was combined with the solid from above and vacuum dried (100° C. at 133 Pa for 14 hours) to give the title compound as an off-white solid (8.52 g, 46%).

$^1$H-NMR (300, DMSO-$d_6$): 8.07 (d, J=6.4 Hz, 1H), 6.44 (d, J=6.4 Hz, 1H), 5.01 (br s, 1H), 4.40 (br s, 1H), 3.42–3.20 (m, 3H), 3.12 (d. J=10.6 Hz, 1H), 2.07–1.80 (m, 2H).

IS-MS, m/e: 165.4 (m+1).

B. N-(5-Chloropyridin-2-yl)-2-[[1-(4-pyridinyl)pyrrolidin-3-yloxycarbonyl]amino]benzamide To as solution of 1-(4-pyridinyl)-3-hydroxypyrrolidine (330 mg, 2.01 mmol) in dichloromethane (30 mL) was added methanesulfonic acid (0.15 mL, 2.31 mmol). After 15 seconds, quinoline (0.3 mL, 2.54 mmol) was added, immediately followed by a toluene solution of phosgene (0.65 mL, 1.25 mmol). After 5 minutes, the reaction was placed in an oil bath at 35° C. After 45 minutes, the reaction was cooled to room temperature. N-(5-Chloropyridin-2-yl)-2-aminobenzamide (498 mg, 2.01 mmol) was added, followed by quinolin (0.3 mL, 2.54 mmol). After stirring overnight, the reaction was diluted with dichloromethane (150 mL) and washed with saturated aqueous sodium carbonate (2×25 mL). The organic layer was concentrated in vacuo and purified by flash column chromatography (100% $CH_2Cl_2$ to 9% MeOH/$CH_2Cl_2$) and then by HPLC to give the title product (181 mg, 0.41 mmol, 21%).

$^1$H-NMR (300 MHz, DMSO-$d_6$): δ 11.01(s, 1H); 9.96(s, 1H); 8.38(d, J=1.8 Hz, 1H); 8.21(m, 2H); 8.06(d, J=9.0 Hz, 1H); 7.88(m, 2H); 7.77(d, J=8.7 Hz, 1H); 7.51(t, J=7.2 Hz, 1H); 7.15(t, J=7.2 Hz, 1H); 6.87(d, J=7.5 Hz, 1H); 6.80(d, J=6.6 Hz, 1H); 5.36(m, 1H); 3.74–3.39(m, 4H); 2.22(m, 2H).

IS-MS, m/e 438.2 (m+1).

Analysis for $C_{22}H_{20}N_5O_3Cl \cdot 1.0HC \cdot 1.25H_2O$: Calcd: C, 53.18; H, 4.77; N, 14.09; Found: C, 53.05; H, 4.64; N, 13.88.

EXAMPLE 5

Preparation of N-(5-Chloropyridin-2-yl)-2-[(1-benzylpyrrolidin-3-ylmethoxycarbonyl)amino]benzamide

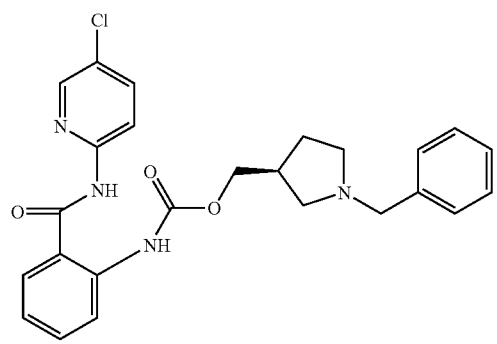

A. 1-Benzylpyrrolidine-3-methanol

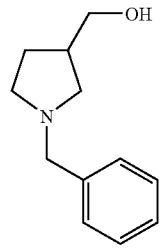

To a mixture of methyl 1-benzylpyrrolidine-3-carboxylate (11.67 g, 50 mmol) and tetrahydrofuran, at 0° C. was added lithium aluminum hydride (3.795 g, 100 mmol). The reaction was warmed to room temperature and refluxed for 24 hours. After cooling to 0° C., the reaction was quenched with saturated sodium sulfate and warmed to room temperature. Tetrahyrofuran (50 mL) and solid sodium sulfate were added to the mixture. After stirring for 1 hour, the mixture was filtered and the filtrate was concentrated and vacuum dried for 3 days to give the title compound as a colorless oil (8.49 g, 88%).

$^1$H-NMR (300 MHz, DMSO-$d_6$): 7.21–7.31 (m, 5H), 4.50 (t. J=5.3 Hz, 1H), 3.51 (s, 2H), 3.20–3.31 (m, 2H), 2.35–2.50 (m, 4H), 2.10–2.27 (m, 1H), 1.70–1.85 (m, 1H), 1.27–1.43 (m, 1H).

IS-MS, m/e: 192.4 (m+1).

B. N-(5-Chloropyridin-2-yl)-2-[(1-benzylpyrrolidin-3-ylmethoxycarbonyl)amino]benzamide Using methods substantially equivalent to those described in example 4-B, N-(5-chloropyridin-2-yl)-2-[(1-benzylpyrrolidin-3-ylmethoxycarbonyl)amino]benzamide (690 mg, 74%) was prepared from N-(5-chloropyridin-2-yl)-2-aminobenzamide and 1-benzylpyrrolidine-3-methanol.

IR($CHCl_3$): 1730, 1507, 1375, 1296.

$^1$H-NMR (400 MHz, DMSO-$d_6$): δ 10.99 (s, 1H); 9.91 (s, 1H); 8.40 (S, 1H); 8.10 (D, J=8.8 Hz, 1H); 7.92 (D, J=9.2 Hz, 1H); 7.87 (D, J=8.01 Hz, 1H); 7.77 (D, J=8.0 Hz, 1H);

7.49 (t, J=7.8 Hz, 1H); 7.27 (m, 5H); 7.13 (t, J=7.6 Hz, 1H); 3.99–3.87 (m, 3H); 3.30 (s, 2H); 2.38 (br s, 3H); 2.24 (br s, 1H); 1.82 (br s, 1H); 1.40 (br s, 1H).

IS-MS, m/e 465.2 (m+1).

Analysis for $C_{25}H_{25}N_4O_3Cl$: Calcd: C, 64.58; H, 5.42; N, 12.05; Found: C, 64.35; H, 5.50; N, 12.04.

EXAMPLE 6

Preparation of N-(5-Chloropyrimidin-2-yl)-2-[[1-(4-pyridinyl)piperidin-4-ylcarbonyl]amino]benzamide

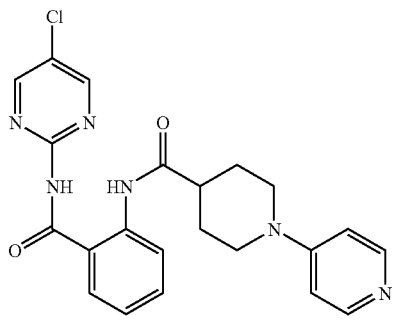

A. N-(5-Chloropyrimidin-2-yl)-2-nitrobenzamide

To a stirred solution of 2-amino-5-chloropyrimidine (2.35 g, 18.14 mmol) in pyridine (10 mL) and dichloromethane (100 mL) was added slowly 2-nitrobenzoyl chloride (5.3 mL, 39.90 mmol). After stirring for 2 h, the solvent was removed in vacuo. The residue was partitioned between ethyl acetate and water, and the layers separated. The organic phase was washed consecutively with 1 N aqueous citric acid, saturated aqueous sodium chloride, saturated aqueous sodium bicarbonate, and saturated aqueous sodium chloride, then dried (magnesium sulfate), filtered, and concentrated in vacuo. The solid was suspended in ether, sonicated, and filtered to give 4.72 g (61%) of a bis-acylated product (IS-MS, m/e 428.1 (m+1).

To a stirring solution of a portion of this material (0.5 g, 1.17 mmol) in p-dioxane (5 mL) was added a solution of lithium hydroxide monohydrate (0.108 g, 2.58 mmol) in water (3 mL). After stirring for 0.5 h, the solvent was removed in vacuo. The residue was washed with THF, then dissolved in water (40 mL) and acidified to pH 3.5 with concentrated hydrochloric acid which resulted in the formation of a precipitate. The mixture was filtered and dried to give 0.275 g (84%) of a tan solid.

$^1$H-NMR

IS-MS, m/e 279.2 (m+1)

Analysis for $C_{11}H_7N_4O_3Cl$: Calcd: C, 47.41; H, 2.53; N, 20.11; Found: C, 47.69; H, 2.55; N, 19.87.

B. N-(5-Chloropyrimidin-2-yl)-2-aminobenzamide

Using methods substantially equivalent to those described in example 2-B, N-(5-chloropyrimidin-2-yl)-2-aminobenzamide (0.17 g, 41%) was prepared from N-(5-chloropyrimidin-2-yl)-2-nitrobenzamide.

$^1$H-NMR

IS-MS, m/e 249.2 (m+1)

Analysis for $C_{11}H_9N_4OCl$: Calcd: C, 53.13; H, 3.65; N, 22.53; Found: C, 53.40; H, 3.68; N, 22.64.

C. N-(5-Chloropyrimidin-2-yl)-2-[[1-(4-pyridinyl)piperidin-4-ylcarbonyl]amino]benzamide Using methods substantially equivalent to those described in example 1-D, N-(5-chloropyrimidin-2-yl)-2-[[1-(4-pyridinyl)piperidin-4-ylcarbonyl]amino]benzamide (0.13 g, 30%) was prepared from N-(5-chloropyrimidin-2-yl)-2-aminobenzamide and 1-(4-pyridinyl)piperidin-4-ylcarbonyl chloride. No purification by HPLC was required.

$^1$H-NMR

IS-MS, m/e 437.3 (m+1)

Analysis for $C_{22}H_{21}N_6O_2Cl$: Calcd: C, 60.48; H, 4.84; N, 19.23; Cl, 8.11; Found: C, 60.41; H, 4.85; N, 19.21; Cl, 8.53.

EXAMPLE 7

Preparation of N-(6-Chloropyridazin-3-yl)-2-[[1-(4-pyridinyl)piperidin-4-ylcarbonyl]amino]benzamide

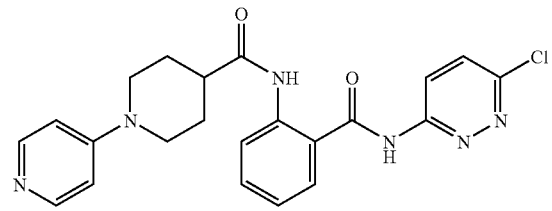

A. N-(6-Chloropyridazin-3-yl)-2-nitrobenzamide

Using the procedure described in example 1-A, 3-amino-6-chloropyridazine (5 g, 39 mmol) yielded 8.1 g (75%) of the title compound.

$^1$H-NMR

FIA-MS, m/e 279.2 (MH+)

Analysis for $C_{11}H_7ClN_4O_3$: Calcd: C, 47.41; H, 2.53; N, 20.11. Found: C, 47.23; H, 2.78; N, 20.01.

B. N-(6-Chloropyridazin-3-yl)-2-[[1-(4-pyridyl)piperidin-4-ylcarbonyl]amino]benzamide Hydrochloride Using the procedure described above in example 1-B, N-(6-chloropyridazin-3-yl)-2-nitrobenzamide (2.0 g, 7.18 mmol) yielded 0.67 g of crude 2-amino-N-(6-chloropyridazin-3-yl)benzamide, which was treated with 1-(4-pyridinyl)piperidin-4-ylcarbonyl chloride (436 mg, 1.9 mmol) using the procedure described in example 1-D to yield 60 mg (1.8%) of the title compound.

$^1$H-NMR

FD-MS, m/e 437.2(M+)

Reverse Phase HPLC (1 mL/min, 0.1% TFA in water/ 0.1% TFA in acetonitrile, linear gradient 98/2 through 70/30 over 45 min)—retention time=32.72 min

EXAMPLE 8

Preparation of N-(5-Chloropyridin-2-yl)-2-[[1-(4-pyridinyl)piperidin-4-yl]methoxy]benzamide Dihydrochloride

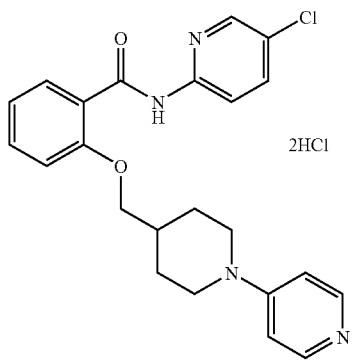

A. N-(5-Chloropyridin-2-yl)-2-hydroxybenzamide

Acetylsalicylic acid chloride was prepared from acetylsalicylic acid using standard oxalyl chloride-methylene chloride conditions. The crude acid chloride was used without purification to acylate commercial 2-amino-5-chloropyridine using standard conditions in methylene chloride to give 2-acetoxy-N-(5-chloropyridin-2-yl)benzamide in 62% yield as a light yellow solid which was used without purification.

2-Acetoxy-N-(5-chloropyridin-2-yl)benzamide (1.45 g, 5 mmol) was saponified in aqueous methanolic NaOH. Standard acid-base workup gave 1.06 g of crude crystalline product which was recrystallized from acetone to give N-(5-chloropyridin-2-yl)-2-hydroxybenzamide (0.79 g, 63% yield).

mp 206–207° C.
$^1$H-NMR
ES-MS for $C_{12}H_9N_2O_2Cl$: Calcd: $M^+$=248; Found: $[M+H]^+$=249; $[M-H]^-$=247.
Anal for $C_{12}H_9N_2O_2Cl$: Calcd: C, 57.96; H, 3.65; N, 11.27; Found: C, 58.23; H, 3.68; N, 11.21.

B. N-(5-Chloropyridin-2-yl)-2-[[1-(4-pyridinyl)piperidin-4-yl]methoxy]benzamide Dihyrochloride 1-(4-Pyridinyl)piperidine-4-methanol was prepared using a procedure similar to the following: A solution of methyl N-(4-pyridinyl)isonipecotate (600 mg, 2.72 mmol) in tetrahydrofuran was added to a solution of lithium aluminum hydride (100 mg) in tetrahydrofuran (14 mL) cooled to 0° C. Upon consumption of the starting material (0.5–2 h), the mixture was treated with water (0.10 mL), 15% aqueous sodium hydroxide (0.10 mL), and water (0.30 mL). After 0.25 h, the mixture was sonicated for 0.25 h, then poured into a mixture of ethyl acetate, water, sodium tartrate, and potassium tartrate. The aqueous layer was extracted twice with ethyl acetate and the combined extracts were dried (magnesium sulfate), filtered, and concentrated in vacuo to yield 357 mg (68%) of 1-(4-pyridyl)piperidine-4-methanol, which was used without further purification.

$^1$H-NMR

N-(5-Chloropyridin-2-yl)-2-hydroxybenzamide (249 mg, 1.0 mmol), [1-(4-pyridinyl)piperidin-4-yl]methanol (192 mg, 1.0 mmol) and triphenylphosphine (262 mg, 1.0 mmol) were dissolved in 4 mL dry THF and 1 mL dry DMF under nitrogen. The solution was cooled to ice-water bath temperature and a solution of diisopropyl azodicarboxylate (202 mg, 0.20 mL, 1.0 mmol) in 2 mL of dry THF was added dropwise over about 45 min. The reaction was allowed to warm to room temperature and stir for 72 h. The solution was evaporated to dryness under vacuum and then dissolved in ethyl acetate. The ethyl acetate solution was washed with water, dilute aqueous sodium bicarbonate, and brine, and was dried over sodium sulphate. Evaporation of the solvent under vacuum gave a colorless glass which was dissolved in 50 mL of methanol and loaded on two 10 g SCX columns. Each column was washed with 150 mL of methanol, and then eluted with 50 mL of 2 M ammonia in methanol. The methanol/ammonia eluates were evaporated to driness under vacuum to give 200 mg of off-white solid. This material was purified by reverse phase HPLC to give N-(5-chloropyridin-2-yl)-2-[[1-(4-pyridinyl)piperidin-4-yl]methoxy]benzamide dihyrochloride as a white solid (151 mg, 30% yield).

$^1$H-NMR
ES-MS for $C_{23}H_{23}N_4O_2Cl$: Calcd: $M^+$=422 Found: $[M+H]^+$=423; $[M-H]^-$=421.
Anal for $C_{23}H_{25}N_4O_2Cl_3$: Calcd: C, 55.47; H, 5.06; N, 11.25; Found: C, 56.85; H, 4.84; N, 11.37.

EXAMPLE 9

Preparation of N-(5-Chloropyridin-2-yl)-2-[[1-(4-pyridinylmethyl)piperidin-4-ylcarbonyl]amino]benzamide

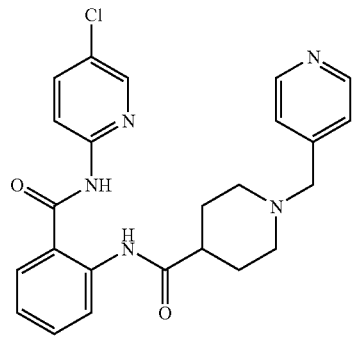

A. N-(5-Chloropyridin-2-yl)-2-[(1-Boc-piperidin-4-ylcarbonyl)amino]benzamide To a stirred solution of N-(5-chloropyridin-2-yl)-2-aminobenzamide (0.5 g, 1.79 mmol) and Boc-isonipecotic acid (0.41 g, 1.79 mmol) in N,N-dimethylformamide (30 mL) was added 1-(3-dimethylaminopropyl)-3-ethylcarbodiimide hydrochloride (0.69 g, 3.58 mmol). After stirring for 15 h, the solvent was removed in vacuo. The residue was partitioned between ethyl acetate and water, and the layers separated. The organic phase was washed with saturated aqueous sodium chloride, dried (magnesium sulfate), filtered, and concentrated in vacuo. The solid was suspended in ether, sonicated, and filtered to give 0.147 g (18%) of a tan solid.

$^1$H-NMR
IS-MS, m/e 459.5 (m+1)

Analysis for $C_{23}H_{27}N_4O_4Cl$: Calcd: C, 60.19; H, 5.93; N, 12.21; Found: C, 60.04; H, 5.81; N, 12.14.

B. N-(5-Chloropyridin-2-yl)-2-[(piperidin-4-ylcarbonyl)amino]benzamide Trifluoroacetate To a stirred solution of N-(5-chloropyridin-2-yl)-2-[(1-Boc-piperidin-4-ylcarbonyl)amino]benzamide (2 g, 4.3 mmol) in dichloromethane (80 mL) and anisole (2.4 mL) was added trifluoroacetic acid (8.4 mL, 109 mmol). After stirring for 4 h, the solvent was removed in vacuo. The residue was suspended in ether, sonicated for 0.25 h, stirred vigorously for 15 h, and filtered to give 1.93 g (94%) of a white solid.

$^1$H-NMR
IS-MS, m/e 359.2 (m+1)
Analysis for $C_{20}H_{20}N_4O_4ClF_3$: Calcd: C, 50.80; H, 4.26; N, 11.85; F, 12.05; Found: C, 50.74; H, 4.28; N, 11.74; F, 12.34.

C. N-(5-Chloropyridin-2-yl)-2-[[1-(4-pyridinylmethyl)piperidin-4-ylcarbonyl]amino]benzamide To a solution of N-(5-chloropyridin-2-yl)-2-[(piperidin-4-ylcarbonyl)amino]benzamide trifluoroacetate (25 mg, 0.053 mmol) in methanol (0.5 mL) was added 4-pyridinecarboxaldehyde (17.1 mg, 0.16 mmol) followed by a solution of sodium cyanoborohydride (7 mg, 0.106 mmol) in 7.5% acetic acid/methanol (1 mL). After shaking for 15 h, the solution was loaded onto an SCX column, which was pretreated with a solution of 5% acetic acid in methanol. The column was washed once with methanol and eluted with 2 N ammonia in methanol. The product containing fractions were combined and concentrated in vacuo. The residue was dissolved in a small amount of methanol and a few drops of acetic anhydride were added. After shaking for 0.5 h, the SCX purification procedure was repeated to give 9.8 mg (41%, 91% pure by HPLC analysis) of the title compound.

IS-MS, m/e 450.1 (m+1)
HPLC, Analytical method, RT=18.56 min.

EXAMPLE 10

Preparation of N-(5-Chloropyridin-2-yl)-2-[[1-(2-furanylmethyl)piperidin-4-ylcarbonyl]amino]benzamide

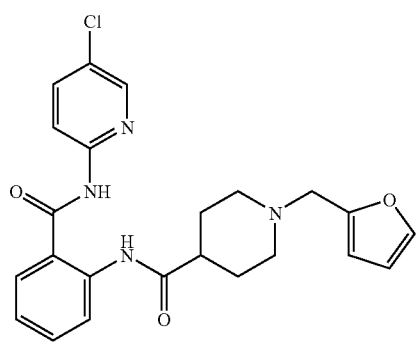

Using procedures substantially equivalent to those described in example 9-C, N-(5-chloropyridin-2-yl)-2-[[1-(2-furanylmethyl)piperidin-4-ylcarbonyl]amino]benzamide (12 mg, 53%, 99% pure by HPLC analysis) was prepared from N-(5-chloropyridin-2-yl)-2-[(piperidin-4-ylcarbonyl)amino]benzamide trifluoroacetate and furan-2-carboxaldehyde.

IS-MS, m/e 439.1 (m+1)
HPLC Analytical method, RT=24.84 min.

EXAMPLE 11

Preparation of N-(5-Chloropyridin-2-yl)-2-[(1-benzylpiperidin-4-ylcarbonyl)amino]benzamide

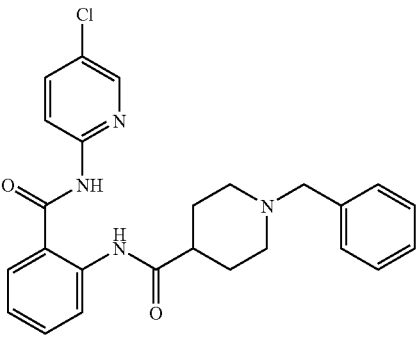

Using procedures substantially equivalent to those described in example 9-C, N-(5-chloropyridin-2-yl)-2-[(1-benzylpiperidin-4-ylcarbonyl)amino]benzamide (6.7 mg, 28%, 98% pure by HPLC analysis) was prepared from N-(5-chloropyridin-2-yl)-2-[(piperidin-4-ylcarbonyl)amino]benzamide trifluoroacetate and benzaldehyde.

FD-MS, m/e 449.1 (m+1)
HPLC, Analytical method, RT=27.70 min.

EXAMPLE 12

Preparation of N-(5-Chloropyridin-2-yl)-2-[[1-(3-pyridinylmethyl)piperidin-4-ylcarbonyl]amino]benzamide

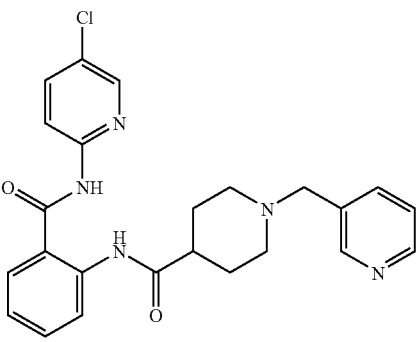

Using procedures substantially equivalent to those described in example 9-C, N-(5-chloropyridin-2-yl)-2-[[1-(3-pyridinylmethyl)piperidin-4-ylcarbonyl]amino]benzamide (17 mg, 70%, 98% pure by HPLC analysis) was prepared from N-(5-chloropyridin-2-yl)-2-[(piperidin-4-ylcarbonyl)amino]benzamide trifluoroacetate and pyridine-3-carboxaldehyde.

IS-MS, m/e 450.2 (m+1)
HPLC, Analytical method, RT=18.87 min.

EXAMPLE 13

Preparation of N-(5-Chloropyridin-2-yl)-2-[[1-(2-thiazolylmethyl)piperidin-4-ylcarbonyl]amino]benzamide

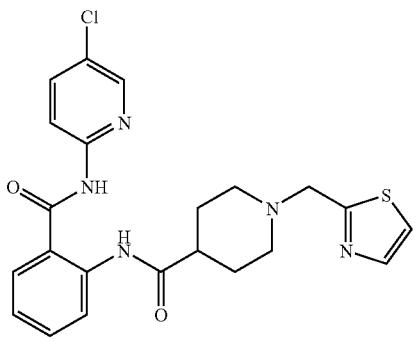

Using procedures substantially equivalent to those described in example 9-C, N-(5-chloropyridin-2-yl)-2-[(1-(2-thiazolylmethyl)piperidin-4-ylcarbonyl)amino]benzamide (7.2 mg, 30%, 88% pure by HPLC analysis) was prepared from N-(5-chloropyridin-2-yl)-2-[(piperidin-4-ylcarbonyl)amino]benzamide trifluoroacetate and thiazole-2-carboxaldehyde.

IS-MS, m/e 456.1 (m+1)

HPLC, Analytical method, RT=22.74 min.

EXAMPLE 14

Preparation of N-(5-Chloropyridin-2-yl)-2-[[1-(2-methylpropyl)piperidin-4-ylcarbonyl]amino]benzamide

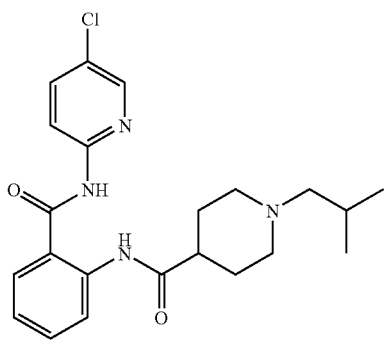

Using procedures substantially equivalent to those described in example 9-C, N-(5-chloropyridin-2-yl)-2-[(1-(2-methylpropyl)piperidin-4-ylcarbonyl)amino]benzamide (17 mg, 78%, 98% pure by HPLC analysis) was prepared from N-(5-chloropyridin-2-yl)-2-[(piperidin-4-ylcarbonyl)amino]benzamide trifluoroacetate and isobutyraldehyde.

IS-MS, m/e 415.2 (m+1)

HPLC, Analytical method, RT=23.92 min.

EXAMPLE 15

Preparation of N-(5-Chloropyridin-2-yl)-2-[[1-(2-ethylbutyl)piperidin-4-ylcarbonyl]amino]benzamide

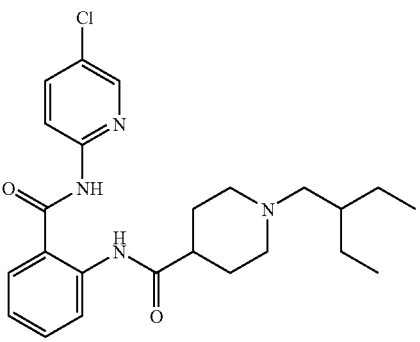

Using procedures substantially equivalent to those described in example 9-C, N-(5-chloropyridin-2-yl)-2-[[1-(2-ethylbutyl)piperidin-4-ylcarbonyl]amino]benzamide (14 mg, 59%, 95% pure by HPLC analysis) was prepared from N-(5-chloropyridin-2-yl)-2-[(piperidin-4-ylcarbonyl)amino]benzamide trifluoroacetate and 2-ethylbutyraldehyde.

IS-MS, m/e 443.2 (m+1)

HPLC, Analytical method, RT=29.94 min.

EXAMPLE 16

Preparation of N-(5-Chloropyridin-2-yl)-2-[(1-propylpiperidin-4-ylcarbonyl)amino]benzamide

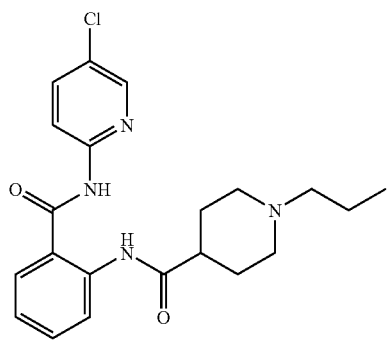

Using procedures substantially equivalent to those described in example 9-C, N-(5-chloropyridin-2-yl)-2-[(1-propylpiperidin-4-ylcarbonyl)amino]benzamide (15 mg, 69%, 94% pure by HPLC analysis) was prepared from N-(5-chloropyridin-2-yl)-2-[(piperidin-4-ylcarbonyl)amino]benzamide trifluoroacetate and propionaldehyde.

IS-MS, m/e 401.1 (m+1)

HPLC, Analytical method, RT=22.50 min.

EXAMPLE 17

Preparation of N-(5-Chloropyridin-2-yl)-2-[(1-cyclopropylmethylpiperidin-4-ylcarbonyl)amino]benzamide

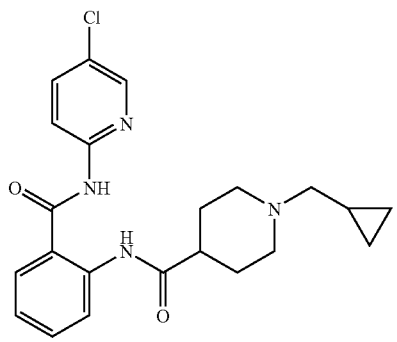

Using procedures substantially equivalent to those described in example 9-C, N-(5-chloropyridin-2-yl)-2-[(1-cyclopropylmethylpiperidin-4-ylcarbonyl)amino]benzamide 116 mg, 72%, 97% pure by HPLC analysis) was prepared from N-(5-chloropyridin-2-yl)-2-[(piperidin-4-ylcarbonyl)amino]benzamide trifluoroacetate and cyclopropanecarboxaldehyde.

IS-MS, m/e 413.2 (m+1)

HPLC, Analytical method, RT=23.38 min.

EXAMPLE 18

Preparation of N-(5-Chloropyridin-2-yl)-2-[[1-(4-quinolinylmethyl)piperidin-4-ylcarbonyl]amino]benzamide

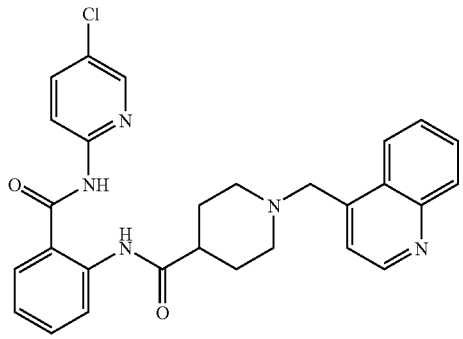

Using procedures substantially equivalent to those described in example 9-C, N-(5-chloropyridin-2-yl)-2-[[1-(4-quinolinylmethyl)piperidin-4-ylcarbonyl]amino]benzamide (13 mg, 52%, 81% pure by HPLC analysis) was prepared from N-(5-chloropyridin-2-yl)-2-[(piperidin-4-ylcarbonyl)amino]benzamide trifluoroacetate and quinoline-4-carboxaldehyde.

IS-MS, m/e 500.1 (m+1)

HPLC, Analytical method, RT=22.59 min.

EXAMPLE 19

Preparation of N-(5-Chloropyridin-2-yl)-2-[[1-(2-pyridylmethyl)piperidin-4-ylcarbonyl]amino]benzamide

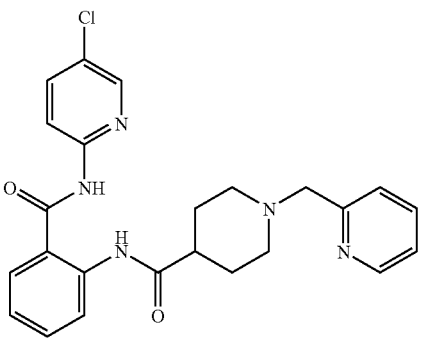

Using procedures substantially equivalent to those described in example 9-C, N-(5-chloropyridin-2-yl)-2-[[1-(2-pyridylmethyl)piperidin-4-ylcarbonyl]amino]benzamide (13 mg, 56%, 100% pure by HPLC analysis) was prepared from N-(5-chloropyridin-2-yl)-2-[(piperidin-4-ylcarbonyl)amino]benzamide trifluoroacetate and pyridine-2-carboxaldehyde.

IS-MS, m/e 450.1 (m+1)

HPLC, Analytical method, RT=23.35 min.

EXAMPLE 20

Preparation of N-(5-Chloropyridin-2-yl)-2-[[1-(3-methylbenzyl)piperidin-4-ylcarbonyl]amino]benzamide

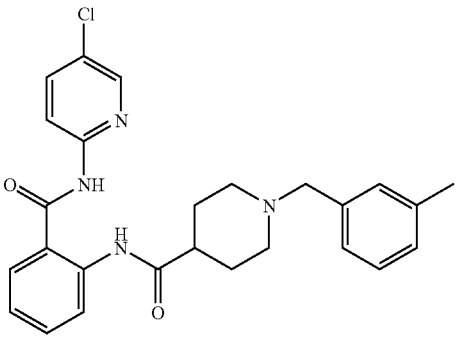

Using procedures substantially equivalent to those described in example 9-C, N-(5-chloropyridin-2-yl)-2-[[1-(3-methylbenzyl)piperidin-4-ylcarbonyl]amino]benzamide (20 mg, 52%, 100% pure by HPLC analysis) was prepared from N-(5-chloropyridin-2-yl)-2-[(piperidin-4-ylcarbonyl)amino]benzamide trifluoroacetate and 3-methylbenzaldehyde.

IS-MS, m/e 463.1 (m+1)

HPLC, Analytical method, RT=31.92 min.

EXAMPLE 21

Preparation of N-(5-Chloropyridin-2-yl)-2-[[1-(2-chlorobenzyl)piperidin-4-ylcarbonyl]amino]benzamide

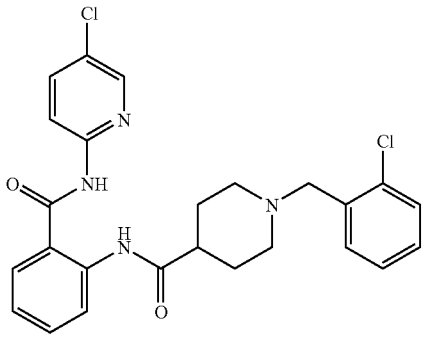

Using procedures substantially equivalent to those described in example 9-C, N-(5-chloropyridin-2-yl)-2-[[1-(2-chlorobenzyl)piperidin-4-ylcarbonyl]amino]benzamide (14 mg, 35%, 98% pure by HPLC analysis) was prepared from N-(5-chloropyridin-2-yl)-2-[(piperidin-4-ylcarbonyl)amino]benzamide trifluoroacetate and 2-chlorobenzaldehyde.

IS-MS, m/e 483.1 (m+1)

HPLC, Analytical method, RT=30.30 min.

EXAMPLE 22

Preparation of N-(5-Chloropyridin-2-yl)-2-[(1-(3-chlorobenzyl)piperidin-4-ylcarbonyl]amino]benzamide

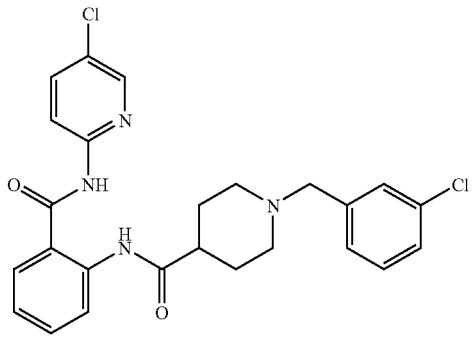

Using procedures substantially equivalent to those described in example 9-C, N-(5-chloropyridin-2-yl)-2-[[1-(3-chlorobenzyl)piperidin-4-ylcarbonyl]amino]benzamide (23 mg, 56%, 100% pure by HPLC analysis) was prepared from N-(5-chloropyridin-2-yl)-2-[(piperidin-4-ylcarbonyl)amino]benzamide trifluoroacetate and 3-chlorobenzaldehyde.

IS-MS, m/e 483.1 (m+1)

HPLC, Analytical method, RT=31.07 min.

EXAMPLE 23

Preparation of N-(5-Chloropyridin-2-yl)-2-[(1-(4-chlorobenzyl)piperidin-4-ylcarbonyl)amino]benzamide

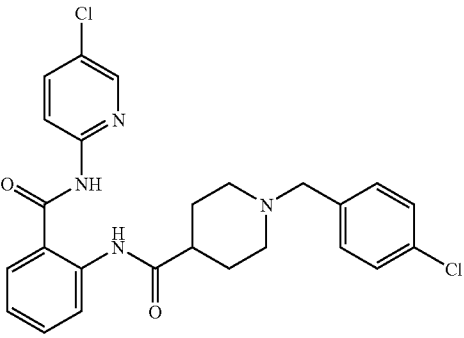

Using procedures substantially equivalent to those described in example 9-C, N-(5-chloropyridin-2-yl)-2-[[1-(4-chlorobenzyl)piperidin-4-ylcarbonyl]amino]benzamide (19 mg, 46%, 100% pure by HPLC analysis) was prepared from N-(5-chloropyridin-2-yl)-2-[(piperidin-4-ylcarbonyl)amino]benzamide trifluoroacetate and 4-chlorobenzaldehyde.

IS-MS, m/e 483.1 (m+1)

HPLC, Analytical method, RT=31.58 min.

EXAMPLE 24

Preparation of N-(5-Chloropyridin-2-yl)-2-[(1-(4-methoxybenzyl)piperidin-4-ylcarbonyl)amino]benzamide

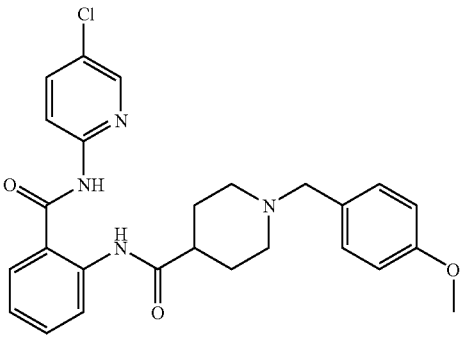

Using procedures substantially equivalent to those described in example 9-C, N-(5-chloropyridin-2-yl)-2-[[1-(4-methoxybenzyl)piperidin-4-ylcarbonyl]amino]benzamide (12 mg, 28%, 97% pure by HPLC analysis) was prepared from N-(5-chloropyridin-2-yl)-2-[(piperidin-4-ylcarbonyl)amino]benzamide trifluoroacetate and 4-methoxybenzaldehyde.

IS-MS, m/e 479.1 (m+1)

HPLC, Analytical method, RT=29.08 min.

EXAMPLE 25

Preparation of N-(5-Chloropyridin-2-yl)-2-[[1-(2-ethylbutyl)-3,4-didehydropiperidin-4-ylcarbonyl]amino]benzamide

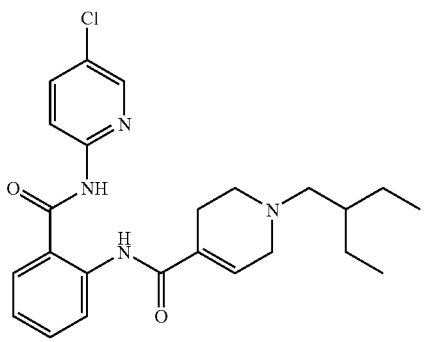

A. 1-Boc-1,2,3,6-Tetrahydro-4-[(trifluoromethyl)sulfonyloxy]pyridine

To a solution of diisopropylamine (38.7 mL, 276 mmol) in tetrahydrofuran (300 mL) at 0° C. under nitrogen was added n-butyllithium (1.6 M in hexane, 172.5 mL, 276 mmol) dropwise via an addition funnel. After stirring for 0.5 h, the solution was cooled to −78° C. A solution of 1-tert-butoxycarbonyl-4-piperidone (50 g, 251 mmol) in tetrahydrofuran (300 mL) was added. After stirring for 0.5 h, a solution of N-phenyltrifluoromethanesulfonimide (96 g, 269 mmol) in tetrahydrofuran (300 mL) was added slowly. The reaction was then warmed to 0° C. and after 3 h, the solvent was removed in vacuo. The residue was chromatographed over alumina, eluting with 5% ethyl acetate in hexanes and the product containing fractions were combined and concentrated in vacuo, then dried under high vacuum for 15 h to give 74.84 g (90%) of a clear oil.
$^1$H-NMR

B. Methyl 1-Boc-1,2,3,6-Tetrahydro-4-pyridinecarboxylate

To a stirred solution of 1-Boc-1,2,3,6-tetrahydro-4-[(trifluoromethyl)sulfonyloxy]pyridine (74.84 g, 226 mmol) in N,N-dimethylformamide (60 mL) was added triethylamine (4.2 mL, 30.2 mmol), palladium acetate (0.100 g, 0.45 mmol), triphenylphosphine (0.235 g, 0.9 mmol), and methanol (24.5 mL) and the solution was placed under an atmosphere of carbon monoxide. After stirring for 48 h, the solvent was removed in vacuo. The residue was chromatographed over silica gel, eluting with 5–10% ethyl acetate in hexane. The product containing fractions were combined and concentrated in vacuo to give 2.35 g (65%) of the title compound as a clear oil.
$^1$H-NMR
FD-MS, m/e 240.2 (m)
Analysis for $C_{12}H_{19}NO_4$: Calcd: C, 59.74; H, 7.94; N, 5.81; Found: C, 59.60; H, 8.07; N, 5.85.

C. 1-Boc-1,2,3,6-Tetrahydro-4-pyridinecarboxylic Acid

To a stirred solution of methyl 1-Boc-1,2,3,6-tetrahydro-4-pyridinecarboxylate (2.22 g, 9.2 mmol) in methanol (10 mL) was added 1.0 N aqueous sodium hydroxide (25 mL). After stirring for 2 h, the solvent was removed in vacuo. The residue was partitioned between diethyl ether and water, and the layers were separated. The aqueous phase was acidified to pH 2.5 with concentrated hydrochloric acid and extracted with ethyl acetate. The organic extract was washed with saturated aqueous sodium chloride, dried (magnesium sulfate), filtered, and concentrated in vacuo to give 1.62 g (78%) of the title compound as a white solid.
$^1$H-NMR
IS-MS, m/e 226.1 (m−1)$^-$
Analysis for $C_{11}H_{17}NO_4$: Calcd: C, 58.14; H, 7.54; N, 6.16; Found: C, 57.41; H, 7.48; N, 6.19.

D. N-(5-Chloropyridin-2-yl)-2-[(1-Boc-3,4-didehydropiperidin-4-ylcarbonyl)amino]benzamide To a stirred solution of 1-Boc-1,2,3,6-tetrahydro-4-pyridinecarboxylic acid (13.39 g, 58.9 mmol) in tetrahydrofuran (250 mL) was added sodium ethoxide (4.01 g, 58.9 mmol). After stirring for 0.25 h, the solvent was removed in vacuo. The residue was suspended in dichloromethane (150 mL); and oxalyl chloride (0.115 mL, 1.32 mmol) was added, followed by a couple drops of N,N-dimethylformamide. After stirring for 0.75 h, the solvent was removed in vacuo. To the (acid chloride) residue was added dichloromethane (75 mL) and then a solution of N-(5-chloropyridine-2-yl)-2-aminobenzamide (0.245 g, 1.0 mmol) and pyridine (25 mL) in dichloromethane (75 mL). After stirring 15 h, the solvent was removed in vacuo. The residue was partitioned between ethyl acetate and water and the layers separated. The organic phase was washed with water, saturated aqueous sodium bicarbonate, saturated aqueous sodium chloride, and then dried (magnesium sulfate), filtered, and concentrated in vacuo. The crude product was chromatographed over silica gel, eluting with a step gradient of 25–40% ethyl acetate in hexane. The product containing fractions were combined and concentrated in vacuo to give 14.65 g (54%) of the title compound as a white solid.
$^1$H-NMR
IS-MS, m/e 457.4 (m+1)
Analysis for $C_{23}H_{25}N_4O_4Cl$: Calcd: C, 60.46; H, 5.51; N, 12.26; Cl, 7.76; Found: C, 61.16; H, 5.60; N, 12.38; Cl, 7.91.

E. N-(5-Chloropyridin-2-yl)-2-[(3,4-didehydropiperidin-4-ylcarbonyl)amino]benzamide Trifluoroacetate Using methods substantially equivalent to those described in example 9-B, N-(5-chloropyridin-2-yl)-2-[(3,4-didehydropiperidin-4-ylcarbonyl)amino]benzamide trifluoroacetate (0.48 g, 74%) was prepared from N-(5-chloropyridin-2-yl)-2-[(1-Boc-3,4-didehydropiperidin-4-ylcarbonyl)amino]benzamide.
$^1$H-NMR

F. N-(5-Chloropyridin-2-yl)-2-[[1-(2-ethylbutyl)-3,4-didehydropiperidin-4-ylcarbonyl]amino]benzamide Using methods substantially equivalent to those described in example 9-C, N-(5-chloropyridin-2-yl)-2-([1-(2-ethylbutyl)-3,4-didehydropiperidin-4-ylcarbonyl)amino]benzamide (43 mg, 46%, 98% pure by HPLC analysis) was prepared from N-(5-chloropyridin-2-yl)-2-[(3,4-didehydropiperidin-4-ylcarbonyl)amino]benzamide trifluoroacetate and 2-ethylbutyraldehyde.

IS-MS, m/e 441.0 (m+1)
HPLC, Analytical method, RT=28.63 min.

EXAMPLE 26

Preparation of N-(5-Chloropyridin-2-yl)-2-[(1-propyl-3,4-didehydropiperidin-4-ylcarbonyl)amino]benzamide

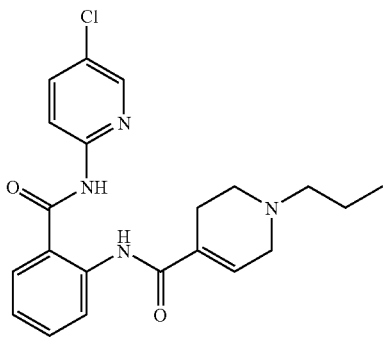

Using methods substantially equivalent to those described in example 9-C, N-(5-chloropyridin-2-yl)-2-[(1-propyl-3,4-didehydropiperidin-4-ylcarbonyl)amino]benzamide (30 mg, 36%, 99% pure by HPLC analysis) was prepared from N-(5-chloropyridin-2-yl)-2-[(3,4-didehydropiperidin-4-ylcarbonyl)amino]benzamide trifluoroacetate and propionaldehyde.

IS-MS, m/e 399.0 (m+1)
HPLC, Analytical method, RT=20.63 min.

EXAMPLE 27

Preparation of N-(5-Chloropyridin-2-yl)-2-[(1-isopropylpiperidin-4-ylcarbonyl)amino]benzamide Hydrochloride

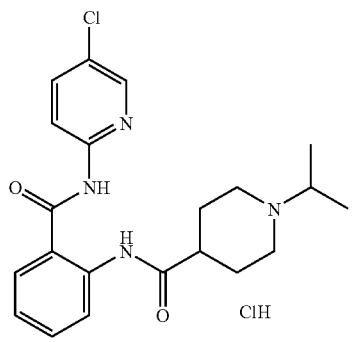

To a stirred suspension of N-(5-chloropyridin-2-yl)-2-[(piperidin-4-ylcarbonyl)amino]benzamide trifluoroacetate (0.4 g, 0.85 mmol) in acetone (6 mL) and 1,2-dichloroethane (10 mL) was added glacial acetic acid (0.2 mL, 3.84 mmol) followed by then sodium triacetoxyborohydride (0.81 g, 3.84 mmol). After stirring for 15 h, saturated aqueous ammonium chloride (10 mL) was added. After stirring for 0.5 h, the mixture was partitioned between dichloromethane and water and the layers separated. The organic phase was washed with saturated aqueous sodium chloride, dried with magnesium sulfate, filtered, and concentrated in vacuo. The residue was then purified by preparative RPHPLC (C18), eluting with a linear gradient of 90/10 to 60/40 (0.01% HCl/acetonitrile) over 180 min. The product containing fractions were combined and lyophilized to give 0.212 g (57%) of the title compound as a white solid.

$^1$H-NMR
IS-MS, m/e 401.2 (m+1)
Analysis for $C_{21}H_{25}N_4O_2Cl \cdot 0.9HCl \cdot 0.1H_2O$: Calcd: C, 57.91; H, 6.04; N, 12.86; Cl, 15.47; Found: C, 57.82; H, 5.95; N, 12.81; Cl, 15.47.

EXAMPLE 28

Preparation of N-(5-Chloropyridin-2-yl)-2-[(1-isopropyl-3,4-didehydropiperidin-4-ylcarbonyl)amino]benzamide Hydrochloride

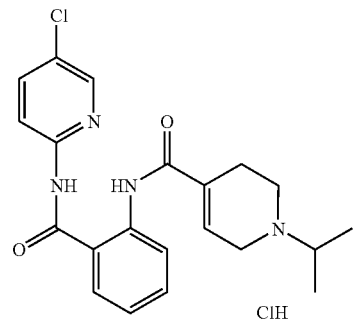

Using methods substantially equivalent to those described in example 27, N-(5-chloropyridin-2-yl)-2-[(1-isopropyl-3,4-didehydropiperidin-4-ylcarbonyl)amino]benzamide hydrochloride (0.21 g, 38%) was prepared from N-(5-chloropyridin-2-yl)-2-[(3,4-didehydropiperidin-4-ylcarbonyl)amino]benzamide trifluoroacetate and acetone. The preparative RPHPLC (C18) purification procedure was elution with a linear gradient of 95/5 to 75/25 (0.01% HCl/acetonitrile) over 180 min.

$^1$H-NMR
IS-MS, m/e 399.2 (m+1)
Analysis for $C_{21}H_{23}N_4O_2Cl \cdot 1.0HCl \cdot 0.7H_2O$: Calcd: C, 56.30; H, 5.72; N, 12.51; Cl, 15.83; Found: C, 56.42; H, 5.35; N, 12.11; Cl, 15.99.

EXAMPLE 29

Preparation of N-(5-Chloropyridin-2-yl)-2-[(1-cyclopentylpiperidin-4-ylcarbonyl)amino]benzamide

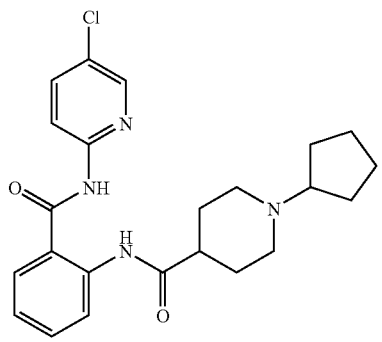

Using procedures substantially equivalent to those described in example 27, N-(5-chloropyridin-2-yl)-2-[(1-cyclopentylpiperidin-4-ylcarbonyl)amino]benzamide (30 mg, 67%, 99% pure by HPLC analysis) was prepared from N-(5-chloropyridin-2-yl)-2-[(piperidin-4-ylcarbonyl)amino]benzamide trifluoroacetate and cyclopentanone.

IS-MS, m/e 427.0 (m+1)

HPLC, Analytical method, RT=21.38 min

EXAMPLE 30

Preparation of N-(5-Chloropyridin-2-yl)-2-[(1-cyclohexylpiperidin-4-ylcarbonyl)amino]benzamide

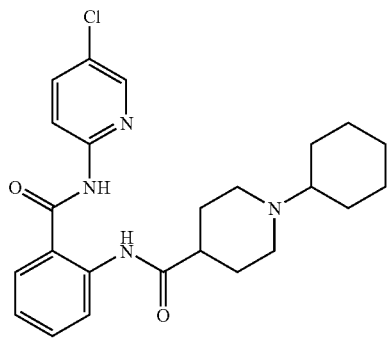

Using procedures substantially equivalent to those described in example 27, N-(5-chloropyridin-2-yl)-2-[(1-cyclohexylpiperidin-4-ylcarbonyl)amino]benzamide (34 mg, 72%, 97% pure by HPLC analysis) was prepared from N-(5-chloropyridin-2-yl)-2-[(piperidin-4-ylcarbonyl)amino]benzamide trifluoroacetate and cyclohexanone.

IS-MS, m/e 441.0 (m+1)

HPLC, Analytical method, RT=24.11 min.

EXAMPLE 31

Preparation of N-(5-chloropyridin-2-yl)-2-[[1-(4-thianyl)-3,4-didebydropiperidin-4-ylcarbonyl)amino]benzamide Hydrochloride

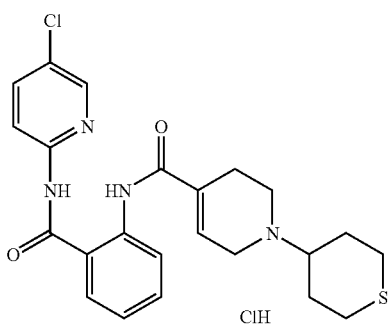

Using methods substantially equivalent to those described in example 27, N-(5-chloropyridin-2-yl)-2-[[1-(4-thianyl)-3,4-didehydropiperidin-4-ylcarbonyl]amino]benzamide hydrochloride (0.26 g, 41%) was prepared from N-(5-chloropyridin-2-yl)-2-[(3,4-didehydropiperidin-4-ylcarbonyl)amino]benzamide trifluoroacetate and tetrahydrothiopyran-4-one. The preparative RPHPLC (C18) purification procedure was elution with a linear gradient of 90/10 to 50/50 (0.01% HCl/acetonitrile) over 180 min.

$^1$H-NMR

IS-MS, m/e 457.4 (m+1)

Analysis for $C_{23}H_{25}N_4O_2Cl.1.0HCl.1.2H_2O$: Calcd: C, 53.63; H, 5.56; N, 10.88; Cl, 13.77; Found: C, 53.58; H, 5.17; N, 10.77; Cl, 13.57.

EXAMPLE 32

Preparation of N-(5-Chloropyridin-2-yl)-2-[[1-(1-ethylpropyl)-3,4-didehydropiperidin-4-ylcarbonyl]amino]benzamide Hydrochloride

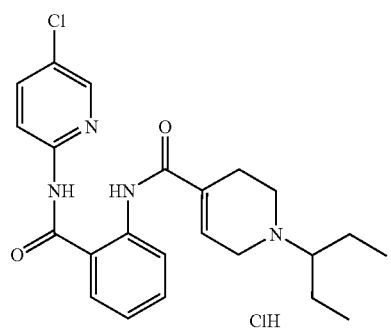

Using methods substantially equivalent to those described in example 27, N-(5-chloropyridin-2-yl)-2-[[1-(1-ethylpropyl)-3,4-didehydropiperidin-4-ylcarbonyl]amino]benzamide hydrochloride (0.14 g, 24%) was prepared from N-(5-chloropyridin-2-yl)-2-[(3,4-didehydropiperidin-4-ylcarbonyl)amino]benzamide trifluoroacetate and 3-pentanone. The preparative RPHPLC (C18) purification procedure was elution with a linear gradient of 95/5 to 75/25 (0.01% HCl/acetonitrile) over 180 min.

IS-MS, m/e 427.1 (m+1)

Analysis for $C_{23}H_{27}N_4O_2Cl.1.5HCl.1.5H_2O$: Calcd: C, 54.31; H, 6.24; N, 11.02; Cl, 17.43; Found: C, 53.94; H, 5.61; N, 10.94; Cl, 17.29.

EXAMPLE 33

Preparation of N-(5-Chloropyridin-2-yl)-2-[[1-(1-propylbutyl)-3,4-didehydropiperidin-4-ylcarbonyl]amino]benzamide

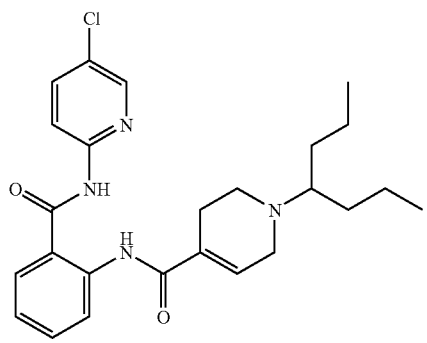

Using methods substantially equivalent to those described in example 27, N-(5-chloropyridin-2-yl)-2-[[1-(1-propylbutyl)-3,4-didehydropiperidin-4-ylcarbonyl]amino]benzamide (5 mg, 10%, 81% pure by HPLC) was prepared from N-(5-chloropyridin-2-yl)-2-[(3,4-didehydropiperidin-4-ylcarbonyl)amino]benzamide trifluoroacetate and 4-heptanone.

IS-MS, m/e 455.1 (m+1)
HPLC, Analytical method, RT=33.28 min.

EXAMPLE 34

Preparation of 4-Chloro-N-(5-chloropyridin-2-yl)-2-[[1-(4-pyridinyl)piperidin-4-ylcarbonyl]amino]benzamide Hydrochloride

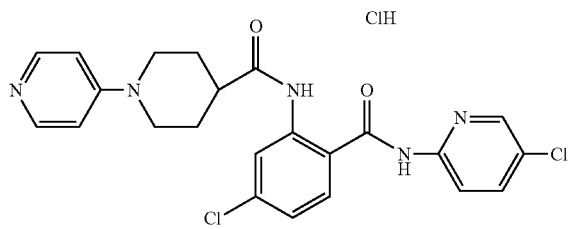

A. 4-Chloro-N-(5-chloropyridin-2-yl)-2-nitrobenzamide

To a stirring suspension of 4-chloro-2-nitrobenzoic acid (20 g, 99 mmol) in dichloromethane (500 mL) was added a few drops of DMF, followed by oxalyl chloride (15.1 g, 119 mmol). After 1 h, the solvent was removed in vacuo and the residue was dissolved in dichloromethane (500 mL). To this stirring solution was added pyridine (24 mL, 297 mmol) followed by 2-amino-5-chloropyridine (12.7 g, 99 mmol). After stirring overnight, the solvents were removed in vacuo and the residue was stirred vigorously with ethyl acetate and water for several hours. The mixture was filtered to give a white solid, which was washed with ethyl acetate and dried in vacuo to give 23 g (74%) of the title compound. The combined ethyl acetate washings and extract were then washed twice with 1 M citric acid, once with brine, twice with saturated aq sodium bicarbonate, and again with brine. The organic phase was then dried with $MgSO_4$, filtered and concentrated in vacuo. The solid was then suspended in diethyl ether, sonicated and filtered to give a second crop of the title compound as a white solid (5.79 g, 19%).

$^1$H-NMR
IS-MS, m/e 312.0 (m)
Analysis for $C_{12}H_7N_3O_3Cl_2$: Calcd: C, 46.18; H, 2.26; N, 13.46; Found: C, 46.24; H, 2.37; N, 13.43.

B. 2-Amino-4-chloro-N-(5-chloropyridin-2-yl)benzamide

Using methods substantially equivalent to those described in example 2-B, 2-amino-4-chloro-N-(5-chloropyridin-2-yl)benzamide (7.85 g, 87%) was prepared from 4-chloro-N-(5-chloropyridin-2-yl)-2-nitrobenzamide.

$^1$H-NMR
IS-MS, m/e 280.2 (m−)
Analysis for $C_{12}H_9N_3OCl_2$: Calcd: C, 51.09; H, 3.22; N, 14.89; Found: C, 51.52; H, 3.56; N, 14.68.

C. 4-Chloro-N-(5-chloropyridin-2-yl)-2-[(1-(4-pyridinyl)piperidin-4-ylcarbonyl)amino]benzamide hydrochloride Using methods substantially equivalent to those described in example 1-D, 4-chloro-N-(5-chloropyridin-2-yl)-2-[(1-(4-pyridinyl)piperidin-4-ylcarbonyl)amino]benzamide hydrochloride (0.2 g, 8%) was prepared from 2-amino-4-chloro-N-(5-chloropyridin-2-yl)benzamide and 1-(4-pyridinyl)piperidin-4-ylcarbonyl chloride. The preparative RPHPLC (C18) purification procedure was elution with a linear gradient of 90/10 to 50/50 (0.01% HCl/acetonitrile) over 180 min.

$^1$H-NMR
IS-MS, m/e 470.2 (m+1)
Analysis for $C_{23}H_{21}N_5O_2 \cdot 1.0HCl \cdot 0.5H_2O$: Calcd: C, 53.55; H, 4.49; N, 13.58; Cl, 20.62; Found: C, 53.75; H, 4.59; N, 13.48; Cl, 20.43.

EXAMPLE 35

Preparation of N-(5-Chloropyridin-2-yl)-4-fluoro-2-[[1-(4-pyridinyl)piperidin-4-ylcarbonyl]amino]benzamide Hydrochloride

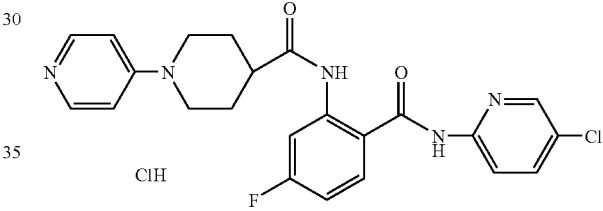

A. 4-Fluoro-2-nitrobenzoic acid

To a stirring solution of $KMnO_4$ (76 g, 483 mmol) in water (1 L) was added 4-fluoro-2-nitrotoluene and the solution was heated to reflux. After 4 h, the hot mixture was filtered and the filtrate was cooled with ice, washed with diethyl ether, acidified with conc HCl, and then extracted twice with diethyl ether. The combined ether extracts were washed with brine, dried with $MgSO_4$, filtered and concentrated in vacuo to give 12.07 g (34%) of a white solid.

$^1$H-NMR
IS-MS, m/e 184.0 (m−1)$^-$
Analysis for $C_7H_4NO_4F$: Calcd: C, 45.42; H, 2.18; N, 7.57; Found: C, 45.63; H, 2.30; N, 7.61.

B. N-(5-Chloropyridin-2-yl)-2-nitro-4-fluorobenzamide

Using methods substantially equivalent to those described in example 34-A, N-(5-chloropyridin-2-yl)-4-fluoro-2-nitrobenzamide (16.06 g, 88%) was prepared from 4-fluoro-2-nitrobenzoic acid and 2-amino-5-chloropyridine.

$^1$H-NMR
IS-MS, m/e 296.2 (m+1)
Analysis for $C_{12}H_7N_3O_3ClF$: Calcd: C, 48.75; H, 2.38; N, 14.21; Found: C, 48.96; H, 2.66; N, 14.40.

C.
2-Amino-N-(5-chloropyridin-2-yl)-4-fluorobenzamide

Using methods substantially equivalent to those described in example 2-B, 2-amino-N-(5-chloropyridin-2-yl)-4-fluorobenzamide (7.98 g, 88%) was prepared from N-(5-chloropyridin-2-yl)-4-fluoro-2-nitrobenzamide.

$^1$H-NMR

IS-MS, m/e 264.2 (m−1)$^−$

Analysis for $C_{12}H_9N_3OClF$: Calcd: C, 54.25; H, 3.42; N, 15.82; Found: C, 54.45; H, 3.65; N, 15.76.

D. N-(5-Chloropyridin-2-yl)-4-fluoro-2-[[1-(4-pyridinyl)piperidin-4-ylcarbonyl]amino]benzamide Hydrochloride Using methods substantially equivalent to those described in example 1-D, N-(5-chloropyridin-2-yl)-4-fluoro-2-[[1-(4-pyridinyl)piperidin-4-ylcarbonyl]amino]benzamide hydrochloride (0.033 g, 2%) was prepared from 2-amino-N-(5-chloropyridin-2-yl)-4-fluorobenzamide and 1-(4-pyridyl)piperidin-4-ylcarbonyl chloride. The preparative RPHPLC (C18) purification procedure was elution with a linear gradient of 90/10 to 50/50 (0.01% HCl/acetonitrile) over 180 min.

$^1$H-NMR

IS-MS, m/e 454.1 (m+1)

EXAMPLE 36

Preparation of 5-Chloro-N-(5-chloropyridin-2-yl)-2-[[1-(4-pyridinyl)piperidin-4-ylcarbonyl]amino]benzamide Hydrochloride

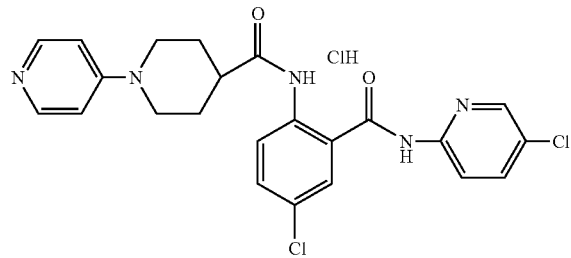

A.
5-Chloro-N-(5-chloropyridin-2-yl)-2-nitrobenzamide

Using methods substantially equivalent to those described in example 34-A, 5-chloro-N-(5-chloropyridin-2-yl)-2-nitrobenzamide (26.4 g, 85%) was prepared from 2-amino-5-chloropyridine and 5-chloro-2-nitrobenzoic acid.

$^1$H-NMR

IS-MS, m/e 312.0 (m+1)

Analysis for $C_{12}H_7N_3O_3Cl_2$: Calcd: C, 46.18; H, 2.26; N, 13.46; Found: C, 46.37; H, 2.41; N, 13.43.

B.
2-Amino-5-chloro-N-(5-chloropyridin-2-yl)benzamide

Using methods substantially equivalent to those described in example 2-B, 2-amino-5-chloro-N-(5-chloropyridin-2-yl)benzamide (7.79 g, 72%) was prepared from 5-chloro-N-(5-chloropyridin-2-yl)-2-nitrobenzamide.

$^1$H-NMR

IS-MS, m/e 282.1 (m+1)

Analysis for $C_{12}H_9N_3OCl_2$: Calcd: C, 51.09; H, 3.22; N, 14.89; Cl, 25.13; Found: C, 51.29; H, 3.36; N, 14.89; Cl, 25.41.

C. 5-Chloro-N-(5-chloropyridin-2-yl)-2-[[1-(4-pyridinyl)piperidin-4-ylcarbonyl]amino]benzamide Hydrochloride Using methods substantially equivalent to those described in example 1-D, 5-chloro-N-(5-chloropyridin-2-yl)-2-[[1-(4-pyridinyl)piperidin-4-ylcarbonyl]amino]benzamide hydrochloride was prepared from 2-amino-5-chloro-N-(5-chloropyridin-2-yl)benzamide and 1-(4-pyridyl)piperidin-4-ylcarbonyl chloride. The preparative RPHPLC (C18) purification procedure was elution with a linear gradient of 90/10 to 50/50 (0.01% HCl/acetonitrile) over 180 min.

$^1$H-NMR

IS-MS, m/e 470.2 (m+1)

Analysis for $C_{23}H_{21}N_5O_2Cl_2 \cdot 1.2C_{10.2}H_2O$: Calcd: C, 53.36; H, 4.40; N, 13.53; Cl, 21.92; Found: C, 53.75; H, 4.65; N, 13.13; Cl, 21.63.

EXAMPLE 37

Preparation of N-(5-Chloropyridin-2-yl)-5-fluoro-2-[[1-(4-pyridinyl)piperidin-4-ylcarbonyl]amino]benzamide Hydrochloride

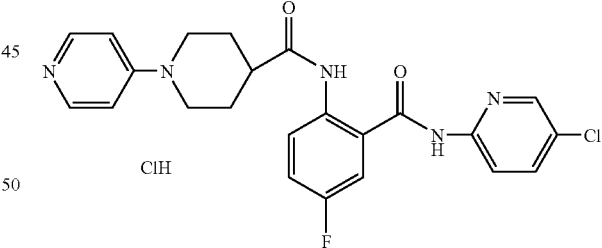

A.
N-(5-Chloropyridin-2-yl)-2-nitro-5-fluorobenzamide

Using methods substantially equivalent to those described in example 34-A, N-(5-chloropyridin-2-yl)-5-fluoro-2-nitrobenzamide (8.7 g, 70%) was prepared from 5-fluoro-2-nitrobenzoic acid and 2-amino-5-chloropyridine.

$^1$H-NMR

IS-MS, m/e 296.2 (m+1)

Analysis for $C_{12}H_7N_3O_3ClF$: Calcd: C, 48.75; H, 2.39; N, 14.21; Found: C, 48.96; H, 2.59; N, 14.02.

B. 2-Amino-N-(5-chloropyridin-2-yl)-5-fluorobenzamide

Using methods substantially equivalent to those described in example 2-B, 2-amino-N-(5-chloropyridin-2-yl)-5-fluorobenzamide (11.6 g, 86%) was prepared from N-(5-chloropyridin-2-yl)-5-fluoro-2-nitrobenzamide.

$^1$H-NMR

IS-MS, m/e 264.1 (m−1)$^-$

Analysis for $C_{12}H_9N_3OClF$: Calcd: C, 54.25; H, 3.42; N, 15.82; Found: C, 54.46; H, 3.58; N, 15.84.

C. N-(5-Chloropyridin-2-yl)-5-fluoro-2-[[1-(4-pyridinyl)piperidin-4-ylcarbonyl]amino]benzamide hydrochloride Using methods substantially equivalent to those described in example 1-D, N-(5-chloropyridin-2-yl)-5-fluoro-2-[[1-(4-pyridinyl)piperidin-4-ylcarbonyl]amino]benzamide hydrochloride (0.47 g, 21%) was prepared from 2-amino-N-(5-chloropyridin-2-yl)-5-fluorobenzamide and 1-(4-pyridyl)piperidin-4-ylcarbonyl chloride. The preparative RPHPLC (C18) purification procedure was elution with a linear gradient of 90/10 to 50/50 (0.01% HCl/acetonitrile) over 180 min.

$^1$H-NMR

IS-MS, m/e 454.0 (m+1)

Analysis for $C_{23}H_{21}N_5O_2Cl_2F$·1.0HCl·0.3H$_2$O: Calcd; C, 55.72; H, 4.59; N, 14.13; Cl, 14.30; Found: C, 55.69; H, 4.66; N, 13.82; Cl, 14.39.

EXAMPLE 38

Preparation of N-(5-Chloropyridin-2-yl)-2-[(1-cyclohexyl-3,4-didehydropiperidin-4-ylcarbonyl)amino]benzamide Hydrochloride

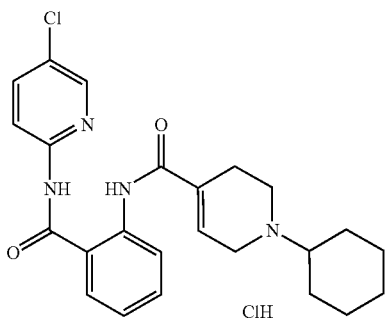

Using methods substantially equivalent to those described in example 27, N-(5-chloropyridin-2-yl)-2-[(1-cyclohexyl-3,4-didehydropiperidin-4-ylcarbonyl)amino]benzamide hydrochloride (0.176 g, 29%) was prepared from N-(5-chloropyridin-2-yl)-2-[(3,4-didehydropiperidin-4-ylcarbonyl)amino]benzamide trifluoroacetate and cyclohexanone. The preparative RPHPLC (C18) purification procedure was elution with a linear gradient of 95/5 to 70/30 (0.01% HCl/acetonitrile) over 200 min.

$^1$H-NMR

IS-MS, m/e 439.2 (m+1)

EXAMPLE 39

Preparation of N-(5-Chloropyridin-2-yl)-2-[[1-(tetrahydropyran-4-yl)-3,4-didehydropiperidin-4-ylcarbonyl)amino]benzamide Hydrochloride

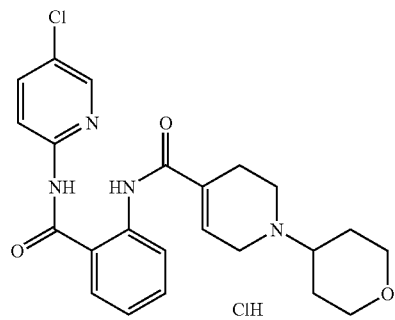

Using methods substantially equivalent to those described in example 27, N-(5-chloropyridin-2-yl)-2-[[1-(tetrahydropyran-4-yl)-3,4-didehydropiperidin-4-ylcarbonyl]amino]benzamide hydrochloride was prepared from N-(5-chloropyridin-2-yl)-2-[(3,4-didehydropiperidin-4-ylcarbonyl)amino]benzamide trifluoroacetate and tetrahydro-4H-pyran-4-one. The preparative RPHPLC (C18) purification procedure was elution with a linear gradient of 95/5 to 70/30 (0.01% HCl/acetonitrile) over 200 min.

$^1$H-NMR

IS-MS, m/e 441.2 (m+1)

Analysis for $C_{23}H_{25}N_4O_3Cl$·1.0HCl·0.2H$_2$O: Calcd: C, 57.43; H, 5.53; N, 11.65; Cl, 14.74; Found: C, 57.31; H, 5.43; N, 11.58; Cl, 15.09.

EXAMPLE 40

Preparation of N-(5-Chloropyridin-2-yl)-2-(4-phenylbenzoylamino)benzamide

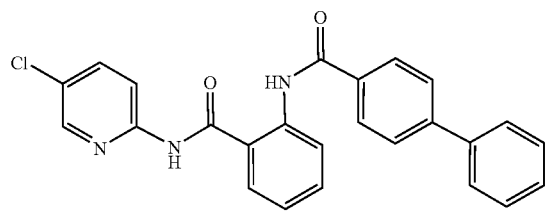

To a solution of N-(5-chloropyridin-2-yl)-2-aminobenzamide (0.247 g, 1 mmol) in dichloromethane (10 mL) and pyridine (0.5 mL) was added a solution of 4-biphenylcarbonyl chloride (0.217 g, 1 mmol) in dichloromethane (5 mL). After stirring overnight the solvent was removed in vacuo. The residue was partitioned between ethyl acetate (50 mL) and water (25 mL). Separate the layers and wash the organic layer with water (2×10 mL), saturated sodium bicarbonate (2×20 mL), hydrochloric acid (0.2 N, 1×20 mL). Dried over MgSO$_4$, filtered and concentrated in vacuo. The residue was then purified by RPHPLC (30% ethyl acetate/hexane) to give 0.4 g (94%) of pure product.

$^1$H-NMR

FD-MS, m/e 426.1 (m−)

Analysis for $C_{25}H_{18}N_3O_2Cl$: Calcd: C, 70.18; H, 4.24; N, 9.82; Found: C, 70.11; H, 4.26; N, 9.87.

EXAMPLE 41

Preparation of N-(5-Chloropyridin-2-yl)-5-fluoro-2-[(1-isopropyl-3,4-didehydropiperidin-4-ylcarbonyl)amino]benzamide Hydrochloride

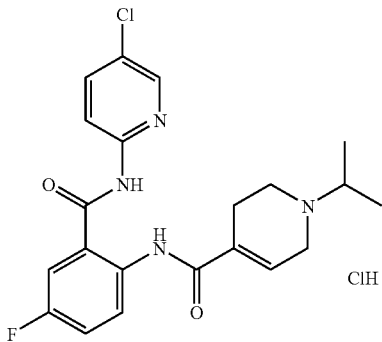

A. N-(5-Chloropyridin-2-yl)-2-[(1-Boc-3,4-didehydropiperidin-4-ylcarbonyl)amino]-5-fluorobenzamide Using methods substantially equivalent to those described in example 25-D, N-(5-chloropyridin-2-yl)-2-[(1-Boc-3,4-didehydropiperidin-4-ylcarbonyl)amino]-5-fluorobenzamide (1.32 g, 67%) was prepared from 2-amino-N-(5-chloropyridin-2-yl)-5-fluorobenzamide.

$^1$H-NMR

B. N-(5-Chloropyridin-2-yl)-5-fluoro-2-[(3,4-didehydropiperidin-4-ylcarbonyl)amino]benzamide Trifluoroacetate Using methods substantially equivalent to those described in example 9-B, N-(5-chloropyridin-2-yl)-5-fluoro-2-[(3,4-didehydropiperidin-4-ylcarbonyl)amino]benzamide trifluoroacetate (1.07 g, 80%) was prepared from N-(5-chloropyridin-2-yl)-2-[(1-Boc-3,4-didehydropiperidin-4-ylcarbonyl)amino]-5-fluorobenzamide.

$^1$H-NMR
IS-MS, m/e 375.0 (m+1)

C. N-(5-Chloropyridin-2-yl)-5-fluoro-2-[(1-isopropyl-3,4-didehydropiperidin-4-ylcarbonyl)amino]benzamide Hydrochloride Using methods substantially equivalent to those described in example 27, N-(5-chloropyridin-2-yl)-5-fluoro-2-[(1-isopropyl-3,4-didehydropiperidin-4-ylcarbonyl)amino]benzamide hydrochloride (0.255 g, 56%) was prepared from acetone and N-(5-chloropyridin-2-yl)-5-fluoro-2-[(3,4-didehydropiperidin-4-ylcarbonyl)amino]benzamide trifluoroacetate. The preparative RPHPLC (C18) purification procedure was elution with a linear gradient of 90/10 to 50/50 (0.01% HCl/acetonitrile) over 180 min, $^1$H-NMR
IS-MS, m/e 417.2 (m+1)

Analysis for $C_{21}H_{22}N_4O_2ClF.1.1HCl.1.3H_2O$: Calcd: C, 52.50; H, 5.39; N, 11.66; Cl, 15.50; Found: C, 52.53; H, 5.16; N, 11.59; Cl, 15.47.

EXAMPLE 42

Preparation of N-(5-Chloropyridin-2-yl)-5-fluoro-2-[(1-isopropylpiperidin-4-ylcarbonyl)amino]benzamide hydrochloride

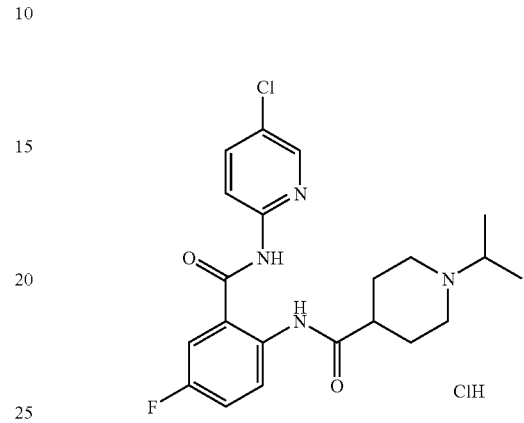

A. N-(5-Chloropyridin-2-yl)-2-[(1-Boc-piperidin-4-ylcarbonyl)amino]-5-fluorobenzamide Using methods substantially equivalent to those described in example 25-D, N-(5-chloropyridin-2-yl)-2-[(1-Boc-piperidin-4-ylcarbonyl)amino]-5-fluorobenzamide (2.15 g, 92%) was prepared from 2-amino-N-(5-chloropyridin-2-yl)-5-fluorobenzamide.

IS-MS, m/e 477.0 (m+1)

B. N-(5-Chloropyridin-2-yl)-5-fluoro-2-[(piperidin-4-ylcarbonyl)amino]benzamide trifluoroacetate Using methods substantially equivalent to those described in example 9-B, N-(5-chloropyridin-2-yl)-5-fluoro-2-[(piperidin-4-ylcarbonyl)amino]benzamide trifluoroacetate (1.7 g, 92%) was prepared from N-(5-chloropyridin-2-yl)-2-[(1-Boc-piperidin-4-ylcarbonyl)amino]-5-fluorobenzamide.

$^1$H-NMR
IS-MS, m/e 377.0 (m+1)

C. N-(5-Chloropyridin-2-yl)-5-fluoro-2-[(1-isopropylpiperidin-4-ylcarbonyl)amino]benzamide Hydrochloride Using methods substantially equivalent to those described in example 27, N-(5-chloropyridin-2-yl)-5-fluoro-2-[(1-isopropylpiperidin-4-ylcarbonyl)amino]benzamide hydrochloride (0.264 g, 58%) was prepared from N-(5-chloropyridin-2-yl)-5-fluoro-2-[(piperidin-4-ylcarbonyl)amino]benzamide trifluoroacetate and acetone. The preparative RPHPLC (C18) purification procedure was elution with a linear gradient of 90/10 to 50/50 (0.01% HCl/acetonitrile) over 180 min.

$^1$H-NMR
IS-MS, m/e 419.2 (m+1)
Analysis for $C_{21}H_{24}N_4O_2ClF.1.1HCl.1.4H_2O$: Calcd: C, 52.09; H, 5.81; N, 11.57; Cl, 15.38; Found: C, 52.11; H, 5.61; N, 11.32; Cl, 15.38.

EXAMPLE 43

Preparation of 5-Chloro-N-(5-chloropyridin-2-yl)-2-[(1-isopropyl-3,4-didehydropiperidin-4-ylcarbonyl)amino]benzamide hydrochloride

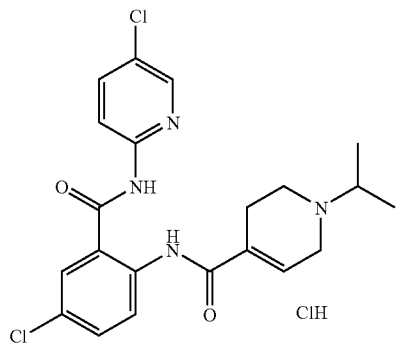

A. N-(5-Chloropyridin-2-yl)-2-[(1-Boc-piperidin-3-ene-4-ylcarbonyl)amino]-5-chlorobenzamide Using methods substantially equivalent to those described in example 25-D, N-(5-chloropyridin-2-yl)-2-[(1-Boc-3,4-didehydropiperidin-4-ylcarbonyl)amino]-5-chlorobenzamide (2.14 g, 99%) was prepared from N-(5-chloropyridin-2-yl)-2-amino-5-chlorobenzamide.

$^1$H-NMR

IS-MS, m/e 490.9 (m+1)

B. N-(5-Chloropyridin-2-yl)-2-[(3,4-didehydropiperidin-4-ylcarbonyl)amino]-5-chlorobenzamide trifluoroacetate Using methods substantially equivalent to those described in example 9-B, N-(5-chloropyridin-2-yl)-2-[(3,4-didehydropiperidin-4-ylcarbonyl)amino]-5-chlorobenzamide trifluoroacetate (1.28 g, 58%) was prepared from N-(5-chloropyridin-2-yl)-2-[(1-Boc-3,4-didehydropiperidin-4-ylcarbonyl)amino]-5-chlorobenzamide.

$^1$H-NMR

IS-MS, m/e 390.9 (m+1)

C. 5-Chloro-N-(5-chloropyridin-2-yl)-2-[(1-isopropyl-3,4-didehydropiperidin-4-ylcarbonyl)amino]benzamide hydrochloride Using methods substantially equivalent to those described in example 27, 5-chloro-N-(5-chloropyridin-2-yl)-2-[(1-isopropyl-3,4-didehydropiperidin-4-ylcarbonyl)amino]benzamide hydrochloride (0.172 g, 38%) was prepared from N-(5-chloropyridin-2-yl)-2-[(3,4-didehydropiperidin-4-ylcarbonyl)amino]-5-chlorobenzamide trifluoroacetate and acetone. The preparative RPHPLC (C18) purification procedure was elution with a linear gradient of 90/10 to 50/50 (0.01% HCl/acetonitrile) over 180 min.

$^1$H-NMR

IS-MS, m/e 433.1 (m+1)

Analysis for $C_{21}H_{22}N_4O_2Cl_2 \cdot 1.5HCl \cdot 0.5H_2O$: Calcd: C, 50.74; H, 4.97; N, 11.27; Cl, 24.97; Found: C, 50.72; H, 4.72; N, 11.19; Cl, 25.25.

EXAMPLE 44

Preparation of 5-Chloro-N-(5-chloropyridin-2-yl)-2-[(1-isopropylpiperidin-4-ylcarbonyl)amino]benzamide Hydrochloride

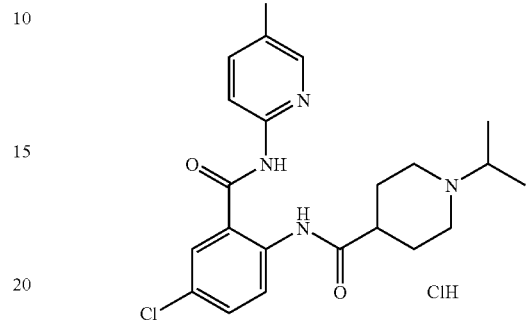

A. N-(5-Chloropyridin-2-yl)-2-[(1-Boc-piperidin-4-ylcarbonyl)amino]-5-chlorobenzamide Using methods substantially equivalent to those described in example 25-D, N-(5-chloropyridin-2-yl)-2-[(1-Boc-piperidin-4-ylcarbonyl)amino]-5-chlorobenzamide (2.8 g, 72%) was prepared from 2-amino-5-chloro-N-(5-chloropyridin-2-yl)benzamide and 1-Boc-piperidin-4-ylcarbonyl chloride.

$^1$H-NMR

IS-MS, m/e 493.0 (m+1)

B. 5-Chloro-N-(5-chloropyridin-2-yl)-2-[(piperidin-4-ylcarbonyl)amino]benzamide trifluoroacetate Using methods substantially equivalent to those described in example 9-B, 5-chloro-N-(5-chloropyridin-2-yl)-2-[(piperidin-4-ylcarbonyl)amino]benzamide trifluoroacetate (2.07 g, 95%) was prepared from N-(5 chloropyridin-2-yl)-2-[(1-Boc-piperidin-4-ylcarbonyl)amino]-5-chlorobenzamide.

$^1$H-NMR

IS-MS, m/e 392.9 (m+1)

C. 5-Chloro-N-(5-chloropyridin-2-yl)-2-[(1-isopropylpiperidin-4-ylcarbonyl)amino]benzamide Hydrochloride Using methods substantially equivalent to those described in example 27, 5-chloro-N-(5-chloropyridin-2-yl)-2-[(1-isopropylpiperidin-4-ylcarbonyl)amino]benzamide hydrochloride (0.103 g, 22%) was prepared from 5-chloro-N-(5-chloropyridin-2-yl)-2-[(piperidin-4-ylcarbonyl)amino]benzamide trifluoroacetate. The preparative RPHPLC (C18) purification procedure was elution with a linear gradient of 90/10 to 50/50 (0.01% HCl/acetonitrile) over 180 min.

$^1$H-NMR

IS-MS, m/e 435.3 (m+1)

Analysis for $C_{21}H_{24}N_4O_2Cl_2 \cdot 1.2HCl \cdot 0.5H_2O$: Calcd: C, 51.67; H, 5.41; N, 11.48; Cl, 23.24; Found: C, 51.52; H, 5.31; N, 11.55; Cl, 23.35.

An alternative preparation for the title compound is as follows:

D. Ethyl 1-Isopropylpiperidine-4-carboxylate

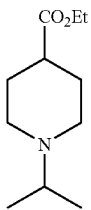

An autoclave was charged with ethyl isonipecotate (50 g, 318.0 mmol), 10% Pd/C (5 g, 10 wt %), acetone (450 mL, 6.13 mol) and ethanol (100 mL). The autoclave was pressurized to 4.1 bar with $H_2$, and the slurry was heated to 35° C. After 14 h the mixture was filtered, rinsed with acetone, and was concentrated to remove excess acetone. The crude material was taken on without any purification:

$^1$H-NMR (500 MHz, CDCl$_3$) δ 4.11 (q, J=7.1 Hz, 2H), 2.84 (m, 2H), 2.68 (hep, J=6.4 Hz, 1H), 2.23 (m, 1H), 2.14 (m, 2H), 1.89 (m, 2H), 1.72 (m, 2H), 1.24 (t, J=7.1 Hz, 3H), 1.01 (d, J=6.6 Hz, 6H).

E. 1-Isopropylpiperidine-4-carboxylic Acid

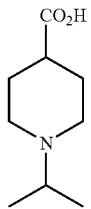

Crude ethyl 1-isopropylpiperidine-4-carboxylate (63.39 g, 318.0 mmol) was dissolved in ethanol (500 mL), and NaOH (25.3 g, 632 mmol) was added. The solution was heated to reflux for 15.75 h at which point it was allowed to cool to 34° C. A solution of ethanolic HCl (220 mL, 2.9 M solution) was added rapidly which caused a mild exotherm and immediate precipitation. The resulting NaCl was filtered using a fritted funnel, and the cloudy filtrate was refiltered through diatomaceous earth. The filtrate was concentrated and dissolved in 50% EtOAc/EtOH (600 mL) and heated on a steam bath. The insoluble material was removed by a filtration through diatomaceous earth, and the resulting filtrate was concentrated to a solid which was dried in a 50° C. vacuum oven to yield 54.09 g of yellow solid (corrected for 0.2 wt % EtOH by $^1$H-NMR analysis) which is a 99% yield over two steps. No further purification was attempted:

$^1$-NMR (500 MHz, MeOD-d$_6$) δ 3.49 (hep, J=6.6 Hz, 1H), 3.41 (m, 2H), 3.06 (m, 2H), 2.40 (m, 1H), 2.14 (m, 2H), 1.96 (m, 2H), 1.37 (d, J=6.6 Hz, 6H); $^{13}$C NMR (75 MHz, MeOD-d$_4$) 181.2, 59.4, 42.8, 28.4, 17.4 ppm; MS (electrospray) m/z 172.2 (MH+), 154.1, 130.1, 112.2.

F. 5-Chloro-N-(5-chloropyridin-2-yl)-2-[(1-isopropylpiperidin-4-ylcarbonyl)amino]benzamide A slurry of 1-isopropylpiperidine-4-carboxylic acid (501.0 mg, 2.92 mmol) and 50% DMF/THF (6.3 mL) was cooled in an ice bath, and a solution of iso-butyl chloroformate (0.34 mL, 2.63 mmol) and 50% DMF/THF (0.7 mL) was added over 10 min via syringe. The ice bath was removed at addition's end, and the mixture was allowed to warm to ambient temperature. After 1 h, 2-amino-5-chloro-N-(5-chloropyridin-2-yl)benzamide (414.8 mg, 1.47 mmol) was added in one portion, and the slurry was heated to 70° C. in an oil bath. Analysis by HPLC after 17 h showed only 2.5% of unacylated amine remained, so the volatiles were removed under reduced pressure, and EtOAc (25 mL) and water (20 mL) were added. The organic layer was extracted with saturated NaHCO$_3$ (2×20 mL), and the combined aqueous layers were back-extracted with CH$_2$Cl$_2$ (2×20 mL). The combined organic layers were dried (Na$_2$SO$_4$), filtered and concentrated to 0.97 g of yellow solid which was found to be contaminated with 45 wt % DMF. Corrected yield was 0.53 g (83% yield), and no further purification was performed:

$^1$H-NMR (500 MHz, CDCl$_3$) δ 10.72 (s, 1H), 8.70 (s, 1H), 8.66 (d, J=9.2 Hz, 1H), 8.26 (m, 2H), 7.75 (dd, J=8.9, 2.7 Hz, 1H), 7.62 (d, J=2.5 Hz, 1H), 7.47 (dd, J=8.9, 2.5 Hz, 1H), 2.96 (m, 2H), 2.74 (hep, J=6.4 Hz, 1H}, 2.30–2.19 (m, 3H), 2.00 (m, 2H), 1.82 (m, 2H), 1.05 (d, J=6.6 Hz, 6H).

G. 5-Chloro-N-(5-chloropyridin-2-yl)-2-[(1-isopropylpiperidin-4-ylcarbonyl)amino]benzamide Hydrochloride A solution of ethereal HCl (1.5 mL, 1 M solution) was added rapidly to a solution of the above crude free base (0.53 g, 1.2 mmol) and CH$_2$Cl$_2$ (16 mL) at 23° C. Precipitation occurred during the addition, and after stirring the resulting slurry for 5 min, Et$_2$O (12 mL) was added. The slurry was cooled in an ice bath for 30 min, at which point it was filtered, and the cake was washed with copious ether to rinse any residual DMF away. The product was dried in a 50° C. vacuum oven to provide 547.9 mg of the title compound as a white solid (97%) which contained 4 wt % H$_2$O by proton NMR analysis:

$^1$H-NMR (500 MHz, DMSO-d$_6$, 3.2:1 mixture of conformational isomers) δ 11.14 (s, 0.8H), 11.06 (s, 0.2H), 10.64 (m, 0.2H), 10.44 (m, 1H), 10.32 (m, 0.8H), 8.43 (d, J=2.7 Hz, 0.8H), 8.41 (d, J=2.7 Hz, 0.2H), 8.11 (d, J=8.9 Hz, 1H), 7.98–7.91 (m, 1.8H), 7.78 (d, J=2.5 Hz, 0.8H), 7.65 (d, J=2.1 Hz, 0.2H), 7.59–7.53 (m, 1.2H), 3.36 (m, 2.4H), 3.26 (m, 0.3H), 3.11 (m, 0.5H), 2.93 (m, 2.4H), 2.64 (m, 0.8H), 2.49 (m, 0.3H), 2.18 (m, 0.5H), 2.03 (m, 3.6H), 1.25 (d, J=6.6 Hz, 4.8H), 1.11 (d, J=6.6 Hz, 1.2H); $^{13}$C NMR (63 MHz, DMSO-d$_6$, mixture of conformational isomers) 172.3, 171.8, 166.0, 150.9, 150.5, 146.4, 137.8, 136.0, 134.7, 131.4, 130.8, 130.0, 128.9, 128.0, 127.5, 126.8, 125.9, 125.5, 124.2, 116.2, 115.6, 57.0, 56.4, 46.9, 44.7, 35.0, 25.4, 24.0, 16.3, 16.0 ppm; IR (KBr) 1301, 1373, 1458, 1512, 1664, 3233 cm$^{-1}$; MS (electrospray) m/z 433 (M–H).

EXAMPLE 45

Preparation of N-(5-Chloropyridin-2-yl)-2-[[4-(4-pyridinyl)piperazin-1-ylmethylcarbonyl]amino]benzamide

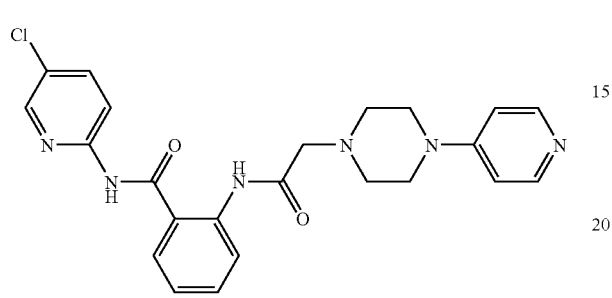

A. 2-(Bromoacetyl)amino-N-(5-chloropyridin-2-yl)benzamide

To a stirred solution of 2-amino-N-(5-chloropyridin-2-yl)benzamide (1.65 g, 6.66 mmol) in tetrahydrofuran (60 mL) and diisopropylethyl amine (1.28 mL) was added bromoacetyl bromide (0.64 mL, 7.32 mmol) dropwise at 0° C. The reaction mixture was warmed to room temperature and stirred overnight. Diluted the reaction mixture with ethyl acetate (120 mL) and water (50 mL). Separated the organic layer and washed with water (25 mL), saturated sodium bicarbonate (50 mL), 0.2 N hydrochloric acid (25 mL), water (50 mL). Dried over sodium sulfate and remove the solvent to get crude product (2.2 g), which was used as such in the following step.

B. N-(5-Chloropyridin-2-yl)-2-[[4-(4-pyridinyl)piperazin-1-ylmethylcarbonyl]amino]benzamide To a solution of 2-(bromoacetyl)amino-N-(5-chloropyridin-2-yl)benzamide (0.369 g, 1 mmol) in dichloromethane (10 ml) was added potassium carbonate (0.169 g, 1.22 mmol) and 1-(4-pyridyl)piperazine (0.171 mg, 1.05 mmol). The reaction was stirred overnight at room temperature. Water (2 mL) was added and the mixture was passed through a column of flux-calcined, high purity, inert diatomaceous earth packed into a polypropylene tube (article number CE 1103 from Varian) to remove water. The solvent was removed and the residue was purified by RPHPLC (CH$_2$Cl$_2$/5% 2 N ammonia in methanol) to give 0.08 g of pure title product.

$^1$H-NMR

FD-MS, m/e 451.0 (m+1)

EXAMPLE 46

Preparation of 2-(4-tert-Butylbenzoylamino)-N-(5-chloropyridin-2-yl)benzamide

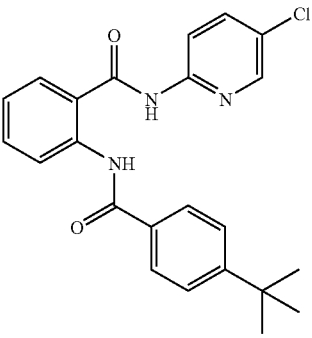

A. Methyl 2-(4-tert-butylbenzoylamino)benzoate

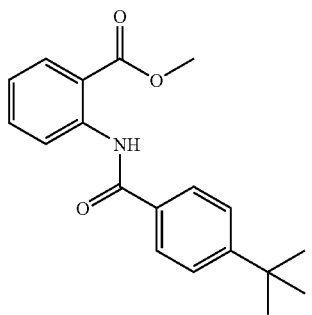

To a stirring solution of methyl 2-aminobenzoate (5 g, 33.1 mmol) and pyridine (5.3 g, 66 mmol) in dichloromethane (100 mL) was added 4-dimethylaminopyridine (0.2 g, 1.6 mmol). The mixture was cooled to 0° C. and treated with 4-tert-butylbenzoyl chloride (6.5 g, 33.1 mmol). After stirring overnight, the reaction mixture was diluted with dichloromethane (100 mL) and washed twice with 1 M aqueous citric acid (100 mL). The organic layer was then washed sequentially with water (100 mL) and 5 N aqueous HCl. It was dried over MgSO$_4$, filtered and concentrated in vacuo to give 10.68 g (quantitative) of a colorless oil.

$^1$H-NMR

FD-MS, m/e 312 (m+1)

Analysis for C$_{19}$H$_{21}$NO$_3$: Calcd: C, 73.29; H, 6.80; N, 4.50; Found: C, 73.09; H, 6.86; N, 5.33.

B. 2-(4-tert-Butylbenzoylamino)benzoic Acid

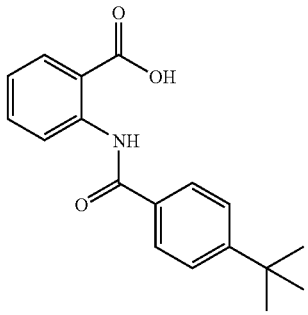

A stirring solution of methyl 2-(4-tert-butylbenzoylamino)benzoate (10.4 g, 33.4 mmol) and THF (200 mL) was treated with 1 M aqueous lithium hydroxide (40 mL) and methanol (80 mL). After stirring over night at room temperature, the mixture was treated with 1 M aqueous HCl (40 mL) and the solvent was removed in vacuo. The residue was partitioned between ethyl acetate (400 mL) and brine (100 mL). The organic phase was separated, then dried with $MgSO_4$, filtered and concentrated in vacuo to give 9.69 g (98%) of a white powder.

$^1$H-NMR

IS-MS, m/e 296 (m−1)

Analysis for $C_{18}H_{19}NO_3$: Calcd: C, 72.71; H, 6.44; N, 4.71; Found: C, 71.04; H, 6.59; N, 6.13.

C. 2-(4-tert-Butylphenyl)-4H-3,1-benzoxazin-4-one

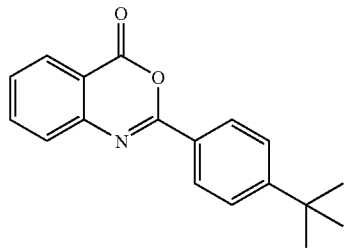

To a stirring mixture of the 2-(4-tert-butylbenzoylamino) benzoic acid (9.5 g, 32 mmol), $CH_2Cl_2$ (200 mL) and 2 drops of DMF was added 2 M oxalyl chloride in $CH_2Cl_2$ (19 mL). After stirring at ambient temperature for 45 minutes, the mixture was concentrated under vacuum to an oil, redissolved in 100 mL $CH_2Cl_2$ and cooled to 0° C. To this was added triethylamine (3.3 g, 33 mmol) at 0° C. for 1 hour. The solvent was removed in vacuo and the residue purified by flash chromatrography using hexanes/EtOAc to give 8.6 g (96%) of a white powder.

$^1$H-NMR

IS-MS, m/e 280 (m+1)

D. N-(5-chloropyridin-2-yl)-2-(4-tert-butylbenzoylamino)benzamide

A mixture of the above benzoxazinone (55 mg, 0.2 mmol), 2-amino-5-chloropyridine (55 mg, 0.43 mmol), KCN (100 mg, 1.54 mmol) and 2 mL of DMF was heated at 100° C. for 4 hours. The mixture was treated with brine (25 mL) and extracted with EtOAc (2×25 mL). The extracts were washed with brine (2×100 mL), dried over $MgSO_4$ and concentrated to dryness in vacuo. The residue was purified by radial chromatography using hexanes/EtOAc to give 35 mg (43%) of a white solid.

$^1$H-NMR

FD-MS, m/e 408 (m+1)

Analysis for $C_{23}H_{22}ClN_3O_2$: Calcd: C, 67.73; H, 5.44; N, 10.30; Found: C, 67.53; H, 5.87; N, 10.60.

EXAMPLE 47

Preparation of N-(5-Chloropyridin-2-yl)-2-(piperidin-4-ylmethylamino)benzamide

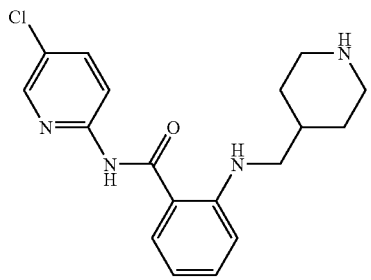

A. 1-tert-Butoxycarbonyl-4-piperidinemethanol

A solution of 1-tert-butoxycarbonyl isonipecotic acid (40 g, 0.17 mol) and N-methylmorpholine (19 mL, 0.17 mol) in tetrahydrofuran (900 mL) at −10° C. was treated with ethyl chloroformate (17 mL, 0.17 mol). After 0.5 h, sodium borohydride was added (19.8 g, 0.5 mol) in one portion followed by slow addition of methanol. After gas evolution ceased, the mixture was concentrated and the residue was diluted with 10% aqueous acetic acid and partitioned between ethyl acetate and water. The aqueous layer was washed with EtOAc (2×) and the combined organic extracts were dried with magnesium sulfate, filtered, and concentrated to a solid residue which was purified by column chromatography ($SiO_2$:10 to 50% EtOAc:hexanes) providing the title compound (33.8 g, 90%) as a white solid.

$^1$H-NMR

B. 1-tert-butoxycarbonyl-4-piperidinecarboxaldehyde

A solution of oxalyl chloride (6 mL, 70 mmol) in dichloromethane (60 mL) at −78° C. was treated dropwise with dimethyl sulfoxide (10 mL, 0.14 mol). After 15 minutes, 1-tert-butoxycarbonyl-4-piperidinemethanol (3.0 g, 14 mmol) was added as a solution in dichloromethane (35 mL). The mixture was stirred at −78° C. for 1 hr, then triethylamine (29 mL, 0.21 mol) was added dropwise. The mixture was warmed to ambient temperature and poured into a saturated ammonium chloride solution (200 mL). The organic layer was separated and the aqueous layer was washed with dichloromethane (75 mL). The organic layers were combined and washed with brine (75 mL); then dried with $MgSO_4$, filtered and concentrated. The residue was redissolved in ethyl acetate-hexanes (1:1) and filtered through Florisil (100–200 mesh). The resulting filtrate was concentrated yielding 3.0 g (100%) of the title aldehyde as a yellow oil; which was used without further purification.
¹H-NMR.

C. N-(5-Chloropyridin-2-yl)-2-(1-Boc-piperidin-4-ylmethylidene)aminobenzamide A solution containing 1-tert-butoxycarbonyl-4-piperidinecarboxaldehyde (500 mg, 2.34 mmol), 2-amino-N-(5-chloropyridin-2-yl)benzamide (580 mg, 0.23 mmol), and pyridinium p-toluenesulfonate (58 mg, 0.23 mmol) in benzene (250 mL) was heated at reflux with azeotropic removal of water. After 16 h, the mixture was concentrated and the residue partitioned between EtOAc (300 mL) and water (150 mL). The organic phase was separated and washed again with water (150 mL), brine (150 mL); then dried with MgSO₄, filtered and concentrated to afford, after purification by column chromatography (SiO₂: 0 to 10% EtOAc:methylene chloride), 750 mg (72%) of the title compound.
¹H-NMR
IS-MS, m/e (m)

D. N-(5-Chloropyridin-2-yl)-2-(piperidin-4-ylmethylamino)benzamide

A solution containing N-(5-chloropyridin-2-yl)-2-(1-Boc-piperidin-4-yl-methylidene)aminobenzamide (1.35 g, 3.05 mmol) and borane trimethylamine complex (667 mg, 9.14 mmol) in glacial acetic acid (50 mL) was heated at reflux for 2 h. The mixture was concentrated and the residue was dissolved in methanol and 12 N HCl. After 24 h, the mixture was concentrated, the residue was dissolved in 2 N ammonia in methanol and concentrated. The residue was triturated from methanol:EtOAc yielding 1.03 g (98%) of the title compound.
¹H-NMR
IS-MS, m/e (m)

EXAMPLE 48

Preparation of N-(5-Chloropyridin-2-yl)-2-(1-isopropylpiperidin-4-ylmethylamino)benzamide

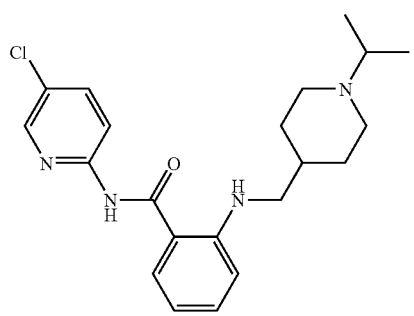

A solution of N-(5-chloropyridin-2-yl)-2-(piperidin-4-ylmethylamino)benzamide (0.152 g, 0.4 mmol) in methanol-acetic acid (95:5) (5 mL) was treated with acetone (5 mL) and sodium cyanoborohydride (0.111 g, 1.8 mmol). The reaction mixture was stirred at room temperature for 24 h, then it was diluted with 1 N NaOH until pH 13 and extracted with dichloromethane. The organic extracts were combined, dried with MgSO₄, filtered and concentrated in vacuo to provide the title compound (0.158 g, 92%). The crude material was triturated in dichloromethane-hexanes, giving a white powder which was filtered and dried under vacuum at 60° C.
¹H-NMR
mp 277.4–280.0° C.
FD-MS, m/e 387.0 (m)
Analysis for C₂₁H₂₇N₄OCl.1CH₂Cl₂.0.68CH₃OH: Calcd: C, 55.18; H, 6.48; N, 11.35; Found: C, 54.78; H, 6.19; N, 11.77.

EXAMPLE 49

Preparation of N-(5-Chloropyridin-2-yl)-2-[(1-methylsulfonylpiperidin-4-ylcarbonyl)amino]benzamide

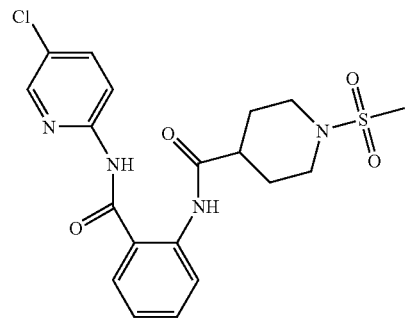

A. Ethyl N-Methylsulfonylisonipecotate

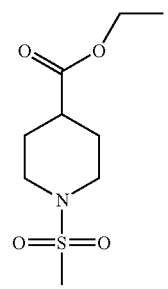

A solution of ethyl isonipecotate (4.9 mL, 31.8 mmol) and pyridine (2.8 mL, 34.6 mmol) was cooled to 0° C. Methanesulfonyl chloride (2.7 mL, 34.9 mmol) was added. After 1.5 hours, the reaction mixture was diluted with CH₂Cl₂ (300 mL) and extracted with saturated aqueous NaHCO₃ (3×100 mL). The organic layer was dried over Na₂SO₄, filtered, and concentrated. The crude material was dissolved in EtOAc (400 mL), extracted with H₂O (3×50 mL), dried over Na₂SO₄, filtered, and concentrated to give the pure product (5.42 g, 22.9 mmol, 72%) as a yellow solid. IR(CHCl₃): 3027, 1726, 1331, 1158, 963.
¹H-NMR (400 MHz, DMSO-d₆): δ 8.08(q, J=7.2 Hz, 2H); 3.44(d, J=11.6 Hz, 2H); 2.81(s, 3H); 2.76(t, J=8.7 Hz, 2H); 2.47(m, 1H); 1.89(d, J=13.2 Hz, 2H); 1.56(m, 2H); 1.15(t, J=7.2 Hz, 3H).
IS-MS, m/e: 236.0 (m+1).
Analysis for C₉H₁₇NO₄S.0.25H₂O: Calcd: C, 45.08; H, 7.36; N, 5.84; Found: C, 45.31; H, 7.08; N, 5.88.

B. N-Methylsulfonylisonipecotic Acid

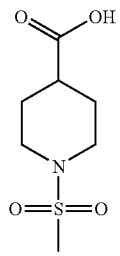

Using a procedure similar to example 46-B, N-methylsulfonylisonipecotic acid (1.6 g, 34%) was prepared from ethyl N-methylsulfonylisonipecotate.

IR(CHCl₃): 1710, 1346, 1331, 1158, 961.

¹H-NMR (300 MHz, DMSO-$d_6$): δ 3.42(d, J=11.7 Hz, 2H); 2.81(s, 3H); 2.75(m, 2H); 2.33(m, 1H); 1.87(d, J=13.8 Hz, 2H); 1.52(m, 2H).

MS-FIA m/e: 208.0 (m+1).

Analysis for $C_7H_{13}NO_4S$: Calcd: C, 40.57; H, 6.32; N, 6.76; Found: C, 40.68; H, 6.24; N, 6.70.

C. N-(5-Chloropyridin-2-yl)-2-[(1-methylsulfonylpiperidin-4-ylcarbonyl)amino]benzamide Using a procedure similar to that used in example 34-A, N-(5-chloropyridin-2-yl)-2-[(1-methylsulfonylpiperidin-4-ylcarbonyl)amino]benzamide (751 mg, 78%) was prepared from 2-amino-N-(5-chloropyridin-2-yl)benzamide and N-methylsulfonylisonipecotic acid.

IR(CHCl₃): 1663, 1588, 1506, 1375.

¹H-NMR (400 MHz, DMSO-$d_6$): d 10.95(s, 1H); 10.34(s, 1H); 8.40(s, 1H); 8.12(d, J=8.0 Hz, 1H); 7.94(d, J=8.4 Hz, 2H); 7.73(d, J=8.0 Hz, 1H); 7.49(t, J=8.0 Hz, 1H); 7.17(d, J=8.0 Hz, 1H); 3.51(d, J=11.6 Hz, 2H); 2.82(s, 3H); 2.73(t, J=11.6 Hz, 2H); 2.47(m, 1H); 1.87(d, J=10.0 Hz, 2H).

MS-FIA m/e: 437.2 (m+1).

EXAMPLE 50

Preparation of 5-Chloro-2-[(1-isopropyl-3,4-didehydropiperidin-4-ylcarbonyl)amino]-N-(5-methylpyridin-2-yl)benzamide Hydrochloride

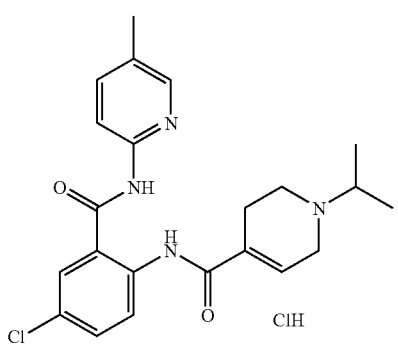

A. 5-Chloro-N-(5-methylpyridin-2-yl)-2-nitrobenzamide

Using methods substantially equivalent to those described in example 34-A, 5-chloro-N-(5-methylpyridin-2-yl)-2-nitrobenzamide (11.4 g, 53%) was prepared from 2-amino-5-methylpyridine and 5-chloro-2-nitrobenzoic acid.

¹H-NMR

IS-MS, m/e 292.0 (m+1)

Analysis for $C_{13}H_{10}N_3O_3Cl$: Calcd: C, 53.53; H, 3.46; N, 14.40; Found: C, 53.76; H, 3.41; N, 14.35.

B. 2-amino-5-chloro-N-(5-methylpyridin-2-yl)benzamide

Using methods substantially equivalent to those described in example 2-B, 2-amino-5-chloro-N-(5-methylpyridin-2-yl)benzamide (2.4 g, 67%) was prepared from 5-chloro-N-(5-methylpyridin-2-yl)-2-nitrobenzamide.

¹H-NMR

IS-MS, m/e 262.0 (m+1)

Analysis for $C_{13}H_{12}N_3OCl$: Calcd: C, 59.66; H, 4.62; N, 16.06; Found: C, 59.89; H, 4.57; N, 15.99.

C. 2-[(1-Boc-3,4-didehydropiperidin-4-ylcarbonyl)amino]-5-chloro-N-(5-methylpyridin-2-yl)benzamide Using methods substantially equivalent to those described in example 25-D, 2-[(1-Boc-3,4-didehydropiperidin-4-ylcarbonyl)amino]-5-chloro-N-(5-methylpyridin-2-yl)benzamide (0.37 g, 39%) was prepared from 2-amino-5-chloro-N-(5-methylpyridin-2-yl)benzamide and 1-Boc-1,2,3,6-tetrahydro-4-pyridinecarboxylic acid.

¹H-NMR

IS-MS, m/e 471.3 (m+1)

D. 5-Chloro-2-[(3,4-didehydropiperidin-4-ylcarbonyl)amino]-N-(5-methylpyridin-2-yl)benzamide trifluoroacetate Using methods substantially equivalent to those described in example 9-B, 5-chloro-2-[(3,4-didehydropiperidin-4-ylcarbonyl)amino]-N-(5-methylpyridin-2-yl)benzamide trifluoroacetate (0.305 g, 95%) was prepared from 2-[(1-Boc-3,4-didehydropiperidin-4-ylcarbonyl)amino]-5-chloro-N-(5-methylpyridin-2-yl)benzamide.

¹H-NMR

IS-MS, m/e 371.1 (m+1)

E. 5-Chloro-2-[(1-isopropyl-3,4-didehydropiperidin-4-ylcarbonyl)amino]-N-(5-methylpyridin-2-yl)benzamide Hydrochloride Using methods substantially equivalent to those described in example 27, 5-chloro-2-[(1-isopropyl-3,4-didehydropiperidin-4-ylcarbonyl)amino]-N-(5-methylpyridin-2-yl)benzamide hydrochloride (90 mg, 35%) was prepared from 5-chloro-2-[(3,4-didehydropiperidin-4-ylcarbonyl)amino]-N-(5-methylpyridin-2-yl)benzamide trifluoroacetate. The preparative RPHPLC (C18) purification procedure was elution with a linear gradient of 90/10 to 50/50 (0.01% HCl/acetonitrile) over 180 min.

¹H-NMR

IS-MS, m/e 413.2 (m+1)

Analysis for $C_{22}H_{25}N_4O_2Cl \cdot 1.4HCl \cdot 0.2H_2O$: Calcd: C, 56.51; H, 5.78; N, 11.98; Cl, 18.20; Found: C, 56.55; H, 5.69; N, 11.84; Cl, 18.06.

EXAMPLE 51

Preparation of 5-Chloro-N-(5-chloropyridin-2-yl)-2-[(4-isopropylpiperazin-1-ylcarbonyl)amino]benzamide Hydrochloride

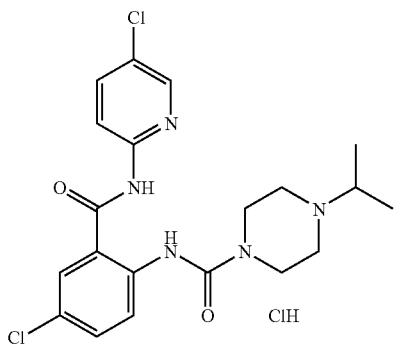

A. 2-[(4-Boc-piperazin-1-ylcarbonyl)amino]-5-chlorobromobenzene

To a stirring solution of triphosgene (2.7 g, 9.0 mmol) in dichloromethane (100 mL) was added, dropwise via an addition funnel, a solution of 2-bromo-4-chloroaniline (5 g, 24.2 mmol) and N,N-diisopropylethylamine (6.9 g, 53.2 mmol) in dichloromethane (50 mL). After complete addition and an additional hour, a solution of N-Boc-piperazine (5 g, 26.6 mmol) in dichloromethane (50 mL) was added. After stirring overnight, the solvent was removed in vacuo and the residue was partitioned between ethyl acetate and water. The organic phase was separated and washed consecutively with 1 M citric acid, brine, sat. aq sodium bicarbonate and finally with brine, then dried with MgSO4, filtered and concentrated in vacuo. The residue was then dissolved in a minimal amount of chloroform and chromatographed over silica gel, eluting with 20% ethyl acetate in hexanes followed by 30% ethyl acetate in hexanes. The product containing fractions were combined and concentrated in vacuo and the resulting solid was suspended in diethyl ether, sonicated and then filtered and dried in vacuo to give 7.2 g (71%) of a white powder.
$^1$H-NMR
IS-MS, m/e 418.2 ((m−1)$^-$

B. 2-[(4-Boc-piperazin-1-ylcarbonyl)amino]-5-chlorobenzoic Acid

To a stirred solution of 2-[(4-Boc-piperazin-1-ylcarbonyl)amino]-5-chlorobromobenzene (0.7 g, 1.67 mmol) in tetrahydrofuran (10 mL) at −78° C. under nitrogen was added methyllithium (1.4 M in ether, 1.2 mL, 1.67 mmol) dropwise via a syringe. After 5 min, tert-butyllithium (1.7 M in pentane, 1.0 mL, 1.67 mmol) was added dropwise via an addition funnel. After another 5 min, carbon dioxide was bubbled through the solution over 30 min as it warmed to room temperature. The solvent was then removed in vacuo and the residue was partitioned between diethyl ether and water. The layers were separated and the aqueous phase was acidified to pH 4 with citric acid and then extracted with ethyl acetate. The organic phase was washed with saturated aqueous sodium chloride, dried (magnesium sulfate), filtered, and concentrated in vacuo to give 0.32 g (50%) of the title compound as a white solid.
$^1$H-NMR
IS-MS, m/e 382–3 (m−1)$^-$
Analysis for $C_{17}H_{22}N_3O_5Cl$: Calcd: C, 53.20; H, 5.78; N, 10.95; Found: C, 52.97; H, 5.53; N, 10.74.

C. 2-(4-Boc-1-piperazinyl)-6-chloro-4H-3,1-benzoxazin-4-one

To a stirring solution of 2-[(4-Boc-piperazin-1-ylcarbonyl)amino]-5-chlorobenzoic acid (1.6 g, 4.17 mmol) in DMF (30 mL) was added 1-(3-dimethylaminopropyl)-3-ethylcarbodiimide hydrochloride (2.4 g, 12.51 mmol). After 30 min, the solvent was removed in vacuo and the residue was partitioned between ethyl acetate and water. The layers were separated and the organic phase was washed consecutively with 1 M citric acid, brine, sat. aq sodium bicarbonate, and brine, then dried with MgSO4, filtered and concentrated in vacuo. The residue was then suspended in diethyl ether, sonicated, filtered and dried in vacuo to give 0.86 g (58%) of the title compound as a white solid.
$^1$H-NMR
IS-MS, m/e 366.1 (m+1)

D. 2-[(4-Boc-piperazin-1-ylcarbonyl)amino]-5-chloro-N-(5-chloropyridin-2-yl)benzamide To a stirred solution of 2-amino-5-chloropyridine (0.6 g, 4.64 mmol) in tetrahydrofuran (80 mL) at 0° C. under nitrogen was added allylmagnesium bromide (1.0 M in ether, 4.7 mL, 4.7 mmol) dropwise via a syringe. After stirring at 0° C. for 10 min, 2-(4-Boc-1-piperazinyl)-6-chloro-4H-3,1-benzoxazin-4-one (0.8 g, 2.19 mmol) was added. After stirring 15 h at room temperature, the solvent was removed in vacuo. The residue was partitioned between ethyl acetate and saturated aqueous sodium chloride and the layers separated. The organic phase was washed with water, dried (magnesium sulfate), filtered, and concentrated in vacuo to give 0.88 g (82%) of the title compound as a white solid.
$^1$H-NMR
IS-MS, m/e 494.1 (m+1)

E. 5-Chloro-N-(5-chloropyridin-2-yl)-2-[(piperazin-1-ylcarbonyl)amino]benzamide trifluoroacetate Using methods substantially equivalent to those described in example 9-B, N-(5-chloropyridin-2-yl)-2-[(piperazin-4-ylcarbonyl)amino]-5-chlorobenzamide trifluoroacetate (0.607 g, 98%) was prepared from 2-[(4-Boc-piperazin-1-ylcarbonyl)amino]-5-chloro-N-(5-chloropyridin-2-yl)benzamide.
$^1$H-NMR
IS-MS, m/e 394.1 (m+1)
Analysis for $C_{17}H_{17}N_5O_2Cl_2$.TFA: Calcd: C, 44.90; H, 3.57; N, 13.78; F, 11.21; Found: C, 44.60; H, 3.53; N, 13.78; F, 11.43.

F. 5-Chloro-N-(5-chloropyridin-2-yl)-2-[(4-isopropylpiperazin-1-ylcarbonyl)amino]benzamide Hydrochloride Using methods substantially equivalent to those described in example 27, 5-chloro-N-(5-chloropyridin-2-yl)-2-[(4-isopropylpiperazin-1-ylcarbonyl)amino]benzamide hydrochloride (0.263 g, 57%) was prepared from 5-chloro-N-(5-chloropyridin-2-yl)-2-[(piperazin-1-ylcarbonyl)amino]benzamide trifluoroacetate.
¹H-NMR
IS-MS, m/e 436.1 (m+1)
Analysis for $C_{20}H_{23}N_5O_2Cl_2 \cdot 2.0HCl \cdot 0.1H_2O$: Calcd: C, 47.00; H, 4.97; N, 13.70; Cl, 27.75; Found: C, 47.07; H, 4.70; N, 13.57; Cl, 27.74.

EXAMPLE 52

Preparation of N-(5-Chloropyridin-2-yl)-2-[1-(4-pyridinyl)piperidin-4-ylmethylamino]benzamide

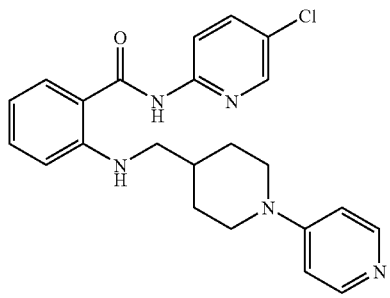

A pressure tube was charged with N-(5-chloropyridin-2-yl)-2-(piperidin-4-ylmethylamino)benzamide (100 mg, 0.29 mmol), 4-chloropyridine hydrochloride (87 mg, 0.58 mmol), triethylamine (59 mg, 0.58 mmol), and ethanol (5 mL), sealed, and placed in a 120° C. bath. After 24 h, the mixture was cooled, concentrated, and the residue purified by column chromatography (SiO₂: 5 to 10% 2 N ammonia in methanol:methylene chloride) affording 70 mg (57%) of the title compound.
¹H-NMR, IR
IS-MS, m/e 422 (m)
Analysis for $C_{23}H_{24}ClN_5O \cdot 0.25H_2O$: Calcd: C, 64.78; H, 5.79; N, 16.42; Found: C, 64.54; H, 6.25; N, 15.58.

EXAMPLE 53

Preparation of 5-Chloro-N-(5-chloropyridin-2-yl)-2-[[1-(1-ethylpropyl)piperidin-4-ylcarbonyl]amino]benzamide Hydrochloride

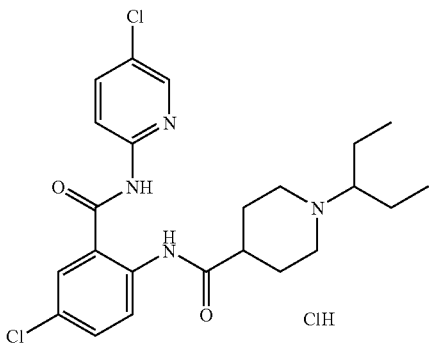

By methods substantially equivalent to those described in Example 27, 5-chloro-N-(5-chloropyridin-2-yl)-2-[[1-(1-ethylpropyl)piperidin-4-ylcarbonyl]amino]benzamide hydrochloride (0.103 g, 21%) was prepared from 5-chloro-N-(5-chloropyridin-2-yl)-2-[(piperidin-4-ylcarbonyl)amino]benzamide trifluoroacetate and 3-pentanone. The product was purified with reverse phase HPLC, eluting with a gradient from 20% through 60% acetonitrile in 0.05% aq HCl.

¹H-NMR
IS-MS, m/e 463.3 (m+1)
Analysis for $C_{23}H_{28}N_4O_2Cl_2 \cdot 1.2HCl \cdot H_2O$: Calcd: C, 52.60; H, 5.99; N, 10.67; Cl, 21.60; Found: C, 52.53; H, 6.08; N, 10.41; Cl, 21.51.

EXAMPLE 54

Preparation of N-(5-Chloropyridin-2-yl)-2-[(1-isopropylazetidin-3-yloxycarbonyl)amino]benzamide

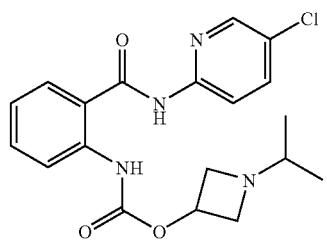

A. N-(5-Chloropyridin-2-yl)-2-[(1-tert-butoxycarbonylazetidin-3-yloxycarbonyl)amino]benzamide Using a similar procedure to that described in example 4-B, 2-amino-N-(5-chloropyridin-2-yl)benzamide (1.07 g, 4.34 mmol) and 1-tert-butoxycarbonyl-3-hydroxyazetidine (1.50 g, 8.67 mmol) yielded 1.43 g (74%) of the title compound.
¹H-NMR
IS-MS, m/e 447 (m+1)

B. N-(5-Chloropyridin-2-yl)-2-[(1-isopropylazetidin-3-yloxycarbonyl)amino]benzamide Using a similar procedure to that described for Example 9-B&C, N-(5-chloropyridin-2-yl)-2-[(1-tert-butoxycarbonylazetidin-3-yloxycarbonyl)amino]benzamide (327 mg, 0.733 mmol) afforded 201 mg (71%) of the title compound.
¹H-NMR
IS-MS, m/e 389 (m)

EXAMPLE 55

Preparation of N-(5-Chloropyridin-2-yl)-2-[(1-isopropylpyrrolidin-3-yloxycarbonyl)amino]benzamide

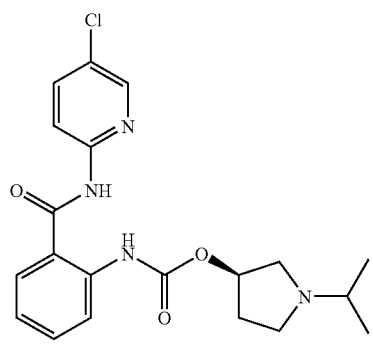

A. N-(5-Chloropyridin-2-yl)-2-[(1-tert-butoxycarbonylpyrrolidin-3-yloxycarbonyl)amino]benzamide Using a similar procedure to that described in Example 4-B, N-(5-chloropyridin-2-yl)-2-aminobenzamide (1.25 g, 5.05 mmol) and 1-tert-butoxycarbonyl-3-hydroxypyrrolidine yielded 2.33 g (99%) of the title compound.

$^1$H-NMR

IS-MS, m/e 461 (m)

B. N-(5-Chloropyridin-2-yl)-2-[(pyrrolidin-3-yloxycarbonyl)amino]benzamide Trifluoroacetate Using a similar procedure to that described in Example 9-B, N-(5-chloropyridin-2-yl)-2-[(1-tert-butoxycarbonylpyrrolidin-3-yloxycarbonyl)amino]benzamide (1.50 g, 3.26 mmol) yielded 1.60 g (94%) of the title compound.

$^1$H-NMR

C. N-(5-Chloropyridin-2-yl)-2-[(1-isopropylpyrrolidin-3-yloxycarbonyl)amino]benzamide Using a similar procedure to that described in Example 9-C, N-(5-chloropyridin-2-yl)-2-[pyrrolidin-3-yloxycarbonyl)amino]benzamide trifluoroacetate (500 mg, 1.06 mmol), acetone (10 mL), and sodium cyanoborohydride (265 mg, 4.22 mmol) yielded 330 mg (77%) of the title compound.

$^1$H-NMR

IS-MS, m/e 403 (m+1)

EXAMPLE 56

Preparation of N-(5-Chloropyridin-2-yl)-2-[(1-cyclohexylpyrrolidin-3-yloxycarbonyl)amino]benzamide

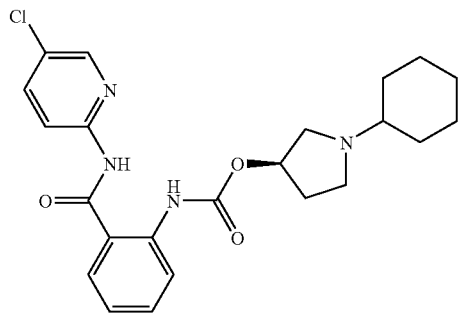

Using a similar procedure to that described in Example 9-C, N-(5-chloropyridin-2-yl)-2-[(pyrolidin-3-yloxycarbonyl)amino]benzamide trifluoroacetate (100 mg, 0.211 mmol), cyclohexanone (0.11 mL, 1.05 mmol), and sodium cyanoborohydride (53 mg, 0.84 mmol) yielded 90 mg (96%) of the title compound.

$^1$H-NMR

IS-MS, m/e 443 (m+1)

EXAMPLE 57

Preparation of N-(5-Chloropyridin-2-yl)-2-[(1-cyclopentylpyrrolidin-3-yloxycarbonyl)amino]benzamide

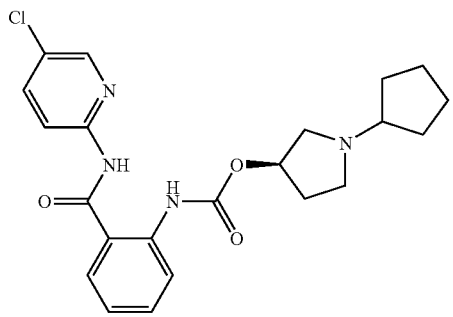

Using a similar procedure to that described in Example 9-C, N-(5-chloropyridin-2-yl)-2-[(pyrrolidin-3-yloxycarbonyl)amino]benzamide trifluoroacetate (100 mg, 0.211 mmol), cyclopentanone (0.095 mL, 1.05 mmol), and sodium cyanoborohydride (53 mg, 0.84 mmol) yielded 78 mg (87%) of the title compound.

$^1$H-NMR

IS-MS, m/e 429 (m+1)

EXAMPLE 58

Preparation of N-(5-Chloropyridin-2-yl)-2-[1-(2-cyanopyridin-4-yl)piperidin-4-ylmethylamino]benzamide

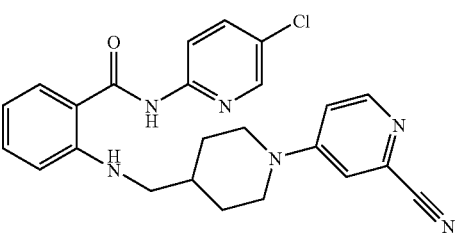

Using a similar procedure to that described in Example 52, N-(5-chloropyridin-2-yl)-2-(piperidin-4-ylmethylamino)benzamide (100 mg, 0.29 mmol), 4-chloro-2-cyanopyridine (80 mg, 0.58 mmol), triethylamine (59 mg, 0.58 mmol), and ethanol (2 mL) yielded 60 mg (46%) of the title compound.

$^1$H-NMR, IR

IS-MS, m/e 447 (m+1)

Analysis for $C_{24}H_{23}ClN_6O \cdot 1.0H_2O$: Calcd: C, 62.00; H, 5.42; N, 18.07; Found: C, 62.14; H, 5.27; N, 17.33.

EXAMPLE 59

Preparation of N-(5-Chloropyridin-2-yl)-5-fluoro-2-(piperidin-4-ylmethylamino)benzamide

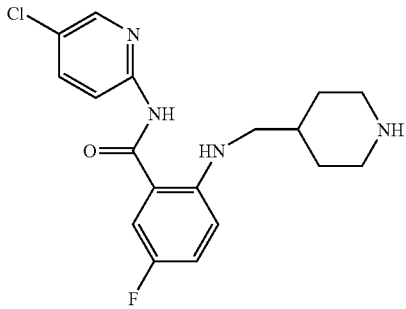

A. 2-(1-Boc-piperidin-4-ylmethylidene)amino-N-(5-chloropyridin-2-yl)-5-fluorobenzamide

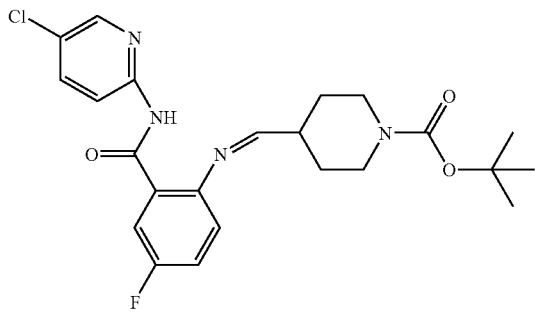

A solution containing 1-Boc-piperidine-4-carboxaldehyde (3.0 g, ca. 14 mmol), 2-amino-N-(5-chloropyridin-2-yl)-5-fluorobenzamide (3.7 g, 14 mmol), and pyridinium p-toluenesulfonate (0.3 g, 1.4 mmol) in benzene (250 mL) was heated at reflux for 24 h with azeotropic removal of water. The solution was allowed to cool to room temperature; then the solvent was removed in vacuo and the residue was partitioned between ethyl acetate (300 mL) and water (150 mL). The organic phase was separated and washed again with water (150 mL) and then brine (150 mL); then dried with MgSO₄, filtered and concentrated in vacuo to give 6.0 g (93%) of the title compound as an orange foam which was used directly in the next step without further purification.

¹H-NMR

FD-MS, m/e 461.1 (m).

B. 2-(1-Boc-piperidin-4-ylmethylamino)-N-(5-chloropyridin-2-yl)-5-fluorobenzamide

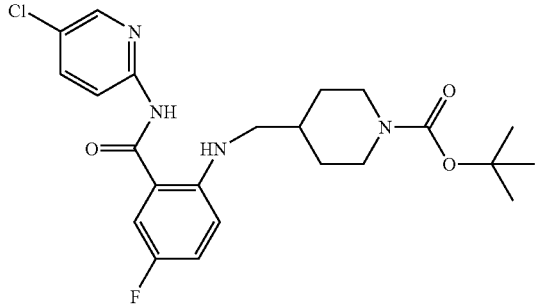

A solution containing 2-(1-Boc-piperidin-4-ylmethylidene)amino-N-(5-chloropyridin-2-yl)-5-fluorobenzamide from above (6.0 g, 13 mmol) and borane trimethylamine complex (2.9 g, 39 mmol) in glacial acetic acid (100 mL) was heated at 70° C. for 24 h. The solution was allowed to cool to room temperature; then the solvent was removed in vacuo, and the residue was partitioned between dichloromethane (200 mL) and water (100 mL). The biphasic mixture was treated with 2 N NaOH until neutral; then the organic layer was separated and the aqueous layer was washed again with dichloromethane (100 mL). The combined organic layers were washed with brine (100 mL), dried with MgSO₄, and filtered. The filtrate was concentrated in vacuo to give 5.85 g (97%) of the title compound as an orange foam which was used directly in the next step without further purification.

¹H-NMR

FD-MS, m/e 463.1 (m).

C. N-(5-Chloropyridin-2-yl)-5-fluoro-2-(piperidin-4-ylmethylamino)benzamide

A solution of 2-(1-Boc-piperidin-4-ylmethylamino)-N-(5-chloropyridin-2-yl)-5-fluorobenzamide from above (5.8 g, 12 mmol) in trifluoroacetic acid (125 mL) was heated at 70° C. for 2 h, then at room temperature for 24 h. The solvent was removed in vacuo; then the residue was directly applied to a silica gel column. Elution with dichloromethane-2 M ammonia in methanol (9:1) afforded 3.8 g (84%) of the title compound as a yellow solid.

¹H-NMR mp 230–233° C.

FD-MS, m/e 363.3 (m)

Analysis for $C_{18}H_{20}ClFN_4O \cdot 1.28 CH_2Cl_2$: Calcd: C, 49.11; H, 4.82; N, 11.88; Found: C, 49.30; H, 4.49; N, 11.49.

EXAMPLE 60

Preparation of 5-Chloro-N-(5-chloropyridin-2-yl)-2-(piperidin-4-ylmethylamino)benzamide

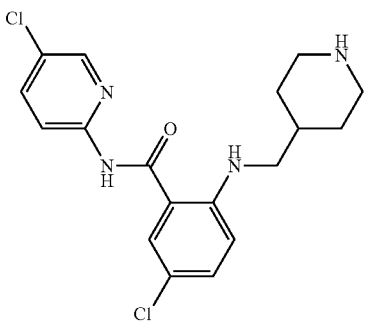

A. 2-(1-Boc-piperidin-4-ylmethylamino)-5-chloro-N-(5-chloropyridin-2-yl)benzamide

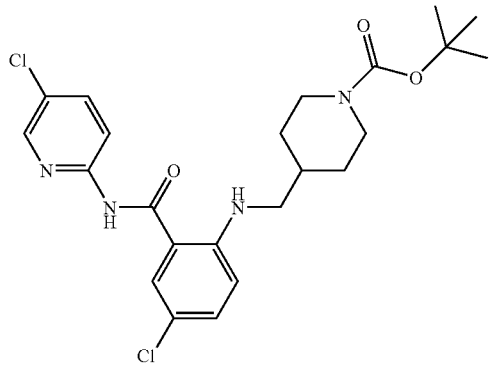

To a solution of 1-Boc-piperidine-4-carboxaldehyde (3.5 g, 14 mmol) and 2-amino-5-chloro-N-(5-chloropyridin-2-yl) benzamide (3.9 g, 14 mmol) in benzene (250 mL), a catalytic amount of pyridinium p-toluenesulfonate (0.35 g, 1.4 mmol) was added, followed by 4 A molecular sieves. The reaction mixture was heated at reflux for 48 h with azeotropic removal of water. The mixture was subsequently filtered through a pad of diatomaceous earth, washing well with ethyl acetate. The filtrate was concentrated in vacuo to a residue that was taken up in acetic acid (100 mL) and treated with borane-trimethylamine complex (3 g, 42 mmol). The mixture was heated at 70° C. for 24 h; then it was diluted with 2 N NaOH and extracted with dichloromethane. The water layer was neutralized with solid sodium bicarbonate, and further extracted with dichloromethane. The combined organic extracts were dried with MgSO$_4$, filtered, and concentrated in vacuo to a solid residue (8 g, >100%) which was identified as the desired product and taken on directly to the next step without further purification.

$^1$H-NMR

FD-MS, m/e 479.0 (m).

B. 5-Chloro-N-(5-chloropyridin-2-yl)-2-(piperidin-4-ylmethylamino)benzamide

Using the procedure described in example 47-D, 2-(1-Boc-piperidin-4-ylmethylamino)-5-chloro-N-(5-chloropyridin-2-yl)benzamide (8 g, 14 mmol) was converted to 5-chloro-N-(5-chloropyridin-2-yl)-2-(piperidin-4-ylmethylamino)benzamide, which was purified via silica gel chromatography. Elution with 9:1 dichloromethane-2 N ammonia in methanol provided clean material identified as the title compound (3.8 g, 72%).

$^1$H-NMR mp 91.4–93.4° C.

FD-MS, m/e 379.1 (m)

Analysis for C$_{18}$H$_{20}$N$_4$OCl$_2$.0.2MeOH: Calcd: C, 56.68; H, 5.44; N, 14.53; Found: C, 56.45; H, 5.13; N, 14.32.

EXAMPLE 61

Preparation of 5-Chloro-N-(5-fluoropyridin-2-yl)-2-[[1-(4-pyridinyl)piperidin-4-ylcarbonyl]amino]benzamide Hydrochloride

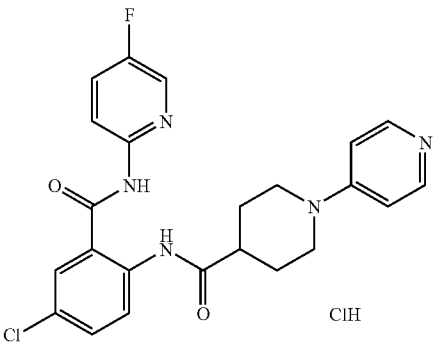

A. 5-Chloro-N-(5-fluoropyridin-2-yl)-2-nitrobenzamide

Using methods substantially equivalent to those described in example 34-A, 5-chloro-N-(5-fluoropyridin-2-yl)-2-nitrobenzamide (4.27 g, 81%) was prepared from 2-amino-5-fluoropyridine and 5-chloro-2-nitrobenzoic acid.

$^1$H-NMR

IS-MS, m/e 296.2 (m+1)

Analysis for C$_{12}$H$_7$N$_3$O$_3$ClF: Calcd: C, 48.75; H, 2.39; N, 14.21; Found: C, 48.97; H, 2.61; N, 14.13.

B. 2-Amino-5-chloro-N-(5-fluoropyridin-2-yl)benzamide

Using methods substantially equivalent to those described in example 2-B, 2-amino-5-chloro-N-(5-fluoropyridin-2-yl) benzamide (1.87 g, 88%) was prepared from 5-chloro-N-(5-fluoropyridin-2-yl)-2-nitrobenzamide.

$^1$H-NMR

IS-MS, m/e 266.0 (m+1)

C. 5-Chloro-N-(5-fluoropyridin-2-yl)-2-[[1-(4-pyridinyl)piperidin-4-ylcarbonyl]amino]benzamide Hydrochloride Using methods substantially equivalent to those described in example 1-D, 5-chloro-N-(5-fluoropyridin-2-yl)-2-[[1-(4-pyridinyl)piperidin-4-ylcarbonyl]amino]benzamide hydrochloride (0.365 g, 40%) was prepared from 2-amino-5-chloro-N-(5-fluoropyridin-2-yl)benzamide and 1-(4-pyridinyl)piperidin-4-ylcarbonyl chloride. The preparative RPHPLC (C18) purification procedure was elution with a linear gradient of 90/10 to 50/50 (0.01% HCl/acetonitrile) over 180 min.

$^1$H-NMR

IS-MS, m/e 455.2 (m+1)

Analysis for C$_{23}$H$_{21}$N$_5$O$_2$ClF.1.1HCl.1.5H$_2$O: Calcd: C, 53.02; H, 4.86; N, 13.44; Cl, 14.29; Found: C, 53.16; H, 4.47; N, 13.29; Cl, 14.25.

EXAMPLE 62

Preparation of N-(5-chloropyridin-2-yl)-5-fluoro-2-(1-isopropylpiperidin-4-ylmethylamino)benzamide

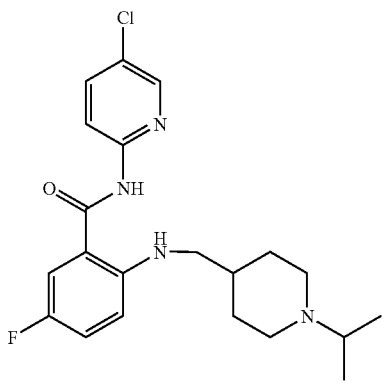

Using the procedure described in example 48, N-(5-chloropyridin-2-yl)-5-fluoro-2-(piperidin-4-ylmethylamino)benzamide (0.7 g, 1.9 mmol) was converted to N-(5-chloropyridin-2-yl)-5-fluoro-2-(1-isopropylpiperidin-4-ylmethylamino)benzamide, which was purified via silica gel chromatography. Elution with dichloromethane-2 M ammonia in methanol (9:1) afforded 0.6 g (83%) of the title compound as a yellow solid.

$^1$H-NMR
mp 142–144° C.
FD-MS, m/e 405.4 (m)
Analysis for $C_{21}H_{26}ClFN_4O$: Calcd: C, 62.29; H, 6.47; N, 13.84; Found: C, 62.03; H, 6.58; N, 13.83.

EXAMPLE 63

Preparation of 5-chloro-N-(5-chloropyridin-2-yl)-2-(1-isopropylpiperidin-4-ylmethylamino)benzamide

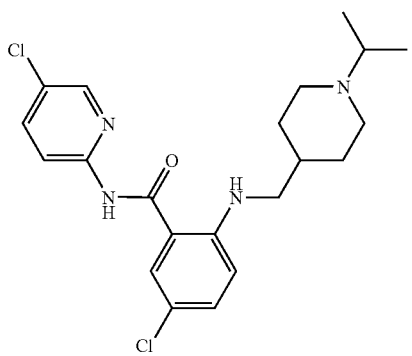

Using the procedure described in example 48, 5-chloro-N-(5-chloropyridin-2-yl)-2-(piperidin-4-ylmethylamino)benzamide (0.626 g, 1.7 mmol) was converted to 5-chloro-N-(5-chloropyridin-2-yl)-2-(1-isopropylpiperidin-4-ylmethylamino)benzamide. The crude reaction mixture was filtered through a pad of diatomaceous earth and concentrated in vacuo. The residue was diluted with methanol and applied to an SCX column, washed with methanol and eluted with 2 N ammonia in methanol. The eluted fractions were combined and concentrated in vacuo to provide a crude residue, which was further purified via silica gel chromatography. Elution with ethyl acetate, then ethyl acetate-2 N ammonia in methanol (95:5), then dichloromethane-2 N ammonia in methanol (90:10) provided the title compound (0.375 g, 54%) as a solid material.

$^1$H-NMR
FD-MS, m/e 421.0 (m)
Analysis for $C_{21}H_{26}N_4OCl_2.0.4CH_3OH$: Calcd: C, 59.20; H, 6.41; N, 12.90; Found: C, 58.91; H, 6.12; N, 12.75.

EXAMPLE 64

Preparation of N-(5-Chloropyridin-2-yl)-2-[[1-(2-methylcyclopentyl)pyrrolidin-3-yloxycarbonyl]amino]benzamide Hydrochloride

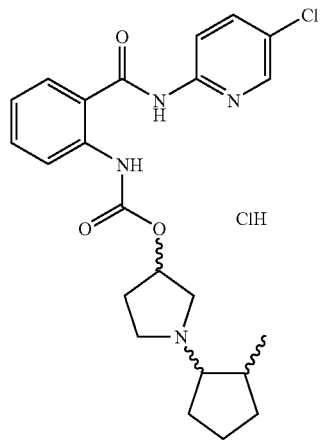

Using a similar procedure to that described in Example 9-C, N-(5-chloropyridin-2-yl)-2-[(pyrrolidin-3-yloxycarbonyl)amino]benzamide trifluoroacetate (100 mg, 0.211 mmol), 2-methylcyclopentanone (0.112 mL, 1.05 mmol), and sodium cyanoborohydride (53 mg, 0.84 mmol) yielded, after treatment with HCl, 80 mg (80%) of the title compound as the hydrochloride salt.

$^1$H-NMR
IS-MS, m/e 443 (m+1)

EXAMPLE 65

Preparation of N-(5-Chloropyridin-2-yl)-2-[[1-(2-methylcyclohexyl)pyrrolidin-3-yloxycarbonyl]amino]benzamide Hydrochloride

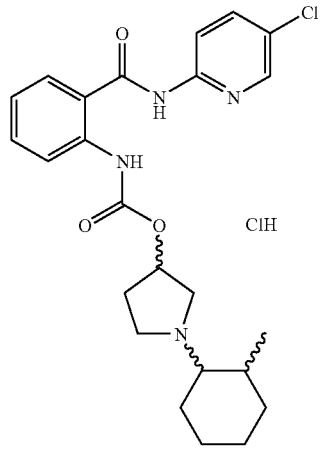

Using a similar procedure to that described in Example 9-C, N-(5-chloropyridin-2-yl)-2-[(pyrrolidin-3-yloxycarbonyl)amino]benzamide trifluoroacetate (100 mg, 0.211 mmol), 2-methylcyclohexanone (0.12 mL, 1.05 mmol), and sodium cyanoborohydride (53 mg, 0.84 mmol) yielded, after treatment with HCl, 82 mg (80%) of the title compound as the hydrochloride salt.

$^1$H-NMR

IS-MS, m/e 443 (m+1).

EXAMPLE 66

Preparation of 2-[1-(3-carboxypyridin-4-yl)piperidin-4-ylmethylamino]-N-(5-chloropyridin-2-yl)benzamide

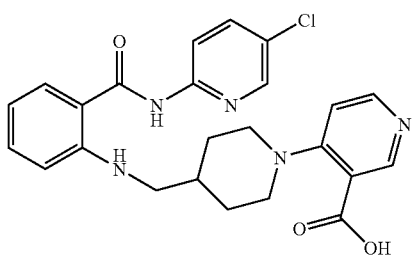

Using a similar procedure to that described in Example 52, N-(5-chloropyridin-2-yl)-2-(piperidin-4-ylmethylamino)benzamide (100 mg, 0.29 mmol), 4-chloronicotinic acid (91 mg, 0.58 mmol), triethylamine (59 mg, 0.58 mmol), and ethanol (5 mL) yielded, after RPHPLC purification, 45 mg (33%) of the title compound as a trifluoroacetate salt.

$^1$H-NMR

IS-MS, m/e 466 (m+1)

Analysis for $C_{24}H_{24}ClN_5O_3$ (1.5$H_2O$, 1.0 $CF_3CO_2H$): Calcd: C, 51.44; H, 4.65; N, 11.54; Found: C, 51.46; H, 4.76; N, 12.02.

EXAMPLE 67

Preparation of N-(5-Chloropyridin-2-yl)-2-[(piperidin-4-ylmethoxycarbonyl)amino]benzamide Trifluoracetic Acid Salt

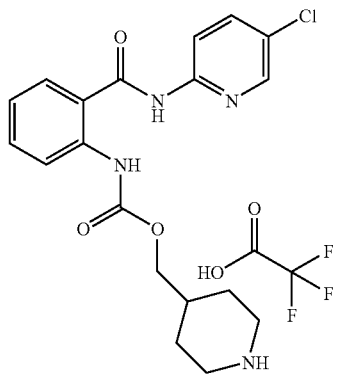

A. N-(5-Chloropyridin-2-yl)-2-[(1-tert-butoxycarbonylpiperidin-4-ylmethoxycarbonyl)amino]benzamide Using a similar procedure to that described in Example 4-B, 2-amino-N-(5-chloropyridin-2-yl)benzamide (1.50 g, 6.07 mmol) and 1-tert-butoxycarbonyl-4-hydroxymethylpiperidine (1.96 g, 9.10 mmol) yielded 2.00 g (67%) of the title compound.

$^1$H-NMR

IS-MS, m/e 489 (m+1)

Analysis for $C_{24}H_{29}N_4O_5Cl$: Calcd: C, 58.95; H, 5.98; N, 11.46; Found: C, 59.23; H, 6.09; N, 11.70.

B. N-(5-Chloropyridin-2-yl)-2-[(piperidin-4-ylmethoxycarbonyl)amino]benzamide Trifluoroacetic Acid Salt Using a similar procedure to that described in Example 9-B, N-(5-chloropyridin-2-yl)-2-[(1-tert-butoxycarbonylpiperidin-4-ylmethoxycarbonyl)amino]benzamide (300 mg, 0.615 mmol) yielded 308 mg (99%) of the title compound as a trifluoroacetate salt.

$^1$H-NMR

IS-MS, m/e 389 (m+1)

Analysis for $C_{21}H_{22}N_4O_5ClF_3$: Calcd: C, 50.16; H, 4.41; N, 11.14; Found: C, 50.39; H, 4.40; N, 11.24.

EXAMPLE 68

Preparation of N-(5-Chloropyridin-2-yl)-2-[(piperidin-4-yloxycarbonyl)amino]benzamide Trifluoroacetic Acid Salt

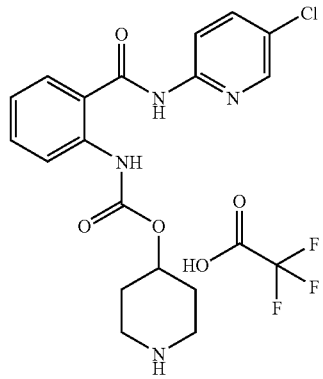

A. N-(5-Chloropyridin-2-yl)-2-[(1-tert-butoxycarbonylpiperidin-4-yloxycarbonyl)amino]benzamide Using a similar procedure to that described in Example 4-B, 2-amino-N-(5-chloropyridin-2-yl)benzamide (1.50 g, 6.07 mmol) and 1-tert-butoxycarbonyl-4-hydroxypiperidine (1.83 g, 9.10 mmol) yielded 2.20 g (76%) of the title compound.

$^1$H-NMR

IS-MS, m/e 475 (m+1)

B. N-(5-Chloropyridin-2-yl)-2-[(piperidin-4-yloxycarbonyl)amino]benzamide Trifluoroacetic Acid Salt Using a similar procedure to that described in Example 9-B, N-(5-chloropyridin-2-yl)-2-[(1-tert-butoxycarbonylpiperidin-4-yloxycarbonyl)amino]benzamide (1.90 g, 4.00 mmol) yielded 1.95 g (99%) of the titled compound as a trifluoroacetate salt.

¹H-NMR
IS-MS, m/e 375 (m+1)
Analysis for $C_{20}H_{20}N_4O_5ClF_3$: Calcd: C, 49.14; H, 4.12; N, 11.46; Found: C, 49.21; H, 4.02; N, 11.57.

EXAMPLE 69

Preparation of 5-Chloro-N-(5-chloropyridin-2-yl)-2-[[1-(tetrahydropyran-4-yl)piperidin-4-ylcarbonyl]amino]benzamide Hydrochloride

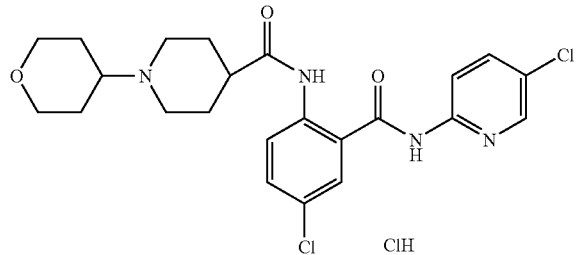

Using methods substantially equivalent to those described in example 27, 5-chloro-N-(5-chloropyridin-2-yl)-2-[[1-(tetrahydropyran-4-yl)piperidin-4-ylcarbonyl]amino]benzamide hydrochloride (0.25 g, 56%) was prepared from 5-chloro-N-(5-chloropyridin-2-yl)-2-[(piperidin-4-ylcarbonyl)amino]benzamide trifluoroacetate and tetrahydro-4H-pyran-4-one. The preparative RPHPLC (C18) purification procedure was elution with a linear gradient of 90/10 to 50/50 (0.01% HCl/acetonitrile) over 180 min.

¹H-NMR
IS-MS, m/e 477.2 (m+1)
Analysis for $C_{23}H_{26}N_4O_3Cl_2 \cdot 0.8HCl \cdot 0.7H_2O$: Calcd: C, 53.21; H, 5.47; N, 10.79; Cl, 19.12; Found: C, 53.24; H, 5.14; N, 10.96; Cl, 19.02.

EXAMPLE 70

Preparation of 5-Chloro-N-(5-chloropyridin-2-yl)-2-[(1-cyclohexylpiperidin-4-ylcarbonyl)amino]benzamide Hydrochloride

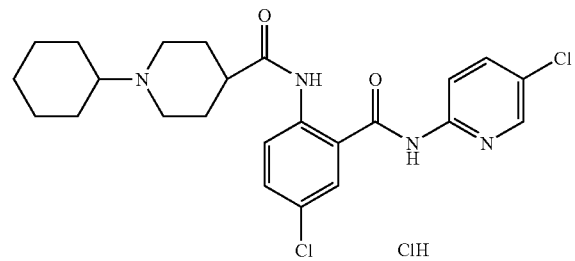

By methods substantially equivalent to those described in example 27, 5-chloro-N-(5-chloropyridin-2-yl)-2-[(1-cyclohexylpiperidin-4-ylcarbonyl)amino]benzamide hydrochloride (0.127 g, 29%) was prepared from 5-chloro-N-(5-chloropyridin-2-yl)-2-[(piperidin-4-ylcarbonyl)amino]benzamide trifluoroacetate and cyclohexanone. The preparative RPHPLC (C18) purification procedure was elution with a linear gradient of 90/10 to 50/50 (0.01% HCl/acetonitrile) over 180 min.

¹H-NMR
IS-MS, m/e 475.1 (m+1)
Analysis for $C_{24}H_{28}N_4O_2Cl_2 \cdot 1.2HCl \cdot 0.8H_2O$: Calcd: C, 54.02; H, 5.82; N, 10.50; Cl, 21.26; Found: C, 54.26; H, 5.56; N, 10.58; Cl, 21.22.

EXAMPLE 71

Preparation of N-(5-Chloropyridin-2-yl)-2-[(1-isopropylpiperidin-4-yloxycarbonyl)amino]benzamide Hydrochloride

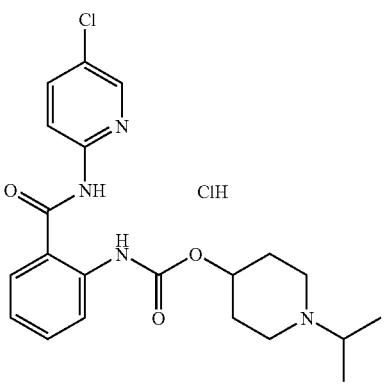

Using a similar procedure to that described in Example 9-C, N-(5-chloropyridin-2-yl)-2-[(piperidin-4-yloxycarbonyl)amino]benzamide (100 mg, 0.205 mmol), acetone (0.075 mL), and sodium cyanoborohydride (51 mg, 0.82 mmol) yielded, after treatment with HCl, 63 mg (67%) of the title compound as a hydrochloride salt.

¹H-NMR
IS-MS, m/e 417 (m+1)

EXAMPLE 72

Preparation of N-(5-Chloropyridin-2-yl)-2-[(1-cyclohexylpiperidin-4-yloxycarbonyl)amino]benzamide Hydrochloride

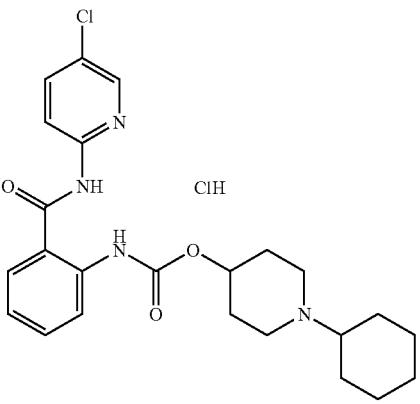

Using a similar procedure to that described in Example 9-C, N-(5-chloropyridin-2-yl)-2-[(piperidin-4-yloxycarbonyl)amino]benzamide (100 mg, 0.205 mmol), cyclohexanone (0.106 mL, 1.02 mmol), and sodium cyanoborohydride (51 mg, 0.82 mmol) yielded, after treatment with HCl, 33 mg (33%) of the title compound as a hydrochloride salt.
¹H-NMR
IS-MS, m/e 457 (m+1)

EXAMPLE 73

Preparation of N-(5-Chloropyridin-2-yl)-2-[(1-cyclopentylpiperidin-4-yloxycarbonyl)amino]benzamide Hydrochloride

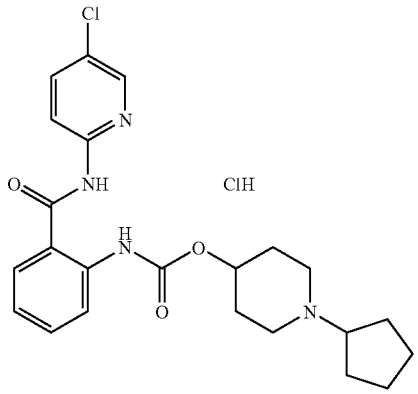

Using a similar procedure to that described in Example 9-C, N-(5-chloropyridin-2-yl)-2-[(piperidin-4-yloxycarbonyl)amino]benzamide (100 mg, 0.205 mmol), cyclopentanone (0.091 mL, 1.02 mmol), and sodium cyanoborohydride (51 mg, 0.82 mmol) yielded, after treatment with HCl, 60 mg (60%) of the title compound as a hydrochloride salt.
¹H-NMR
IS-MS, m/e 443 (m+1)

EXAMPLE 74

Preparation of N-(5-Chloropyridin-2-yl)-2-[(1-isopropylpiperidin-4-ylmethoxycarbonyl)amino]benzamide Hydrochloride

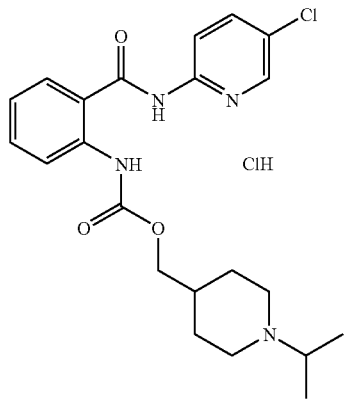

Using a similar procedure to that described in Example 9-C, N-(5-chloropyridin-2-yl)-2-[(piperidin-4-ylmethoxycarbonyl)amino]benzamide (100 mg, 0.199 mmol), acetone (0.075 mL), and sodium cyanoborohydride (50 mg, 0.80 mmol) yielded, after treatment with HCl, 25 mg of the title compound as a hydrochloride salt.
¹H-NMR
IS-MS, m/e 431 (m+1)

EXAMPLE 75

Preparation of 2-[1-(2-Carboxypyridin-4-yl)piperidin-4-ylmethylamino]-N-(5-chloropyridin-2-yl)benzamide

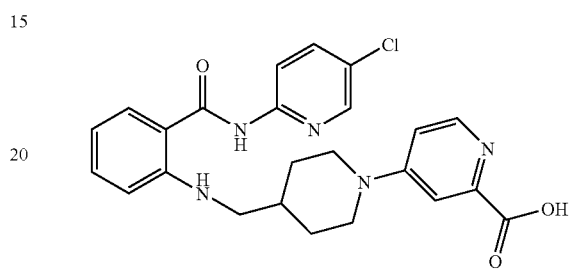

Using a similar procedure to that described in Example 52, N-(5-chloropyridin-2-yl)-2-(piperidin-4-ylmethylamino)benzamide (150 mg, 0.43 mmol), 4-chloropicolinic acid (95 mg, 0.60 mmol), triethylamine (87 mg, 0.86 mmol), and ethanol (2 mL) yielded 50 mg (25%) of the title compound.
¹H-NMR, IR
IS-MS, m/e 466 (m+1)
Analysis for $C_{24}H_{24}ClN_5O_3$ (1.5 $H_2O$): Calcd: C, 58.47; H, 5.52; N, 14.21; Found: C, 58.37; H, 5.08; N, 13.96.

EXAMPLE 76

Preparation of N-(5-Chloropyridin-2-yl)-2-(1-isopropylpiperidin-4-ylmethoxy)benzamide Hydrochloride

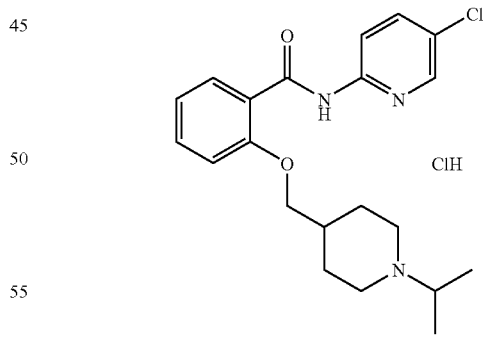

A. N-(5-Chloropyridin-2-yl)-2-(1-tert-butoxycarbonylpiperidin-4-ylmethoxy)benzamide A solution of N-(5-chloropyridin-2-yl)-2-hydroxybenzamide (200 mg, 0.806 mmol), 1-tert-butoxycarbonylpiperidine-4-methanol (191 mg, 0.887 mmol), and triphenylphosphine (232 mg, 0.887 mmol) in THF was treated dropwise with a THF solution of diethyl diazodicarboxylate (DEAD) (0.14 mL, 0.887 mmol in 1 mL of THF). After 16 h, the mixture was treated with an additional equivalent of triphenylphosphine and DEAD. After 2 h, the mixture was concentrated, diluted with methylene chloride, and filtered. The solid collected was the desired product (128 mg, 36%). The filtrate was purified by column chromatography (SiO$_2$; 4:1 hexanes:EtOAc) providing an additional 142 mg (40%) of the title compound.

$^1$H-NMR
IS-MS, m/e 446 (m+1)
Analysis for $C_{23}H_{28}ClN_3O_4$: Calcd: C, 61.95; H, 6.33; N, 9.42; Found: C, 61.67; H, 6.63; N, 9.33.

B. N-(5-Chloropyridin-2-yl)-2-(piperidin-4-ylmethoxy)benzamide

Using a similar procedure to that described in Example 9-B, N-(5-chloropyridin-2-yl)-2-(1-tert-butoxycarbonylpiperidin-4-ylmethoxy)benzamide (240 mg, 0.539 mmol) yielded 350 mg of the title compound as a trifluoroacetate salt which was used without further purification.

C. N-(5-Chloropyridin-2-yl)-2-(1-isopropylpiperidin-4-ylmethoxy)benzamide

Using a similar procedure to that described in Example 9-C, N-(5-chloropyridin-2-yl)-2-(piperidin-4-ylmethoxy)benzamide (100 mg, 0.218 mmol) yielded, after treatment with HCl, 64 mg (70%) of the title compound as a hydrochloride salt.

$^1$H-NMR
IS-MS, m/e 388 (m+1)

EXAMPLE 77

Preparation of N-(5-Chloropyridin-2-yl)-5-(methylsulfonylamino)-2-[1-(4-pyridinyl)piperidin-4-ylmethylamino]benzamide Dihydrochloride

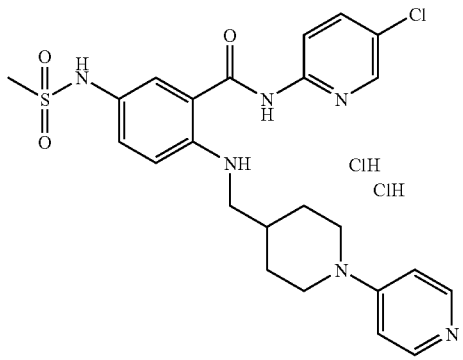

A. Methyl 2-Fluoro-5-nitrobenzoate

A solution of 2-fluoro-5-nitrobenzoic acid (200 mg, 1.08 mmol) in 0.7 M HCl in methanol was stirred for 5 h. The mixture was concentrated yielding 210 mg (99%) of the title compound; which was used without further purification.
$^1$H-NMR

B. 1-(4-Pyridyl)piperidine-4-methylamine

A solution of 1-(4-pyridinyl)piperidine-4-methanol (5.87 g, 30.6 mmol), phthalimide (4.59 g, 31.2 mmol), and triphenylphosphine (8.10 g, 30.9 mmol) in 125 mL of THF at −5° C. was treated with a solution of diethyl azodicarboxylate (5.38 g, 30.9 mmol) in THF (40 mL). After 16 h, the mixture was poured into EtOAc and 1 N HCl. The aqueous layer was washed with EtOAC (2×), pH adjusted to 12 by addition of 5 N NaOH, and washed with EtOAc (3×). The combined organic extracts were dried (K$_2$CO$_3$) and concentrated yielding 8.45 g (86%) of crude phthalimide. The crude material (5.47 g, 17.0 mmol) was then treated with hydrazine hydrate (3.5 mL, 60.0 mmol) in EtOH (50 mL). The mixture was heated at 75° C. for 5 h, cooled, diluted with CH$_2$Cl$_2$ (100 mL), and cooled to 0° C. The solid was removed by filtration and the filtrat was concentrated yielding 3.32 g of the title compound which was used without further purification.

$^1$H-NMR, IR
FD-MS, m/e 191 (m)

C. Methyl 5-Nitro-2-[1-(4-pyridyl)piperidin-4-ylmethylamino]benzoate

A solution of 1-(4-pyridyl)piperidine-4-methylamine (1.13 g, 5.92 mmol) and potassium carbonate (816 mg, 5.92 mmol) in dimethyl sulfoxide (12 mL) was treated with methyl 2-fluoro-5-nitrobenzoate (1.18 g, 5.92 mmol). After 17 h, the mixture was cooled, diluted with EtOAc, and filtered. The filtrate was concentrated and partitioned between EtOAc and 10% HCl. The aqueous layer was washed with EtOAc (1×), pH adjusted (>10) by addition of NaOH, and washed with EtOAC (3×). The combined extracts were washed with H$_2$O (5×), brine, dried (sodium sulfate), and concentrated. The residue was purified by column chromatography (SiO$_2$, 1 to 3% [2 N NH$_3$ in MeOH]:chloroform) yielding 920 mg (42%) of the title compound.

$^1$H-NMR
IS-MS, m/e 381 (m+1)

D. 5-Amino-N-(5-chloropyridin-2-yl)-2-[1-(4-pyridinyl)piperidin-4-ylmethylamino]benzamide A solution of methyl 5-nitro-2-[1-(4-pyridinyl)piperidin-4-ylmethylamino]benzoate (400 mg, 1.08 mmol) was treated with the magnesium salt of 2-amino-5-chloropyridine [freshly prepared by the addition of methyl magnesium bromide (2.16 mmol) to a solution of 2-amino-5-chloropyridine (2.16 mmol) in THF (11 mL)] and the mixture was heated at reflux. After 3 h, the mixture was cooled, sonicated, and the resulting solid (645 mg) collected by filtration. Using a similar procedure to that described in Example 2-B, the crude material was reduced to yield 370 mg of the titled compound; which was used without further purification.

$^1$H-NMR

E. N-(5-Chloropyridin-2-yl)-5-(methylsulfonylamino)-2-[1-(4-pyridinyl)piperidin-4-ylmethylamino]benzamide Dihydrochloride A solution of 5-amino-N-(5-chloropyridin-2-yl)-2-[1-(4-pyridinyl)piperidin-4-ylmethylamino]benzamide (90 mg, 0.21 mmol) and diisopropyl ethylamine (0.036 mL) in methylene chloride (2 mL) was treated with methanesulfonyl chloride (0.016 mL, 0.21 mmol). After 0.25 h, the mixture was concentrated and the residue partitioned between EtOAc and water. The aqueous layer was treated with 1 N NaOH and the resulting solid collected by filtration. The material was further purified by RPHPLC yielding the title compound as a hydrochloride salt.

¹H-NMR

IS-MS, m/e 515 (m+1)

Analysis for $C_{24}H_{30}N_6O_3SCl_4 \cdot 0.5H_2O$: Calcd: C, 45.52; H, 4.93; N, 13.27; Found: C, 45.65; H, 4.92; N, 13.36.

EXAMPLE 78

Preparation of N-(5-Chloropyridin-2-yl)-2-[1-(cylopropylmethyl)piperidin-4-ylmethylamino]benzamide

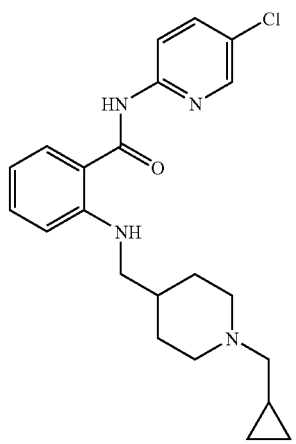

To a small sample of N-(5-chloropyridin-2-yl)-2-(piperidin-4-ylmethylamino)benzamide (0.034 g, 0.1 mmol) weighed out in a 1 mL sealable vial, dichloroethane was added (300 μL), followed by excess of cyclopropanecarboxaldehyde (20 μL, >0.15 mmol) and sodium triacetoxyborohydride (200 μL of a 1.5 M solution in N-methylpyrrolidinone). The vial was capped and placed in a shaker at 70° C. overnight. After an additional 24 h at room temperature, methanol was added (400 μL) and the vial was shaken for a few minutes. The reaction mixture was then applied to a 2 g SCX column, washed with methanol (30 mL) and gravity-eluted with 1 N ammonia in methanol (20 mL). The yellow fractions were combined and concentrated in vacuo to a dry residue (0.040 g, >100%), which was identified as the title compound by LC-MS (Method A).

LC-MS: 95% pure, $R_t$=2.859 min, m/e 399.2 (m).

EXAMPLE 79

Preparation of N-(5-Chloropyridin-2-yl)-2-[1-(pyridin-4-ylmethyl)piperidin-4-ylmethylamino]benzamide

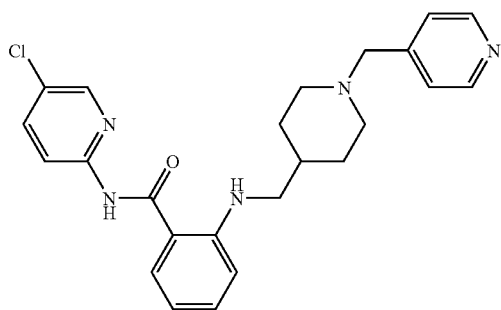

N-(5-Chloropyridin-2-yl)-2-(piperidin-4-ylmethylamino) benzamide (0.034 g, 0.1 mmol) was converted to the title compound (0.050 g, >100%) using the procedure described in example 78. The product was obtained as an oily residue which was further purified on silica gel. Elution with ethyl acetate-methanol (9:1) followed by trituration with acetonitrile afforded a solid which was identified by LC-MS (Method A).

LC-MS: 80% pure, $R_t$=1.509 min, m/e 436.1 (m).

EXAMPLE 80

Preparation of N-(5-chloropyridin-2-yl)-5-fluoro-2-[1-(4-pyridinyl)piperidin-4-ylmethylamino]benzamide

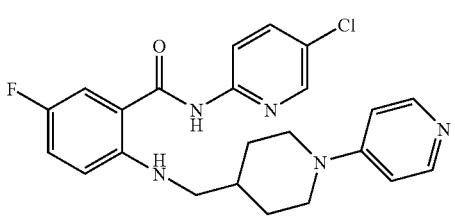

Using a similar procedure to that described in Example 52, N-(5-chloropyridin-2-yl)-5-fluoro-2-(piperidin-4-ylmethyl)aminobenzamide (343 mg, 0.95 mmol), 4-chloropyridine hydrochloride (709 mg, 4.73 mmol), triethylamine (479 mg, 4.73 mmol), and ethanol (3 mL) yielded 100 mg (24%) of the title compound.

¹H-NMR, IR

IS-MS, m/e 440 (m+1)

Analysis for $C_{23}H_{23}ClFN_5O$ (EtOH): Calcd: C, 61.79; H, 6.01; N, 14.41; Found: C, 61.93; H, 5.56; N, 14.68.

EXAMPLE 81

Preparation of N-(5-Chloropyridin-2-yl)-2-(1-propylpiperidin-4-ylmethylamino)benzamide

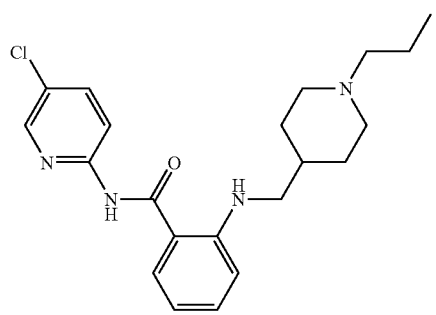

N-(5-Chloropyridin-2-yl)-2-(piperidin-4-ylmethylamino) benzamide (0.114 g, 0.33 mmol) was converted to the title compound (0.084 g, 66%) using the procedure described in example 78. The product was obtained as an oily residue which was further purified on silica gel. Elution with ethyl acetate-2 N ammonia in methanol (95:5) followed by trituration with diethyl ether afforded a solid which was identified by LC-MS (Method A).

LC-MS: 82% pure, $R_t$=2.682 min, m/e 387.2 (m).

EXAMPLE 82

Preparation of N-(5-Chloropyridin-2-yl)-2-[1-(2,2-dimethylpropyl)piperidin-4-ylmethylamino]benzamide

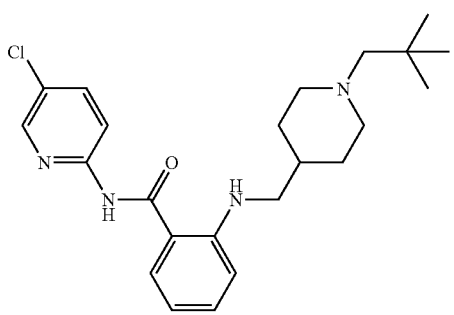

N-(5-Chloropyridin-2-yl)-2-(piperidin-4-ylmethylamino) benzamide (0.114 g, 0.33 mmol) was converted to the title compound (0.060 g, 44%) using the procedure described in example 78. The product was obtained as an oily residue which was further purified on silica gel. Elution with ethyl acetate-2 N ammonia in methanol (95:5) followed by trituration with diethyl ether afforded a solid which was identified by LC-MS (Method A).

LC-MS: 92% pure, $R_t$=3.626 min. m/e 415.1 (m).

EXAMPLE 83

Preparation of 5-Chloro-N-(5-chloropyridin-2-yl)-2-[1-(4-pyridinyl)piperidin-4-ylmethylamino]benzamide

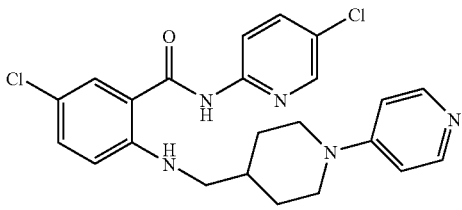

Using a similar procedure to that described in Example 52, 5-chloro-N-(5-chloropyridin-2-yl)-2-(piperidin-4-ylmethyl)aminobenzamide (400 mg, 1.05 mmol), 4-chloropyridine hydrochloride (791 mg, 5.27 mmol), triethylamine (533 mg, 5.27 mmol), and ethanol (3 mL) yielded 70 mg (15%) of the title compound.

$^1$H-NMR, IR

IS-MS, m/e 456 (m+1)

Analysis for $C_{23}H_{23}Cl_2N_5O$ 0.5 $H_2O$: Calcd: C, 59.36; H, 5.20; N, 15.05; Found: C, 59.84; H, 5.14; N, 14.82.

EXAMPLE 84

Preparation of 5-Chloro-N-(5-fluoropyridin-2-yl)-2-[(1-isopropylpiperidin-4-ylcarbonyl)amino]benzamide Hydrochloride

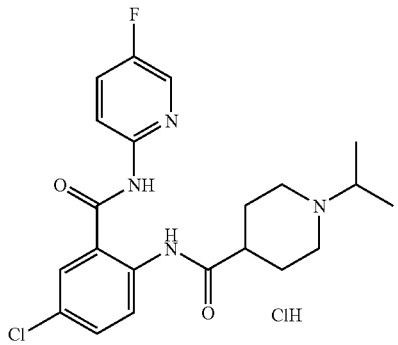

A. 2-[(1-Boc-piperidin-4-ylcarbonyl)amino]-5-chloro-N-(5-fluoropyridin-2-yl)benzamide Using methods substantially equivalent to those described in example 25-D, 2-[(1-Boc-piperidin-4-ylcarbonyl)amino]-5-chloro-N-(5-fluoropyridin-2-yl)benzamide (0.91 g, 79%) was prepared from 2-amino-5-chloro-N-(5-fluoropyridin-2-yl)benzamide and 1-Boc-piperidin-4-ylcarbonyl chloride.

$^1$H-NMR

IS-MS, m/e 477.2 (m+1)

Analysis for $C_{23}H_{26}N_4O_4ClF$: Calcd: C, 57.92; H, 5.49; N, 11.75; Found: C, 58.04; H, 5.61; N, 11.51.

B. 5-Chloro-N-(5-fluoropyridin-2-yl)-2-[(piperidin-4-ylcarbonyl)amino]benzamide trifluoroacetate Using methods substantially equivalent to those described in example 9-B, 5-chloro-N-(5-fluoropyridin-2-yl)-2-[(piperidin-4-ylcarbonyl)amino]benzamide trifluoroacetate (0.805 g, 93%) was prepared from 2-[(1-Boc-piperidin-4-ylcarbonyl)amino]-5-chloro-N-(5-fluoropyridin-2-yl)benzamide.

$^1$H-NMR

IS-MS, m/e 377.3 (m+1)

C. 5-Chloro-N-(5-fluoropyridin-2-yl)-2-[(1-isopropylpiperidin-4-ylcarbonyl)amino]benzamide Hydrochloride Using methods substantially equivalent to those described in example 27, 5-chloro-N-(5-fluoropyridin-2-yl)-2-[(1-isopropylpiperidin-4-ylcarbonyl)amino]benzamide hydrochloride (0.167 g, 60%) was prepared from 5-chloro-N-(5-fluoropyridin-2-yl)-2-[(piperidin-4-ylcarbonyl)amino] benzamide trifluoroacetate. The preparative RPHPLC (C18) purification procedure was elution with a linear gradient of 90/10 to 55/45 (0.01% HCl/acetonitrile) over 180 min.

$^1$H-NMR

IS-MS, m/e 419.2 (m+1)

Analysis for $C_{21}H_{24}N_4O_2ClF \cdot 1.0HCl \cdot 0.8H_2O$: Calcd: C, 53.69; H, 5.71; N, 11.93; Cl, 15.09; Found: C, 53.52; H, 5.39; N, 11.84; Cl, 15.20.

EXAMPLE 85

Preparation of N-(3-Chloropyridin-2-yl)-2-[1-(2-methylpyridin-4-yl)piperidin-4-ylmethylamino]benzamide

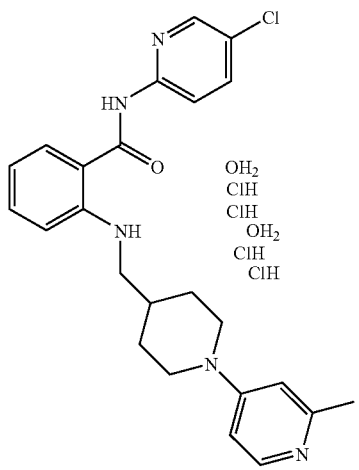

To a solution of N-(5-chloropyridin-2-yl)-2-(piperidin-4-ylmethylamino)benzamide (0.130 g, 0.38 mmol) in ethanol (10 mL) was added 4-chloro-2-picoline (0.1 mL). The reaction mixture was heated in a sealed tube for 24 hours. The reaction mixture was concentrated and the residue was purified by RPHPLC. The pure product containing fractions were combined and lyophilized to give 155 mg (66%) of a tan powder.

$^1$H-NMR

FD-MS, m/e 436.3 (m+1)

Analysis for $C_{24}H_{26}ClN_5O.4HCl.2H_2O$: Calcd: C, 46.66; H, 5.55; N, 11.34; Found: C, 47.02; H, 5.32; N, 11.26.

EXAMPLE 86

Preparation of 2-[1-(2-Carboxypyridin-4-yl)piperidin-4-ylmethylamino]-5-chloro-N-(5-chloropyridin-2-yl)benzamide

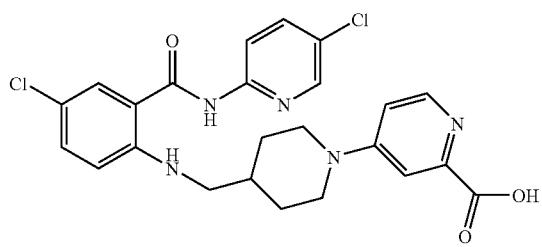

Using a similar procedure to that described in Example 52, 5-chloro-N-(5-chloropyridin-2-yl)-2-(piperidin-4-ylmethyl)aminobenzamide (166 mg, 0.44 mmol), 4-chloropicolinic acid (103 mg, 0.66 mmol), triethylamine (89 mg, 0.88 mmol), and ethanol (3 mL) yielded 180 mg (82%) of the title compound.

$^1$H-NMR, IR

IS-MS, m/e 500 (m+1)

Analysis for $C_{24}H_{23}Cl_2N_5O_3.3.0 H_2O$: Calcd: C, 51.99; H, 5.27; N, 12.63; Found: C, 51.77; H, 4.94; N, 12.98.

EXAMPLE 87

Preparation of N-(5-Chloropyridin-2-yl)-2-[(1-isopropylpyrrolidin-3-ylaminocarbonyl)amino]benzamide Hydrochloride

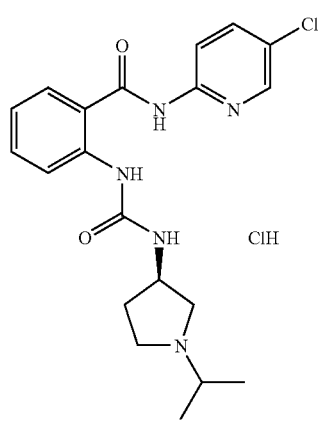

A. 2-[(1-tert-Butoxycarbonylpyrrolidin-3-ylaminocarbonyl)amino]-N-(5-chloropyridin-2-yl)benzamide A solution of 3-amino-1-tert-butoxycarbonylpyrrolidine (200 mg, 1.08 mmol; prepared from 1-tert-butoxycarbonyl-3-hydroxy-pyrrolidine using a similar procedure to that described in Example 77-B) and triethylamine (0.38 mL) in methylene chloride (3.5 mL) was added dropwise to a solution of triphosgene (120 mg, 0.403 mmol) in methylene chloride (2 mL). After complete addition, a solution of 2-amino-N-(5-chloropyridin-2-yl)benzamide (242 mg, 0.983 mmol) and triethylamine (0.38 mL) in methylene chloride (3.5 mL) was added in one portion. After 16 h, the mixture was treated with an additional equivalent of the isocyanate. After 1 h, the mixture was concentrated and the residue was partitioned between EtOAc and water. The organic layer was washed with 0.5 N HCl (2×), satd sodium bicarbonate (1×), water, brine, dried with sodium sulfate, and concentrated. The residue was purified by column chromatography (SiO$_2$: 40 to 50% EtOAc in hexanes) affording 160 mg (35%) of the title compound.

$^1$H-NMR

IS-MS, m/e 460 (m+1)

Analysis for $C_{22}H_{26}Cl_4N_5O_4$: Calcd: C, 57.45; H, 5.70; N, 15.23; Found: C, 57.27; H, 5.79; N, 15.06.

B. N-(5-Chloropyridin-2-yl)-2-[(pyrrolidin-3-ylaminocarbonyl)amino]benzamide Trifluoroacetate Using a similar procedure to that described in Example 9-B, 2-[(1-tert-butoxycarbonylpyrrolidin-3-ylaminocarbonyl)amino]-N-(5-chloropyridin-2-yl)benzamide (100 mg, 0.218 mmol) yielded the titled compound as a trifluoroacetate salt, which was used without further purification.

$^1$H-NMR

IS-MS, m/e 360 (m+1)

C. N-(5-Chloropyridin-2-yl)-2-[(1-isopropylpyrrolidin-3-ylaminocarbonyl)amino]benzamide Hydrochloride Using a similar procedure to that described in Example 9-C, N-(5-chloropyridin-2-yl)-2-[(pyrrolidin-3-ylaminocarbonyl)amino]benzamide trifluoroacetate (100 mg, 0.211 mmol) yielded, after purification of the mixture by column chromatography (3% [2 N $NH_3$ in methanol]:chloroform) and treatment with HCl, 65 mg of the title compound as a hydrochloride salt.

$^1$H-NMR
IS-MS, m/e 402 (m+1)

EXAMPLE 88

Preparation of 2-[(4-Aminocyclohexylcarbonyl)amino]-5-chloro-N-(5-chloropyridin-2-yl)benzamide

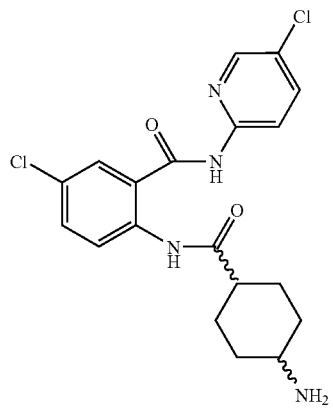

A. 4-(tert-Butoxycarbonylamino)cyclohexanecarboxylic Acid

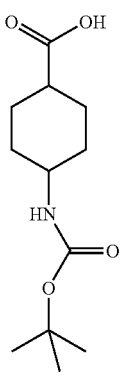

To a suspension of of 4-aminocyclohexanecarboxylic acid (9.3 g, 65 mmol), potassium carbonate (9.88 g, 71.5 mmol), di-t-butyl dicarbonate (15.6 g, 71.5 mmol) and acetone (500 ml) was added water (100 mL). The reaction was stirred for 16 hours and the organic solvent was removed in vacuo. A solution of 3:1 hexane:ether (8 mL) was added to the reaction mixture and then the mixture was acidified with saturated citric acid. The solid was filtered with water and 3:1 hexane:ether washes. The product was air dried and vacuum dried to give the title compound as a white solid (14.7 g, 93%).

$^1$H-NMR (300 MHz, $CDCl_3$): 4.57 (br s, 0.7H), 4.38 (br s, 0.3H), 3.61 (br s, 0.7H), 3.20 (br s, 0.3H), 2.52 (br s, 1H), 2.00–2.16 (m, 1H), 1.42 (s, 9H), 1.00–2.00 (m, 7H).

IS-MS, m/e: 244.2 (m+1).

B. 2-[[4-(tert-Butoxycarbonylamino)cyclohexylcarbonyl]amino]-5-chloro-N-(5-chloropyridin-2-yl)benzamide

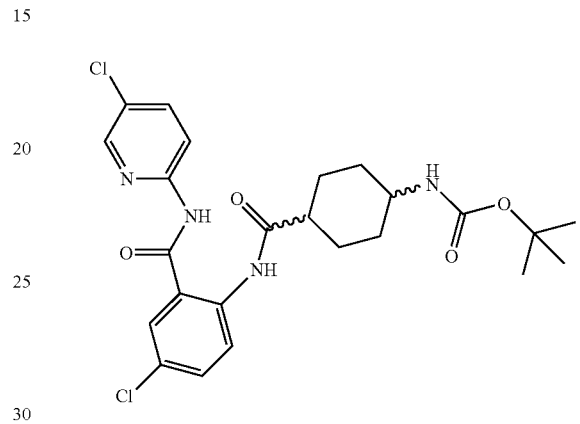

Using a procedure similar to that described in example 34-A, 2-[[4-(tert-butoxycarbonylamino)cyclohexylcarbonyl]amino]-5-chloro-N-(5-chloropyridin-2-yl)benzamide (2.91 g, 52%) was prepared from 2-amino-N-(5-methylpyridin-2-yl)benzamide and 4-(tert-butoxycarbonylamino)cyclohexanecarboxylic acid.

$^1$H-NMR (400 MHz, DMSO-$d_6$): δ 11.10(s, 1H); 10.24(s, 1H); 8.41(d, J=2.0 Hz, 1H); 8.10(d, J=9.2 Hz, 1H); 8.01(d, J=9.2 Hz, 1H); 7.93(dd, J=2.4, 9.2 Hz, 1H); 7.78(d, J=2.4 Hz, 1H); 7.55(dd, J=2.4, 8.8 Hz, 1H); 6.69(m, 1H); 3.36(m, 1H); 2.37(m, 1H); 1.79–1.45(m, 8H); 1.33(s, 9H).

MS-FIA m/e: 507.2 (m+1).

Analysis for $C_{24}H_{28}N_4O_4Cl_2 \cdot 0.35CH_2Cl_2$: Calcd: C, 54.80; H, 5.34; N, 10.35; Found: C, 54.58; H, 5.25; N, 10.57.

C. 2-[(4-Aminocyclohexylcarbonyl)amino]-5-chloro-N-(5-chloropyridin-2-yl)benzamide 2-[[4-(tert-Butoxycarbonylamino)cyclohexylcarbonyl]amino]-5-chloro-N-(5-chloropyridin-2-yl)benzamide (2.90 g, 5.71 mmol) was dissolved in TFA (10 mL). After 5 minutes, the reaction was concentrated in vacuo. The residue was diluted with methylene chloride and methanol. The organics were washed with saturated aqueous sodium carbonate (2×50 mL) and water (50 mL). The organic layer was dried over sodium sulfate, filtered and concetrated to give the title product (1.86 g, 4.56 mmol, 80%) as a white solid.

$^1$H-NMR (300 MHz, DMSO-$d_6$): δ 8.33(s, 1H); 8.13(m, 2H); 7.85(s, 1H); 7.83(d, J=9.9 Hz, 1H); 7.46(d, J=8.4 Hz, 1H); 2.91(m, 1H); 2.39(m, 1H); 1.87(m, 2H); 1.48(m, 6H).

MS-FIA m/e: 407.3 (m+1).

Analysis for $C_{19}H_{20}N_4O_2Cl_2$: Calcd: C, 56.03; H, 4.95; N, 13.76; Found: C, 55.91; H, 5.05; N, 13.58.

EXAMPLE 89

Preparation of 5-Chloro-N-(5-chloropyridin-2-yl)-2-[4-(N,N-dimethylamino)cyclohexylcarbonylamino]benzamide

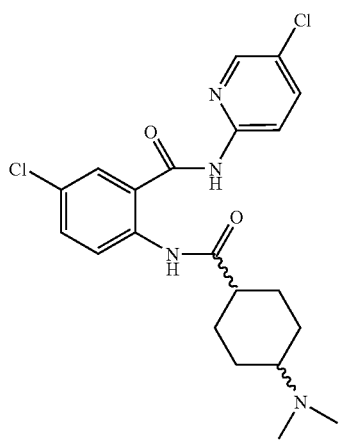

Using a procedure similar to example 9-C, 5-chloro-N-(5-chloropyridin-2-yl)-2-[4-(N,N-dimethylamino)cyclohexylcarbonylamino]benzamide (121 mg, 38%) was prepared from 2-[(4-aminocyclohexylcarbonyl)amino]-5-chloro-N-(5-chloropyridin-2-yl)benzamide.

$^1$H-NMR (400 MHz, DMSO-d$_6$): δ 8.38(s, 1H); 8.10(d, J=8.8 Hz, 1H); 7.96(m, 1H); 7.90(m, 1H); 7.83(d, J=3.2 Hz, 1H); 7.51(d, J=9.2 Hz, 1H); 3.29(m, 1H); 2.47(m, 1H); 1.86–1.38 (m, 8H);

MS-FD m/e: 435.1 (m+1);

Analysis for $C_{21}H_{24}N_4O_2Cl_2.0.2CH_2Cl_2$: Calcd: C, 55.45; H, 5.31; N, 12.20; Found: C, 55.76; H, 5.29; N, 12.01.

EXAMPLE 90

Preparation of 5-Chloro-N-(5-chloropyridin-2-yl)-2-[(1-cyclopentylpiperidin-4-ylcarbonyl)amino]benzamide Hydrochloride

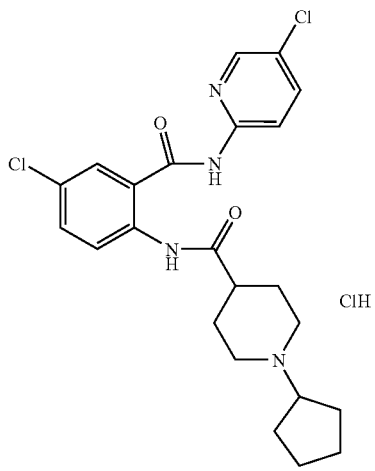

Using methods substantially equivalent to those described in example 27, 5-chloro-N-(5-chloropyridin-2-yl)-2-[(1-cyclopentylpiperidin-4-ylcarbonyl)amino]benzamide hydrochloride (0.122 g, 25%) was prepared from 5-chloro-N-(5-chloropyridin-2-yl)-2-[(piperidin-4-ylcarbonyl)amino] benzamide trifluoroacetate and cyclopentanone. The preparative RPHPLC (C18) purification procedure was elution with a linear gradient of 80/20 to 50/50 (0.01% HCl/acetonitrile) over 180 min.

$^1$H-NMR

IS-MS, m/e 461.3 (m+1)

Analysis for $C_{23}H_{26}N_4O_2Cl_2.1.2HCl.1.7H_2O$: Calcd: C, 51.56; H, 5.76; N, 10.46; Cl, 21.18; Found: C, 51.78; H, 5.82; N, 10.30; Cl, 21.24.

EXAMPLE 91

Preparation of 5-Chloro-N-(5-chloropyridin-2-yl)-2-[[1-(4-pyridinylmethyl)piperidin-4-ylcarbonyl]amino]benzamide Hydrochloride

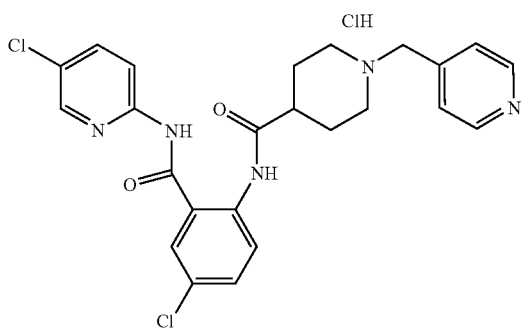

Using methods substantially equivalent to those described in example 27, 5-chloro-N-(5-chloropyridin-2-yl)-2-[[1-(4-pyridinylmethyl)piperidin-4-ylcarbonyl]amino]benzamide hydrochloride 10.21 g, 40%) was prepared from 5-chloro-N-(5-chloropyridin-2-yl)-2-[(piperidin-4-ylcarbonyl)amino] benzamide trifluoroacetate and pyridine-4-carboxaldehyde. The preparative RPHPLC (C18) purification procedure was elution with a linear gradient of 80/20 to 50/50 (0.01% HCl/acetonitrile) over 180 min.

$^1$H-NMR

IS-MS, m/e 484.4 (m+1)

Analysis for $C_{24}H_{23}N_5O_2Cl_2.2.6HCl.1.6H_2O$: Calcd: C, 47.41; H, 4.77; N, 11.52; Cl, 26.82; Found: C, 47.40; H, 4.41; N, 11.16; Cl, 26.89.

EXAMPLE 92

Preparation of 5-Chloro-N-(5-chloropyridin-2-yl)-2-[[1-(4-thianyl)piperidin-4-ylcarbonyl]amino]benzamide Hydrochloride

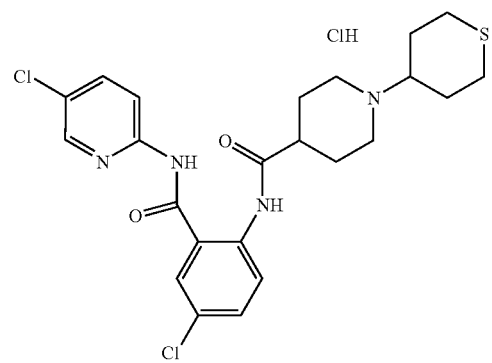

Using methods substantially equivalent to those described in example 27, 5-chloro-N-(5-chloropyridin-2-yl)-2-[[1-(4-thianyl)piperidin-4-ylcarbonyl]amino]benzamide hydrochloride (0.080 g, 15%) was prepared from 5-chloro-N-(5- chloropyridin-2-yl)-2-[(piperidin-4-ylcarbonyl)amino]
benzamide trifluoroacetate and tetrahydrothiopyran-4-one.
The preparative RPHPLC (C18) purification procedure was
elution with a linear gradient of 80/20 to 50/50 (0.01%
HCl/acetonitrile) over 180 min.

$^1$H-NMR

IS-MS, m/e 493.2 (m+1)

Analysis for $C_{23}H_{26}N_4O_2Cl_2S \cdot HCl \cdot 0.1H_2O$; Calcd: C, 51.95; H, 5.16; N, 10.54; Cl, 20.00; Found: C, 51.87; H, 5.03; N, 10.57; Cl, 20.24.

EXAMPLE 93

Preparation of 2-[1-(2-Carboxypyridin-4-yl)piperidin-4-ylmethylamino]-N-(5-chloropyridin-2-yl)-5-fluorobenzamide

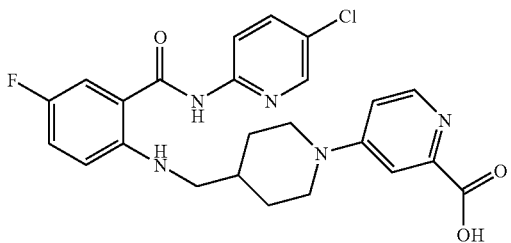

Using a similar procedure to that described in Example 52, N-(5-chloropyridin-2-yl)-5-fluoro-2-(piperidin-4-ylmethyl)aminobenzamide (200 mg, 0.55 mmol), 4-chloropicolinic acid (130 mg, 0.83 mmol), triethylamine (111 mg, 1.10 mmol), and ethanol (4 mL) yielded 120 mg (45%) of the title compound.

$^1$H-NMR, IR

IS-MS, m/e 485 (m+1)

Analysis for $C_{24}H_{23}ClFN_5O_3$ (2.5H$_2$O): Calcd: C, 54.50; H, 5.34; N, 3.23; Found: C, 54.32; H, 4.56; N, 12.90.

EXAMPLE 94

Preparation of 2-(4-Acetylaminobenzyl)amino-5-chloro-N-(5-chloropyridin-2-yl)benzamide

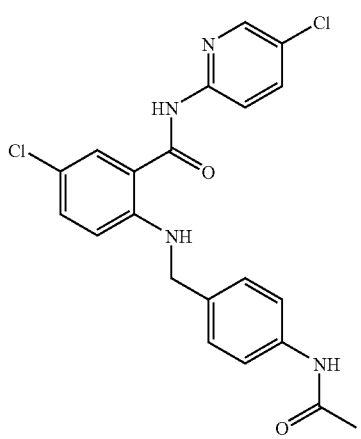

To a small sample of 2-amino-5-chloro-N-(5-chloropyridin-2-yl)benzamide (0.01 g, 0.035 mmol) weighed out in a sealable vial toluene was added (200 µL), followed by 4-acetamidobenzaldehyde (0.006 g, 0.035 mmol) and pyridinium p-toluenesulfonate (catalytic amount). A few molecular sieves were added; then the vial was sealed and placed in a shaker at 75° C. After 18 h, the reaction mixture was treated with borane-trimethylamine complex (100 µL of a 1 M solution in acetic acid) and the vial was placed in the shaker at room temperature for an additional 5 h. The reaction mixture was then diluted with methanol and applied to a 0.5 g SCX column, washed with methanol and gravity-eluted with 1 N ammonia in methanol. The product fractions were combined and concentrated in vacuo to a residue which was triturated in acetonitrile to provide the title compound as a yellowish powder (0.015 g, 100%) in 98% purity by LC-MS (method A).

LC-MS: 98% pure, Rt=6.647 min, m/e 429.2 (m).

EXAMPLE 95

Preparation of 2-[[4-(1-Azetedinyl)piperidin-1-ylcarbonyl]amino]-N-(5-chloropyridin-2-yl)benzamide

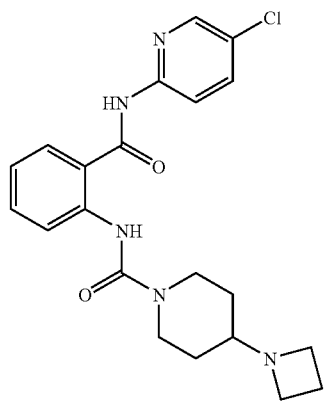

A. Methyl 2-(1,4-Dioxa-8-azaspiro[4.5]decan-8-ylcarbonyl)aminobenzoate

A solution of 2-carbomethoxyphenyl isocyanate (10.0 g, 56.5 mmol) in methylene chloride (300 mL) was treated with the ethylene glycol ketal of 4-piperidinone (7.93 mL, 62.1 mmol). After 17 h, the mixture was concentrated and the residue partitioned between EtOAc and 1 N HCl. The organic layer was washed with 1 N HCl (1×), 1 N NaOH (2×), brine, dried with sodium sulfate, and concentrated yielding 17.2 g of the title compound; which was used without further purification.

$^1$H-NMR

B. 2-(1,4-Dioxa-8-azaspiro[4.5]decan-8-ylcarbonyl)aminobenzoic Acid

A solution of methyl 2-(1,4-dioxa-8-azaspiro[4.5]decan-8-ylcarbonyl)aminobenzoate (2.00 g, 6.25 mmol) in dioxane (30 mL) was treated with 5 N NaOH (12.5 mL). After 1 h, the mixture was poured into EtOAc and water, and the aqueous layer was washed with EtOAc. The pH of the aqueous layer was then adjusted to 2–3 by addition of 5 N HCl and washed with EtOAc (3×). The combined organic layers were washed with brine, dried with sodium sulfate, and concentrated, yielding the title compound; which was used without further purification.

1H-NMR

IS-MS, m/e 307 (m+1)

C. 2-(1,4-dioxa-8-azaspiro[4.5]decan-8-yl)-4H-3,1-benzoxazin-4-one

Using a similar procedure to that described in Example 51-C, 2-(1,4-dioxa-8-azaspiro[4.5]decan-8-ylcarbonyl)aminobenzoic acid (1.91 g, 6.25 mmol) yielded 1.36 g of the title compound; which was used without further purification.

$^1$H-NMR

IS-MS, m/e 288 (m)

Analysis for $C_{15}H_{16}N_2O_4$: Calcd: C, 62.49; H, 5.59; N, 9.72; Found: C, 63.17; H, 5.66; N, 9.94.

D. N-(5-Chloropyridin-2-yl)-2-(1,4-dioxa-8-azaspiro[4.5]decan-8-ylcarbonyl)aminobenzamide Using a similar procedure to that described in example 51-D, 2-(1,4-dioxa-8-azaspiro[4.5]decan-8-yl)-4H-3,1-benzoxazin-4-one (1.30 g, 4.51 mmol) and 2-amino-5-chloropyridine (573 mg, 4.51 mmol) yielded, after recrystallization from EtOAc, 880 mg (47%) of the titled compound.

$^1$H-NMR

IS-MS, m/e 417 (m+1)

Analysis for $C_{20}H_{21}ClN_4O_4$: Calcd: C, 57.63; H, 5.08; N, 13.44; Found: C, 58.10; H, 4.97; N, 13.78.

E. N-(5-Chloropyridin-2-yl)-2-(4-oxopiperidin-1-ylcarbonyl)aminobenzamide

A solution of N-(5-chloropyridin-2-yl)-2-(1,4-dioxa-8-azaspiro[4.5]decan-8-ylcarbonyl)aminobenzamide (120 mg, 0.289 mmol) in dioxane (1 mL) and water (0.25 mL) was treated with 12 N HCl (0.25 mL). After 1.5 h, the mixture was poured into EtOAc and water. The organic layer was washed with satd sodium bicarbonate (2×), brine, dried with sodium sulfate, and concentrated yielding 100 mg of the title compound; which was used without further purification.

$^1$H-NMR

IS-MS, m/e 373 (m+1)

F. 2-[[4-(1-Azetedinyl)piperidin-1-ylcarbonyl]amino]-N-(5-chloropyridin-2-yl)benzamide Using a similar procedure to that described in Example 9-C, N-(5-chloropyridin-2-yl)-2-(4-oxopiperidin-1-ylcarbonyl)aminobenzamide 100 mg, 0.268 mmol) and azetidine (0.036 mL, 0.54 mmol) yielded the title compound.

$^1$H-NMR

IS-MS, m/e 414 (m+1)

EXAMPLE 96

Preparation of N-(5-Chloropyridin-2-yl)-2-[[4-(1-pyrrolidinyl)piperidin-1-ylcarbanyl]amino]benzamide

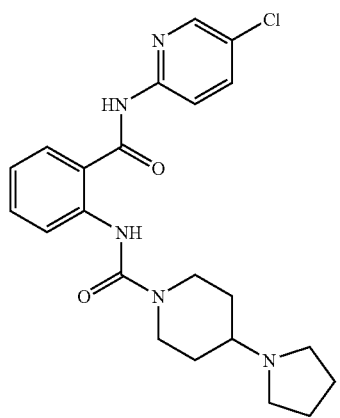

Using a similar procedure to that described in Example 9-C, N-(5-chloropyridin-2-yl)-2-(4-oxopiperidin-1-ylcarbonyl)aminobenzamide (100 mg, 0.268 mmol) and pyrolidine (0.045 mL, 0.54 mmol) yielded the title compound.

$^1$H-NMR

IS-MS, m/e 428 (m+1)

EXAMPLE 97

Preparation of N-(5-Chloropyridin-2-yl)-2-[1-(2-methoxycarbonylpyridin-4-yl)piperidin-4-ylmethyl)amino]benzamide

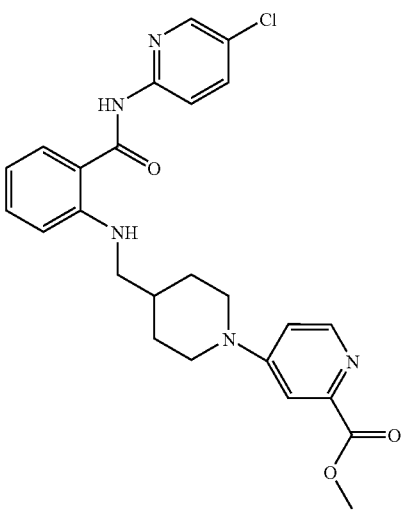

A slurry of 2-[1-(2-carboxypyridin-4-yl)piperidin-4-ylmethylamino]-N-(5-chloropyridin-2-yl)benzamide (100 mg, 0.21 mmol) in 4:1 methylene chloride:methanol (10 mL) was treated with trimethylsilyl diazomethane (2 M solution in hexanes, 0.21 mL, 0.42 mmol). After 1 h, the mixture was concentrated and the residue was purified by column chromatography (SiO$_2$: 1:1 methylene chloride:EtOAc) yielding 50 mg (49%) of the title compound.

$^1$H-NMR, IR

IS-MS, m/e 460 (m+1)

Analysis for C$_{25}$H$_{26}$ClN$_5$O$_3$ (1.0 H$_2$O): Calcd: C, 60.30; H, 5.67; N, 14.06; Found: C, 60.30; H, 5.46; N, 13.68.

EXAMPLE 98

Preparation of N-(5-Chloropyridin-2-yl)-2-[[4-(N,N-dimethylamino)piperidin-1-ylcarbonyl]amino]benzamide Hydrochloride

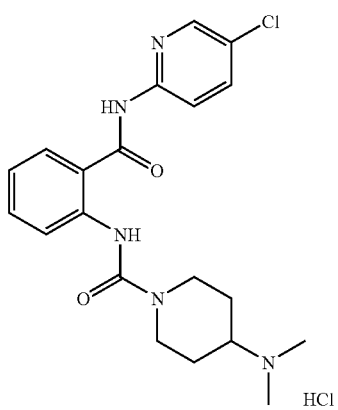

Using a similar procedure to that described in Example 27, N-(5-chloropyridin-2-yl)-2-(4-oxopiperidin-1-ylcarbonyl)aminobenzamide (100 mg, 0.268 mmol) and dimethylamine (2.0 M solution, 2.7 mL, 5.4 mmol) yielded, after treatment with HCl, 100 mg of the title compound as a hydrochloride salt.

$^1$H-NMR

IS-MS, m/e 402 (m+1)

EXAMPLE 99

Preparation of 5-Chloro-2-(1-isopropylpiperidin-4-ylmethylamino)-N-(5-methylpyridin-2-yl)benzamide

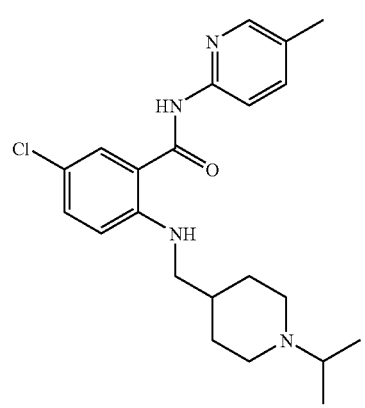

A. 5-Chloro-N-(5-methylpyridin-2-yl)-2-(piperidin-4-ylmethylamino)benzamide

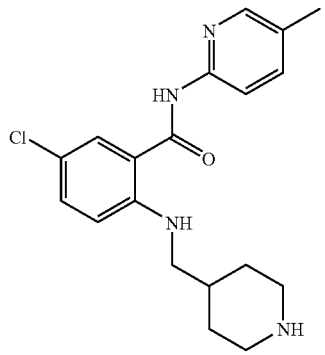

Utilizing a procedure analogous to the one described in example 60-A, 5-chloro-N-(5-methylpyridin-2-yl)-2-(piperidin-4-ylmethylamino)benzamide was prepared from 1-Boc-piperidine-4-carboxaldehyde (3.8 g, 11.5 mmol) and 2-amino-5-chloro-N-(5-methylpyridin-2-yl)benzamide (3 g, 11.5 mmol). The crude reaction product was purified on silica gel. Elution with ethyl acetate-hexanes (1:2) provided the title compound (0.48 g, 10%), which was taken on directly to the next step without further purification.

$^1$H-NMR

FD-MS, m/e 359.1 (m).

B. 5-Chloro-2-(1-isopropylpiperidin-4-ylmethylamino)-N-(5-methylpyridin-2-yl)benzamide Using the procedure described in example 48, 5-chloro-N-(5-methylpyridin-2-yl)-2-(piperidin-4-ylmethylamino) benzamide from above (0.448 g, 1.3 mmol) was converted into the title compound (0.500 g, 100%). The crude product was triturated in acetonitrile, providing analytically pure material which was identified by LC-MS (Method B).

$^1$H-NMR mp 147.0–148.4° C.

LC-MS: 96% pure, R$_t$=5.044 min, m/e 401.3 (m)

FTIR

Analysis for C$_{22}$H$_{29}$N$_4$OCl.0.25MeOH: Calcd: C, 65.35; H, 7.39; N, 13.70; Found: C, 65.01; H, 7.15; N, 13.49.

EXAMPLE 100

Preparation of 5-Chloro-N-(5-chloropyridin-2-yl)-2-[[4-(1-pyrrolidinyl)cyclohexylcarbonyl]amino]benzamide hydrochloride

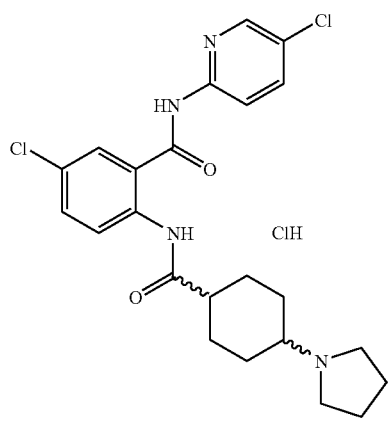

2-[(4-Aminocyclohexylcarbonyl)amino]-5-chloro-N-(5-chloropyridin-2-yl)benzamide (300 mg, 0.74 mmol) was diluted with dimethylformamide (8 mL); Potassium carbonate (307 mg, 2.22 mmol) and 1,4-dibromobutane (88 mL, 0.74 mmol) were added. The reaction was heated to 80° C. over the weekend. The reaction was cooled to room temperature, diluted with ethyl acetate (50 mL) and washed with water (5×10 mL). The ethyl acetate layer was dried over sodium sulfate, filtered and concentrated. The crude material was purified by HPLC to give 284 mg (77%) of the title compound as a white solid.

$^1$H-NMR (300 MHz, DMSO-d$_6$): δ 8.44(d, J=2.3 Hz, 1H); 8.13(d, J=9.0 Hz, 1H); 7.97(m, 1H); 7.92(s, 1H); 7.59(dd, J=2.4, 8.9 Hz, 1H); 3.12(m, 1H); 2.95(m, 2H); 2.64 (t, J=4.3 Hz, 1H); 2.07–1.52 (m, 14H).

MS-FIA m/e: 461.3 (m+1).

Analysis for C$_{23}$H$_{26}$N$_4$O$_2$Cl$_2$.0.25HCl: Calcd: C, 58.71; H, 5.62; N, 11.91; Found: C, 58.75; H, 5.33; N, 12.20.

EXAMPLE 101

Preparation of N-(5-Chloropyridin-2-yl)-2-[(4-isopropylpiperazin-1-ylcarbonyl)amino]-5-methylbenzamide Hydrochloride

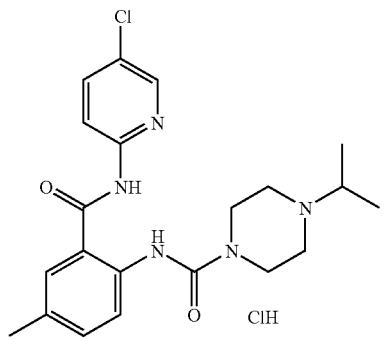

A. 2-[(4-Boc-piperazin-1-ylcarbonyl)amino]-5-methylbromobenzene

Using methods substantially equivalent to those described in example 51-A, 2-[(4-Boc-piperazin-1-ylcarbonyl)amino]-5-methylbromobenzene (7.9 g, 73%) was prepared from 4-Boc-piperazine and 2-bromo-4-methylaniline.

$^1$H-NMR

IS-MS, m/e 398.1 (m+1)

B. 2-[(4-Boc-piperazin-1-ylcarbonyl)amino]-5-methylbenzoic Acid

Using methods substantially equivalent to those described in example 51-B, 2-[(4-Boc-piperazin-1-ylcarbonyl)amino]-5-methylbenzoic acid (1.1 g, 60%) was prepared from 2-[(4-Boc-piperazin-1-ylcarbonyl)amino]-5-methylbromobenzene.

C. 2-(4-Boc-piperazin-1-yl)-6-methyl-4H-3,1-benzoxazin-4-one

Using methods substantially equivalent to those described in example 51-C, 2-(4-Boc-piperazin-1-yl)-6-methyl-4H-3,1-benzoxazin-4-one (0.88 g, 93%) was prepared from N-(5-chloropyridin-2-yl)-2-[(piperazin-1-ylcarbonyl)amino]-5-methylbenzoic acid.

$^1$H-NMR

IS-MS, m/e 346.2 (m+1)

Analysis for C$_{18}$H$_{23}$N$_3$O$_4$: Calcd: C, 62.59; H, 6.71; N, 12.17; Found: C, 62.32; H, 6.67; N, 12.15.

D. 2-[(1-Boc-piperazin-1-ylcarbonyl)amino]-N-(5-chloropyridin-2-yl)-5-methylbenzamide Using methods substantially equivalent to those described in example 51-D, 2-[(1-Boc-piperazin-1-ylcarbonyl)amino]-N-(5-chloropyridin-2-yl)-5-methylbenzamide (0.51 g, 50%) was prepared from 2-(4-Boc-piperazin-1-yl)-6-methyl-4H-3,1-benzoxazin-4-one.

$^1$H-NMR

IS-MS, m/e 474.1 (m+1)

Analysis for C$_{23}$H$_{28}$N$_5$O$_4$Cl: Calcd: C, 58.29; H, 5.95; N, 14.78; Found: C, 58.30; H, 5.68; N, 14.85.

E. N-(5-Chloropyridin-2-yl)-2-[(piperazin-1-ylcarbonyl)amino]-5-methylbenzamide trifluoroacetate Using methods substantially equivalent to those described in example 9-B, N-(5-chloropyridin-2-yl)-2-[(piperazin-1-ylcarbonyl)amino]-5-methylbenzamide trifluoroacetate (0.391 g, 95%) was prepared from 2-[(1-Boc-piperazin-1-ylcarbonyl)amino]-N-(5-chloropyridin-2-yl)-5-methylbenzamide.

$^1$H-NMR

IS-MS, m/e 374.2 (m+1)

Analysis for C$_{18}$H$_{20}$N$_5$O$_2$Cl.TFA: Calcd: C, 49.24; H, 4.34; N, 14.35; F, 11.68; Found: C, 48.82; H, 3.84; N, 14.00; F, 11.95.

F. N-(5-Chloropyridin-2-yl)-2-[(4-isopropylpiperazin-1-ylcarbonyl)amino]-5-methylbenzamide hydrochloride Using methods substantially equivalent to those described in example 27, N-(5-chloropyridin-2-yl)-2-[(4-isopropylpiperazin-1-ylcarbonyl)amino]-5-methylbenzamide hydrochloride (55 mg, 17%) was prepared from N-(5-chloropyridin-2-yl)-2-[(piperazin-1-ylcarbonyl)amino]-5-methylbenzamide trifluoroacetate and acetone. The preparative RPHPLC (C18) purification procedure was elution with a linear gradient of 80/20 to 50/50 (0.01% HCl/acetonitrile) over 180 min.

$^1$H-NMR

IS-MS, m/e 416.3 (m+1)

Analysis for C$_{21}$H$_{26}$N$_5$O$_2$Cl.1.7HCl.2.2H$_2$O: Calcd: C, 48.73; H, 6.25; N, 13.53; Cl, 18.50; Found: C, 49.10; H, 5.98; N, 13.17; Cl, 18.62.

EXAMPLE 102

Preparation of 5-Chloro-N-(5-chloropyridin-2-yl)-2-[[(1-phenylethyl)piperidin-4-ylcarbonyl]amino]benzamide Hydrochloride

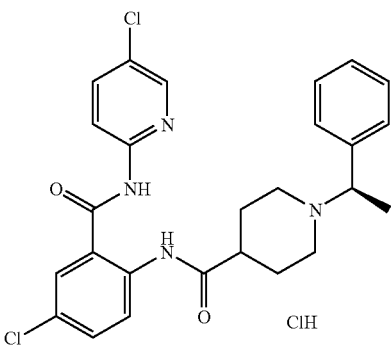

To a stirred solution of 5-chloro-N-(5-chloropyridin-2-yl)-2-[(4-piperidinylcarbonyl)amino]benzamide trifluoroacetate (0.2 g, 0.39 mmol) and triethylamine (0.115 mL, 0.82 mmol) in N,N-dimethylformamide (5 mL) was added (1-bromoethyl)benzene (0.065 mL, 0.47 mmol). After stirring for 72 h at room temperature, the solution was passed through an SCX column (2 N ammonia in methanol) and concentrated in vacuo. The preparative RPHPLC (C18) purification procedure was elution with a linear gradient of 80/20 to 50/50 (0.01% HCl/acetonitrile) over 180 min. The product containing fractions were combined and lyophilized to give 0.091 g (44%) of the title compound as a white solid.

$^1$H-NMR

IS-MS, m/e 497.2

Analysis for $C_{26}H_{26}N_4O_2.Cl_2.1.1HCl.0.3H_2O$: Calcd: C, 57.52; H, 5.14; N, 10.32; Cl, 20.24; Found: C, 57.52; H, 4.99; N, 10.35; Cl, 20.35.

EXAMPLE 103

Preparation of N-(5-Chloropyridin-2-yl)-2-[[1-[1-(4-pyridinyl)ethyl]piperidin-4-ylmethyl]amino]benzamide

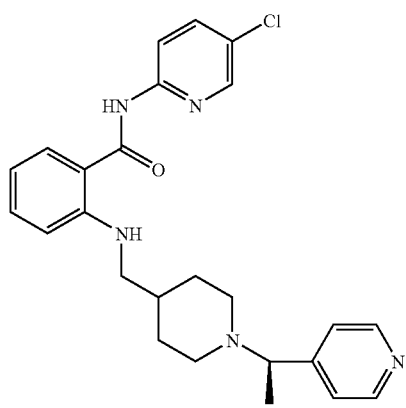

To a small sample of N-(5-chloropyridin-2-yl)-2-(piperidin-4-ylmethylamino)benzamide (0.03 g, 0.1 mmol) weighed out in a 1 mL sealable vial, excess 4-acetylpyridine was added (100 µL, ca. 1 mmol) followed by sodium cyanoborohydride (360 µL of a 1 M solution in tetrahydrofuran) and methanol-acetic acid (95:5). The vial was capped and placed in a shaker at 50° C. for several days until reasonable conversion by TLC was evident. The reaction mixture was then diluted with methanol, shaken well for several minutes, and allowed to stand for 0.5 h before applying it to a 2 g SCX column. After washing well with methanol, the product was gravity-eluted from the column with 2 M ammonia in methanol. The product fractions were combined and concentrated in vacuo to a residue which was triturated in acetonitrile, giving rise to the title compound as a powdery solid (0.03 g, 74%) in >98% purity by HPLC.

FD-MS, m/e 450.2 (m).

EXAMPLE 104

Preparation of N-(5-Chloropyridin-2-yl)-3-[[1-[1-(3-thiophenyl)ethyl]piperidin-4-ylmethyl]amino]benzamide

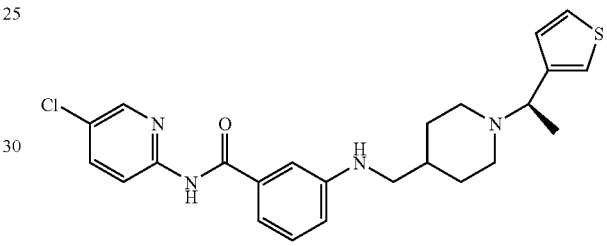

Using the procedure described in example 103, N-(5-chloropyridin-2-yl)-2-(piperidin-4-ylmethylamino)benzamide (0.03 g, 0.1 mmol) was converted to the title compound (0.038 g, 93%), which was identified by LC-MS (Method A).

LC-MS: 87% pure, $R_t$=3.825 min, m/e 455.2 (m).

EXAMPLE 105

Preparation of N-(5-Chloropyridin-2-yl)-2-[[1-[2-(N-hydroxycarbamimidoyl)pyridin-4-yl]piperidin-4-ylmethyl]amino]benzamide

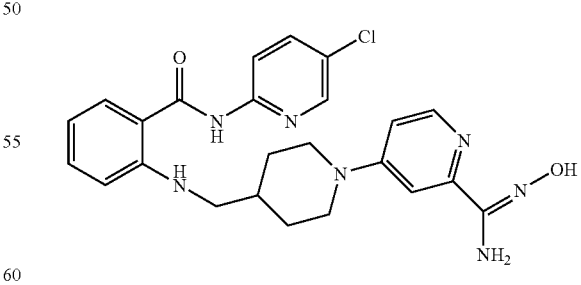

A solution of N-(5-chloropyridin-2-yl)-2-[1-(3-cyanopyridin-4-yl)piperidin-4-ylmethylamino]benzamide (50 mg, 0.11 mmol) and triethylamine (22 mg, 0.22 mmol) in ethanol (5 mL) was treated with hydroxylamine hydrochloride (12 mg, 0.17 mmol). After 16 h, the mixture was concentrated and the residue was purified by column chromatography (SiO₂; 5% methanol in methylene chloride) yielding 40 mg (75%) of the title compound.

¹H-NMR, IR
IS-MSS, m/e 480 (m+1)
Analysis for $C_{24}H_{26}ClN_7O_2$: Calcd: C, 60.06; H, 5.46; N, 20.43; Found: C, 59.57; H, 5.64; N, 19.61.

EXAMPLE 106

Preparation of N-(5-Chloropyridin-2-yl)-5-fluoro-2-[(4-isopropylpiperazin-1-ylcarbonyl)amino]benzamide Hydrochloride

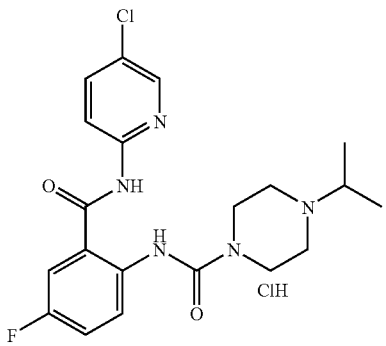

A. 2-[(4-Boc-piperazin-1-ylcarbonyl)amino]-5-fluorobromobenzene

By methods substantially equivalent to those described in example 51-A, 2-[(1-Boc-piperazin-4-ylcarbonyl)amino]-5-fluorobromobenzene (6.4 g, 59%) was prepared from 2-bromo-4-fluoroaniline.

¹H-NMR
IS-MS, m/e 402.2 (m−)
Analysis for $C_{16}H_{21}N_3O_3BrF$: Calcd: C, 47.77; H, 5.26; N, 10.45; Found: C, 47.77; H, 5.00; N, 10.52.

B. 2-[(4-Boc-piperazin-1-ylcarbonyl)amino]-5-fluorobenzoic Acid

By methods substantially equivalent to those described in example 51-B, 2-[(4-Boc-piperazin-1-ylcarbonyl)amino]-5-fluorobenzoic acid (1.68 g, 46%) was prepared from 2-[(4-Boc-piperazin-1-ylcarbonyl)amino]-5-fluorobromobenzene.

¹H-NMR
IS-MS, m/e 368.2 (m+1)
Analysis for $C_{17}H_{22}N_3O_5F$ Calcd: C, 55.58; H, 6.04; N, 11.44; Found: C, 56.34; H, 6.03; N, 11.46.

C. 2-(4-Boc-piperazin-1-yl)-6-fluoro-4H-3,1-benzoxazin-4-one

By methods substantially equivalent to those described in example 51-C, 2-[4-Boc-piperazin-1-yl]-6-fluoro-4H-3,1-benzoxazin-4-one (1.35 g, 94%) was prepared from 2-[(4-Boc-piperazin-1-ylcarbonyl)amino]-5-fluorobenzoic acid.

¹H-NMR
FD-MS, m/e 349 (m)
Analysis for $C_{17}H_{20}N_3O_4F$: Calcd: C, 58.45; H, 5.77; N, 12.03; Found: C, 58.11; H, 5.61; N, 11.35.

D. 2-[(4-Boc-piperazin-1-ylcarbonyl)amino]-N-(5-chloropyridin-2-yl)-5-fluorobenzamide By methods substantially equivalent to those described in example 51-D, 2-[(4-Boc-piperazin-1-ylcarbonyl)amino]-N-(5-chloropyridin-2-yl)-5-fluorobenzamide (1.35 g, 77%) was prepared from 2-[4-Boc-piperazin-1-yl]-6-fluoro-4H-3,1-benzoxazin-4-one.

¹H-NMR
IS-MS, m/e 478.2 (m+1)
Analysis for $C_{22}H_{25}N_5O_4ClF$: Calcd: C, 55.29; H, 5.27; N, 14.65; Found: C, 55.57; H, 5.27; N, 14.58.

E. N-(5-Chloropyridin-2-yl)-5-fluoro-2-[(piperazin-1-ylcarbonyl)amino]benzamide trifluoroacetate By methods substantially equivalent to those described in example 9-B, N-(5-chloropyridin-2-yl)-5-fluoro-2-[(piperazin-1-ylcarbonyl)amino]benzamide trifluoroacetate (0.96 g, 93%) was prepared from 2-[(4-Boc-piperazin-1-ylcarbonyl)amino]-N-(5-chloropyridin-2-yl)-5-fluorobenzamide.

¹H-NMR
IS-MS, m/e 378.4 (m+1)
Analysis for $C_{17}H_{17}N_5O_2ClF$: Calcd: C, 46.40; H, 3.69; N, 14.24; Found: C, 46.22; H, 3.66; N, 13.94.

F. N-(5-Chloropyridin-2-yl)-5-fluoro-2-[(4-isopropylpiperazin-1-ylcarbonyl)amino]benzamide Hydrochloride By methods substantially equivalent to those described in example 27, N-(5-chloropyridin-2-yl)-5-fluoro-2-[(4-isopropylpiperazin-1-ylcarbonyl)amino]benzamide hydrochloride (0.11 g, 20%) was prepared from N-(5-chloropyridin-2-yl)-5-fluoro-2-[(piperazin-1-ylcarbonyl)amino]benzamide trifluoroacetate. The product was purified by preparative RPHPLC (C18), eluting with a linear gradient from 80/20 through 50/50 (0.01% HCl/acetonitrile) over 180 min.

¹H-NMR
IS-MS, m/e 420.2 (m+1)
Analysis for $C_{20}H_{23}N_5O_2ClF \cdot 1.3HCl \cdot 0.2H_2O$: Calcd: C, 51.01; H, 5.29; N, 14.87; Cl, 17.32; Found: C, 51.13; H, 5.46; N, 14.53; Cl, 17.32.

EXAMPLE 107

Preparation of N-(5-Chloropyridin-2-yl)-2-[(4-isopropylpiperazin-1-ylcarbonyl)amino]benzamide Hydrochloride

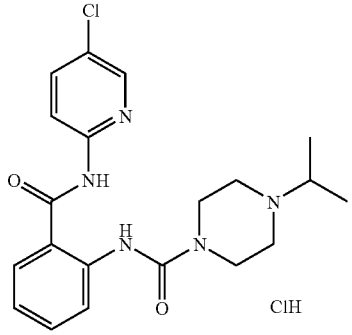

A. Methyl 2-[4-Boc-piperazine-1-ylcarbonyl]aminobenzoate

To a stirring solution of 2-methoxycarbonylphenyl isocyanate (5.44 g, 30.71 mmol) in 1,2-dichloroethane (30 mL)

was added Boc-piperazine (5.72 g, 30.71 mmol). After 1.5 h, the solvent was removed in vacuo and the solid residue was suspended in diethyl ether with vigorous stirring, then filtered and dried to give 6.15 g (55%) of a white solid. A second crop was isolated by adding hexanes to the mother liquor. The precipitate was again filtered and dried in vacuo to give 3.32 g (30%) of a white solid.
$^1$H-NMR
IS-MS, m/e 364.3 (m+1)

B. 2-[4-Boc-piperazine-1-ylcarbonyl]aminobenzoic Acid

To a stirring solution of methyl 2-[4-Boc-piperazine-1-ylcarbonyl]aminobenzoate (2.42 g, 6.7 mmol) in methanol (15 mL) was added 5 N sodium hydroxide (15 mL). After 45 min, the solution was partially concentrated in vacuo to a volume of about 10 mL and the solution was diluted with water and washed with diethyl ether. The aqueous phase was then acidified with conc HCl and extracted with ethyl acetate. The ethyl acetate solution was then washed with brine, dried with MgSO$_4$, filtered and concentrated in vacuo to give 2.03 g (87%) of an off-white solid.
$^1$H-NMR
IS-MS, m/e 350.4 (m+1)

C. 2-[4-Boc-piperazine-1-yl]-4H-3,1-benzoxazin-4-one

By methods substantially equivalent to those described in example 51-C, 2-[4-Boc-piperazine-1-yl]-4H-3,1-benzoxazin-4-one (1.76 g, 96%) was prepared from 2-[4-Boc-piperazine-1-ylcarbonyl]aminobenzoic acid.
$^1$H-NMR
IS-MS, m/e 332.2
Analysis for C$_{17}$H$_{21}$N$_3$O$_4$: Calcd: C, 61.62; H, 6.39; N, 12.68; Found: C, 61.92; H, 6.36; N, 12.75.

D. 2-[(4-Boc-piperazin-1-ylcarbonyl)amino]-N-(5-chloropyridin-2-yl)benzamide By methods substantially equivalent to those described in example 51-D, 2-[(4-Boc-piperazin-1-ylcarbonyl)amino]-N-(5-chloropyridin-2-yl)benzamide (0.87 g, 90%) was prepared from 2-[4-Boc-piperazine-1-yl]-4H-3,1-benzoxazin-4-one.
$^1$H-NMR
IS-MS, m/e 460.0

E. N-(5-Chloropyridin-2-yl)-2-[(piperazin-1-ylcarbonyl)amino]benzamide trifluoroacetate By methods substantially equivalent to those described in example 9-B, N-(5-chloropyridin-2-yl)-2-[(piperazin-1-ylcarbonyl)amino]benzamide trifluoroacetate (0.62 g, 86%) was prepared from 2-[(4-Boc-piperazin-1-ylcarbonyl)amino]-N-(5-chloropyridin-2-yl)benzamide.
$^1$H-NMR
IS-MS, m/e 360.2 (m+1)

F. N-(5-Chloropyridin-2-yl)-2-[(4-isopropylpiperazin-1-ylcarbonyl)amino]benzamide Hydrochloride By methods substantially equivalent to those described in example 27, N-(5-chloropyridin-2-yl)-2-[(4-isopropylpiperazin-1-ylcarbonyl)amino]benzamide hydrochloride (0.155 g, 33%, 97% pure by RPHPLC analysis) was prepared from N-(5-chloropyridin-2-yl)-2-[(piperazin-4-ylcarbonyl)amino]benzamide trifluoroacetate. The product was purified by preparative RPHPLC (C18), eluting with a linear gradient from 90/10 through 60/40 (0.01% HCl/acetonitrile) over 180 min.
$^1$N-NMR
IS-MS, m/e 402.1 (m+1)
Analytical HPLC, RT=24.32 min (90/10–60/40, 40 min)

EXAMPLE 108

Preparation of N-(5-Chloropyridin-2-yl)-2-[(4-isopropylpiperazin-1-ylcarbonyl)amino]-5-trifluoromethylbenzamide Hydrochloride

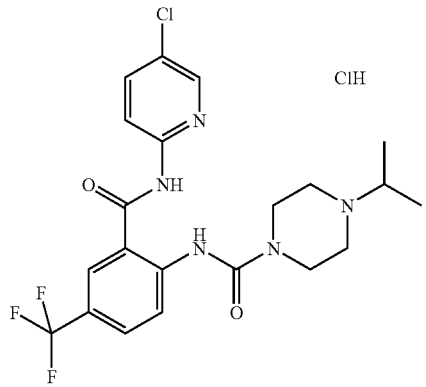

A. 2-(4-Boc-piperazin-1-ylcarbonyl)amino-5-(trifluoromethyl)bromobenzene

By methods substantially equivalent to those described in example 51-A, 2-(4-Boc-piperazin-1-ylcarbonyl)amino-5-(trifluoromethyl)bromobenzene (6.4 g, 93%) was prepared from 2-bromo-4-(trifluoromethyl)aniline.
$^1$H-NMR
IS-MS, m/e 452.2 (m–)
Analysis for C$_{17}$H$_{21}$N$_3$O$_3$BrF$_3$: Calcd: C, 45.15; H, 4.68; N, 9.29; Found: C, 45.01; H, 4.40; N, 9.15.

B. 2-(4-Boc-piperazin-1-ylcarbonyl)amino-5-trifluoromethylbenzoic Acid

By methods substantially equivalent to those described in example 51-B, 2-(4-Boc-piperazin-1-ylcarbonyl)amino-5-trifluoromethylbenzoic acid (2.58 g, 70%) was prepared from 2-(4-Boc-piperazin-1-ylcarbonyl)amino-5-(trifluoromethyl)bromobenzene.
$^1$H-NMR
IS-MS, m/e 416.2 (m–)

C. 2-(4-Boc-piperazin-1-yl)-6-trifluoromethyl-4H-3,1-benzoxazin-4-one

By methods substantially equivalent to those described in example 51-C, 2-(4-Boc-piperazin-1-yl)-6-trifluoromethyl-4H-3,1-benzoxazin-4-one (1.75 g, 71%) was prepared from 2-(4-Boc-piperazin-1-ylcarbonyl)amino-5-trifluoromethylbenzoic acid.
$^1$H-NMR
FD-MS, m/e 399.2 (m)

D. 2-[(4-Boc-piperazin-1-ylcarbonyl)amino]-N-(5-chloropyridin-2-yl)-5-trifluoromethylbenzamide By methods substantially equivalent to those described in example 51-D, 2-[(4-Boc-piperazin-1-ylcarbonyl)amino]-N-(5-chloropyridin-2-yl)-5-trifluoromethylbenzamide (0.71 g, 60%) was prepared from 2-(4-Boc-piperazin-1-yl)-6-trifluoromethyl-4H-3,1-benzoxazin-4-one.

$^1$H-NMR
IS-MS, m/e 528.1 (m+1)

E. N-(5-Chloropyridin-2-yl)-2-[(piperazin-1-ylcarbonyl)amino]-5-trifluoromethylbenzamide trifluoroacetate By methods substantially equivalent to those described in example 9-B, N-(5-chloropyridin-2-yl)-2-[(piperazin-1-ylcarbonyl)amino]-5-trifluoromethylbenzamide trifluoroacetate (0.525 g, 85%) was prepared from 2-[(4-Boc-piperazin-1-ylcarbonyl)amino]-N-(5-chloropyridin-2-yl)-5-trifluoromethylbenzamide.

$^1$H-NMR
IS-MS, m/e 428.1 (m+1)

F. N-(5-Chloropyridin-2-yl)-2-[(4-isopropylpiperazin-1-ylcarbonyl)amino]-5-trifluoromethylbenzamide Hydrochloride By methods substantially equivalent to those described in example 27, N-(5-chloropyridin-2-yl)-2-[(4-isopropylpiperazin-1-ylcarbonyl)amino]-5-trifluoromethylbenzamide hydrochloride (0.37 g, 86%, 99% pure by analytical HPLC) was prepared from N-(5-chloropyridin-2-yl)-2-[(piperazin-1-ylcarbonyl)amino]-5-trifluoromethylbenzamide trifluoroacetate.

$^1$H-NMR
IS-MS, m/e 470.2 (m+1)
Analytical HPLC, RT=21.59 min (80/20–40/60, 40 min)

EXAMPLE 109

Preparation of N-(5-Chloropyridin-2-yl)-2-[(4-isopropylpiperazin-1-ylcarbonyl)amino]-5-trifluoromethoxybenzamide Hydrochloride

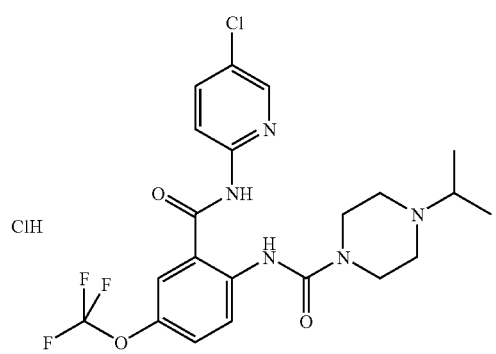

A. 2-(4-Boc-piperazin-1-ylcarbonyl)amino-5-(trifluoromethoxy)bromobenzene

By methods substantially equivalent to those described in example 51-A, 2-(4-Boc-piperazin-1-ylcarbonyl)amino-5-(trifluoromethoxy)bromobenzene (7.1 g, 56%) was prepared from 2-bromo-4-(trifluoromethoxy)aniline.

$^1$H-NMR
IS-MS, m/e 466.1 (m−)

B. 2-(1-Boc-piperazin-4-ylcarbonyl)amino-5-trifluoromethoxybenzoic Acid

By methods substantially equivalent to those described in example 51-B, 2-(4-Boc-piperazin-1-ylcarbonyl)amino-5-trifluoromethoxybenzoic acid (3.7 g, 100%) was prepared from 2-(4-Boc-piperazin-1-ylcarbonyl)amino-5-(trifluoromethoxy)bromobenzene.

$^1$H-NMR
IS-MS, m/e 433.3 (m−)

C. 2-(4-Boc-piperazin-1-yl)-6-trifluoromethoxy-4H-3,1-benzoxazin-4-one

By methods substantially equivalent to those described in example 51-C, 2-(4-Boc-piperazin-1-yl)-6-trifluoromethoxy-4H-3,1-benzoxazin-4-one (1.91 g, 56%) was prepared from 2-(4-Boc-piperazin-1-ylcarbonyl)amino-5-trifluoromethoxybenzoic acid.

$^1$H-NMR
IS-MS, m/e 416 (m)
Analysis for $C_{18}H_{20}N_3O_5F_3$: Calcd: C, 52.05; H, 4.85; N, 10.12; Found: C, 52.34; H, 4.82; N, 10.51.

D. 2-[(4-Boc-piperazin-1-ylcarbonyl)amino]-N-(5-chloropyridin-2-yl)-5-trifluoromethoxybenzamide By methods substantially equivalent to those described in example 51-D, 2-[(4-Boc-piperazin-1-ylcarbonyl)amino]-N-(5-chloropyridin-2-yl)-5-trifluoromethoxybenzamide (0.78 g 74%) was prepared from 2-(4-Boc-piperazin-1-yl)-6-trifluoromethoxy-4H-3,1-benzoxazin-4-one.

$^1$H-NMR
IS-MS, m/e 544.3 (m+1)

E. N-(5-Chloropyridin-2-yl)-2-[(piperazin-4-ylcarbonyl)amino]-5-trifluoromethoxybenzamide trifluoroacetate By methods substantially equivalent to those described in example 9-B, N-(5-chloropyridin-2-yl)-2-[(piperazin-4-ylcarbonyl)amino]-5-trifluoromethoxybenzamide trifluoroacetate (0.67 g, 93%) was prepared from 2-[(4-Boc-piperazin-1-ylcarbonyl)amino]-N-(5-chloropyridin-2-yl)-5-trifluoromethoxybenzamide.

$^1$H-NMR
IS-MS, m/e 444.1 (m+1)

F. N-(5-Chloropyridin-2-yl)-2-[(4-isopropylpiperazin-1-ylcarbonyl)amino]-5-trifluoromethoxybenzamide hydrochloride By methods substantially equivalent to those described in example 27, N-(5-chloropyridin-2-yl)-2-[(4-isopropylpiperazin-1-ylcarbonyl)amino]-5-trifluoromethoxybenzamide hydrochloride (0.347 g, 62%) was prepared from N-(5-chloropyridin-2-yl)-2-[(piperazin-4-ylcarbonyl)amino]-5-trifluoromethoxybenzamide trifluoroacetate.
$^1$H-NMR
IS-MS, m/e 486.5 (m+1)
Analysis for $C_{21}H_{23}N_5O_3ClF_3 \cdot 1.0HCl \cdot 0.05H_2O$: Calcd: C, 47.47; H, 4.74; N, 13.18; Found: C, 47.28; H, 4.66; N, 12.90.

EXAMPLE 110

Preparation of 5-Chloro-N-(5-fluoropyridin-2-yl)-2-[(4-isopropylpiperazin-1-ylcarbonyl)amino]benzamide Hydrochloride

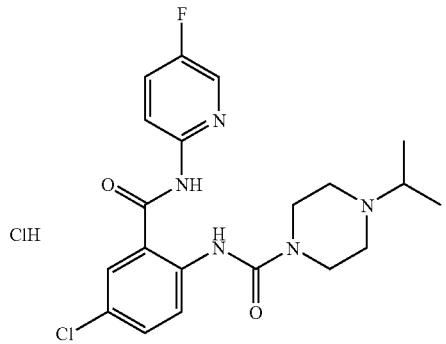

A. 2-[(4-Boc-piperazin-1-ylcarbonyl)amino]-5-chloro-N-(5-fluoropyridin-2-yl)benzamide By methods substantially equivalent to those described in example 51-D, 2-[(4-Boc-piperazin-1-ylcarbonyl)amino]-5-chloro-N-(5-fluoropyridin-2-yl)benzamide (0.75 g, 71%) was prepared from 6-chloro-2-[4-Boc-piperazin-1-yl]-4H-3,1-benzoxazin-4-one and 2-amino-5-fluoropyridine.
$^1$H-NMR
IS-MS, m/e 478.2 (m+1)
Analysis for $C_{22}H_{25}N_5O_4ClF$: Calcd: C, 55.29; H, 5.27; N, 14.65; Found: C, 55.58; H, 5.32; N, 14.81.

B. 5-Chloro-N-(5-fluoropyridin-2-yl)-2-[(piperazin-1-ylcarbonyl)amino]benzamide Trifluoroacetate By methods substantially equivalent to those described in example 9-B, 5-chloro-N-(5-fluoropyridin-2-yl)-2-[(piperazin-1-ylcarbonyl)amino]benzamide trifluoroacetate (0.619 g, 93%) was prepared from 2-[(4-Boc-piperazin-1-ylcarbonyl)amino]-5-chloro-N-(5-fluoropyridin-2-yl)benzamide.
$^1$H-NMR
IS-MS, m/e 378.4 (m+1)
Analysis for $C_{17}H_{17}N_5O_2ClF \cdot CF_3COOH$: Calcd: C, 46.40; H, 3.69; N, 14.24; F, 15.45; Found: C, 46.01; H, 3.67; N, 14.03; F, 15.40.

C. 5-Chloro-N-(5-fluoropyridin-2-yl)-2-[(4-isopropylpiperazin-1-ylcarbonyl)amino]benzamide Hydrochloride By methods substantially equivalent to those described in example 27, 5-chloro-N-(5-fluoropyridin-2-yl)-2-[(4-isopropylpiperazin-1-ylcarbonyl)amino]benzamide hydrochloride (0.310 g, 68%) was prepared from 5-chloro-N-(5-fluoropyridin-2-yl)-2-[(piperazin-1-ylcarbonyl)amino]benzamide trifluoroacetate.
$^1$H-NMR
IS-MS, m/e 420.2 (m+1)
Analysis for $C_{20}H_{23}N_5O_2ClF \cdot 1.5HCl \cdot 0.2H_2O$: Calcd: C, 50.23; H, 5.25; N, 14.65; Cl, 18.54; Found: C, 50.07; H, 4.97; N, 14.44; Cl, 18.81.

EXAMPLE 111

Preparation of 5-Chloro-2-[(4-isopropylpiperazin-1-ylcarbonyl)amino]-N-(5-methylpyridin-2-yl)benzamide Hydrochloride

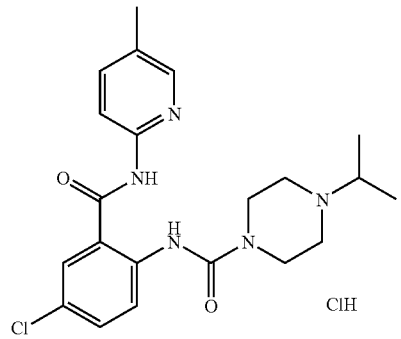

A. 2-[(4-Boc-piperazin-1-ylcarbonyl)amino]-5-chloro-N-(5-methylpyridin-2-yl)benzamide By methods substantially equivalent to those described in example 51-D, 2-[(4-Boc-piperazin-1-ylcarbonyl)amino]-5-chloro-N-(5-methylpyridin-2-yl)benzamide (0.667 g, 74%) was prepared from 2-[4-Boc-piperazin-1-yl]-6-chloro-4H-3,1-benzoxazin-4-one and 2-amino-5-methylpyridine.
$^1$H-NMR
IS-MS, m/e 474.1 (m+1)
Analysis for $C_{23}H_{28}N_5O_4Cl$: Calcd: C, 58.29; H, 5.95; N, 14.78; Found: C, 58.42; H, 6.15; N, 14.57.

B. 5-Chloro-N-(5-methylpyridin-2-yl)-2-[(piperazin-1-ylcarbonyl)amino]benzamide Trifluoroacetate By methods substantially equivalent to those described in example 9-B, 5-chloro-N-(5-methylpyridin-2-yl)-2-[(piperazin-1-ylcarbonyl)amino]benzamide trifluoroacetate (4.07 g, 99%) was prepared from 2-[(4-Boc-piperazin-1-ylcarbonyl)amino]-5-chloro-N-(5-methylpyridin-2-yl)benzamide.
$^1$H-NMR
IS-MS, m/e 374.1 (m+1)
Analysis for $C_{18}H_{20}N_5O_2Cl \cdot 2.1TFA$: Calcd: C, 43.48; H, 3.63; N, 11.42; F, 19.52; Found: C, 43.49; H, 3.61; N, 11.40; F, 19.98.

C. 5-Chloro-2-[(4-isopropylpiperazin-1-ylcarbonyl)amino]-N-(5-methylpyridin-2-yl)benzamide Hydrochloride By methods substantially equivalent to those described in example 27, 5-chloro-2-[(4-isopropylpiperazin-1-ylcarbonyl)amino]-N-(5-methylpyridin-2-yl)benzamide hydrochloride (0.263 g, 71%) was prepared from 5-chloro-N-(5-methylpyridin-2-yl)-2-[(piperazin-1-ylcarbonyl)amino]benzamide trifluoroacetate. The product was purified by reverse phase HPLC, eluting with a gradient from 5% through 35% acetonitrile in 0.05% aq HCl over 200 min.

$^1$H-NMR

IS-MS, m/e 416.3 (m+1)

Analysis for $C_{21}H_{26}N_5O_2Cl.2.1HCl.0.3H_2O$: Calcd: C, 50.66; H, 5.81; N, 14.07; Cl, 22.08; Found: C, 50.69; H, 5.58; N, 14.08; Cl, 22.03.

EXAMPLE 112

Preparation of 5-Chloro-N-(5-chloropyridin-2-yl)-2-[1-(4-thianyl)piperidin-4-ylmethylamino]benzamide

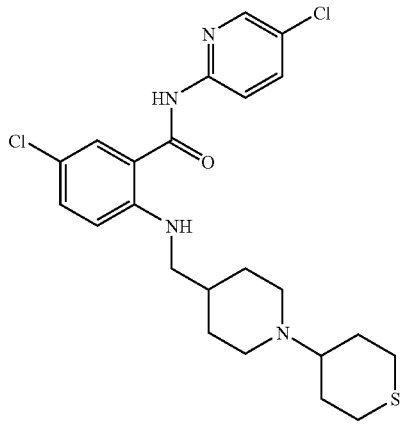

A solution of 5-chloro-N-(5-chloropyridin-2-yl)-2-(piperidin-4-ylmethylamino)benzamide (0.44 g, 1.2 mmol) in methanol-acetic acid (95:5) (10 mL) was treated with tetrahydrothiopyran-4-one (1.34 g, 11.5 mmol) and sodium cyanoborohydride (4.6 mL of a 1 M solution in tetrahydrofuran). The reaction mixture was stirred at room temperature for 48 h, then heated at 50° C. for an additional 60 h. After cooling to room temperature, the solvent was removed in vacuo; the resulting residue was redissolved in methanol and directly applied to 5×10 g SCX columns, washed with methanol and eluted with dichloromethane-2 N ammonia in methanol (1:1). The product fractions were concentrated in vacuo and the residue was purified via silica gel chromatography. Elution with ethyl acetate followed by ethyl acetate-methanol (9:1) afforded the title compound (0.46 g, 84%) as a yellow solid, which was further purified via trituration in acetonitrile followed by separation of the yellow mother liquor.

$^1$H-NMR mp 200.2–202.9° C.

FD-MS, m/e 479.2 (m)

Analysis for $C_{23}H_{28}N_4OSCl_2$: Calcd: C, 57.62; H, 5.89; N, 11.69; Found: C, 57.39; H, 6.05; N, 11.51.

EXAMPLE 113

Preparation of 5-Chloro-N-(5-chloropyridin-2-yl)-2-[1-(1-ethylpropyl)piperidin-4-ylmethylamino]benzamide

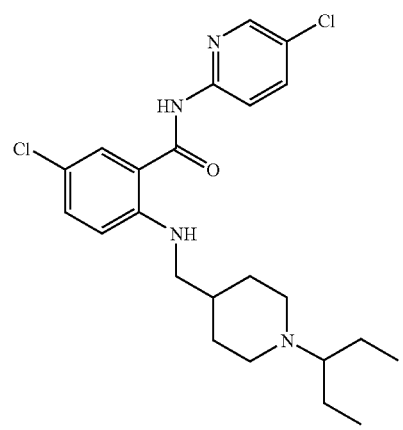

Using the procedure described in example 112, 5-chloro-N-(5-chloropyridin-2-yl)-2-(piperidin-4-ylmethylamino)benzamide (0.59 g, 1.5 mmol) was converted to the title compound (0.5 g, 72%). The material was further purified via trituration in acetonitrile followed by separation of the yellow mother liquor.

$^1$H-NMR mp 135.7–138.3° C.

FD-MS, m/e 449.2 (m)

Analysis for $C_{23}H_{30}N_4OCl_2.0.095H_2O$: Calcd: C, 61.23; H, 6.75; N, 12.42; Found: C, 60.83; H, 6.34; N, 12.31.

EXAMPLE 114

Preparation of 5-Chloro-N-(5-chloropyridin-2-yl)-2-(1-isobutylpiperidin-4-ylmethylamino)benzamide

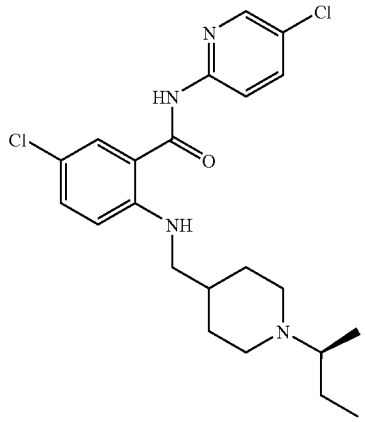

Using the procedure described in example 112 5-chloro-N-(5-chloropyridin-2-yl)-2-(piperidin-4-ylmethylamino)benzamide (0.42 g, 1.1 mmol) was converted to the title compound (0.4 g, 85%). The material was further purified via trituration in acetonitrile followed by separation of the yellow mother liquor.

$^1$H-NMR
mp 121.3–122.2° C.
FD-MS, m/e 435.2 (m)
Analysis for $C_{22}H_{26}N_4OCl_2$: Calcd: C, 60.69; H, 6.48; N, 12.87; Found: C, 60.39; H, 6.39; N, 12.68.

EXAMPLE 115

Preparation of N-(5-Chloropyridin-2-yl)-2-[[1-(4-hydroxybenzyl)piperidin-4-ylmethyl]amino]benzamide

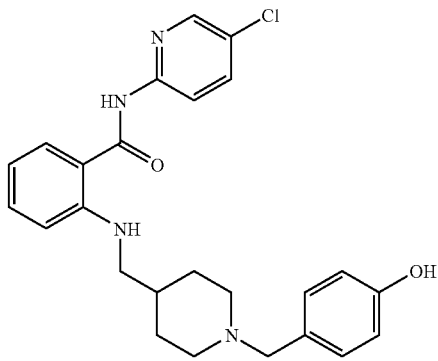

N-(5-Chloropyridin-2-yl)-2-(piperidin-4-ylmethylamino) benzamide (0.034 g, 0.1 mmol) was converted to the title compound (0.0430 g, 94%) using the procedure described in example 78. The product was obtained as an oily residue which was triturated in diethyl ether to afford a solid which was identified by LC-MS (Method A).

LC-MS: 91% pure, $R_t$=2.750 min, m/e 451.2 (m).

EXAMPLE 116

Preparation of N-(5-Chloropyridin-2-yl)-2-[[1-(3-thiophenylmethyl)piperidin-4-ylmethyl]amino]benzamide

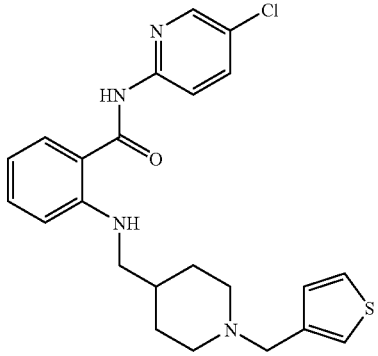

N-(5-Chloropyridin-2-yl)-2-(piperidin-4-ylmethylamino) benzamide (0.034 g, 0.1 mmol) was converted to the title compound (0.042 g, 95%) using the procedure described in example 78. The product was obtained as an oily residue which was further purified on silica gel. Elution with ethyl acetate-2 N ammonia in methanol (95:5) followed by trituration with diethyl ether-acetonitrile afforded a solid which was identified by LC-MS (Method A).

LC-MS: 89% pure, $R_t$=3.421 min, m/e 441.1 (m).

EXAMPLE 117

Preparation of N-(5-Chloropyridin-2-yl)-2-[[1-(2-pyridinylmethyl)piperidin-4-ylmethyl]amino]benzamide

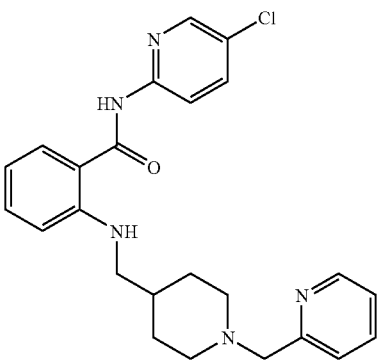

N-(5-Chloropyridin-2-yl)-2-(piperidin-4-ylmethylamino) benzamide (0.114 g, 0.33 mmol) was converted to the title compound (0.093 g, 65%) using the procedure described in example 78. The product was obtained as an oily residue which was further purified on silica gel. Elution with ethyl acetate-2 N ammonia in methanol (95:5) followed by trituration with acetonitrile afforded a solid which was identified by LC-MS (Method A).

LC-MS: 97% pure, $R_t$=2.631 min, m/e 436.2 (m).

EXAMPLE 118

Preparation of N-(5-Chloropyridin-2-yl)-2-[[1-(2-methylbenzyl)piperidin-4-ylmethyl]amino]benzamide

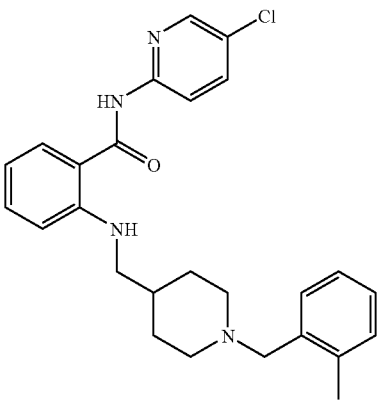

N-(5-Chloropyridin-2-yl)-2-(piperidin-4-ylmethylamino) benzamide (0.034 g, 0.1 mmol) was converted to the title compound (0.017 g, 38%) using the procedure described in example 78. The product was obtained as an oily residue

EXAMPLE 119

Preparation of N-(5-Chloropyridin-2-yl)-2-[[1-(2-methoxybenzyl)piperidin-4-ylmethyl]amino]benzamide

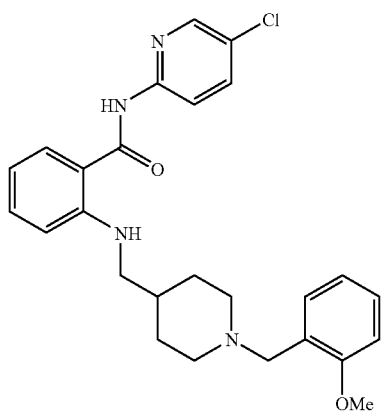

N-(5-Chloropyridin-2-yl)-2-(piperidin-4-ylmethylamino)benzamide (0.034 g, 0.1 mmol) was converted to the title compound (0.041 g, 88%) using the procedure described in example 78. The product was obtained as an oily residue which was triturated in diethyl ether-acetonitrile to provide a solid which was identified as the title compound by LC-MS (Method A).

LC-MS: 95% pure, $R_t$=4.278 min, m/e 465.2 (m).

EXAMPLE 120

Preparation of N-(5-Chloropyridin-2-yl)-2-[[1-(4-methoxybenzyl)piperidin-4-ylmethyl]amino]benzamide

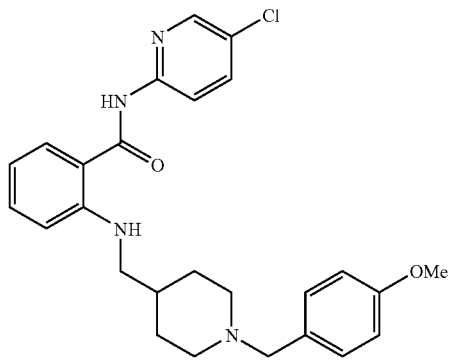

N-(5-Chloropyridin-2-yl)-2-(piperidin-4-ylmethylamino)benzamide (0.034 g, 0.1 mmol) was converted to the title compound (0.044 g, 94%) using the procedure described in example 78. The product was obtained as an oily residue which was triturated in diethyl ether-acetonitrile to provide a solid which was identified as the title compound by LC-MS (Method A).

LC-MS: 91% pure, $R_t$=3.938 min, m/e 465.2 (m).

EXAMPLE 121

Preparation of N-(5-Chloropyridin-2-yl)-2-[[1-(3-hydroxybenzyl)piperidin-4-ylmethyl]amino]benzamide

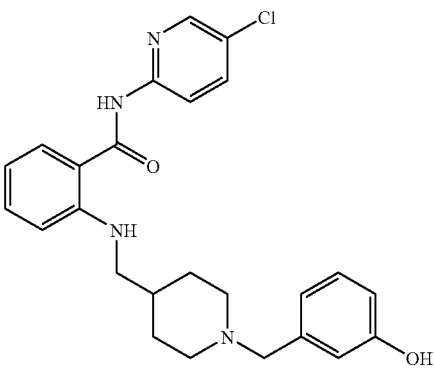

N-(5-Chloropyridin-2-yl)-2-(piperidin-4-ylmethylamino)benzamide (0.034 g, 0.1 mmol) was converted to the title compound (0.043 g, 95%) using the procedure described in example 78. The product was obtained as an oily residue which was triturated in diethyl ether-acetonitrile to provide a solid which was identified as the title compound by LC-MS (Method A).

LC-MS: 91% pure, $R_t$=2.839 min, m/e 451.1 (m).

EXAMPLE 122

Preparation of N-(5-Chloropyridin-2-yl)-2-[[1-(2-thiophenylmethyl)piperidin-4-ylmethyl]amino]benzamide

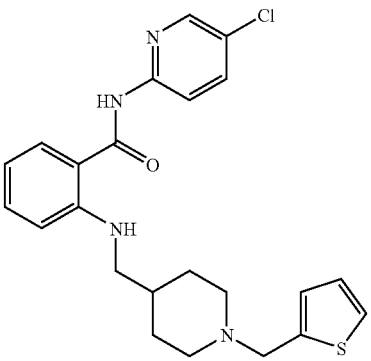

N-(5-Chloropyridin-2-yl)-2-(piperidin-4-ylmethylamino)benzamide (0.034 g, 0.1 mmol) was converted to the title compound (0.041 g, 92%) using the procedure described in example 78. The product was obtained as an oily residue which was further purified on silica gel. Elution with ethyl acetate-2 N ammonia in methanol (95:5) followed by trituration with diethyl ether afforded a solid which was identified by LC-MS (Method A).

LC-MS: 88% pure, $R_t$=3.377 min, m/e 441.1 (m).

EXAMPLE 123

Preparation of N-(5-Chloropyridin-2-yl)-2-[[1-(2-chlorobenzyl)piperidin-4-ylmethyl]amino]benzamide

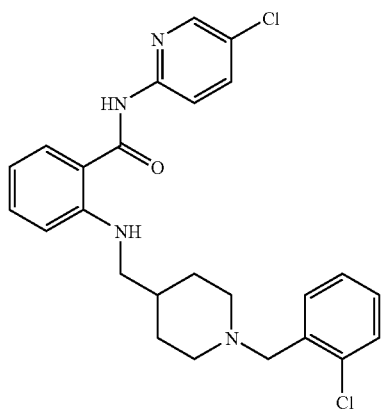

N-(5-Chloropyridin-2-yl)-2-(piperidin-4-ylmethylamino)benzamide (0.034 g, 0.1 mmol) was converted to the title compound (0.025 g, 53%) using the procedure described in example 78. The product was obtained as an oily residue which was triturated in diethyl ether-acetonitrile to provide a solid which was identified as the title compound by LC-MS (Method A).

LC-MS: 91% pure, $R_t$=4.175 min, m/e 469.1 (m).

EXAMPLE 124

Preparation of N-(5-Chloropyridin-2-yl)-2-[[1-(2-fluorobenzyl)piperidin-4-ylmethyl]amino]benzamide

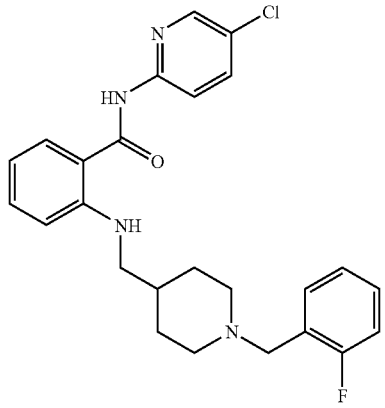

N-(5-Chloropyridin-2-yl)-2-(piperidin-4-ylmethylamino)benzamide (0.034 g, 0.1 mmol) was converted to the title compound (0.045 g, 100%) using the procedure described in example 78. The product was obtained as an oily residue which was triturated in diethyl ether-acetonitrile to provide a solid which was identified as the title compound by LC-MS (Method A).

LC-MS: 92% pure, $R_t$=3.752 min, m/e 453.1 (m).

EXAMPLE 125

Preparation of N-(5-Chloropyridin-2-yl)-2-[[1-(3-fluorobenzyl)piperidin-4-ylmethyl]amino]benzamide

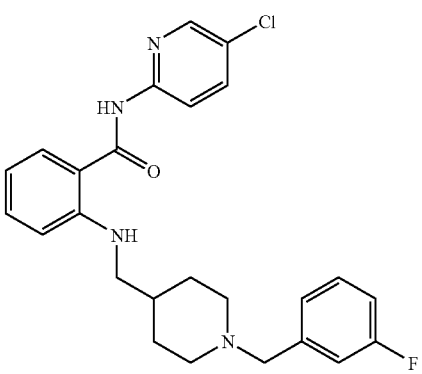

N-(5-Chloropyridin-2-yl)-2-(piperidin-4-ylmethylamino)benzamide (0.034 g, 0.1 mmol) was converted to the title compound (0.044 g, 97%) using the procedure described in example 78. The product was obtained as an oily residue which was triturated in diethyl ether-acetonitrile to provide a solid which was identified as the title compound by LC-MS (Method A).

LC-MS: 94% pure, $R_t$=3.831 min, m/e 453.1 (m).

EXAMPLE 126

Preparation of N-(5-Chloropyridin-2-yl)-2-[(1-benzylpiperidin-4-ylmethyl)amino]benzamide

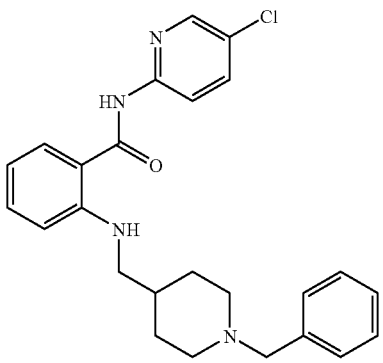

N-(5-Chloropyridin-2-yl)-2-(piperidin-4-ylmethylamino)benzamide (0.114 g, 0.33 mmol) was converted to the title compound (0.144 g, 100%) using the procedure described in example 78. The product was obtained as an oily residue which was further purified on silica gel. Elution with ethyl acetate-2 N ammonia in methanol (95:5) followed by trituration with diethyl ether afforded a solid which was identified by LC-MS (Method A).

LC-MS: 97% pure, $R_t$=3.713 min, m/e 435.1 (m).

EXAMPLE 127

Preparation of N-(5-Chloropyridin-2-yl)-2-[[1-(4-ethylbenzyl)piperidin-4-ylmethyl]amino]benzamide

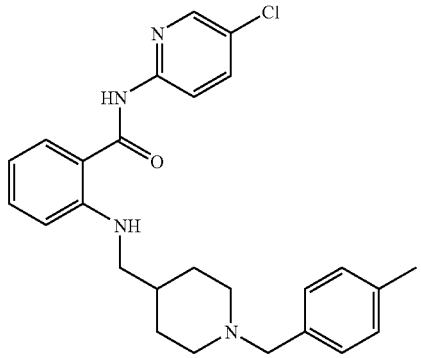

N-(5-Chloropyridin-2-yl)-2-(piperidin-4-ylmethylamino)benzamide (0.034 g, 0.1 mmol) was converted to the title compound (0.04 g, 88%) using the procedure described in example 78. The product was obtained as an oily residue which was triturated in diethyl ether-acetonitrile to provide a solid which was identified as the title compound by LC-MS (Method A).

LC-MS: 88% pure, $R_t$=4.388 min, m/e 449.2 (m).

EXAMPLE 128

Preparation of N-(5-Chloropyridin-2-yl)-2-[[1-(4-chlorobenzyl)piperidin-4-ylmethyl]amino]benzamide

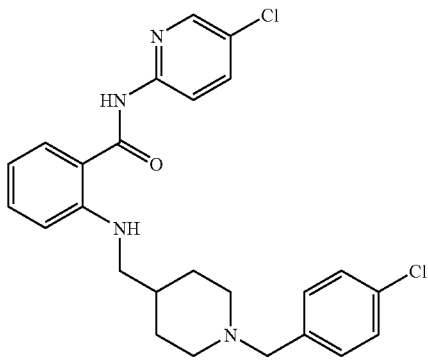

N-(5-Chloropyridin-2-yl)-2-(piperidin-4-ylmethylamino)benzamide (0.034 g, 0.1 mmol) was converted to the title compound (0.046 g, 98%) using the procedure described in example 78. The product was obtained as an oily residue which was triturated in diethyl ether-acetonitrile to provide a solid which was identified as the title compound by LC-MS (Method A).

LC-MS: 99% pure, $R_t$=4.407 min, m/e 469.1 (m).

EXAMPLE 129

Preparation of N-(5-Chloropyridin-2-yl)-2-[[1-(3-methoxybenzyl)piperidin-4-ylmethyl]amino]benzamide

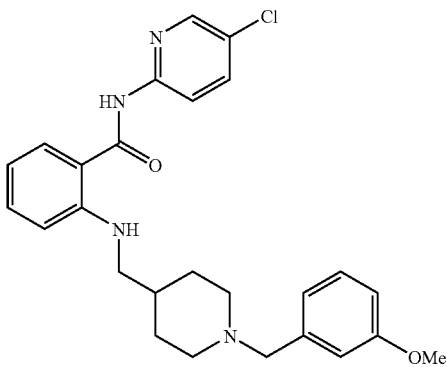

N-(5-Chloropyridin-2-yl)-2-(piperidin-4-ylmethylamino)benzamide (0.034 g, 0.1 mmol) was converted to the title compound (0.046 g, 99%) using the procedure described in example 78. The product was obtained as an oily residue which was triturated in diethyl ether-acetonitrile to provide a solid which was identified as the title compound by LC-MS (Method A).

LC-MS: 87% pure, $R_t$=4.003 min, m/e 465.2 (m).

EXAMPLE 130

Preparation of N-(5-Chloropyridin-2-yl)-2-[[1-(4-bromobenzyl)piperidin-4-ylmethyl]amino]benzamide

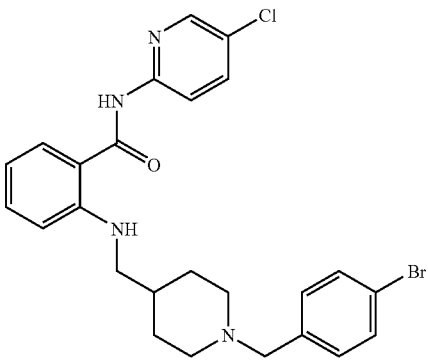

N-(5-Chloropyridin-2-yl)-2-(piperidin-4-ylmethylamino)benzamide (0.034 g, 0.1 mmol) was converted to the title compound (0.052 g, 100%) using the procedure described in example 78. The product was obtained as an oily residue which was triturated in diethyl ether-acetonitrile to provide a solid which was identified as the title compound by LC-MS (Method A).

LC-MS: 91% pure, $R_t$=4.532 min, m/e 515.1 (m+1).

EXAMPLE 131

Preparation of N-(5-Chloropyridin-2-yl)-2-[[1-(2-bromobenzyl)piperidin-4-ylmethyl]amino]benzamide

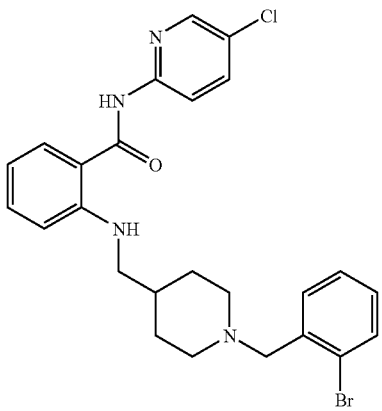

N-(5-Chloropyridin-2-yl)-2-(piperidin-4-ylmethylamino)benzamide (0.034 g, 0.1 mmol) was converted to the title compound (0.031 g, 61%) using the procedure described in example 78. The product was obtained as an oily residue which was triturated in diethyl ether-acetonitrile to provide a solid which was identified as the title compound by LC-MS (Method A).

DC-MS: 86% pure, $R_t$=4.335 min, m/e 515.1 (m+1)

EXAMPLE 132

Preparation of N-(5-Chloropyridin-2-yl)-2-[[1-(3-methylbenzyl)piperidin-4-ylmethyl]amino]benzamide

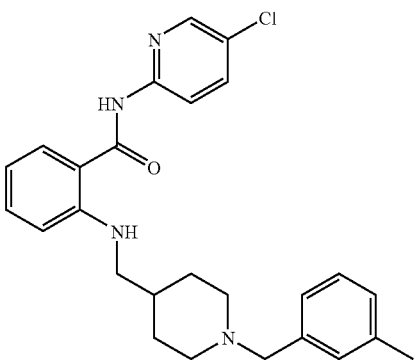

N-(5-Chloropyridin-2-yl)-2-(piperidin-4-ylmethylamino)benzamide (0.034 g, 0.1 mmol) was converted to the title compound (0.045 g, 100%) using the procedure described in example 78. The product was obtained as an oily residue which was triturated in diethyl ether-acetonitrile to provide a solid which was identified as the title compound by LC-MS (Method A).

LC-MS: 88% pure, $R_t$=4.326 min, m/e 449.2 (m).

EXAMPLE 133

Preparation of N-(5-Chloropyridin-2-yl)-2-[1-(cyclohexylmethyl)piperidin-4-ylmethyl)amino]benzamide

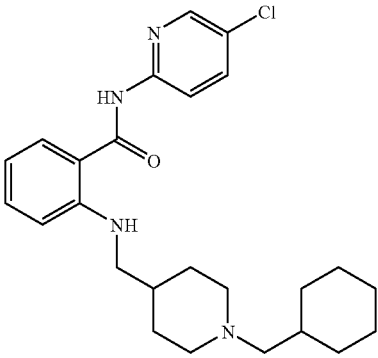

N-(5-Chloropyridin-2-yl)-2-(piperidin-4-ylmethylamino) benzamide (0.034 g, 0.1 mmol) was converted to the title compound (0.039 g, 88%) using the procedure described in example 78. The product was obtained as an oily residue which was triturated in diethyl ether-acetonitrile to provide a solid which was identified as the title compound by LC-MS (Method A).

LC-MS: 89% pure, $R_t$=4.535 min, m/e 441.2 (m).

EXAMPLE 134

Preparation of N-(5-Chloropyridin-2-yl)-2-[[1-(3-furanylmethyl)piperidin-4-ylmethyl]amino]benzamide

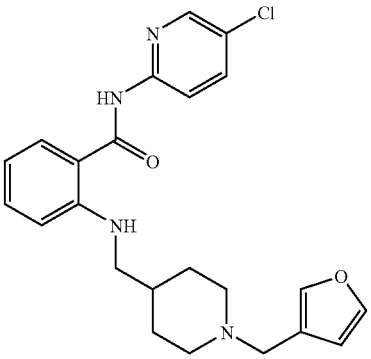

N-(5-Chloropyridin-2-yl)-2-(piperidin-4-ylmethylamino) benzamide (0.034 g, 0.1 mmol) was converted to the title compound (0.039 g, 92%) using the procedure described in example 78. The product was obtained as an oily residue which was was further purified on silica gel. Elution with ethyl acetate afforded an oily material which was identified by LC-MS (Method A).

LC-MS: 90% pure, $R_t$=3.082 min, m/e 425.2 (m).

EXAMPLE 135

Preparation of N-(5-Chloropyridin-2-yl)-2-[[1-(4-imidazolylmethyl)piperidin-4-ylmethyl]amino]benzamide

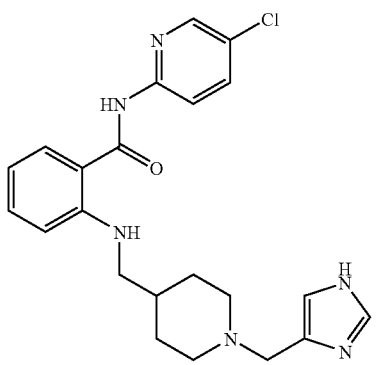

N-(5-Chloropyridin-2-yl)-2-(piperidin-4-ylmethylamino)benzamide (0.034 g, 0.1 mmol) was converted to the title compound (0.030 g, 71%) using the procedure described in example 78. The product was obtained as an oily residue which was was further purified on silica gel. Elution with dichloromethane-methanol (9:1) afforded an oily material which was identified by LC-MS (Method A).

LC-MS: 96% pure, $R_t$=1.407 min, m/e 425.1 (m).

EXAMPLE 136

Preparation of N-(5-Chloropyridin-2-yl)-2-[[1-(2-furanylmethyl)piperidin-4-ylmethyl]amino]benzamide

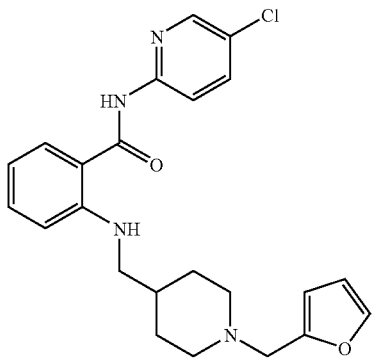

N-(5-Chloropyridin-2-yl)-2-(piperidin-4-ylmethylamino)benzamide (0.034 g, 0.1 mmol) was converted to the title compound (0.032 g, 75%) using the procedure described in example 78. The product was obtained as an oily residue which was was further purified on silica gel. Elution with ethyl acetate afforded an oily material which was identified by LC-MS (Method A).

LC-MS: 90% pure, $R_t$=3.066 min, m/e 425.1 (m).

EXAMPLE 137

Preparation of N-(5-Chloropyridin-2-yl)-2-[[1-(3-pyridinylmethyl)piperidin-4-ylmethyl]amino]benzamide

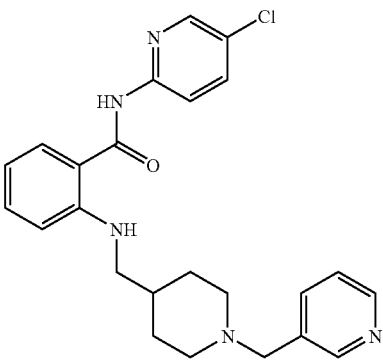

N-(5-Chloropyridin-2-yl)-2-(piperidin-4-ylmethylamino)benzamide (0.034 g, 0.1 mmol) was converted to the title compound (0.058 g, 100%) using the procedure described in example 78. The product was obtained as an oily residue which was was further purified on silica gel. Elution with dichloromethane-methanol (9:1) afforded an oily material which was identified by LC-MS (Method A).

LC-MS: 87% pure, $R_t$=1.632 min, m/e 436.1 (m).

EXAMPLE 138

Preparation of N-(5-Chloropyridin-2-yl)-2-[[1-(2-imidazolylmethyl)piperidin-4-ylmethyl]amino]benzamide

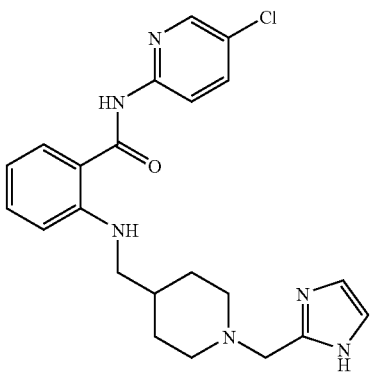

N-(5-Chloropyridin-2-yl)-2-(piperidin-4-ylmethylamino)benzamide (0.034 g, 0.1 mmol) was converted to the title compound (0.029 g, 68%) using the procedure described in example 78. The product was obtained as an oily residue which was was further purified on silica gel. Elution with ethyl acetate-2 N ammonia in methanol (95:5) followed by trituration with diethyl ether-acetonitrile afforded a solid which was identified by LC-MS (Method A).

LC-MS: 66% pure, $R_t$=1.481 min, m/e 425.1 (m).

EXAMPLE 139

Preparation of N-(5-Chloropyridin-2-yl)-2-[[1-[1-(4-methoxyphenyl)ethyl]piperidin-4-ylmethyl]amino]benzamide

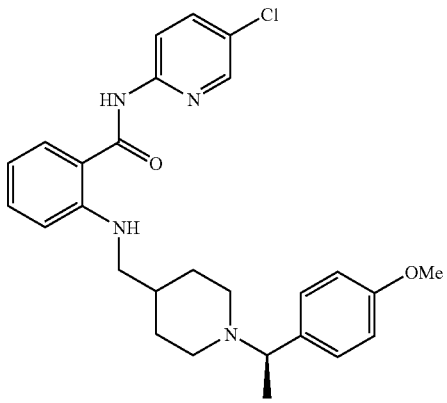

Using the procedure described in example 103, N-(5-chloropyridin-2-yl)-2-(piperidin-4-ylmethylamino)benzamide (0.03 g, 0.1 mmol) was converted to the title compound (0.027 g, 63%), which was identified by LC-MS (Method A).

LC-MS: 95% pure, $R_t$=4.229 min, m/e 479.3 (m).

EXAMPLE 140

Preparation of N-(5-Chloropyridin-2-yl)-2-[[1-[1-(2-thiophenyl)ethyl]piperidin-4-ylmethyl]amino]benzamide

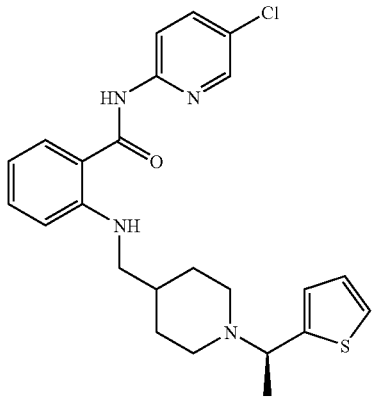

Using the procedure described in example 103, N-(5-chloropyridin-2-yl)-2-(piperidin-4-ylmethylamino)benzamide (0.03 g, 0.1 mmol) was converted to the title compound (0.039 g, 95%), which was identified by LC-MS (Method A).

LC-MS: 91% pure, $R_t$=3.868 min, m/e 455.2 (m).

EXAMPLE 141

Preparation of N-(5-Chloropyridin-2-yl)-2-[[1-[1-(4-bromophenyl)ethyl]piperidin-4-ylmethyl]amino]benzamide

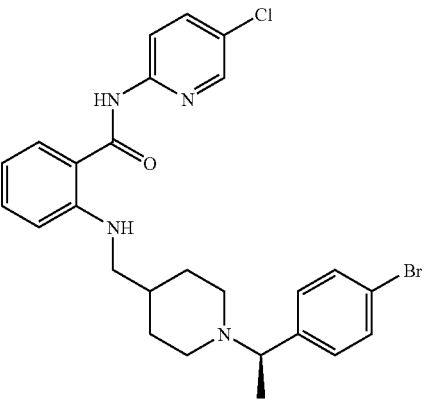

Using the procedure described in example 103, N-(5-chloropyridin-2-yl)-2-(piperidin-4-ylmethylamino)benzamide (0.03 g, 0.1 mmol) was converted to the title compound (0.041 g, 86%), which was identified by LC-MS (Method A).

LC-MS: 97% pure, $R_t$=4.878 min, m/e 529.2 (m+1).

EXAMPLE 142

Preparation of N-(5-Chloropyridin-2-yl)-2-[[1-[1-(4-chlorophenyl)ethyl]piperidin-4-ylmethyl]amino]benzamide

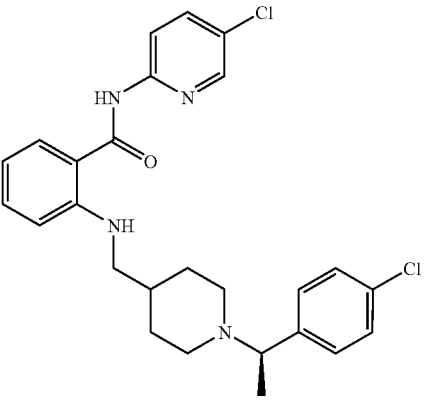

Using the procedure described in example 103, N-(5-chloropyridin-2-yl)-2-(piperidin-4-ylmethylamino)benzamide (0.03 g, 0.1 mmol) was converted to the title compound (0.043 g, 99%), which was identified by LC-MS (Method A).

LC-MS: 92% pure, $R_t$=5.001 min, m/e 483.2 (m).

EXAMPLE 143

Preparation of N-(5-Chloropyridin-2-yl)-2-[[1-[1-(2,5-dimethylfuran-3-yl)ethyl]piperidin-4-ylmethyl]amino]benzamide

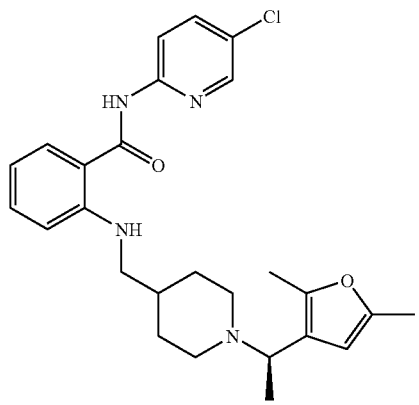

Using the procedure described in example 103, N-(5-chloropyridin-2-yl)-2-(piperidin-4-ylmethylamino)benzamide (0.03 g, 0.1 mmol) was converted to the title compound (0.030 g, 71%), which was identified by LC-MS (Method A).

LC-MS: 96% pure, $R_t$=4.624 min, m/e 467.3 (m).

EXAMPLE 144

Preparation of N-(5-Chloropyridin-2-yl)-2-[[1-[1-(3-chlorophenyl)ethyl]piperidin-4-ylmethyl]amino]benzamide

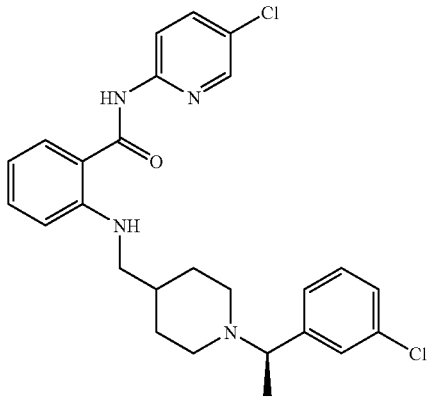

Using the procedure described in example 103, N-(5-chloropyridin-2-yl)-2-(piperidin-4-ylmethylamino)benzamide (0.03 g, 0.1 mmol) was converted to the title compound (0.026 g, 60%), which was identified by LC-MS (Method B).

LC-MS: 99% pure, $R_t$=7.883 min, m/e 483.2 (m).

EXAMPLE 145

Preparation of N-(5-Chloropyridin-2-yl)-2-[[1-(1-methylpropyl)piperidin-4-ylmethyl]amino]benzamide

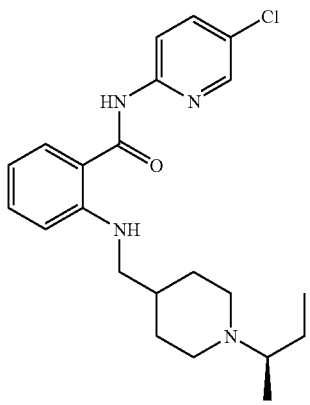

Using the procedure described in example 103, N-(5-chloropyridin-2-yl)-2-(piperidin-4-ylmethylamino)benzamide (0.03 g, 0.1 mmol) was converted to the title compound (0.034 g, 94%), which was identified by LC-MS (Method A).

LC-MS: 85% pure, $R_t$=3.060 min, m/e 401.3 (m).

EXAMPLE 146

Preparation of N-(5-Chloropyridin-2-yl)-2-[[1-(1-ethylpropyl)piperidin-4-ylmethyl]amino]benzamide

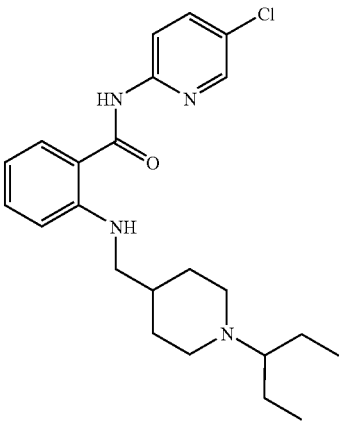

Using the procedure described in example 103, N-(5-chloropyridin-2-yl)-2-(piperidin-4-ylmethylamino)benzamide (0.03 g, 0.1 mmol) was converted to the title compound (0.035 g, 94%), which was identified by LC-MS (Method A).

LC-MS: 92% pure, $R_t$=3–440 min, m/e 415.3 (m).

EXAMPLE 147

Preparation of N-(5-Chloropyridin-2-yl)-2-[[1-(4-thianyl)piperidin-4-ylmethyl]amino]benzamide

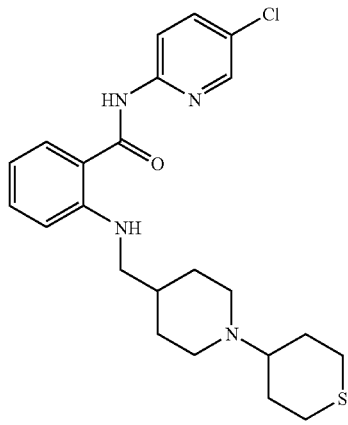

Using the procedure described in example 103, N-(5-chloropyridin-2-yl)-2-(piperidin-4-ylmethylamino)benzamide (0.03 g, 0.1 mmol) was converted to the title compound (0.039 g, 97%), which was identified by LC-MS (Method A).

LC-MS: 99% pure, $R_t$=3.063 min, m/e 445.5 (m).

EXAMPLE 148

Preparation of N-(5-Chloropyridin-2-yl)-2-[[1-(1-cyclopropylethyl)piperidin-4-ylmethyl]amino]benzamide

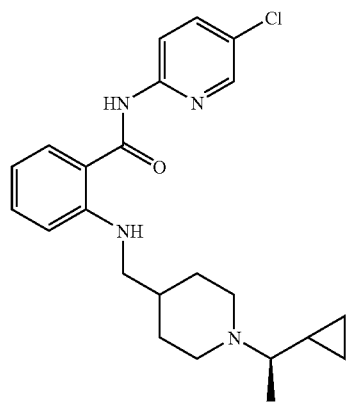

Using the procedure described in example 103, N-(5-chloropyridin-2-yl)-2-(piperidin-4-ylmethylamino)benzamide (0.03 g, 0.1 mmol) was converted to the title compound (0.032 g, 86%), which was identified by LC-MS (Method A).

LC-MS: 91% pure, $R_t$=3.276 min, m/e 413.3 (m).

EXAMPLE 149

Preparation of N-(5-Chloropyridin-2-yl)-2-[(1-cyclohexylpiperidin-4-ylmethyl)amino]benzamide

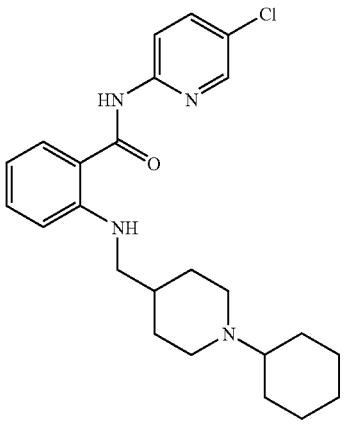

Using the procedure described in example 103, N-(5-chloropyridin-2-yl)-2-(piperidin-4-ylmethylamino)benzamide (0.03 g, 0.1 mmol) was converted to the title compound, which was identified by LC-MS (Method A). Further purification on silica gel provided clean material (0.015 g, 39%) 96% pure by HPLC.

LC-MS: $R_t$=3.598 min, m/e 427.3 (m).

EXAMPLE 150

Preparation of N-(5-Chloropyridin-2-yl)-2-[[1-(4-tetrahydropyran-4-yl)piperidin-4-ylmethyl]amino]benzamide

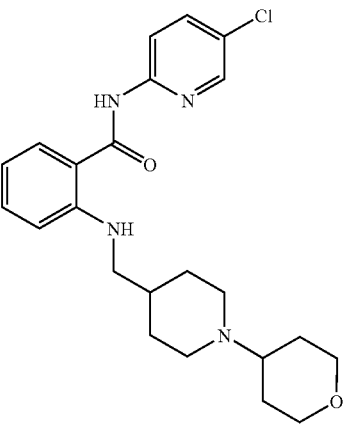

Using the procedure described in example 103, N-(5-chloropyridin-2-yl)-2-(piperidin-4-ylmethylamino)benzamide (0.03 g, 0.1 mmol) was converted to the title compound, which was identified by LC-MS (Method A). Further purification on silica gel provided clean material (0.022 g, 57%) 87% pure by HPLC.

LC-MS: $R_t$=2.150 min, m/e 429.3 (m).

EXAMPLE 151

Preparation of N-(5-Chloropyridin-2-yl)-2-[[1-(3-thiolanyl)piperidin-4-ylmethyl]amino]benzamide

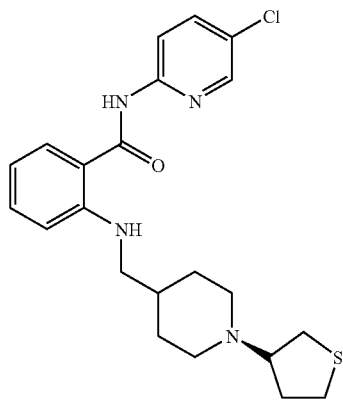

Using the procedure described in example 103, N-(5-chloropyridin-2-yl)-2-(piperidin-4-ylmethylamino)benzamide (0.03 g, 0.1 mmol) was converted to the title compound, which was identified by LC-MS (Method A). Further purification on silica gel provided clean material (0.012 g, 31%) 90% pure by HPLC.

LC-MS: $R_t$=2.625 min. m/e 431.2 (m).

EXAMPLE 152

Preparation of N-(5-Chloropyridin-2-yl)-2-[(1-cyclopentylpiperidin-4-ylmethyl)amino]benzamide

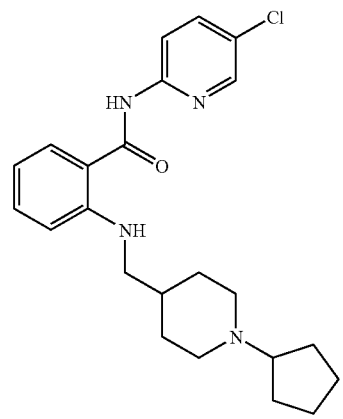

Using the procedure described in example 103, N-(5-chloropyridin-2-yl)-2-(piperidin-4-ylmethylamino)benzamide (0.03 g, 0.1 mmol) was converted to the title compound (0.031 g, 83%), which was identified by LC-MS (Method A).

LC-MS: 87% pure, $R_t$=3.141 min, m/e 413.3 (m).

EXAMPLE 153

Preparation of N-(5-Chloropyridin-2-yl)-2-[[1-[1-(2-pyridyl)ethyl]piperidin-4-ylmethyl]amino]benzamide

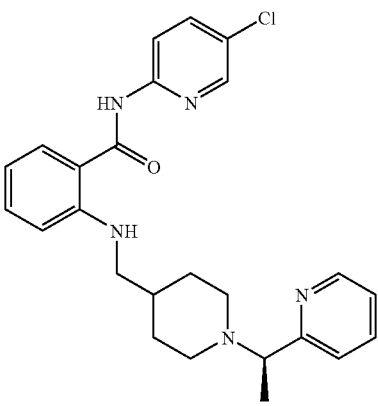

Using the procedure described in example 103, N-(5-chloropyridin-2-yl)-2-(piperidin-4-ylmethylamino)benzamide (0.03 g, 0.1 mmol) was converted to the title compound (0.035 g, 86%), which was identified by LC-MS (Method A).

LC-MS: 88% pure, $R_t$=2.934 min, m/e 450.3 (m).

EXAMPLE 154

Preparation of N-(5-Chloropyridin-2-yl)-2-[(1-cyclobutylpiperidin-4-ylmethyl)amino]benzamide

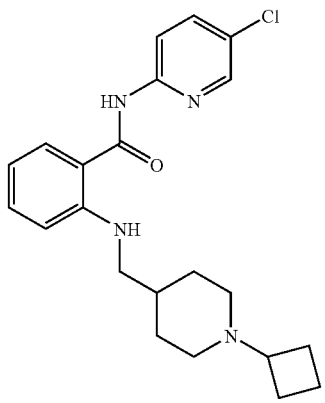

Using the procedure described in example 103, N-(5-chloropyridin-2-yl)-2-(piperidin-4-ylmethylamino)benzamide (0.03 g, 0.1 mmol) was converted to the title compound (0.034 g, 95%), which was identified by LC-MS (Method A).

LC-MS: 51% pure, $R_t$=2.793 min, m/e 399.2 (m).

EXAMPLE 155

Preparation of N-(5-Chloropyridin-2-yl)-2-[[1-(1-propylbutyl)piperidin-4-ylmethyl]amino]benzamide

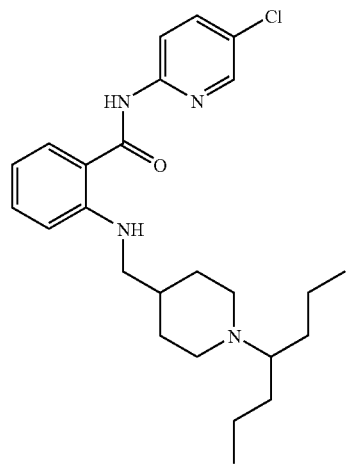

Using the procedure described in example 103, N-(5-chloropyridin-2-yl)-2-(piperidin-4-ylmethylamino)benzamide (0.03 g, 0.1 mmol) was converted to the title compound (0.026 g, 65%), which was identified by LC-MS (Method A).

LC-MS: 98% pure, $R_t$=4.759 min, m/e 443.3 (m).

EXAMPLE 156

Preparation of N-(5-Chloropyridin-2-yl)-2-[[1-(2-indanyl)piperidin-4-ylmethyl]amino]benzamide

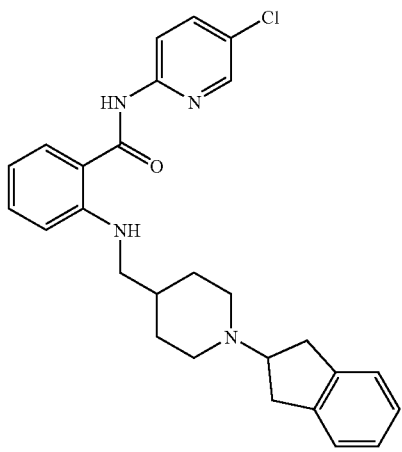

Using the procedure described in example 103, N-(5-chloropyridin-2-yl)-2-(piperidin-4-ylmethylamino)benzamide (0.03 g, 0.1 mmol) was converted to the title compound (0.027 g, 65%), which was identified by LC-MS (Method A).

LC-MS: ca. 85% pure, $R_t$=4.197 min, m/e 461.3 (m).

EXAMPLE 157

Preparation of N-(5-Chloropyridin-2-yl)-2-[[1-[1-(2-thiazolyl)ethyl]piperidin-4-ylmethyl)amino]benzamide

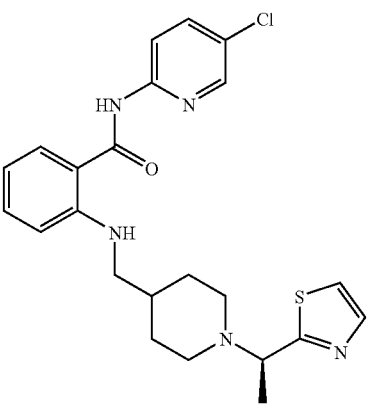

Using the procedure described in example 103, N-(5-chloropyridin-2-yl)-2-(piperidin-4-ylmethylamino)benzamide (0.03 g, 0.1 mmol) was converted to the title compound (0.020 g, 49%), which was identified by LC-MS (Method A).

LC-MS: 100% pure, $R_t$=2.785 min, m/e 456.2 (m).

EXAMPLE 158

Preparation of N-(5-Chloropyridin-2-yl)-2-[[1-[1-(3-pyridinyl)ethyl]piperidin-4-ylmethyl]amino]benzamide

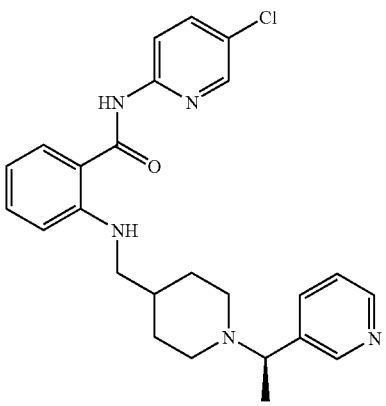

Using the procedure described in example 103, N-(5-chloropyridin-2-yl)-2-(piperidin-4-ylmethylamino)benzamide (0.03 g, 0.1 mmol) was converted to the title compound, which was purified on silica gel to afford clean material (0.024 g, 59%) 98% pure by HPLC.

FD-MS, m/e 450.2 (m).

EXAMPLE 159

Preparation of N-(5-Chloropyridin-2-yl)-2-[[1-[1-(2-furanyl)ethyl]piperidin-4-ylmethyl]amino]benzamide

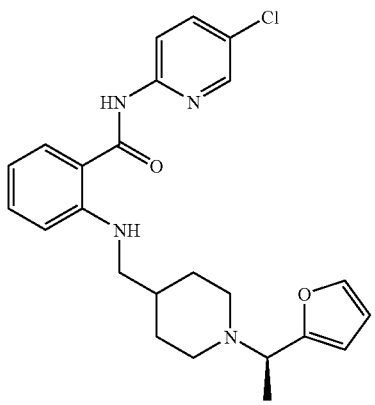

Using the procedure described in example 103, N-(5-chloropyridin-2-yl)-2-(piperidin-4-ylmethylamino)benzamide (0.03 g, 0.1 mmol) was converted to the title compound (0.022 g, 56%), which was identified by LC-MS (Method A).

LC-MS: 90% pure, $R_t$=3.442 min, m/e 439.2 (m).

EXAMPLE 160

Preparation of N-(5-Chloropyridin-2-y)-2-[[1-[1-(3-fluorophenyl)ethyl]piperidin-4-ylmethyl]amino]benzamide

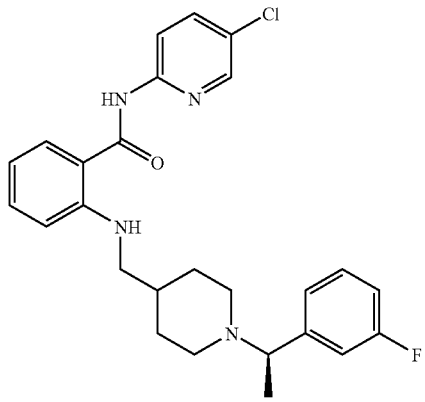

Using the procedure described in example 103, N-(5-chloropyridin-2-yl)-2-(piperidin-4-ylmethylamino)benzamide (0.03 g, 0.1 mmol) was converted to the title compound (0.036 g, 86%), which was identified by LC-MS (Method A).

LC-MS: ca. 90% pure, $R_t$=4.193 min, m/e 467.3 (m).

EXAMPLE 161

Preparation of N-(5-Chloropyridin-2-yl)-2-[[1-[1-(4-fluorophenyl)ethyl]piperidin-4-ylmethyl]amino]benzamide

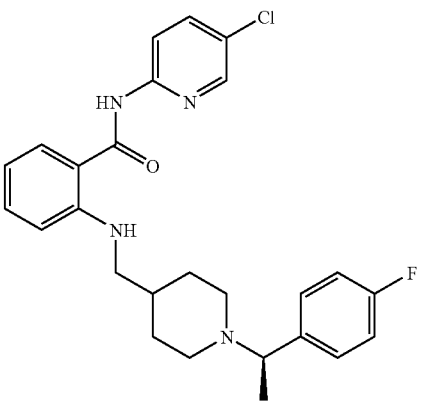

Using the procedure described in example 103, N-(5-chloropyridin-2-yl)-2-(piperidin-4-ylmethylamino)benzamide (0.03 g, 0.1 mmol) was converted to the title compound (0.036 g, 86%), which was identified by LC-MS (Method A).

LC-MS: 92% pure, $R_t$=4.185 min, m/e 467.3 (m).

EXAMPLE 162

Preparation of N-(5-Chloropyridin-2-yl)-2-[[1-[1-(2-methoxyphenyl)ethyl]piperidin-4-ylmethyl]amino]benzamide

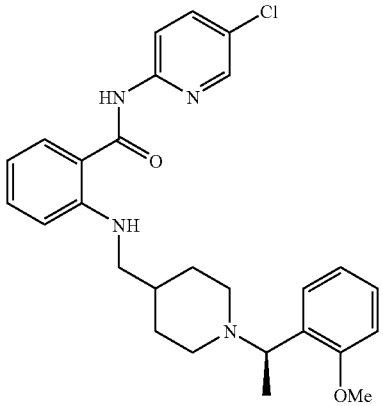

Using the procedure described in example 103, N-(5-chloropyridin-2-yl)-2-(piperidin-4-ylmethylamino)benzamide (0.03 g, 0.1 mmol) was converted to the title compound (0.040 g, 93%), which was identified by LC-MS (Method A).

LC-MS: 100% pure, $R_t$=4.588 min. m/e 479.3 (m).

EXAMPLE 163

Preparation of N-(5-Chloropyridin-2-yl)-2-[[1-[1-(4-methylphenyl)ethyl]piperidin-4-ylmethyl]amino]benzamide

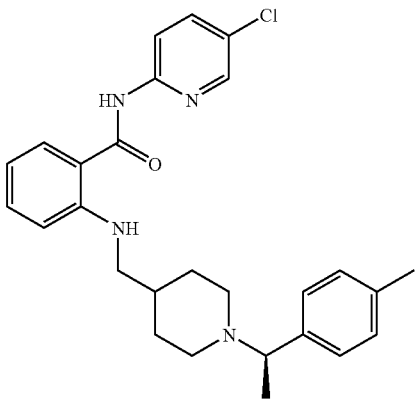

Using the procedure described in example 103, N-(5-chloropyridin-2-yl)-2-(piperidin-4-ylmethylamino)benzamide (0.03 g, 0.1 mmol) was converted to the title compound (0.036 g, 86%), which was identified by LC-MS (Method A).

LC-MS: ca. 95% pure, $R_t$=4.656 min, m/e 463.3 (m).

EXAMPLE 164

Preparation of N-(5-Chloropyridin-2-yl)-2-[[1-[1-(3-methoxyphenyl)ethyl]piperidin-4-ylmethyl]amino]benzamide

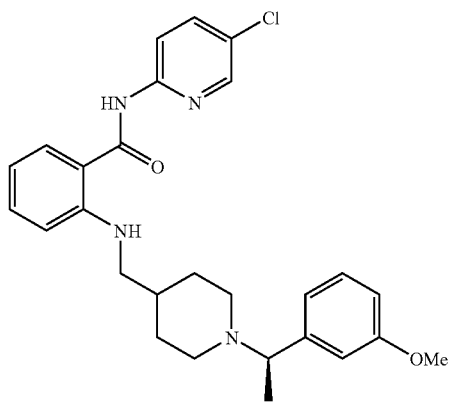

Using the procedure described in example 103, N-(5-chloropyridin-2-yl)-2-(piperidin-4-ylmethylamino)benzamide (0.03 g, 0.1 mmol) was converted to the title compound (0.039 g, 90%), which was identified by LC-MS (Method A).

LC-MS: 96% pure, $R_t$=4.296 min, m/e 479.3 (m).

EXAMPLE 165

Preparation of N-(5-Chloropyridin-2-yl)-2-[[1-[1-(3-hydroxyphenyl)ethyl]piperidin-4-ylmethyl]amino]benzamide

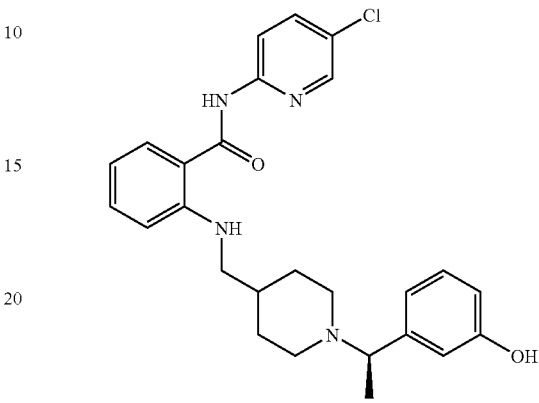

Using the procedure described in example 103, N-(5-chloropyridin-2-yl)-2-(piperidin-4-ylmethylamino)benzamide (0.03 g, 0.1 mmol) was converted to the title compound (0.031 g, 74%), which was identified by LC-MS (Method A).

LC-MS: ca. 100% pure, $R_t$=3.016 min, m/e 465.3 (m).

EXAMPLE 166

Preparation of N-(5-Chloropyridin-2-yl)-2-[[1-[1-(2-hydroxyphenyl)ethyl]piperidin-4-ylmethyl]amino]benzamide

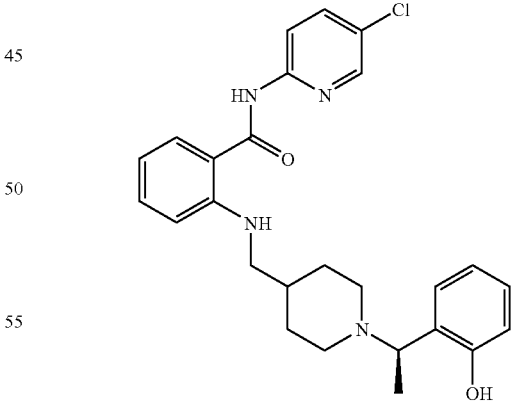

Using the procedure described in example 103, N-(5-chloropyridin-2-yl)-2-(piperidin-4-ylmethylamino)benzamide (0.03 g, 0.1 mmol) was converted to the title compound (0.020 g, 48%), which was identified by LC-MS (Method A).

LC-MS: 100% pure, $R_t$=3.830 min, m/e 465.3 (m).

EXAMPLE 167

Preparation of N-(5-Chloropyridin-2-yl)-2-[[1-[1-(2-methylphenyl)ethyl]piperidin-4-ylmethyl]amino]benzamide

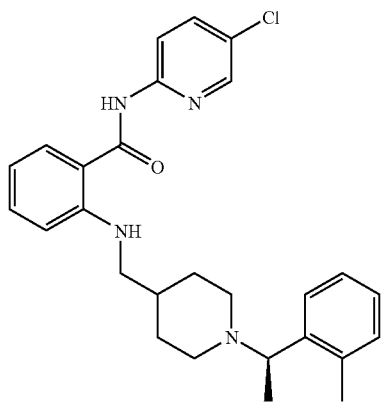

Using the procedure described in example 103, N-(5-chloropyridin-2-yl)-2-(piperidin-4-ylmethylamino)benzamide (0.03 g, 0.1 mmol) was converted to the title compound (0.025 g, 60%), which was identified by LC-MS (Method A).

LC-MS: 94% pure, $R_t$=4.463 min, m/e 463.3 (m).

EXAMPLE 168

Preparation of N-(5-Chloropyridin-2-yl)-2-[[1-(1-phenylethyl)piperidin-4-ylmethyl]amino]benzamide

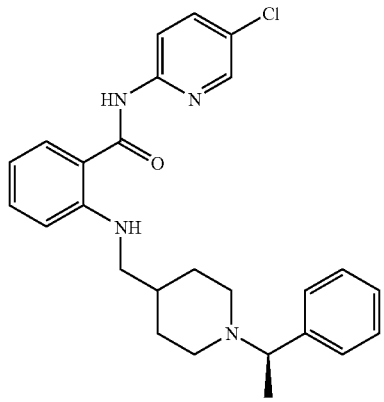

Using the procedure described in example 103, N-(5-chloropyridin-2-yl)-2-(piperidin-4-ylmethylamino)benzamide (0.03 g, 0.1 mmol) was converted to the title compound (0.035 g, 87%), which was identified by LC-MS (Method A).

LC-MS: 100% pure, $R_t$=3.828 min, m/e 449.3 (m).

EXAMPLE 169

Preparation of N-(5-Chloropyridin-2-yl)-2-[[1-[1-(2-fluorophenyl)ethyl]piperidin-4-ylmethyl]amino]benzamide

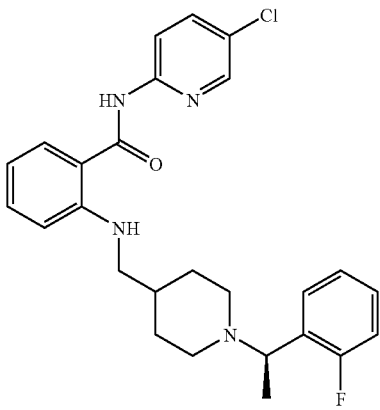

Using the procedure described in example 103, N-(5-chloropyridin-2-yl)-2-(piperidin-4-ylmethylamino)benzamide (0.03 g, 0.1 mmol) was converted to the title compound (0.023 g, 55%), which was identified by LC-MS (Method A).

LC-MS: ca. 95% pure, $R_t$=4.114 min, m/e 467.3 (m).

EXAMPLE 170

Preparation of N-(5-Chloropyridin-2-yl)-2-[[1-[1-(3-methylphenyl)ethyl]piperidin-4-ylmethyl]amino]benzamide

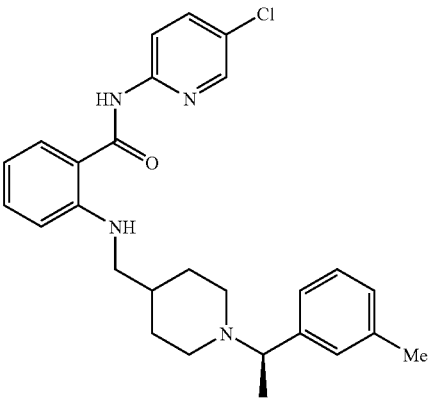

Using the procedure described in example 103, N-(5-chloropyridin-2-yl)-2-(piperidin-4-ylmethylamino)benzamide (0.03 g, 0.1 mmol) was converted to the title compound (0.026 g, 62%), which was identified by LC-MS (Method A).

LC-MS: ca. 95% pure, $R_t$=4.692 min, m/e 463.3 (m).

EXAMPLE 171

Preparation of N-(5-Chloropyridin-2-yl)-2-[[1-(1-methylpiperidin-4-yl)piperidin-4-ylmethyl]amino]benzamide

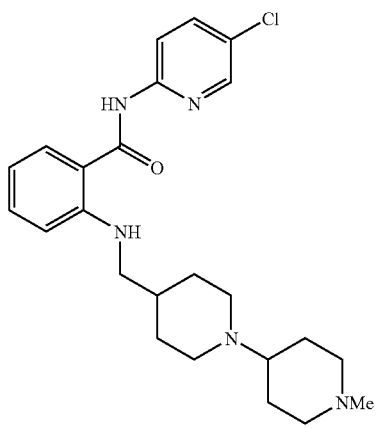

Using the procedure described in example 103, N-(5-chloropyridin-2-yl)-2-(piperidin-4-ylmethylamino)benzamide (0.03 g, 0.1 mmol) was converted to the title compound (0.032 g, 80%), which was identified by LC-MS (Method A).

LC-MS: 94% pure, $R_t$=1.387 min, m/e 442.3 (m).

EXAMPLE 172

Preparation of N-(5-Chloropyridin-2-yl)-2-[(1-methylpiperidin-4-ylmethyl)amino]benzamide Hydrochloride

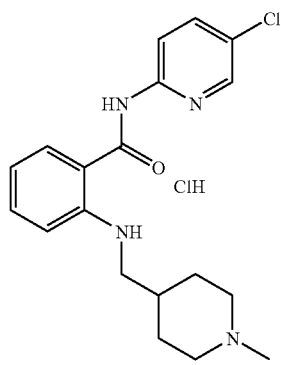

To a solution of N-(5-chloropyridin-2-yl)-2-(piperidin-4-ylmethylamino)benzamide (0.132 g, 0.4 mmol) in ethanol (5 mL), 88% formic acid was added (160 μL, 1.9 mmol) followed by 36% aqueous formaldeyde (80 μL, 1.9 mmol). The reaction mixture was heated at 80° C. for 16 h; then it was allowed to cool to room temperature before directly applying it to an SCX column. After washing well with methanol, the product was gravity-eluted with 1 N ammonia in methanol. The product fractions were concentrated in vacuo, giving rise to 0.12 g of an oily residue which corresponded to a 1:2 mixture of the title compound to bis-methylated product, as determined by LC-MS (Method B). The title compound was isolated from the mixture as the pure HCl salt utilizing preparative HPLC methods.

$^1$H-NMR

LC-MS: 86% pure, $R_t$=6.120 min, m/e 359.2 (m).

EXAMPLE 173

Preparation of N-(5-Chloropyridin-2-yl)-2-[(1-isopropylpiperidin-4-ylcarbonyl)amino]-5-methylsulfonylbenzamide Hydrochloride

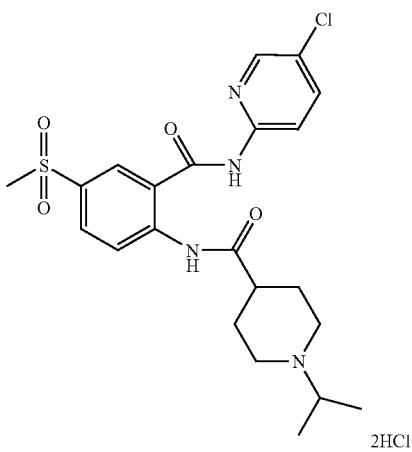

A. 4-(Methylsulfonyl)nitrobenzene

To a stirring solution of methyl 4-nitrophenyl sulfide (10 g, 59.1 mmol) in chloroform at 0° C. was added m-chloroperoxybenzoic acid (55.6 g, 177.3 mmol). After 3 h, ethyl acetate (1.2 L) was added followed by satd aq sodium bisulfite. After stirring overnight, the layers were separated and the organic phase was washed with satd aq sodium bicarbonate (3×200 mL), followed by brine, and then dried over MgSO$_4$, filtered and concentrated in vacuo to give 11.27 g (95%) of the title compound.

$^1$H-NMR

FD-MS, m/e 201.1 (m+)

Analysis for $C_7H_7NO_4S$: Calcd: C, 41.79; H, 3.51; N, 6.96; Found: C, 41.79; H, 3.59; N, 6.82.

B. 4-(Methylsulfonyl)aniline

A solution of 4-(methylsulfonyl)nitrobenzene (6.26 g, 31.1 mmol) in THF (200 mL) and ethanol (100 mL) was placed in a high pressure reaction vessel and to this solution was added 5% Pd/C (1.6 g). The vessel was shaken for 8 h under an atmosphere of hydrogen (60 psi). The solution was then filtered through diatomaceous earth, partially concentrated in vacuo, and diluted with diethyl ether. The resulting precipitate was filtered and dried in vacuo to give 4.84 g (91%) of a tan solid.

$^1$H-NMR

IS-MS, m/e 172.1 (m+1)

Analysis for $C_7H_9NO_2S$: Calcd: C, 49.11; H, 5.30; N, 8.18; Found: C, 49.28; H, 5.48; N, 7.91.

C. 2-Iodo-4-(methylsulfonyl)aniline

To a solution of iodine (20.8 g, 81.8 mmol) and silver sulfate (25.5 g, 81.8 mmol) in ethanol (1 L) was added 4-(methylsulfonyl)aniline (14 g, 81.8 mmol). After stirring overnight, the solution was filtered. The precipitate was then suspended in THF and stirred for 48 h, then filtered again and the filtrate was concentrated in vacuo to give 15.5 g (64%) of tan solid. The original filtrate was also concentrated in vacuo and then suspended in ethanol with stirring, then filtered and dried in vacuo to give another 7.92 g (33%) of tan solid.

$^1$H-NMR
IS-MS, m/e 298.3 (m+1)

Analysis for $C_7H_8NO_2IS$: Calcd: C, 28.30; H, 2.71; N, 4.71; Found: C, 28.60; H, 2.64; N, 4.54.

D. 2-[(1-Boc-piperidin-4-ylcarbonyl)amino]-5-methylsulfonyliodobenzene

Using methods substantially equivalent to those described in Example 25-D, 2-[(1-Boc-piperidin-4-ylcarbonyl)amino]-5-methylsulfonyliodobenzene (6.88 g, 40%) was prepared from 2-iodo-4-(methylsulfonyl)aniline and 1-Boc-piperidin-4-ylcarbonyl chloride.

$^1$H-NMR
IS-MS, m/e 507.0 (m−1)$^-$

Analysis for $C_{18}H_{25}N_2O_5IS$: Calcd: C, 42.53; H, 4.96; N, 5.51; Found: C, 42.29; H, 4.87; N, 5.43.

E. 2-[1-Boc-piperidin-4-yl]-6-methylsulfonyl-4H-3,1-benzoxazin-4-one

To a stirring solution of 2-[(1-Boc-piperidin-4-ylcarbonyl)amino]-5-methylsulfonyliodobenzene (1.89 g, 3.72 mmol) in acetonitrile (50 mL) was added $K_2CO_3$ (2.53 g, 18.6 mmol) followed by Pd(PPh$_3$)$_4$ (0.22 g, 0.19 mmol) and CuI (0.036 g, 0.19 mmol). The mixture was placed under an atmosphere of CO and heated to 75° C. After 2 h, the heat was removed and the mixture was diluted with ethyl acetate and washed with water, then brine. The organic phase was then dried with MgSO$_4$, filtered and concentrated in vacuo. The residue was chromatographed over silica gel, eluting with a gradient of 10% to 20% ethyl acetate in dichloromethane. The product containing fractions were combined and concentrated in vacuo to give 0.485 g (32%) of a white solid.

$^1$H-NMR
FD-MS, m/e 408.0 (m+)

Analysis for $C_{19}H_{24}N_2O_6S$: Calcd: C, 55.87; H, 5.92; N, 6.86; Found: C, 56.00; H, 5.94; N, 6.74.

F. 2-[(1-Boc-piperidin-4-ylcarbonyl)amino]-N-(5-chloropyridin-2-yl)-5-methylsulfonylbenzamide Using methods substantially equivalent to those described in Example 51-D, 2-[(1-Boc-piperidin-4-ylcarbonyl)amino]-N-(5-chloropyridin-2-yl)-5-methylsulfonylbenzamide (0.947 g, 89%) was prepared from 2-[1-Boc-piperidin-4-yl]-6-methylsulfonyl-4H-3,1-benzoxazin-4-one.

$^1$H-NMR
IS-MS, m/e 537.3 (m+1)

G. N-(5-Chloropyridin-2-yl)-2-[(piperidin-4-ylcarbonyl)amino]-5-methylsulfonylbenzamide Trifluoroacetate Using methods substantially equivalent to those described in Example 9-B, N-(5-chloropyridin-2-yl)-2-[(piperidin-4-ylcarbonyl)amino]-5-methylsulfonylbenzamide trifluoroacetate (0.845 g, 91%) was prepared from 2-[(1-Boc-piperidin-4-ylcarbonyl)amino]-N-(5-chloropyridin-2-yl)-5-methylsulfonylbenzamide.

$^1$H-NMR
IS-MS, m/e 437.2 (m+1)

H. N-(5-Chloropyridin-2-yl)-2-[(1-isopropylpiperidin-4-ylcarbonyl)amino]-5-methylsulfonylbenzamide Hydrochloride Using methods substantially equivalent to those described in Example 27, N-(5-chloropyridin-2-yl)-2-[(1-isopropylpiperidin-4-ylcarbonyl)amino]-5-methylsulfonylbenzamide hydrochloride (0.375 g, 50%) was prepared from N-(5-chloropyridin-2-yl)-2-[(piperidin-4-ylcarbonyl)amino]-5-methylsulfonylbenzamide trifluoroacetate. The product was purified using reverse phase HPLC, eluting with a gradient of 10% through 40% acetonitrile in 0.05% aq HCl over 200 min.

$^1$H-NMR
IS-MS, m/e 479.1 (m+1)

Analysis for $C_{22}H_{27}N_4O_4SCl.1.5HCl.0.2H_2O$: Calcd: C, 49.18; H, 5.42; N, 10.43; Found: C, 49.14; H, 5.18; N, 10.10.

EXAMPLE 174

Preparation of N-(5-Chloropyridin-2-yl)-5-(N,N-dimethylaminosulfonyl)-2-[(1-isopropylpiperidin-4-ylcarbonyl)amino]benzamide Hydrochloride

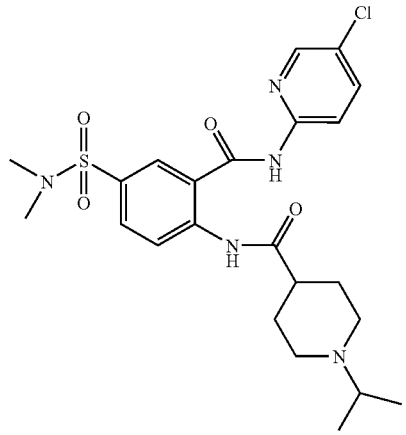

A. 4-(N,N-Dimethylaminosulfonyl)nitrobenzene

To a stirring solution of dimethylamine (180 mL, 40% in water, 1.57 mol) in methanol (180 mL) at 0° C., was slowly added 4-nitrobenzenesulfonyl chloride (69.5 g, 314 mmol). After complete addition, the cold bath was removed; and, after stirring overnight, the mixture was filtered and the precipitate was washed with water and dried in vacuo to give 68 g (94%) of tan solid.

¹H-NMR
IS-MS, m/e 231.1 (m+1)
Analysis for $C_8H_{10}N_2O_4S$: Calcd: C, 41.73; H, 4.38; N, 12.17; Found: C, 41.44; H, 4.42; N, 12.04.

B. 4-(N,N-Dimethylaminosulfonyl)aniline

Using methods substantially equivalent to those described in Example 173-B, 4-(N,N-dimethylaminosulfonyl)aniline (11.7 g, 85%) was prepared from 4-(N,N-dimethylaminosulfonyl)nitrobenzene.
¹H-NMR
IS-MS, m/e 201.2 (m+1)
Analysis for $C_8H_{12}N_2O_2S$: Calcd: C, 47.98; H, 6.04; N, 13.99; Found: C, 48.30; H, 6.03; N, 13.74.

C. 2-Iodo-4-(N,N-dimethylaminosulfonyl)aniline

Using methods substantially equivalent to those described in Example 173-C, 2-iodo-4-(N,N-dimethylaminosulfonyl)aniline (12.8 g, 68%) was prepared from 4-(N,N-dimethylaminosulfonyl)aniline.
¹H-NMR
IS-MS, m/e 327.1 (m+1)
Analysis for $C_8H_{11}N_2O_2IS$: Calcd: C, 29.46; H, 3.40; N, 8.59; Found: C, 29.47; H, 3.16; N, 8.37.

D. 2-[(1-Boc-piperidin-4-ylcarbonyl)amino]-5-(N,N-dimethylaminosulfonyl)iodobenzene Using methods substantially equivalent to those described in Example 25-D, 2-[(1-Boc-piperidin-4-ylcarbonyl)amino]-5-(N,N-dimethylaminosulfonyl)iodobenzene (6.65 g, 40%) was prepared from 2-iodo-4-(N,N-dimethylaminosulfonyl)aniline and 1-Boc-piperidin-4-ylcarbonyl chloride.
¹H-NMR
IS-MS, m/e 536.2 (m−1)⁻
Analysis for $C_{19}H_{28}N_3O_5IS$: Calcd: C, 42.46; H, 5.25; N, 7.82; Found: C, 42.32; H, 5.30; N, 7.65.

E. 2-(1-Boc-piperidin-4-yl)-6-(N,N-dimethylaminosulfonyl)-4H-3,1-benzoxazin-4-one Using methods substantially equivalent to those described in Example 173-E, 2-(1-Boc-piperidin-4-yl)-6-(N,N-dimethylaminosulfonyl)-4H-3,1-benzoxazin-4-one (0.87 g, 53%) was prepared from 2-[(1-Boc-piperidin-4-ylcarbonyl)amino]-5-(N,N-dimethylaminosulfonyl)iodobenzene.
¹H-NMR
Analysis for $C_{20}H_{27}N_3O_6S$: Calcd: C, 54.91; H, 6.22; N, 9.60; Found: C, 54.80; H, 6.28; N, 9.60.

F. 2-[(1-Boc-piperidin-4-ylcarbonyl)amino]-N-(5-chloropyridin-2-yl)-5-(N,N-dimethylaminosulfonyl)benzamide Using methods substantially equivalent to those described in Example 51-D, 2-[(1-Boc-piperidin-4-ylcarbonyl)amino]-N-(5-chloropyridin-2-yl)-5-(N,N-dimethylaminosulfonylbenzamide (0.912 g, 85%) was prepared from 2-(1-Boc-piperidin-4-yl)-6-(N,N-dimethylaminosulfonyl)-4H-3,1-benzoxazin-4-one and 2-amino-5-chloropyridine.
¹H-NMR
IS-MS, m/e 566.5 (m+1)
Analysis for $C_{25}H_{32}N_5O_6ClS$: Calcd: C, 53.05; H, 5.70; N, 12.37; Found: C, 53.45; H, 5.88; N, 11.79.

G. N-(5-Chloropyridin-2-yl)-5-(N,N-dimethylaminosulfonyl)-2-[(piperidin-4-ylcarbonyl)amino]benzamide Trifluoroacetate Using methods substantially equivalent to those described in Example 9-B, N-(5-chloropyridin-2-yl)-5-(N,N-dimethylaminosulfonyl)-2-[(piperidin-4-ylcarbonyl)amino]benzamide trifluoroacetate (0.745 g, 92%) was prepared from N-(5-chloropyridin-2-yl)-2-[(1-Boc-piperidin-4-ylcarbonyl)amino]-5-(N,N-dimethylaminosulfonyl)benzamide.
¹H-NMR
IS-MS, m/e 466.1 (m+1)
Analysis for $C_{20}H_{24}N_5O_4SCl \cdot CF_3OH$: Calcd: C, 45.56; H, 4.34; N, 12.08; F, 9.83; Found: C, 45.85; H, 4.39; N, 11.87; F, 10.68.

H. N-(5-Chloropyridin-2-yl)-5-(N,N-dimethylaminosulfonyl)-2-[(1-isopropylpiperidin-4-ylcarbonyl)amino]benzamide Hydrochloride Using methods substantially equivalent to those described in Example 27, N-(5-chloropyridin-2-yl)-5-(N,N-dimethylaminosulfonyl)-2-[(1-isopropylpiperidin-4-ylcarbonyl)amino]benzamide hydrochloride (0.605 g, 86%) was prepared from N-(5-chloropyridin-2-yl)-5-(N,N-dimethylaminosulfonyl)-2-[(piperidin-4-ylcarbonyl)amino]benzamide trifluoroacetate.
¹H-NMR
IS-MS, m/e 508.1 (m+1)
Analysis for $C_{23}H_{30}N_5O_4SCl \cdot 1.5HCl \cdot 1.8H_2O$: Calcd: C, 46.41; H, 5.94; N, 11.77; Cl, 14.89; Found: C, 46.70; H, 5.55; N, 11.47; Cl, 15.22.

EXAMPLE 175

Preparation of N-(5-Chloropyridin-2-yl)-2-[(4-isopropylpiperazin-1-ylcarbonyl)amino]-5-(methylsulfonyl)benzamide

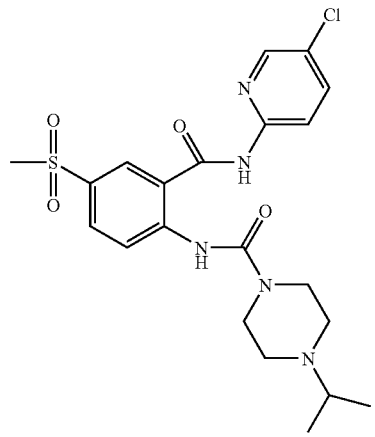

A. 2-[(4-Boc-piperazin-1-ylcarbonyl)amino]-5-(methylsulfonyl)iodobenzene

Using methods substantially equivalent to those described in Example 51-A, 2-[(1-Boc-piperazin-4-ylcarbonyl)

amino]-5-(methylsulfonyl)iodobenzene (7.42 g, 86%) was prepared from Boc-piperazine and 2-iodo-4-(methylsulfonyl)aniline.

¹H-NMR

IS-MS, m/e 508.1 (m−1)⁻

Analysis for C₁₇H₂₄N₃O₅IS: Calcd: C, 40.09; H, 4.75; N, 8.25; Found: C, 39.81; H, 4.67; N, 7.99.

B. 2-[1-Boc-piperazin-4-yl]-6-methylsulfonyl-4H-3,1-benzoxazin-4-one

Using methods substantially equivalent to those described in Example 173-E, 2-[1-Boc-piperazin-4-yl]-6-methylsulfonyl-4H-3,1-benzoxazin-4-one (1.05 g, 63%) was prepared from 2-[(1-Boc-piperazin-4-ylcarbonyl)amino]-5-(methylsulfonyl)iodobenzene.

¹H-NMR

IS-MS, m/e 410.1 (m+1)

Analysis for C₁₈H₂₃N₃O₆S: Calcd: C, 52.80; H, 5.66; N, 10.26; Found: C, 52.59; H, 5.47; N, 9.97.

C. 2-[(1-Boc-piperazin-4-ylcarbonyl)amino]-N-(5-chloropyridin-2-yl)-5-(methylsulfonyl)benzamide Using methods substantially equivalent to those described in Example 51-D, 2-[(1-Boc-piperazin-4-ylcarbonyl)amino]-N-(5-chloropyridin-2-yl)-5-(methylsulfonyl)benzamide (0.565 g, 85%) was prepared from 2-[1-Boc-piperazin-4-yl]-6-methylsulfonyl-4H-3,1-benzoxazin-4-one.

¹H-NMR

IS-MS, m/e 538.1 (m+1)

D. N-(5-Chloropyridin-2-yl)-5-(methylsulfonyl)-2-[(piperazin-4-ylcarbonyl)amino]benzamide trifluoroacetate Using methods substantially equivalent to those described in Example 9-B, N-(5-chloropyridin-2-yl)-5-(methylsulfonyl)-2-[(piperazin-4-ylcarbonyl)amino]benzamide trifluoroacetate (1.02 g, 96%) was prepared from 2-[(1-Boc-piperazin-4-ylcarbonyl)amino]-N-(5-chloropyridin-2-yl)-5-(methylsulfonyl)benzamide.

¹H-NMR

IS-MS, m/e 438.0 (m+1)

E. N-(5-Chloropyridin-2-yl)-2-[(1-isopropylpiperazin-4-ylcarbonyl)amino]-5-(methylsulfonyl)benzamide Using methods substantially equivalent to those described in Example 27, N-(5-chloropyridin-2-yl)-2-[(1-isopropylpiperazin-4-ylcarbonyl)amino]-5-(methylsulfonyl)benzamide (0.34 g, 77%) was prepared from N-(5-chloropyridin-2-yl)-5-(methylsulfonyl)-2-[(piperazin-4-ylcarbonyl)amino]benzamide trifluoroacetate.

¹H-NMR

IS-MS, m/e 480.1 (m+1)

Analysis for C₂₁H₂₆N₅O₄SCl: Calcd: C, 52.55; H, 5.46; N, 14.59; Found: C, 52.25; H, 5.33; N, 14.23.

EXAMPLE 176

Preparation of N-(5-Chloropyridin-2-yl)-5-(N,N-dimethylaminosulfonyl)-2-[(4-isopropylpiperazin-1-ylcarbonyl)amino]benzamide Hydrochloride

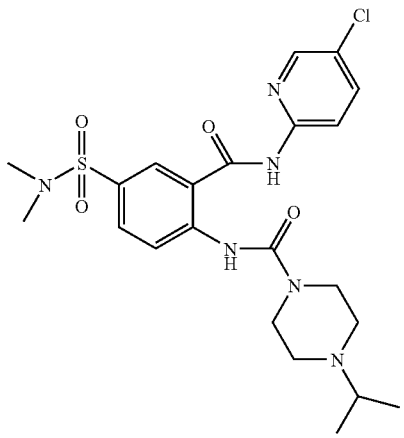

A. 2-[(1-Boc-piperazin-4-ylcarbonyl)amino]-5-(N,N-dimethylaminosulfonyl)iodobenzene Using methods substantially equivalent to those described in Example 51-A, 2-[(1-Boc-piperazin-4-ylcarbonyl)amino]-5-(N,N-dimethylaminosulfonyl)iodobenzene (6.58 g, 79%) was prepared from 2-iodo-4-(N,N-dimethylaminosulfonyl)aniline.

¹H-NMR

IS-MS, m/e 537.1 (m−1)⁻

B. 2-(1-Boc-piperazin-4-yl)-6-(N,N-dimethylaminosulfonyl)-4H-3,1-benzoxazin-4-one Using methods substantially equivalent to those described in Example 173-E, 2-(1-Boc-piperazin-4-yl)-6-(N,N-dimethylaminosulfonyl)-4H-3,1-benzoxazin-4-one (0.98 g, 60%) was prepared from 2-[(1-Boc-piperazin-4-ylcarbonyl)amino]-5-(N,N-dimethylaminosulfonyl)iodobenzene.

¹H-NMR

IS-MS, m/e 438.1 (m+1)

Analysis for C₁₉H₂₆N₄O₆S: Calcd: C, 52.04; H, 5.98; N, 12.78; Found: C, 52.10; H, 5.90; N, 12.73.

C. 2-[(1-Boc-piperazin-4-ylcarbonyl)amino]-N-(5-chloropyridin-2-yl)-5-(N,N-dimethylaminosulfonyl)benzamide Using methods substantially equivalent to those described in Example 51-D, 2-[(1-Boc-piperazin-4-ylcarbonyl)amino]-N-(5-chloropyridin-2-yl)-5-(N,N-dimethylaminosulfonyl)benzamide (0.963 g, 82%) was prepared from 2-(1-Boc-piperazin-4-yl)-6-(N,N-dimethylaminosulfonyl)-4H-3,1-benzoxazin-4-one.

¹H-NMR

IS-MS, m/e 567.1 (m+1)

D. N-(5-Chloropyridin-2-yl)-5-(N,N-dimethylaminosulfonyl)-2-[(piperazin-4-ylcarbonyl)amino]benzamide trifluoroacetate Using methods substantially equivalent to those described in Example 9-B, N-(5-chloropyridin-2-yl)-5-(N,N-dimethylaminosulfonyl)-2-[(piperazin-4-ylcarbonyl)amino]benzamide trifluoroacetate (0.908 g, 94%) was prepared from 2-[(1-Boc-piperazin-4-ylcarbonyl)amino]-N-(5-chloropyridin-2-yl)-5-(N,N-dimethylaminosulfonyl)benzamide.

¹H-NMR

IS-MS, m/e 467.1 (m+1)

Analysis for $C_{19}H_{23}N_6O_4SCl \cdot 1.1TFA$: Calcd: C, 42.98; H, 4.10; N, 14.19; F, 10.58; Found: C, 43.05; H, 4.01; N, 13.85; F, 10.40.

E. N-(5-Chloropyridin-2-yl)-5-(N,N-dimethylaminosulfonyl)-2-[(1-isopropylpiperazin-4-ylcarbonyl)amino]benzamide hydrochloride Using methods substantially equivalent to those described in Example 27, N-(5-chloropyridin-2-yl)-5-(N,N-dimethylaminosulfonyl)-2-[(1-isopropylpiperazin-4-ylcarbonyl)amino]benzamide hydrochloride (0.616 g, 84%) was prepared from N-(5-chloropyridin-2-yl)-5-(N,N-dimethylaminosulfonyl)-2-[(piperazin-4-ylcarbonyl)amino]benzamide trifluoroacetate.

¹H-NMR

IS-MS, m/e 509.1 (m+1)

Analysis for $C_{22}H_{29}N_6O_4SCl \cdot 1.8HCl \cdot 1.6H_2O$: Calcd: C, 43.65; H, 5.70; N, 13.89; Cl, 16.40; Found: C, 43.72; H, 5.56; N, 13.54; Cl, 16.46.

EXAMPLE 177

Preparation of N-(5-Chloropyridin-2-yl)-2-(1-isopropylpiperidin-4-ylmethylamino)-4-methoxycarbonylbenzmide

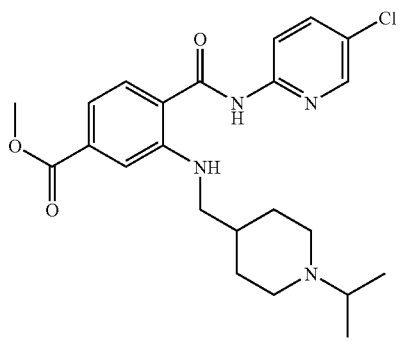

A. N-(5-Chloropyridin-2-yl)-4-methoxycarbonyl-2-nitrobenzamide

Using a similar procedure to that described in Example 1-A, 4-methoxycarbonyl-2-nitrobenzoic acid (1.87 g, 8.31 mmol) and 2-amino-5-chloropyridine (1.16 g, 9.14 mmol) afforded 2.05 g (74%) of the title compound.

¹H-NMR, IR

IS-MS, m/e 336 (m+1)

Analysis for $C_{14}H_{10}ClN_3O_5$: Calcd: C, 50.09; H, 3.00; N, 12.52; Found: C, 49.73; H, 2.94; N, 12.19.

B. 2-Amino-N-(5-chloropyridin-2-yl)-4-methoxycarbonylbenzamide

Using a similar procedure to that described in Example 2-B, N-(5-chloropyridin-2-yl)-4-methoxycarbonyl-2-nitrobenzamide (2.00 g, 5.99 mmol) afforded 1.50 g (82%) of the title compound.

¹H-NMR, IR

IS-MS, m/e 305 (m+1)

Analysis for $C_{14}H_{12}ClN_3O_3$: Calcd: C, 55.00; H, 3.96; N, 13.74; Found: C, 54.43; H, 3.68; N, 13.64.

C. N-(5-Chloropyridin-2-yl)-4-methoxycarbonyl-2-(piperidin-4-ylmethylamino)benzamide Using a similar procedure to that described in Example 47-C&D, 2-amino-N-(5-chloropyridin-2-yl)-4-methoxycarbonylbenzamide (1.00 g, 3.28 mmol), 1-tert-butoxycarbonylpiperidine-4-carboxaldehyde (1.05 g, 4.92 mmol), and borane trimethylamine complex (717 mg, 9.94 mmol) afforded 1.10 g (84%) of the title compound.

¹H-NMR

IS-MS, m/e 403 (m+1)

D. N-(5-Chloropyridin-2-yl)-2-(1-isopropylpiperidin-4-ylmethylamino)-4-methoxycarbonylbenzamide Using a similar procedure to that described in Example 9-C, N-(5-chloropyridin-2-yl)-4-methoxycarbonyl-2-(piperidin-4-ylmethylamino)benzamide (230 mg, 0.572 mmol) afforded 168 mg (66%) of the title compound.

¹H-NMR

IS-MS, m/e 445 (m+1)

EXAMPLE 178

Preparation of N-(5-chloropyridin-2-yl)-4-methoxycarbonyl-2-[1-(4-pyridinyl)piperidin-4-ylmethylamino]benzamide

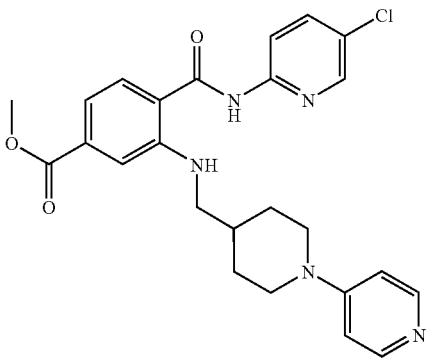

Using a similar procedure to that described in Example 52, N-(5-chloropyridin-2-yl)-4-methoxycarbonyl-2-(piperidin-4-ylmethylamino)benzamide (700 mg, 1.74 mmol) afforded 380 mg (45%) of the title compound.

¹H-NMR, IR

IS-MS, m/e 480 (m+1)

Analysis for $C_{25}H_{26}ClN_6O_3$: Calcd: C, 62.56; H, 5.46; N, 14.59; Found: C, 62.58; H, 5.52; N, 14.51.

EXAMPLE 179

Preparation of 4-Carboxy-N-(5-chloropyridin-2-yl)-2-(1-isopropylpiperidin-4-ylmethylamino)benzamide Hydrochloride

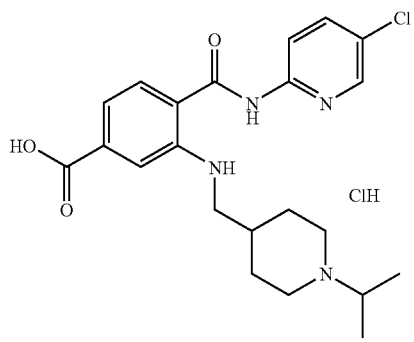

A solution of N-(5-chloropyridin-2-yl)-2-(1-isopropylpiperidin-4-ylmethylamino)-4-methoxycarbonylbenzamide (100 mg, 0.225 mmol) in 4:1 tetrahydrofuran:water (2.5 mL) was treated with lithium hydroxide (20 mg, 0.90 mmol). After 17 h, the pH of the mixture was adjusted to 2–3 by addition of 1 N HCl. The mixture was then concentrated and the residue purified by RPHPLC affording 32 mg (30%) of the title compound as a hydrochloride salt.

$^1$H-NMR
IS-MS, m/e 431 (m+1)

EXAMPLE 180

Preparation of 4-Carboxy-N-(5-chloropyridin-2-yl)-2-[1-(4-pyridinyl)piperidin-4-ylmethylamino]benzamide Dihydrochloride

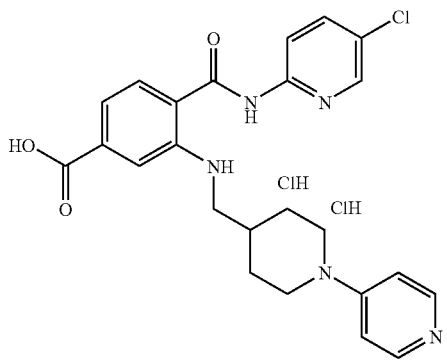

Using a similar procedure to that described in Example 179, N-(5-chloropyridin-2-yl)-4-methoxycarbonyl-2-[1-(4-pyridinyl)piperidin-4-ylmethylamino]benzamide (180 mg, 0.376 mmol) afforded 125 mg (62%) of the title compound as a hydrochloride salt.

$^1$H-NMR, IR
IS-MS, m/e 466 (m+1)
Analysis for $C_{24}H_{24}ClN_5O_3$ (3.0 HCl, 1.5 $H_2O$): Calcd: C, 47.86; H, 5.02; N, 11.63; Found: C, 47.81; H, 4.91; N, 11.43.

EXAMPLE 181

Preparation of N-(5-Chloropyridin-2-yl)-2-[1-(2-thiocarbamoylpyridin-4-yl)piperidin-4-ylmethylamino]benzamide

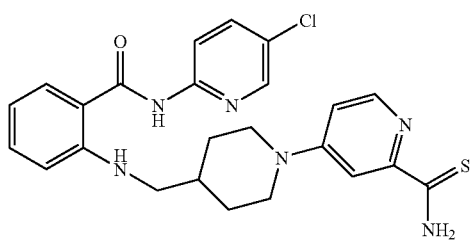

A pressure tube was charged with N-(5-chloropyridin-2-yl)-2-[1-(2-cyanopyridin-4-yl)piperidin-4-ylmethylamino]benzamide (50 mg, 0.11 mmol) and 1:2 methanol:tetrahydrofuran (3 mL); and the solution was treated with ammonia (g), sealed, and allowed to stir for 2 days. The mixture was then treated with hydrogen sulfide (g), sealed and allowed to stir for 2 days. The mixture was concentrated and the residue purified by column chromatography ($SiO_2$: 2% methanol in methylene chloride) affording 38 mg (70%) of the title compound.

$^1$H-NMR, IR
IS-MS, m/e 481 (m+1)
Analysis for $C_{24}H_{25}ClN_6OS$ 0.25 $H_2O$: Calcd: C, 59.37; H, 5.29; N, 17.31; Found: C, 59.04; H, 5.04; N, 16.65.

EXAMPLE 182

Preparation of N-(5-Chloropyridin-2-yl)-2-[1-(2-carbamoylpyridin-4-yl)piperidin-4-ylmethylamino]benzamide

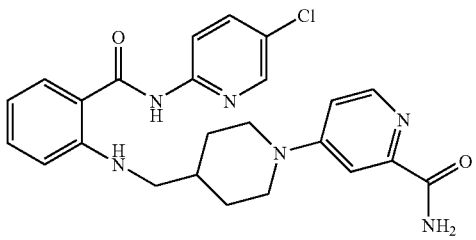

A pressure tube was charged with N-(5-chloropyridin-2-yl)-2-[[1-(3-methoxycarbonylpyridin-4-yl)piperidin-4-ylmethyl]amino]benzamide (50 mg, 0.10 mmol) and 2 N ammonia in methanol (5 mL), sealed, and placed in a 110° C. bath. After 4 h, the mixture was transfered to a 60° C. bath. After 3 days, the mixture was cooled, concentrated, and the residue purified by column chromatography ($SiO_2$, 2% methanol in methylene chloride) affording 48 mg (96%) of the title compound.

$^1$H-NMR, IR
IS-MS, m/e 465 (m+1)

EXAMPLE 183

Preparation of N-(5-Chloropyridin-2-yl)-2-[1-[2-(hydroxymethyl)pyridin-4-yl]piperidin-4-ylmethylamino]benzamide Trifluoroacetic Acid Salt

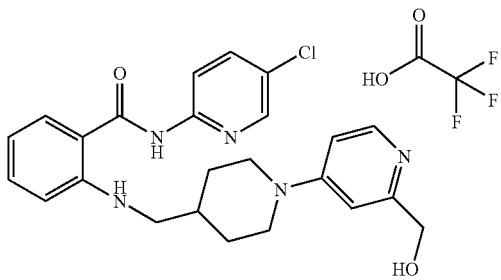

A solution of N-(5-chloropyridin-2-yl)-2-[[1-(3-methoxycarbonylpyridin-4-yl)piperidin-4-ylmethyl]amino]benzamide (200 mg, 0.42 mmol) in tetrahydrofuran was treated with lithium aluminum hydride (1 M in THF, 0.83 mL, 0.83 mmol). After 2 h, additional lithium aluminum hydride was introduced (0.42 mL, 0.42 mmol). After 0.5 h, the mixture was treated with water, 1 N NaOH, and a saturated aqueous solution of sodium potassium tartrate. The mixture was washed with EtOAc (3×) and the combined extracts were dried with magnesium sulfate, filtered, concentrated, and the residue purified by RPHPLC affording 17 mg (7%) of the title compound as a trifluoroacetate salt.

$^1$H-NMR, IR

IS-MS, m/e 452 (m+1)

Analysis for $C_{26}H_{27}ClF_3N_5O_4$ (6.0 $H_2O$): Calcd: C, 46.33; H, 5.83; N, 10.38; Found: C, 46.08; H, 5.68; N, 11.01.

EXAMPLE 184

Preparation of 5-Chloro-N-(5-methylpyridin-2-yl)-2-{[1-(tetrahydrothiopyran-4-yl)piperidin-4-yl]methylamino}benzamide

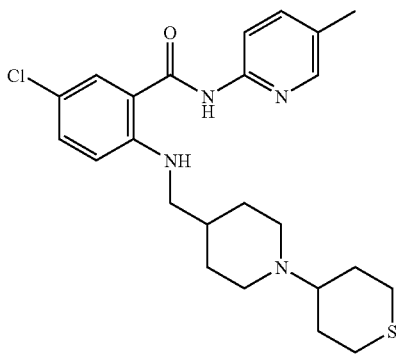

5-Chloro-N-(5-methylpyridin-2-yl)-2-[(4-piperidinylmethyl)amino]benzamide from Example 99-A (0.45 g, 1.25 mmol) was dissolved in 95:5 methanol-acetic acid (10 mL), followed by addition of tetrahydrothiopyran-4-one (1.46 g, 12.6 mmol) and sodium cyanoborohydride (5.0 mL of a 1 M solution in tetrahydrofuran, 6.0 mmol). After stirring at 50° C. for 96 h, the mixture was concentrated in vacuo; and the residue was directly subjected to silica gel chromatography. Elution with 9:1 dichloromethane-methanol provided 0.23 g (40%) of the title product as a yellow solid.

$^1$NMR mp 173–176° C.

MS, m/e 459.3 (M+).

Analysis for $C_{24}H_{32}ClN_4OS$: Calcd: C, 62.80; H, 6.81; N, 12.20; Found: C, 62.75; H, 6.71; N, 12.05.

EXAMPLE 185

Preparation of 5-Chloro-N-(5-methylpyridin-2-yl)-2-([1-(1,1-dioxohexabydro-1$\lambda^6$-thiopyran-4-yl)piperidine-4-yl]methylamino)benzamide

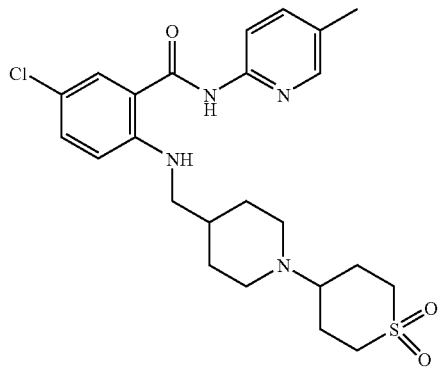

To a solution of 5-chloro-N-(5-methylpyridin-2-yl)-2-([1-(tetrahydrothiopyran-4-yl)piperidin-4-yl]methylamino)benzamide from Example 184 (1.0 g, 2.2 mmol) in 20 mL of dichloromethane, 50% m-chloroperoxybenzoic acid was added (1.88 g, 10.9 mmol). The solution was stirred at room temperature overnight, then concentrated in vacuo and taken up in a few mL of methanol. The crude solution was directly applied to a 10 g SCX column, flushed with methanol, and eluted with 9:1 dichloromethane-2 M ammonia in methanol. Two products were isolated; the minor one (18 mg of an orange solid) was identified as the title product by MS.

mp 154–156° C.

$^{1,13}$NMR, IR

MS, m/e 491.0 (M+).

EXAMPLE 186

Preparation of 5-Chloro-N-(5-methylpyridin-2-yl)-2-[(1-cycloheptylpiperidin-4-yl)methylamino]benzamide

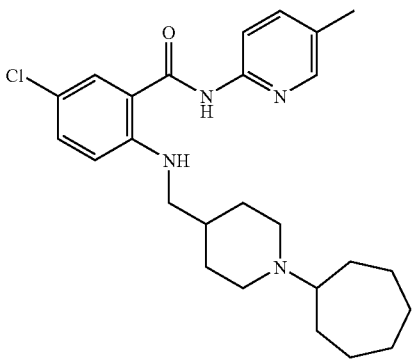

A solution of 5-chloro-N-(5-methylpyridin-2-yl)-2-[(4-piperidinylmethyl)amino]benzamide from Example 99-A (0.45 g, 1.25 mmol) in 10 mL of 95:5 methanol-acetic acid was treated with excess cycloheptanone (1.48 mL, 12.5 mmol), followed by sodium cyanoborohydride (5.0 ml of a 1 M solution in tetrahydrofuran, 6.0 mmol). After stirring at 50° C. for 96 h, the mixture was concentrated in vacuo; and the residue was subjected to silica gel chromatography. Elution with 9:1 dichloromethane-methanol provided 0.41 g (72%) of the title compound as an off-white solid.

¹NMR
mp 159–161° C.
MS, m/e 455.3 (M+).
Analysis for $C_{26}H_{35}ClN_4O \cdot 0.5H_2O$: Calcd: C, 67.30; H, 7.82; N, 12.07; Found: C, 67.85; H, 7.48; N, 12.09.

EXAMPLE 187

Preparation of 5-Chloro-N-(5-methylpyridin-2-yl)-2-[(1-sec-butylpiperidin-4-yl)methylamino]benzamide

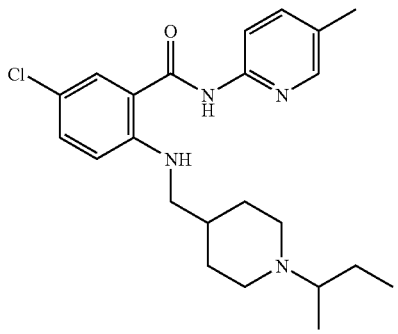

A solution of 5-chloro-N-(5-methylpyridin-2-yl)-2-[(4-piperidinylmethyl)amino]benzamide from Example 99-A (0.45 g, 1.25 mmol) in 10 mL of 95:5 methanol-acetic acid was treated with methylethyl ketone (1.12 mL, 12.5 mmol), followed by sodium cyanoborohydride (5.0 ml of a 1 M solution in tetrahydrofuran, 6.0 mmol). After stirring at 50° C. for 96 h, the mixture was concentrated in vacuo; and the residue was subjected to silica gel chromatography. Elution with 9:1 dichloromethane-methanol afforded 0.26 g (50%) of the title compound as a tan solid.

¹NMR
mp 126–128° C.
MS, m/e 415.2 (M+).
Analysis for $C_{23}H_{31}ClN_4O \cdot 1H_2O$: Calcd: C, 63.80; H, 7.68; N, 12.93; Found: C, 63.99; H, 7.20; N, 12.93

EXAMPLE 188

Preparation of 5-Chloro-N-(5-methylpyridin-2-yl)-2-{[1-(3-pentyl)piperidin-4-yl]methylamino}benzamide

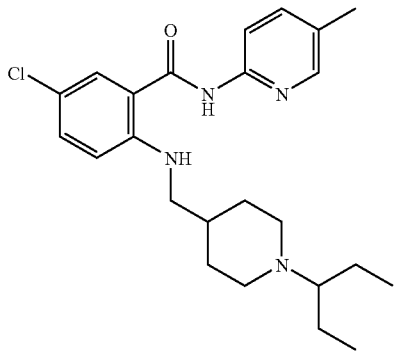

A solution of 5-chloro-N-(5-methylpyridin-2-yl)-2-[(4-piperidinylmethyl)amino]benzamide from Example 99-A (0.45 g, 1.25 mmol) in 10 mL of 95:5 methanol-acetic acid was treated with excess 3-pentanone (1.32 mL, 12.5 mmol), followed by sodium cyanoborohydride (5.0 ml of a 1 M solution in tetrahydrofuran, 6.0 mmol). After stirring at 50° C. for 96 h, the mixture was concentrated in vacuo; and the residue was subjected to silica gel chromatography. Elution with 9:1 dichloromethane-methanol furnished 0.21 g (39%) of the title compound as a yellow solid.

¹NMR
mp 122–124° C.
MS, m/e 429.3 (M+).
Analysis for $C_{23}H_{31}ClN_4O$: Calcd: C, 67.19; H, 7.75; N, 13.06; Found: C, 66.71; H, 7.59; N, 12.96.

EXAMPLE 189

Preparation of 5-Chloro-N-(5-methylpyridin-2-yl)-2-[(1-cyclohexylpiperidin-4-yl)methylamino]benzamide

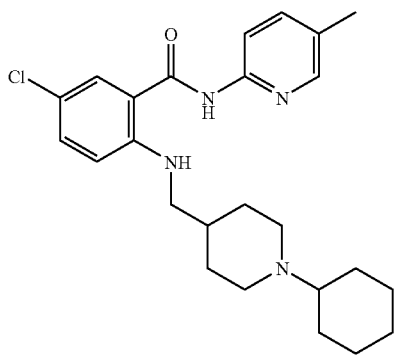

A solution of 5-chloro-N-(5-methylpyridin-2-yl)-2-[(4-piperidinylmethyl)amino]benzamide from Example 99-A (0.45 g, 1.25 mmol) in 10 ml of 95:5 methanol-acetic acid was treated with excess cyclohexanone (1.30 mL, 12.5 mmol), followed by sodium cyanoborohydride (5.0 ml of a 1 M solution in tetrahydrofuran, 6.0 mmol). After stirring at 50° C. for 48 h, the mixture was concentrated in vacuo; and the residue was subjected to silica gel chromatography. Elution with 9:1 dichloromethane-methanol afforded 0.34 g (62%) of the title compound as a yellow solid.

¹NMR
mp 176.4–177.8° C.
MS, m/e 441.3 (M+).
Analysis for $C_{25}H_{33}ClN_4O$: Calcd: C, 68.09; H, 7.54; N, 12.70; Found: C, 68.37; H, 7.67; N, 12.78.

EXAMPLE 190

Preparation of 5-Chloro-N-(5-methylpyridin-2-yl)-2-{[1-(tetrahydropyran-4-yl)piperidin-4-yl]methylamino}benzamide

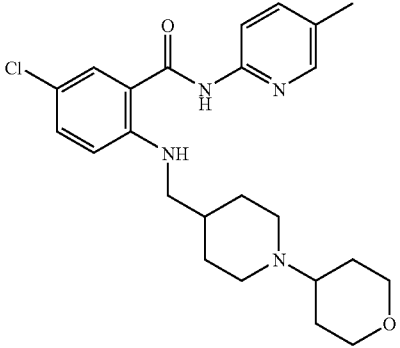

A solution of 5-chloro-N-(5-methylpyridin-2-yl)-2-[(4-piperidinylmethyl)amino]benzamide from Example 99-A (0.45 g, 1.25 mmol) in 10 mL of 95:5 methanol-acetic acid was treated with excess tetrahydro-4H-pyran-4-one (1.16 mL, 12.5 mmol), followed by sodium cyanoborohydride (5.0 ml of a 1 M solution in tetrahydrofuran, 6.0 mmol). After stirring at 50° C. for 36 h, the mixture was concentrated in vacuo; and the residue was subjected to silica gel chromatography. Elution with 9:1 dichloromethane-2 M ammonia in methanol afforded 0.51 g (93%) of the title compound as a yellow solid.

¹NMR mp 166–168° C.

MS, m/e 443.2 (M+).

Analysis for $C_{24}H_{31}ClN_4O_2$: Calcd: C, 65.07; H, 7.05; N, 12.65; Found: C, 65.04; H, 6.84; N, 12.56.

EXAMPLE 191

Preparation of 5-Chloro-N-(5-methylpyridin-2-yl)-2-{[1-(tetrahydrothiophen-3-yl)piperidin-4-yl]methylamino}benzamide

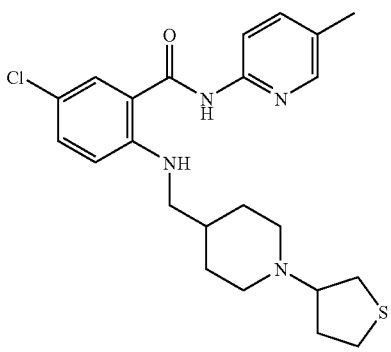

A solution of 5-chloro-N-(5-methylpyridin-2-yl)-2-[(4-piperidinylmethyl)amino]benzamide from Example 99-A (0.45 g, 1.25 mmol) in 10 mL of 95:5 methanol-acetic acid was treated with excess tetrahydrothiophen-3-one (1.07 mL, 12.5 mmol), followed by sodium cyanoborohydride (5.0 ml of a 1 M solution in tetrahydrofuran, 6.0 mmol). After stirring at 50° C. for 96 h, the mixture was concentrated in vacuo; and the residue was subjected to silica gel chromatography. Elution with 9:1 dichloromethane-2 M ammonia in methanol afforded 0.43 g (77%) of the title compound as a yellow solid.

¹NMR mp 151–153° C.

MS, m/e 445.2 (M+).

Analysis for $C_{23}H_{29}ClN_4OS$: Calcd: C, 62.08; H, 6.57; N, 12.59; Found: C, 62.83; H, 6.63; N, 12.52.

EXAMPLE 192

Preparation of 5-chloro-N-(5-methylpyridin-2-yl)-2-{[1-(1,1-dioxotetrahydro-1λ⁶-thiophen-3-yl)piperidin-4-yl]methylamino}benzamide

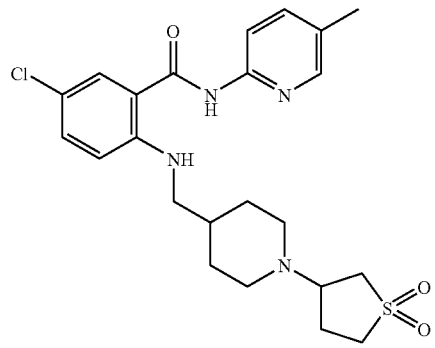

A solution of 5-chloro-N-(5-methylpyridin-2-yl)-2-{[1-(tetrahydrothiophen-3-yl)piperidin-4-yl]methylamino}benzamide from example 191 (0.1 g, 0.22 mmol) in dichloromethane at 0° C. was treated with m-chloroperoxybenzoic acid (84 mg, 0.24 mmol). After 5 h at 0° C., an identical portion of 50% m-chloroperoxybenzoic acid was added. The reaction mixture was kept at 0° C. overnight, before directly applying it to an SCX column. After a thorough wash with methanol, elution with 9:1 dichloromethane-2 M ammonia in methanol provided a crude product, which was submitted to preparative thin layer chromatography. Elution with 9:1 dichloromethane-methanol provided three different product bands. The product with the highest $R_f$ value was assigned to the title sulfone by LC-MS (method B). Isolation of this band provided 30 mg (30%) of the title compound as a yellow foam.

LC-MS: 86% pure, $R_t$=5.425 min, m/e 477.1 (M).

¹NMR, IR.

EXAMPLE 193

Preparation of 5-Chloro-N-(5-methylpyridin-2-yl)-2-[(1-cyclopentylpiperidin-4-yl)methylamino]benzamide

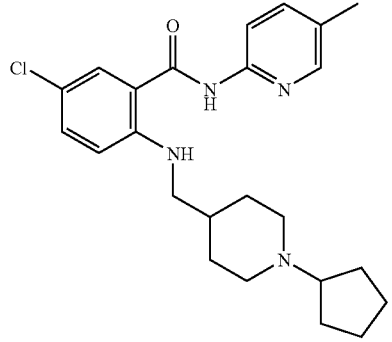

A solution of 5-chloro-N-(5-methylpyridin-2-yl)-2-[(4-piperidinylmethyl)amino]benzamide from Example 99-A (0.45 g, 1.25 mmol) in 10 mL of 95:5 methanol-acetic acid was treated with excess cyclopentanone (1.11 mL, 12.5 mmol), followed by sodium cyanoborohydride (5.0 ml of a 1 M solution in tetrahydrofuran, 6.0 mmol). After stirring at 50° C. for 36 h, the mixture was concentrated in vacuo; and the residue was subjected to silica gel chromatography.

Elution with 9:1 dichloromethane-2 M ammonia in methanol afforded 0.31 g (58%) of the title compound as a yellow solid.

$^1$NMR mp 150–152° C.

MS, m/e 427.2 (M+).

Analysis for $C_{24}H_{31}ClN_4O$: Calcd: C, 67.51; H, 7.32; N, 13.12; Found: C, 66.91; H, 7.12; N, 13.17.

EXAMPLE 194

Preparation of 5-Chloro-N-(5-methylpyridin-2-yl)-2-{[1-(1-cyclopropylethyl)piperidin-4-yl]methylamino}benzamide hydrochloride

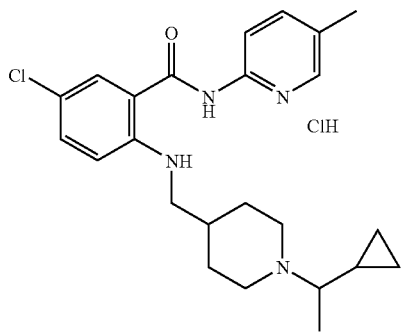

A solution of 5-chloro-N-(5-methylpyridin-2-yl)-2-[(4-piperidinylmethyl)amino]benzamide from Example 99-A (0.45 g, 1.25 mmol) in 10 mL of 95:5 methanol-acetic acid was treated with excess cyclopropylmethyl ketone (1.24 mL, 12.5 mmol), followed by sodium cyanoborohydride (5.0 ml of a 1 M solution in tetrahydrofuran, 6.0 mmol). After stirring at 50° C. for 48 h, the mixture was concentrated in vacuo; and the residue was subjected to silica gel chromatography. Elution with 9:1 dichloromethane-2 M ammonia in methanol afforded 0.27 g of impure free-base product. Subsequent purification by reverse phase HPLC provided 34 mg of the pure title hydrochloride as a yellow solid.

$^1$NMR

MS, m/e 461.0 (M+).

Analysis for $C_{24}H_{31}ClN_4O \cdot 2.5$ HCl: Calcd: C, 55.63; H, 6.52; N, 10.81; Found: C, 56.30; H, 6.54; N, 10.32.

EXAMPLE 195

Preparation of 5-Chloro-N-(5-chloropyridin-2-yl)-2-{[1-(1-cyclopropylethyl)piperidin-4-yl]methylamino}benzamide

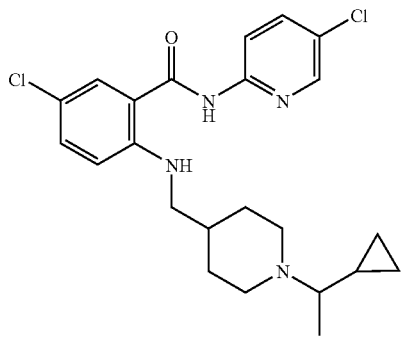

A solution of 5-chloro-N-(5-chloropyridin-2-yl)-2-[(4-piperidinylmethyl)amino]benzamide from Example 60 (60 mg, 0.16 mmol) in 500 μL of 95:5 methanol-acetic acid was prepared in a 4 mL sealable vial. To this was added excess cyclopropylmethyl ketone (156 μL, 1.6 mmol), followed by sodium cyanoborohydride (630 μl of a 1 M solution in tetrahydrofuran, 0.63 mmol). The vial was capped and placed in a shaker, heated at 50° C. for 96 h. The reaction mixture was then applied to an SCX column, washed with methanol and eluted with 1 N ammonia in methanol. The yellow fractions were combined and concentrated in vacuo to a dry residue, which was purified by preparative thin layer chromatography. Elution with 9:1 dichloromethane-methanol provided 13 mg (18%) of a yellow residue, which was identified as the title compound by LC-MS (Method A).

$^1$NMR

LC-MS: 97% pure, $R_t$=7.958 min, m/e 447.1 (M+).

EXAMPLE 196

Preparation of 5-chloro-N-(5-chloropyridin-2-yl)-2-[(1-cyclopentylpiperidin-4-yl)methylamino]benzamide

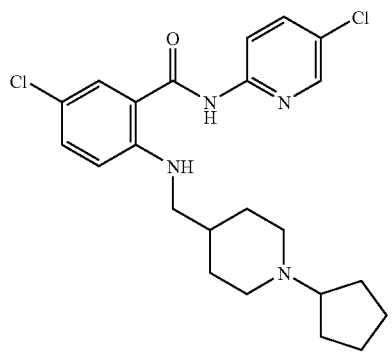

In a manner similar to that described in Example 195, 5-chloro-N-(5-chloropyridin-2-yl)-2-[(4-piperidinylmethyl)amino]benzamide from Example 60 (60 mg, 0.16 mmol) was converted to the title compound (46 mg, 65%), which was identified as by LC-MS (Method A).

$^1$NMR mp 169.5–171.0° C.

LC-MS: 99% pure, $R_t$=7.911 min, m/e 447.1 (M+).

Analysis for $C_{23}H_{28}Cl_2N_4O$: Calcd: C, 61.75; H, 6.31; N, 12.52; Found: C, 61.19; H, 6.21; N, 12.25.

EXAMPLE 197

Preparation of 5-Chloro-N-(5-chloropyridin-2-yl)-2-[(1-cyclohexylpiperidin-4-yl)methylamino]benzamide

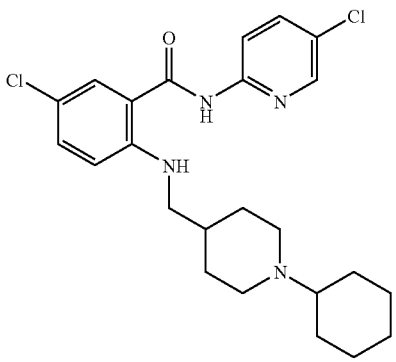

In a manner similar to that described in Example 195, 5-chloro-N-(5-chloropyridin-2-yl)-2-[(4-piperidinylmethyl)

amino]benzamide from Example 60 (60 mg, 0.16 mmol) was converted to the title compound (49 mg, 67%), which was identified by LC-MS (Method A).
¹NMR
mp 186–188° C.
LC-MS: 90% pure, $R_t$=8.310 min, m/e 461.1 (M+).
Analysis for $C_{24}H_{30}Cl_2N_4O$: Calcd: C, 62.47; H, 6.55; N, 12.14; Found: C, 62.21; H, 6.27; N, 12.20.

EXAMPLE 198

Preparation of 5-Chloro-N-(5-chloropyridin-2-yl)-2-{[1-(tetrahydropyran-4-yl)piperidin-4-yl]methylamino}benzamide

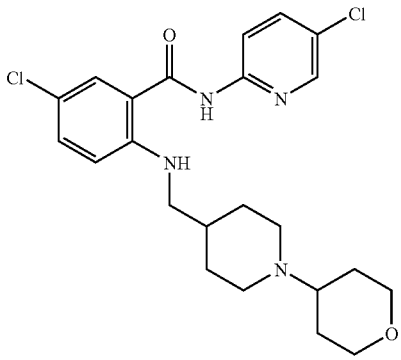

In a manner similar to that described in Example 195, 5-chloro-N-(5-chloropyridin-2-yl)-2-[(4-piperidinylmethyl)amino]benzamide from Example 60 (60 mg, 0.16 mmol) was converted to the title compound (60 mg, 82%), which was identified by LC-MS (Method A).
¹NMR
mp 192–194° C.
LC-MS: 94% pure, $R_t$=7.169 min, m/e 463.1 (M+).
Analysis for $C_{23}H_{28}Cl_2N_4O_2 \cdot 0.1\ CH_2Cl_2$: Calcd: C, 58.90; H, 6.00; N, 11.84; Found: C, 58.83; H, 6.04; N, 11.66.

EXAMPLE 199

Preparation of 5-Chloro-N-(5-chloropyridin-2-yl)-2-[(1-cycloheptylpiperidin-4-yl)methylamino]benzamide

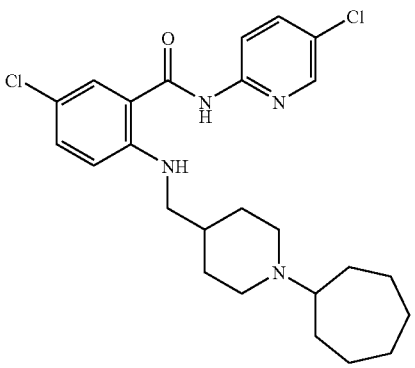

In a manner similar to that described in Example 195, 5-chloro-N-(5-chloropyridin-2-yl)-2-[(4-piperidinylmethyl)amino]benzamide from Example 60 (60 mg, 0.16 mmol) was converted to the title compound (44 mg, 59%), which was identified by LC-MS (Method A).
¹NMR
mp 170.0–171.5° C.

LC-MS: 98% pure, $R_t$=8.652 min, m/e 475.2 (M+).
Analysis for $C_{25}H_{32}Cl_2N_4O$: Calcd: C, 63.15; H, 6.78; N, 11.78; Found: C, 62.93; H, 6.82; N, 11.69.

EXAMPLE 200

Preparation of 5-Chloro-N-(5-chloropyridin-2-yl)-2-{[1-(4,4,4-trifluorobut-2-yl)piperidin-4-yl]methylamino}benzamide

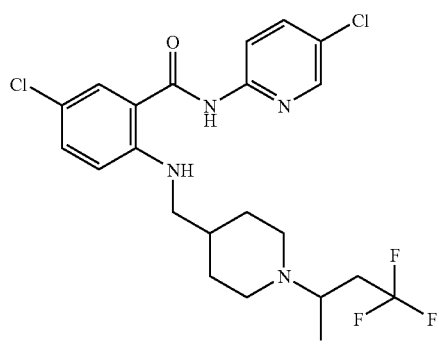

A solution of 5-chloro-N-(5-chloropyridin-2-yl)-2-[(4-piperidinylmethyl)amino]benzamide from Example 60 (0.37 g, 1 mmol) in 11 mL of 95:5 methanol-acetic acid was treated with excess of 4,4,4-trifluorobutan-2-one (1 g, 7.9 mmol), followed by sodium cyanoborohydride (0.25 g, 4 mmol). The reaction mixture was heated at 70° C. overnight, after which a small trace of the desired product was detected by LC-MS analysis. The crude reaction mixture was directly submitted to silica gel chromatography; elution with 9:1 dichloromethane-2 M ammonia in methanol provided a small amount of impure product. Further purification by preparative thin layer chromatography afforded 10 mg of the title compound, identified by LC-MS (Method A).
LC-MS: 91% pure, $R_t$=4.967 min, m/e 489.1 (M+).

EXAMPLE 201

Preparation of 5-Chloro-N-(5-chloropyridin-2-yl)-2-{[1-(tetrahydrothiophen-3-yl)piperidin-4-yl]methylamino}benzamide

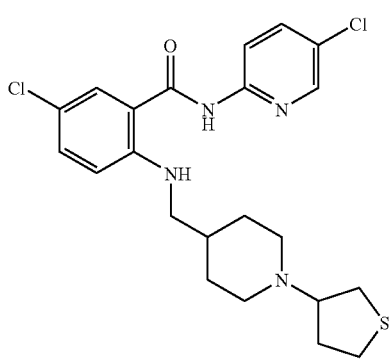

In a manner similar to that described in Example 191, 5-chloro-N-(5-chloropyridin-2-yl)-2-[(4-piperidinylmethyl)amino]benzamide from Example 60 (2.0 g, 5.3 mmol) was converted to the title compound (1.7 g, 69%), which was identified by LC-MS (method A).
¹NMR, IR
mp 177.6–180.6° C.
LC-MS: 98% pure, $R_t$=4.720 min, m/e 465.2 (M+).
Analysis for $C_{22}H_{26}Cl_2N_4OS$: Calcd: C, 56.77; H, 5.63; N, 12.04; Found: C, 56.64; H, 5.67; N, 12.08.

EXAMPLE 202

Preparation of 5-Chloro-N-(5-chloropyridin-2-yl)-2-{[1-(1,1-dioxohexahydro-1λ$^6$-thiopyran-4-yl)piperidin-4-yl]methylamino}benzamide

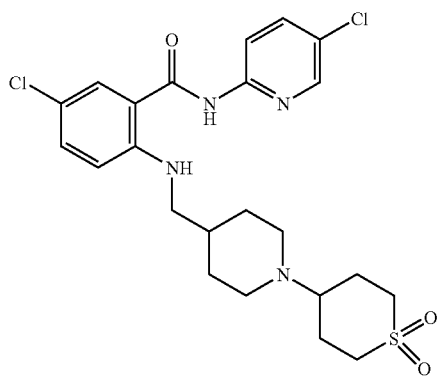

To a solution of 5-chloro-N-(5-chloropyridin-2-yl)-2-{[1-(1,1-hexahydro-1λ$^6$-thiopyran-4-yl)piperidine-4-yl]methylamino}benzamide (0.13 g, 0.27 mol) from Example 112 in 9 mL of chloroform at 0° C., 50% m-chloroperoxybenzoic acid was added (0.13 g, 0.74 mmol). After 4 h at 0° C., the reaction mixture was warmed to room temperature and kept stirring overnight. Since examination of the reaction mixture by LC-MS indicated the presence of starting material, more 50% m-chloroperoxybenzoic acid was added and the reaction was stirred at room temperature for an additional 24 h. The crude mixture was then directly submitted to silica gel chromatography, eluting with 19:1 dichloromethane-2 M ammonia in methanol. Two product bands where thus isolated and identified by LC-MS analysis (method B): the high $R_f$ band corresponded to the title sulfone, and the lower $R_f$ band was assigned as the corresponding sulfoxide described in Example 203. The crude sulfone was further purified by preparative thin layer chromatography, providing the pure title compound (41 mg, 30%) as a white solid.
$^1$NMR
LC-MS: 95% pure, $R_t$=6.919 min, m/e 511.2 (M+).

EXAMPLE 203

Preparation of 5-Chloro-N-(5-chloropyridin-2-yl)-2-{[1-(1-oxohexahydro-1λ$^4$-thiopyran-4-yl)piperidin-4-yl]methylamino}benzamide

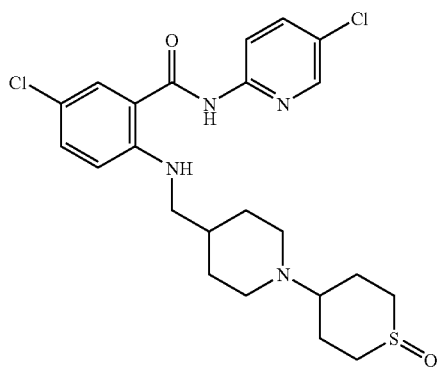

As described in Example 202, 5-chloro-N-(5-chloropyridin-2-yl)-2-{[1-(1,1-hexahydro-1λ$^6$-thiopyran-4-yl)piperidin-4-yl]methylamino}benzamide was converted to the title sulfoxide upon treatment with 50% m-chloroperoxybenzoic acid. The crude product was further purified by preparative thin layer chromatography, which afforded the pure title compound (58 mg, 43%) as a white solid.
$^1$NMR
LC-MS: 95% pure, $R_t$=6.397 min, m/e 495.2 (M+).

EXAMPLE 204

Preparation of N-(5-Chloropyridin-2-yl)-5-methyl-2-[(4-piperidinylmethyl)amino]benzamide

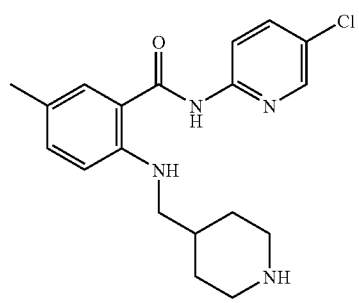

In a manner similar to that described in Example 59, 2-amino-N-(5-chloropyridin-2-yl)-5-methylbenzamide (4.0 g, 15.3 mmol) was converted to the title compound (3.7 g, 67%), which was isolated as a pale-yellow solid.
$^1$NMR
mp 229–231° C.
MS, m/e 358.9 (M+).

EXAMPLE 205

Preparation of N-(5-Chloropyridin-2-yl)-2-[(1-isopropylpiperidin-4-yl)methylamino]-5-methylbenzamide

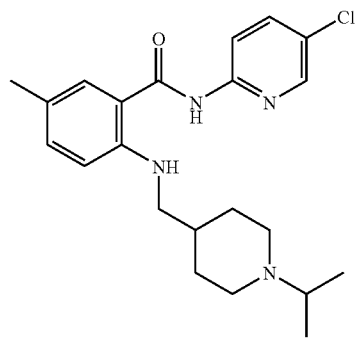

A solution of N-(5-chloropyridin-2-yl)-2-[(4-piperidinylmethyl)amino]-5-methylbenzamide from Example 204 (1.0 g, 2.78 mmol) in 20 mL of acetone and 6 mL of 95:5 methanol-acetic acid was treated with sodium cyanoborohydride (0.70 g, 11.1 mmol). After stirring at room temperature for 24 h, the reaction mixture was applied to a 10 g SCX column, washed with methanol and eluted with 1 N ammonia in methanol. The yellow fractions were combined and concentrated in vacuo, affording 0.76 g (69%) of the title compound as a yellow solid.

¹NMR
mp 172–174° C.
MS, m/e 401.3 (M+).
Analysis for $C_{22}H_{29}ClN_4O$: Calcd: C, 65.90; H, 7.29; N, 13.97; Found: C, 65.65; H, 6.95; N, 13.83.

EXAMPLE 206

Preparation of N-(5-Chloropyridin-2-yl)-2-{[1-(1-cyclopropylethyl)piperidin-4-yl]methylamino}-5-methylbezamide

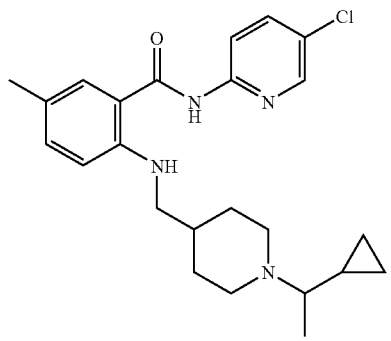

A solution of N-(5-chloropyridin-2-yl)-2-[(4-piperidinylmethyl)amino]-5-methylbenzamide from Example 204 (1.0 g, 2.78 mmol) in 6 mL of 95:5 methanol-acetic acid was treated with excess cyclopropylmethyl ketone (5.52 mL, 55.6 mmol), followed by sodium cyanoborohydride (0.65 g, 10.3 mmol). After stirring at room temperature for 24 hr, the reaction mixture was concentrated in vacuo; and the residue was subjected to silica gel chromatography. Elution with 9:1 dichloromethane-methanol afforded 0.76 g (64%) of the title compound as a yellow solid.
¹NMR
mp 79–81° C.
MS, m/e 427.0 (M+).
Analysis for $C_{24}H_{31}ClN_4O \cdot 0.25CH_2Cl_2$: Calcd: C, 64.51; H, 7.04; N, 12.38; Found: C, 64.59; H, 7.82; N, 14.42.

EXAMPLE 207

Preparation of N-(5-Chloropyridin-2-yl)-2-[(1-cyclohexylpiperidin-4-yl)methylamino]-5-methylbenzamide

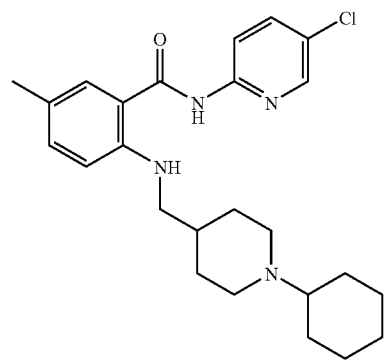

In a manner similar to that described in Example 206, N-(5-chloropyridin-2-yl)-2-[(4-piperidinylmethyl)amino]-5-methylbenzamide from Example 204 (0.45 g, 1.16 mmol) was converted to the title compound (0.34 g, 62%), which was isolated as a yellow solid.
¹NMR
mp 179–182° C.
MS, m/e 441.0 (M+).
Analysis for $C_{25}H_{33}ClN_4O$: Calcd: C, 68.09; H, 7.54; N, 12.70; Found: C, 67.81; H, 7.61; N, 12.76.

EXAMPLE 208

Preparation of N-(5-Chloropyridin-2-yl)-2-[(1-cyclopentylpiperidin-4-yl)methylamino]-5-methylbenzamide

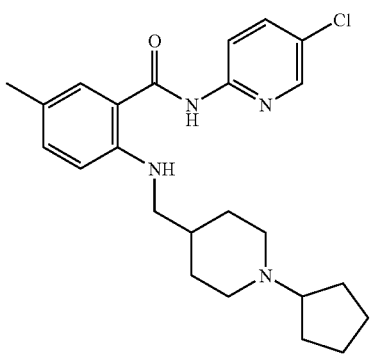

In a manner similar to that described in Example 206, N-(5-chloropyridin-2-yl)-2-[(4-piperidinylmethyl)amino]-5-methylbenzamide from Example 204 (0.45 g, 1.16 mmol) was converted to the title compound (0.28 g, 52%), which was isolated as a yellow solid.
¹NMR
mp 173–175° C.
MS, m/e 427.1 (M+).
Analysis for $C_{24}H_{31}ClN_4O$: Calcd: C, 67.51; H, 7.32; N, 13.12; Found: C, 67.57; H, 7.33; N, 13.07.

EXAMPLE 209

Preparation of N-(5-Chloropyridin-2-yl)-5-methyl-2-{[1-(tetrahydropyran-4-yl)piperidin-4-yl]methylamino}benzamide

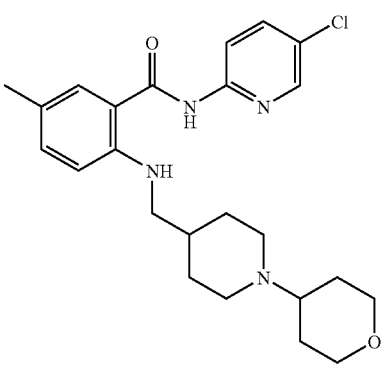

In a manner similar to that described in Example 206, N-(5-chloropyridin-2-yl)-2-[(4-piperidinylmethyl)amino]-5-methylbenzamide from Example 204 (0.45 g, 1.16 mmol)

was converted to the title compund (0.40 g, 73%), which was isolated as a yellow solid.

$^1$NMR mp 178–182° C.

MS, m/e 443.2 (M+).

Analysis for $C_{24}H_{31}ClN_4O_2$: Calcd: C, 65.07; H, 7.05; N, 12.65; Found: C, 64.43; H, 7.07; N, 12.27.

EXAMPLE 210

Preparation of N-(5-Fluoropyridin-2-yl)-2-[(1-isopropylpiperidin-4-yl)methylamino]-5-methylbenzamide

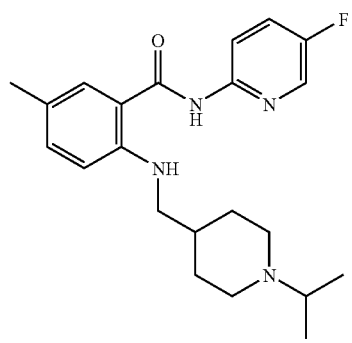

A. N-(5-Fluoropyridin-2-yl)-5-methyl-2-[(4-piperidinylmethyl)amino]benzamide

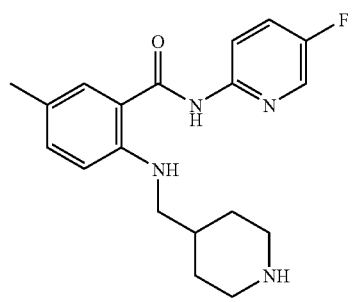

In a manner similar to that described in Example 59, 2-amino-N-(5-fluoropyridin-2-yl)-5-methylbenzamide (3.0 g, 12.2 mmol) was converted to the title compound (3.3 g, 78%), which was isolated as a yellow solid.

$^{1,13}$NMR, IR mp 146.9–149.0° C.

LC-MS (method B): 98% pure, $R_t$=5.897 min, m/e 343.2 (M+1).

Analysis for $C_{19}H_{23}FN_4O\cdot 0.1CH_2Cl_2$: Calcd: C, 65.38; H, 6.66; N, 15.96; Found: C, 65.74; H, 6.43; N, 15.79.

B. N-(5-Fluoropyridin-2-yl)-2-[(1-isopropylpiperidin-4-yl)methylamino]-5-methylbenzamide In a manner similar to that described in Example 205, N-(5-fluoropyridin-2-yl)-5-methyl-2-[(4-piperidinylmethyl)amino]benzamide from Example 210-A (0.43 g, 1.24 mmol) was converted to the title compound (0.30 g, 63%), which was isolated as a yellow solid.

$^1$NMR mp 58–60° C.

MS, m/e 385.1 (M+).

Analysis for $C_{22}H_{29}FN_4O\cdot 1.6H_2O$: Calcd: C, 63.93; H, 7.85; N, 13.55; Found: C, 63.93; H, 7.79; N, 16.14.

EXAMPLE 211

Preparation of 2-[(1-Butyrylpiperidin-4-yl)methylamino]-5-chloro-N-(5-chloropyridin-2-yl)benzamide

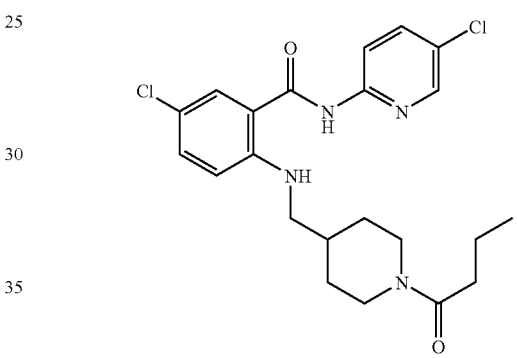

A small sample of 5-chloro-N-(5-chloropyridin-2-yl)-2-[(4-piperidinylmethyl)amino]benzamide from Example 60 (60 mg, 0.16 mmol) was weighed out in a 4 mL sealable vial, followed by (piperidinomethyl)polystyrene (0.12 g, 0.32 mmol). To this was added 10 mL of amylene-stabilized chloroform and butyryl chloride (18.0 µL, 0.17 mmol). The vial was capped and placed in a shaker, where it was kept at room temperature for 24 h, then at 50° C. for 36 h. The crude reaction mixture was then applied to a 2 g SCX column, washed with methanol and eluted with 1 N ammonia in methanol. The yellow fractions were combined and concentrated in vacuo to a dry residue, which was purified by preparative thin layer chromatography. Elution with 9:1 dichloromethane-methanol provided the title compound (9 mg, 13%), isolated in 98% purity by HPLC analysis (Method C: gradient from 50% acetonitrile-50% water with 0.1% trifluoroacetic acid to 90% acetonitrile-10% water with 0.1% trifluoroacetic acid over 10 min; hold 2 min; back to 50% acetonitrile-10% water with 0.1% trifluoroacetic acid over 1 min; hold 2 min; 0.5 ml/min; Waters Symmetry $Cl_{18}$, 3.5 µM column, 4.6 by 75 mm; 25° C.).

$^1$NMR

HPLC: 98% pure, $R_t$=9.967 min.

MS, m/e 448.9 (M+).

EXAMPLE 212

Preparation of 5-Chloro-N-(5-chloropyridin-2-yl)-2-[(1-isobutyrylpiperidin-4-yl)methylamino]benzamide

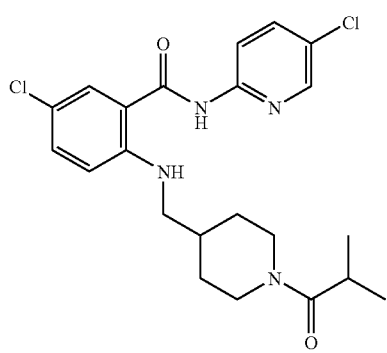

In a manner similar to that described in Example 211, a small sample of 5-chloro-N-(5-chloropyridin-2-yl)-2-[(4-piperidinylmethyl)amino]benzamide from Example 60 (60 mg, 0.16 mmol) was converted to the title compound (23 mg, 33%), isolated in 99% purity by HPLC analysis (Method C, described in Example 211).
$^1$NMR
mp 99–101° C.
HPLC: 99% pure, $R_f$=9.836 min
MS, m/e 448.9 (M+).

EXAMPLE 213

Preparation of 5-Chloro-N-(5-chloropyridin-2-yl)-2-{[1-(thiophene-2-carbonyl)piperidin-4-yl]methylamino}benzamide

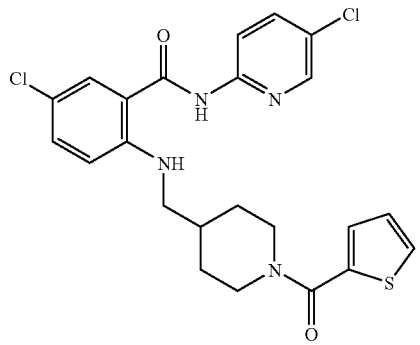

In a manner similar to that described in Example 211, a small sample of 5-chloro-N-(5-chloropyridin-2-yl)-2-[(4-piperidinylmethyl)amino]benzamide from Example 60 (60 mg, 0.16 mmol) was converted to the title compound (38 mg, 49%), isolated in 99% purity by HPLC analysis (method C, described in Example 211).
$^1$NMR
mp 163–165° C.
HPLC: 99% pure, $R_f$=10.542 min, m/e 488.9 (M+).
Analysis for $C_{23}H_{22}Cl_2N_4O_2S \cdot 1.0H_2O$: Calcd: C, 54.44; H, 4.77; N, 11.04; Found: C, 54.87; H, 4.29; N, 10.72.

EXAMPLE 214

Preparation of 5-Chloro-N-(5-chloropyridin-2-yl)-2-{[1-(morpholin-4-ylcarbonyl)piperidin-4-yl]methylamino}benzamide

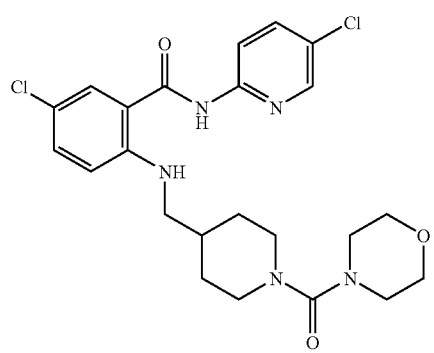

In a manner similar to that described in Example 211, a small sample of 5-chloro-N-(5-chloropyridin-2-yl)-2-[(4-piperidinylmethyl)amino]benzamide from Example 60 (60 mg, 0.16 mmol) was converted to the title compound (35 mg, 45%), isolated in 97% purity by HPLC analysis (Method C, described in Example 211).
$^1$NMR
mp 105–107° C.
HPLC: 97% pure, $R_f$=14.003 min.
MS, m/e 491.9 (M+).
Analysis for $C_{23}H_{27}Cl_2N_5O_3 \cdot 0.5CH_2Cl_2$: Calcd: C, 52.77; H, 5.28; N, 13.09; Found: C, 52.71; H, 5.38; N, 12.68.

EXAMPLE 215

Preparation of 5-Chloro-N-(5-chloropyridin-2-yl)-2-{[1-(3-methoxycarbonylpropionyl)piperidin-4-yl]methylamino}benzamide

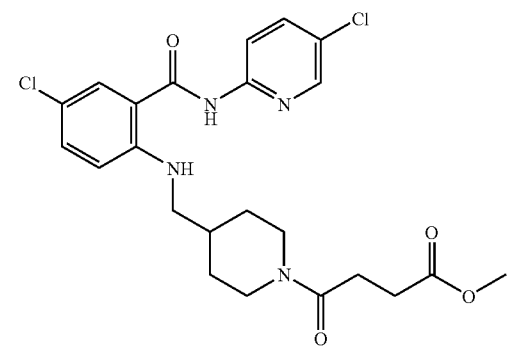

In a manner similar to that described in Example 211, a small sample of 5-chloro-N-(5-chloropyridin-2-yl)-2-[(4-piperidinylmethyl)amino]benzamide from Example 60 (60 mg, 0.16 mmol) was converted to the title compound (23 mg, 29%), isolated in 97% purity by HPLC analysis (Method D, gradient from 20% acetonitrile-80% water with 0.1% trifluoroacetic acid to 70% acetonitrile-30% water with 0.1% trifluoroacetic acid over 10 min; hold 2 min; back to 20% acetonitrile-80% water with 0.1% trifluoroacetic acid over 1 min; hold 2 min; 0.5 mL/min; Waters Symmetry $C_{18}$ 3.5 μM column, 4.6 by 75 mm; 25° C.).

¹NMR
mp 71–74° C.
HPLC: 97% pure, $R_t$=12.692 min.
MS, m/e 492.9 (M+).

EXAMPLE 216

Preparation of 5-Chloro-N-(5-chloropyridin-2-yl)-2-[(1-ethoxycarbonylmethylpiperidin-4-yl)methylamino]benzamide

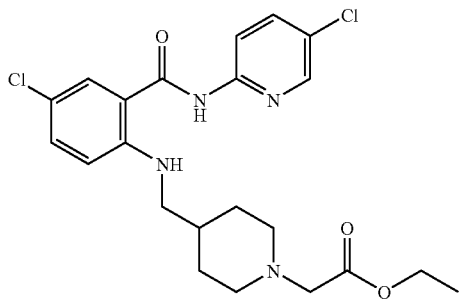

A solution of 5-chloro-N-(5-chloropyridin-2-yl)-2-[(4-piperidinylmethyl)amino]benzamide from Example 60 (0.5 g, 1.32 mmol) in 30 mL of dimethylformamide was treated with excess ethyl bromoacetate (0.7 mL, 6.60 mmol). After heating at 70° C. for 1 h, triethylamine (0.9 ml, 6.6 mmol) was added dropwise; the reaction mixture was then heated at 70° C. for an additional 30 min, after which it was partitioned between saturated sodium bicarbonate and dichloromethane. The organic extract was concentrated in vacuo, and the residue was applied to a 10 g SCX column which was washed with methanol and eluted with 1 N ammonia in methanol. The yellow fractions were combined and concentrated in vacuo to afford an orange oil, which was subjected to silica gel chromatography. Elution with 9:1 dichloromethane-methanol, then 9:3 dichloromethane-methanol provided 0.31 g (51%) of the title compound as a yellow solid.
¹NMR
mp 61–63° C.
MS, m/e 441.3 (M+).
Analysis for $C_{22}H_{26}Cl_2N_4O_3$: Calcd: C, 56.78; H, 5.63; N, 12.04; Found: C, 56.86; H, 5.75; N, 12.23.

EXAMPLE 217

Preparation of 2-[(1-Carboxymethylpiperidin-4-yl)methylamino]-5-chloro-N-(5-chloropyridin-2-yl)benzamide

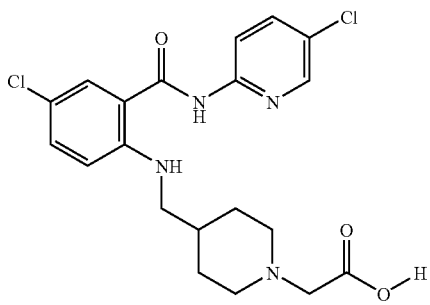

A solution of 5-chloro-N-(5-chloropyridin-2-yl)-2-[(1-ethoxycarbonylmethylpiperidin-4-yl)methylamino]benzamide from Example 216 (1.5 g, 3.2 mmol) in 40 mL of 1:1 tetrahydrofuran-water was treated with sodium hydroxide (0.14 g, 3.50 mmol). After stirring at room temperature for 24 h, the mixture was treated with 3.5 mL of 1 N hydrochloric acid and concentrated in vacuo to remove the tetrahydrofuran. Filtration of the yellow solid formed upon concentration provided the title amino acid (1.35 g, 95%) in 97% purity by HPLC analysis (Method D, described in Example 215).
¹NMR
mp 114–118° C.
HPLC: 97% pure, $R_t$=8.768 min.
MS, m/e 436.9 (M+).

EXAMPLE 218

Preparation of 5-Chloro-N-(5-fluoropyridin-2-yl)-2-[(4-piperidinylmethyl)amino]benzamide

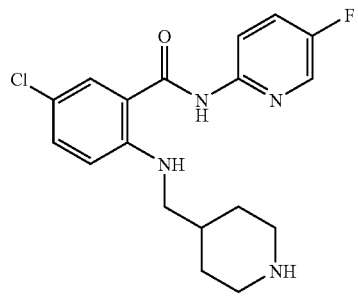

In a manner similar to that described in Example 59, 2-amino-5-chloro-N-(5-fluoropyridin-2-yl)benzamide (5 g, 19 mmol) was converted to the title compound (4.9 g, 71%), which was isolated as a yellow solid.
¹NMR
mp 243–246° C.
MS, m/e 362.9 (M+).
Analysis for $C_{18}H_{20}ClFN_4O\cdot4.0H_2O$: Calcd: C, 49.71; H, 6.49; N, 12.88; Found: C, 49.23; H, 4.75; N, 13.65.

EXAMPLE 219

Preparation of 5-Chloro-N-(5-fluoropyridin-2-yl)-2-[(1-isopropylpiperidin-4-yl)methylamino]benzamide

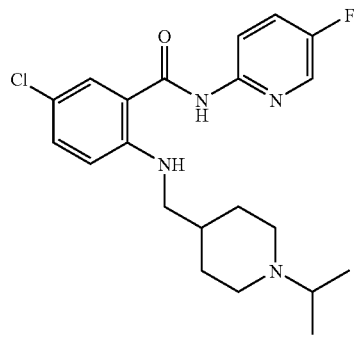

A solution of 5-chloro-N-(5-fluoropyridin-2-yl)-2-[(4-piperidinylmethyl)amino]benzamide from Example 218 (0.50 g, 1.37 mmol) in 10 mL of acetone and 6 mL of 95:5 methanol-acetic acid was treated with sodium cyanoborohydride (0.35 g, 5.5 mmol). After stirring at 50° C. for 24 h, the solution was concentrated in vacuo; and the residue was subjected to silica gel chromatography. Elution with 98:2 dichloromethane-methanol furnished the title compound (0.12 g, 21%) as a yellow solid.
$^1$NMR
mp 72–74° C.
MS, m/e 405.0 (M+).
Analysis for $C_{21}H_{26}ClFN_4O.1.0H_2O$: Calcd: C, 58.40; H, 6.77; N, 13.00; Found: C, 58.22; H, 6.67; N, 14.91.

EXAMPLE 220

Preparation of 5-Chloro-N-(5-chloropyridin-2-yl)-2-{[1-(3-methoxycarbonylpropyl)piperidin-4-yl]methylamino}benzamide

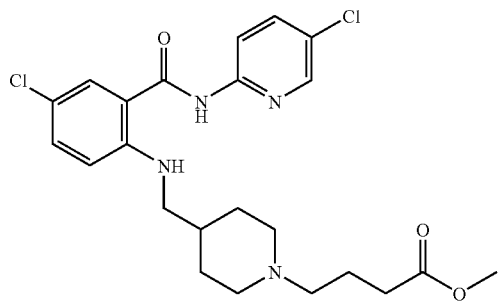

A small sample of 5-chloro-N-(5-chloropyridin-2-yl)-2-[(4-piperidinylmethyl)amino]benzamide from Example 60 (60 mg, 0.16 mmol) was weighed out in a 4 mL sealable vial, followed by methyl 4-bromobutyrate (35 μL, 0.32 mmol). To this was added tetrahydrofuran (1.0 mL) and triethylamine (44 μL, 0.32 mmol). The vial was capped and placed in a shaker where it was kept at 50° C. for 36 h, after which the crude reaction mixture submitted to preparative thin layer chromatography. Elution with 19:1 dichloromethane-methanol provided a tan residue (55 mg, 72%), which was identified as the title compound by LC-MS (Method A).
$^1$NMR
LC-MS: 99% pure, $R_t$=3.819 min. m/e 479.2 (M+).

EXAMPLE 221

Preparation of 2-[(1-Acetylpiperidin-4-yl)methylamino]-5-chloro-N-(5-chloropyridin-2-yl)benzamide

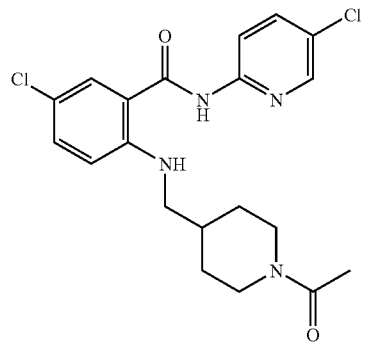

A small sample of 5-chloro-N-(5-chloropyridin-2-yl)-2-[(4-piperidinylmethyl)amino]benzamide from Example 60 (40 mg, 0.11 mmol) was weighed out in a 4 mL sealable vial, followed by addition of acetyl chloride (8 μL, 0.11 mmol), dichloromethane (500 μL) and triethylamine (15 μL, 0.11 mmol). The vial was capped and placed in a shaker, where it was kept at room temperature for 48 h, followed by heating at 50° C. for 96 h. The crude reaction mixture was then submitted to preparative thin layer chromatography to afford a yellow residue (7 mg, 16%), which was identified as the title compound by LC-MS (Method A).
$^1$NMR
LC-MS: 97% pure, $R_t$=7.111 min. m/e 421.1 (M+).

EXAMPLE 222

Preparation of 2-{[1-(3-Carboxypropyl)piperidin-4-yl]methylamino}-5-chloro-N-(5-chloropyridin-2-yl)benzamide

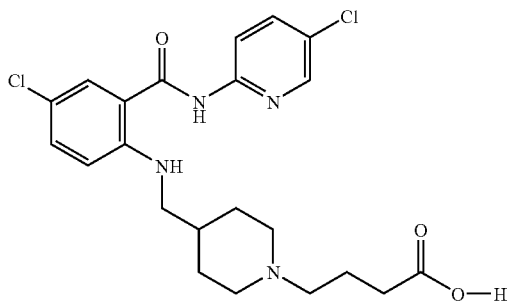

A solution of 5-chloro-N-(5-chloropyridin-2-yl)-2-{[1-(3-methoxycarbonylpropyl)piperidin-4-yl]methylamino}benzamide from Example 220 (32 mg, 0.067 mmol) in 1:1 water-tetrahydrofuran (400 μL) was treated with 1 N aqueous sodium hydroxide (73 μL, 0.073 mmol). The vial was capped and placed in a shaker, heated at 50° C. for 24 h. The crude reaction mixture was directly submitted to preparative thin layer chromatography. Elution with 19:1 dichloromethane-2 M ammonia in methanol furnished a yellow residue (17 mg, 56%), which was identified as the title compound by LC-MS (Method A).
LC-MS: 99% pure, $R_t$=2.891 min, m/e 465.1 (M+).

EXAMPLE 223

Preparation of 5-Chloro-N-(5-chloropyridin-2-yl)-2-{[1-(2-cyano-1-methylethyl)piperidin-4-yl]methylamino}benzamide

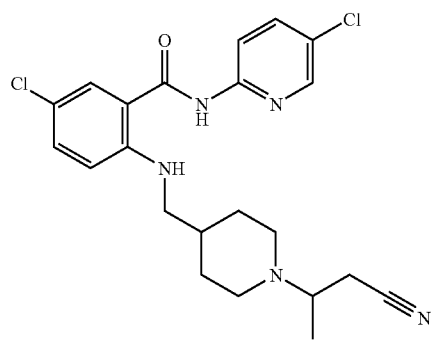

To a sample of 5-chloro-N-(5-chloropyridin-2-yl)-2-[(4-piperidinylmethyl)amino]benzamide from Example 60 (32 mg, 0.067 mmol) in a 4 mL sealable glass vial, was added crotonitrile (26 μL, 0.32 mmol), tetraethyl orthosilicate (70 μL, 0.32 mmol), cesium fluoride (2 mg, 0.016 mmol), and N-methylpyrrolidinone (500 μL). The vial was capped and placed in a shaker, heated at 70° C. for 72 h. The reaction mixture was concentrated in vacuo, and the residue was subjected to silica gel chromatography. Elution with 9:1 dichloromethane-methanol provided a yellow solid (9 mg, 12%), which was identified as the title compound by LC-MS (Method A).

LC-MS: 97% pure, $R_t$=3.272 min, m/e 446.1 (M+).

EXAMPLE 224

Preparation of 5-Chloro-N-(5-chloropyridin-2-yl)-2-{[1-(2-methoxycarbonyl-1-methylethyl)piperidin-4-yl]methylamino}benzamide

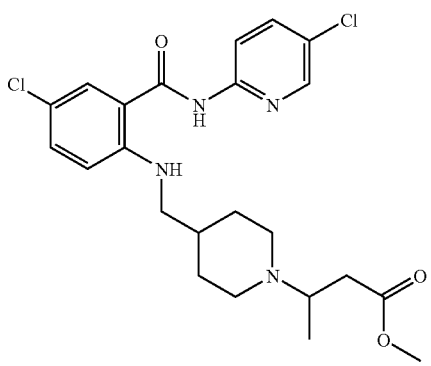

In a manner similar to that described in Example 223, 5-chloro-N-(5-chloropyridin-2-yl)-2-[(4-piperidinylmethyl)amino]benzamide from Example 60 (32 mg, 0.067 mol) was converted to the title compound (7 mg, 9%), which was isolated as a yellow film in 98% purity by HPLC analysis (Method C, described in Example 211).

HPLC: 98% pure, $R_t$=8.024 min.
MS, m/e 477.9 (M+).

EXAMPLE 225

Preparation of 5-Chloro-N-(5-chloropyridin-2-yl)-2-{[1-(2-carbamoylethyl)piperidin-4-yl]methylamino}benzamide

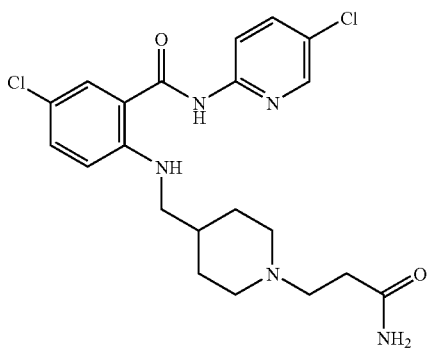

In a manner similar to that described in Example 223, 5-chloro-N-(5-chloropyridin-2-yl)-2-[(4-piperidinylmethyl)amino]benzamide from Example 60 (60 mg, 0.16 mmol) was converted to the title compound (35 mg, 49%), which was isolated as a yellow solid and identified by LC-MS analysis (Method A).

mp 193–196° C.
LC-MS: 99% pure, $R_t$=2.289 min. m/e 450.1 (M+).

EXAMPLE 226

Preparation of 2-{[1-(2-Carboxyethyl)piperidin-4-yl]methylamino}-5-chloro-N-(5-chloropyridin-2-yl)benzamide

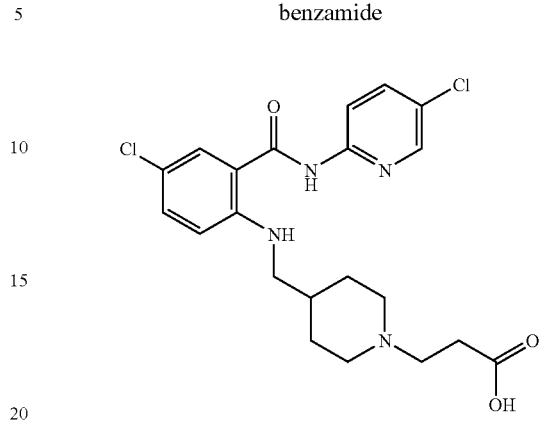

In a manner similar to that described in Example 223, 5-chloro-N-(5-chloropyridin-2-yl)-2-[(4-piperidinylmethyl)amino]benzamide from Example 60 (60 mg, 0.16 mmol) was converted to the title compound (32 mg, 45%), which was isolated as a tan film and identified by LC-MS analysis (Method A).

LC-MS: 99% pure, $R_t$=2.755 min, m/e 451.1 (M+).

EXAMPLE 227

Preparation of N-(5-Chloropyridin-2-yl)-2-[(1-isopropylpiperidin-4-yl)methylamino]-5-methylsulfonylaminobenzamide

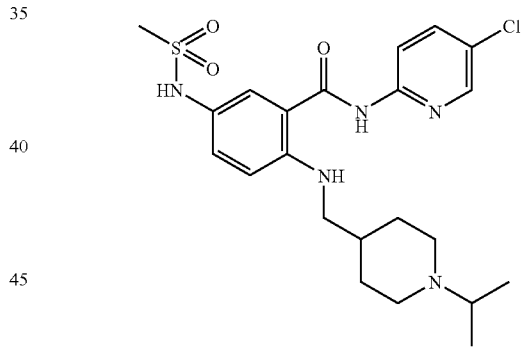

A. N-(5-Chloropyridin-2-yl)-2-[(4-piperidinyl)methylamino]-5-methanesulfonylaminobenzamide

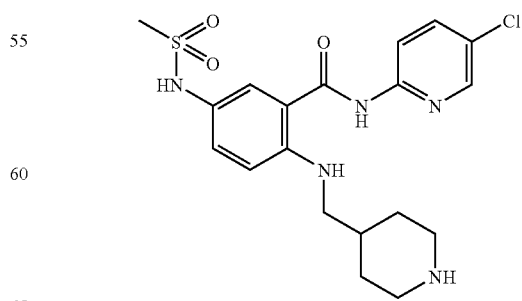

A suspension of 5-amino-N-(5-chloropyridin-2-yl)-2-[(1-Boc-piperidin-4-yl)methylamino]benzamide (0.55 g, 1.2 mmol) in 12 mL of dichloromethane at 0° C. was treated with ethyldiisopropylamine (231 µL, 1.3 mmol) followed by methanesulfonyl chloride (93 µL, 1.2 mmol). The reaction mixture was allowed to reach room temperature overnight, then it was concentrated in vacuo to a crude residue. The residue was directly applied to an SCX column, which was washed with methanol and allowed to stand overnight. Elution with 1:1 dichloromethane-1 N ammonia in methanol provided yellow fractions, which were combined and concentrated in vacuo to a crude residue. Purification by silica gel chromatography, eluting with 9:1 dichloromethane-2 N ammonia in methanol, afforded solid material which was taken up in acetonitrile and sonicated for several minutes. The resulting suspension was filtered, giving rise to the title compound (0.29 g, 56%) as a pale-yellow solid.

$^1$NMR, IR mp 222.8–226.0° C.

MS, m/e 438.2 (M+).

Analysis for $C_{22}H_{30}ClN_5O_3S$: Calcd: C, 52.11; H, 5.52; N, 15.99; Found: C, 52.16; H, 5.39; N, 15.96.

B. N-(5-Chloropyridin-2-yl)-2-[(1-isopropylpiperidin-4-yl)methylamino]-5-methanesulfonylaminobenzamide In a manner similar to that described in Example 205, N-(5-chloropyridin-2-yl)-2-[(piperidin-4-yl)methylamino]-5-methanesulfonylaminobenzamide from Example 227-A (0.29 g, 0.67 mmol) was converted to the title compound (0.29 g, 91%), which was isolated as a pale-yellow solid.

$^1$NMR, IR mp 203.7–205.4° C.

MS, m/e 480.2 (M+).

Analysis for $C_{22}H_{30}ClN_5O_3S$: Calcd: C, 55.05; H, 6.30; N, 14.59; Found: C, 54.84; H, 6.20; N, 14.66.

EXAMPLE 228

Preparation of 5-Chloro-N-(5-chloropyridin-2-yl)-2-{[1-(2-methoxycarbonylethyl)piperidin-4-yl]methylamino}benzamide

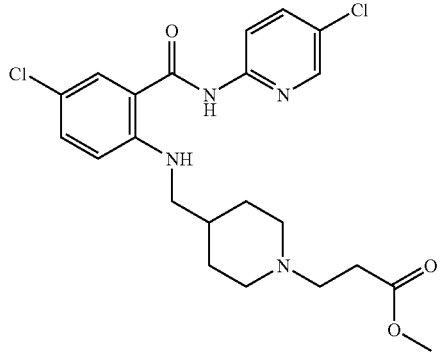

In a manner similar to that described in Example 223, 5-chloro-N-(5-chloropyridin-2-yl)-2-[(4-piperidinylmethyl)amino]benzamide from Example 60 (60 mg, 0.16 mmol) was converted to the title compound (41 mg, 55%), which was isolated as a yellow residue of 98% purity by HPLC analysis (Method D, described in Example 215).

HPLC: 98% pure, $R_t$=9.425 min.

MS, m/e 464.8 (M+).

EXAMPLE 229

Preparation of 5-Chloro-N-(5-chloropyridin-2-yl)-2-{[1-(2-cyanoethyl)piperidin-4-yl]methylamino}benzamide

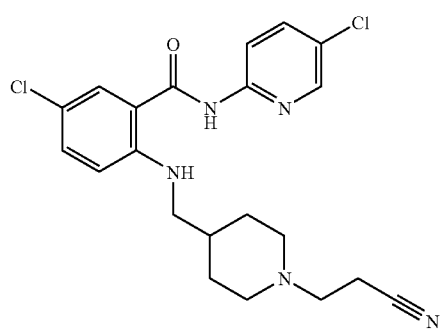

In a manner similar to that described in Example 223, 5-chloro-N-(5-chloropyridin-2-yl)-2-[(4-piperidinylmethyl)amino]benzamide from Example 60 (60 mg, 0.16 mmol) was converted to the title compound (64 mg, 94%), which was isolated as a yellow residue of 98% purity by HPLC analysis (Method D, described in Example 215).

HPLC: 98% pure, $R_t$=9.127 min.

MS, m/e 431.9 (M+).

EXAMPLE 230

Preparation of 2-[(4-tert-Butylpiperazin-1-ylcarbonyl)amino]-N-(5-chloropyridin-2-yl)benzamide

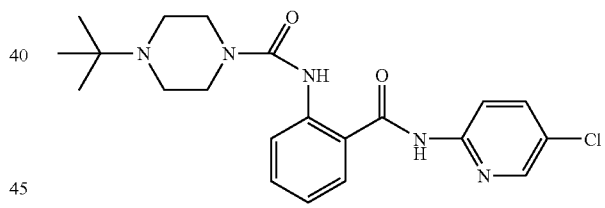

A. 3-(2-Hydroxyethyl)oxazolidin-2-one

A mixture of diethanolamine (12.55 g), diethyl carbonate (16.2 mL), and sodium methoxide (80 mg) was heated to 130–140° C. for 1.5 h and distilled during the reaction using a Dean-Stark trap. The remaining liquid was concentrated in vacuo to give 15.11 g (97%) as a yellow oil.

$^1$H NMR.

B. 3-[2-(4-Toluenesulfonyloxy)ethyl]oxazolidin-2-one

To an ice cold stirring solution of crude 3-(2-hydroxyethyl)oxazolidin-2-one (15.1 g, 115 mmol) in dichloromethane (40 mL) was added triethylamine (18 mL, 129 mmol), and 4-(N,N-dimethylamino)pyridine (0.143 g, 1.2 mmol). A slurry of 4-toluenesulfonyl chloride (25.0 g, 131 mmol) in dichloromethane (50 mL) was then added dropwise. The reaction mixture was stirred for 3 d at room temperature, washed with saturated aqueous sodium bicarbonate, dried over magnesium sulfate, filtered, and concentrated in vacuo. The residue was slurried in isopropanol and filtered to give 23.88 g (73%) of a white solid.

IS-MS, m/e 286.0 (m+1).

C. 3-[2-(tert-Butylamino)]ethyl]oxazolidin-2-one

To a mixture of 3-[2-(4-toluenesulfonyloxy)ethyl]oxazolidin-2-one (2.01 g, 7.04 mmol) and potassium carbonate (0.99 g, 7.2 mmol) in acetonitrile (19 mL) was added tert-butylamine (15 mL). The mixture was heated at reflux for 4 h, and partitioned between dichloromethane and water. The organic phase was dried over magnesium sulfate, filtered, and concentrated in vacuo to give 1.18 g (91%) of a yellow oil.

$^1$H NMR
IS-MS, m/e 187.1 (m+1).

D. 1-tert-Butylpiperazine Dihydrobromide

To crude 3-[2-(tert-butylamino)ethyl]oxazolidin-2-one (1.18 g, 6.33 mmol) was added acetic acid (8.8 mL) and then 45% hydrobromic acid in acetic acid (19.5 mL). The reaction solution was stirred at room temperature for 3 d, poured into dichloromethane (250 mL), and filtered to give 1.87 g of a brown solid. The solid was heated at reflux in n-butanol for 2 d and the reaction mixture concentrated in vacuo. The residual solid was slurried in 3:1 diethyl ether:dichloromethane and filtered. The filtered solid was heated in ethanol, cooled to room temperature, and filtered to give 0.57 g (30%) of a white solid.

$^1$H NMR
IS-MS, m/e 143.1 (m+1);
Analysis for $C_8H_{18}N_2O_4 \cdot 2HBr$: Calcd: C, 24.89; H, 5.74; N, 7.26; Br, 41.40; Found: C, 31.88; H, 6.53; N, 9.16; Br, 52.22.

E. Methyl 2-[(4-tert-Butylpiperazin-1-ylcarbonyl)amino]benzoate

To an ice cold solution of methyl 2-isocyanatobenzoate (0.18 g, 1.0 mmol) in dichloromethane (3 mL) was added dropwise a solution of 1-tert-butylpiperazine dihydrobromid (0.28 g, 0.92 mmol) and N,N-diisopropylethylamine (0.36 mL, 2.1 mmol) in N,N-dimethylformamide (5 mL). The reaction solution was stirred at room temperature for 1 h, diluted with ethyl acetate, washed with saturated aqueous sodium bicarbonate, dried over magnesium sulfate, filtered, and concentrated in vacuo to give 0.28 g (95%) of a yellow oil.

$^1$H NMR
IS-MS, m/e 320.2 (m+1);
Analysis for $C_{17}H_{25}N_3O_3$: Calcd: C, 63.93; H, 7.89; N, 13.16; Found: C, 62.79; H, 7.73; N, 13.07.

F. 2-[(4-tert-Butylpiperazin-1-ylcarbonyl)amino]benzoic Acid Hydrochloride

To an ice cold solution of methyl 2-[(4-tert-butylpiperazin-1-ylcarbonyl)amino]benzoate (0.24 g, 0.75 mmol) in tetrahydrofuran (12 mL) and water (3 mL) was added dropwise 1 N aqueous lithium hydroxide (0.95 mL, 0.95 mmol). The reaction solution was stirred at room temperature for 22 h, concentrated in vacuo, and the residue partitioned between water and diethyl ether. The aqueous phase was acidified to pH 2 using 1 N hydrochloric acid and lyophilized to give 0.25 g of crude material as a white solid.

$^1$H NMR
IS-MS, m/e 306.1 (m+1), 304.2 (m–1).

G. 2-(4-tert-Butylpiperazin-1-yl)-4H-3,1-benzoxazin-4-one

Using methods substantially equivalent to those described in Example 51-C, 2-(4-tert-butylpiperazin-1-yl)-4H-3,1-benzoxazin-4-one (0.13 g, 75%) was prepared from 2-[(4-tert-butylpiperazin-1-ylcarbonyl)amino]benzoic acid hydrochloride (0.22 g, 0.6 mmol) and 1-(3-dimethylaminopropyl)-3-ethyl-carbodiiimide hydrochloride in the presence of N,N-diisopropylethylamine (0.14 mL, 0.8 mmol).

$^1$H NMR
IS-MS, m/e 288.1 (m+1).

H. 2-[(4-tert-Butylpiperazin-1-ylcarbonyl)amino]-N-(5-chloropyridin-2-yl)benzamide Using methods substantially equivalent to those described in Example 51-D, 2-[(4-tert-butylpiperazin-1-ylcarbonyl)amino]-N-(5-chloropyridin-2-yl)benzamide (62 mg, 33%) was prepared from 2-[(4-tert-butylpiperazin-1-yl)-4H-3,1-benzoxazin-4-one (0.13 g, 0.45 mmol) and 2-amino-5-chloropyridine. The crude product was suspended in ether and filtered.

$^1$H NMR
IS-MS, m/e 416.1(m+1), 471.3 (m–1);
Analysis for $C_{21}H_{26}ClN_5O_2 \cdot 0.5H_2O$: Calcd: C, 59.36; H, 6.40; N, 16.48; Found: C, 59.09; H, 6.12; N, 16.09.

EXAMPLE 231

Preparation of N-(5-Chloropyridin-2-yl)-2-[(1-isopropylpiperidin-4-ylcarbonyl)amino]-5-methylbenzamide Hydrochloride

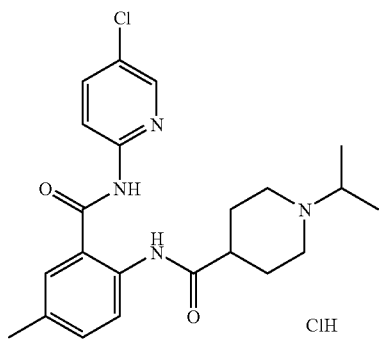

A. N-(5-Chloropyridin-2-yl)-5-methyl-2-nitrobenzamide

To a stirring suspension of 5-methyl-2-nitrobenzoic acid (23.36 g, 129 mmol) in dichloromethane (100 mL) was added a couple of drops of N,N-dimethylformamide followed by oxalyl chloride (12.36 mL, 142 mmol). The reaction was stirred at room temperature overnight and the residue transferred slowly to an ice cold solution of 2-amino-5-chloropyridine (16 g, 126 mmol) and pyridine (30 mL) in dichloromethane (200 mL). The reaction was stirred overnight, treated with water (100 mL), and concentrated. The resulting mixture was treated with ethyl acetate (2 L), washed consecutively with aqueous citric acid, saturated aqueous sodium bicarbonate, dried over magnesium sulfate, filtered, and concentrated in vacuo. The crude product was purified by recrystallization from toluene to give 26 g (69%) of a white solid.

$^1$H NMR
ESI+MS, m/e 292.0 (m+1);
Analysis for $C_{13}H_{10}ClN_3O_3$: Calcd: C, 53.53; H, 3.46; N, 14.41; Found: C, 53.52; H, 3.56; N, 14.49.

B. 2-Amino-N-(5-chloropyridin-2-yl)-5-methylbenzamide

Using methods substantially equivalent to those described in Example 2-B, 2-amino-5-methyl-N-(5-chloropyridin-2-yl)benzamide (19 g, 88%) was prepared from N-(5-chloropyridin-2-yl)-5-methyl-2-nitrobenzamide.

$^1$H NMR
ESI+MS, m/e 262.0 (m+1);
Analysis for $C_{13}H_{12}ClN_3O$: Calcd: C, 59.66; H, 4.62; N, 16.06; Found: C, 64.32; H, 4.81; N, 17.59.

C. 2-[(1-tert-Butoxycarbonylpiperidin-4-ylcarbonyl)amino]-N-(5-chloropyridin-2-yl)-5-methylbenzamide Using methods substantially equivalent to those described in Example 25-D, 2-[(1-tert-butoxycarbonylpiperidin-4-ylcarbonyl)amino]-N-(5-chloropyridin-2-yl)-5-methylbenzamide (4.3 g, 79%) was prepared from 2-amino-N-(5-chloropyridin-2-yl)-5-methylbenzamide.

$^1$H NMR
IS-MS, m/e 473.2 (m+1), 471.3 (m−1);
Analysis for $C_{24}H_{29}ClN_4O_4$: Calcd: C, 60.95; H, 6.18; N, 11.85; Found: C, 61.17; H, 6.41; N, 11.90.

D. N-(5-Chloropyridin-2-yl)-5-methyl-2-[(4-piperidinylcarbonyl)amino]benzamide Trifluoroacetate Using methods substantially equivalent to those described in Example 9-B, N-(5-chloropyridin-2-yl)-2-[(4-piperidinylcarbonyl)amino]-5-methylbenzamide trifluoroacetate (4.7 g, 100%) was prepared from 2-[(1-tert-butoxycarbonylpiperidin-4-ylcarbonyl)amino]-N-(5-chloropyridin-2-yl)-5-methylbenzamide.

$^1$H NMR
IS-MS, m/e 373.2 (m+1), 371.1 (m−1);
Analysis for $C_{19}H_{20}ClN_4O_2 \cdot 1.6C_2HF_3O_2$: Calcd: C, 48.02; H, 4.10; N, 10.09; F, 16.42; Found: C, 48.34; H, 3.98; N, 10.06; F, 17.50.

E. N-(5-Chloropyridin-2-yl)-2-[(1-isopropylpiperidin-4-ylcarbonyl)amino]-5-methylbenzamide Hydrochloride To a stirring suspension of N-(5-chloropyridin-2-yl)-5-methyl-2-[(4-piperidinylcarbonyl)amino]benzamide trifluoroacetate (1.0 g, 2.05 mmol) in methanol (30 mL) was added acetone (15 mL), followed by acetic acid (0.6 mL, 10.5 mmol), and then sodium cyanoborohydride (0.165 g, 2.46 mmol). After stirring overnight, the solution was treated with saturated aqueous ammonium chloride solution, concentrated, and partitioned between dichloromethane and saturated aqueous sodium bicarbonate. The organic phase was washed with brine, dried over magnesium sulfate, filtered, and concentrated. The crude product was purified by chromatography over silica gel, eluting with a step gradient of 0–10% 2 M solution of ammonia/methanol in dichloromethane. To a stirring solution of the chromatography product in dichloromethane was added 1.0 N hydrochloric acid in diethyl ether until precipitate formed. The mixture was filtered to give 0.81 g (88%) of a white solid.

$^1$H NMR
IS-MS, m/e 415.2 (m+1), 413.2 (m−1);
Analysis for $C_{22}H_{27}ClN_4O_2 \cdot 2.0HCl \cdot 0.1H_2O$: Calcd: C, 53.96; H, 6.01; N, 11.44; Cl, 21.72; Found: C, 54.09; H, 6.00; N, 11.39; Cl, 21.75.

EXAMPLE 232

Preparation of 2-[(4-tert-Butylpiperazin-1-ylcarbonyl)amino]-5-chloro-N-(5-chloropyridin-2-yl)benzamide Hydrochloride

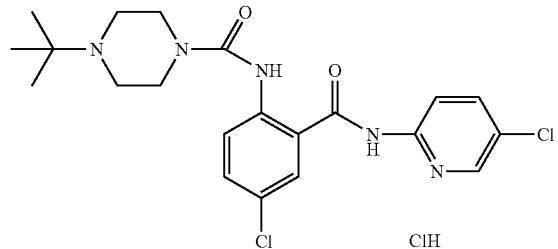

A. 4-Chloro-2-iodoaniline

Using methods substantially equivalent to those described in Example 173-C, 4-chloro-2-iodoaniline (50.92 g, 51%) was prepared from 4-chloroaniline.

$^1$H NMR
EI-MS, m/e 252.9 (m);
Analysis for $C_6H_5ClIN$: Calcd: C, 28.43; H, 1.99; N, 5.53; Found: C, 28.35; H, 2.02; N, 5.52.

B. 2-[(4-tert-Butylpiperazin-1-ylcarbonyl)amino]-5-chloro-1-iodobenzene

To a stirring solution of triphosgene (0.35 g, 1.16 mmol) in dichloromethane (12 mL) was added dropwise a solution of 4-chloro-2-iodoaniline (0.80 g, 3.15 mmol). The reaction mixture was stirred for 30 min. Then, using methods substantially equivalent to those described in Example 230-E, 2-[(4-tert-butylpiperazin-1-ylcarbonyl)amino]-5-chloro-1-iodobenzene was prepared from 1-tert-butylpiperazine dihydrobromide (1.03 g, 3.4 mmol).

$^1$H NMR
IS-MS, m/e 421.9 (m+1), 420.0 (m−1);
Analysis for $C_{15}H_{21}ClIN_3O$: Calcd: C, 42.72; H, 5.01; N, 9.97; Found: C, 42.16; H, 5.11; N, 9.60.

C. 2-(4-tert-Butylpiperazin-1-yl)-6-chloro-4H-3,1-benzoxazin-4-one

Using methods substantially equivalent to those described in Example 173-D, crude 2-(4-tert-butylpiperazin-1-yl)-6-chloro-4H-3,1-benzoxazin-4-one (0.49 g) was prepared from 2-[(4-tert-butylpiperazin-1-ylcarbonyl)amino]-5-chloro-1-iodobenzene.

$^1$H NMR

IS-MS, m/e 322.0 (m+1).

D. 2-[(4-tert-Butylpiperazin-1-ylcarbonyl)amino]-5-chloro-N-(5-chloropyridin-2-yl)benzamide Hydrochloride Using methods substantially equivalent to those described in Example 51-D, 2-[(4-tert-butylpiperazin-1-ylcarbonyl)amino]-5-chloro-N-(5-chloropyridin-2-yl)benzamide hydrochloride (0.15 g, 44%) was prepared from 2-(4-tert-butylpiperazin-1-yl)-6-chloro-4H-3,1-benzoxazin-4-one (0.49 g, 0.8 mmol) and 2-amino-5-chloropyridine. The product was purified with reverse phase HPLC, eluting with a gradient from 20% through 60% acetonitrile in 0.05% aqueous hydrochloric acid.

$^1$H NMR

IS-MS, m/e 448.1 (m−1);

Analysis for $C_{21}H_{25}Cl_2N_5O_2 \cdot 2.0Cl \cdot 0.5H_2O$: Calcd: C, 47.38; H, 5.30; N, 13.16; Cl, 26.64; Found: C, 47.45; H, 4.91; N, 12.76; Cl, 25.44.

EXAMPLE 233

Preparation of N-(5-Chloropyridin-2-yl)-2-[(1-isopropylpiperidin-4-ylcarbonyl)amino]-3-methylbenzamide Hydrochloride

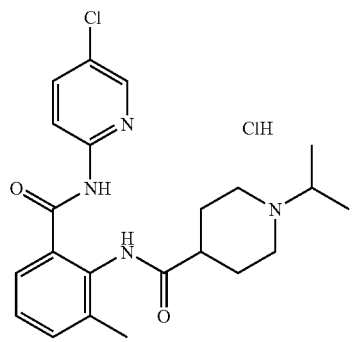

A. N-(5-Chloropyridin-2-yl)-3-methyl-2-nitrobenzamide

Using methods substantially equivalent to those described in Example 231-A, N-(5-chloropyridin-2-yl)-3-methyl-2-nitrobenzamide (36 g, 74%) was prepared from 3-methyl-2-nitrobenzoic acid.

$^1$H NMR

ESI+MS, m/e 292.0 (m+1);

Analysis for $C_{13}H_{10}ClN_3O_3$: Calcd: C, 53.53; H, 3.46; N, 14.41; Found: C, 53.49; H, 3.40; N, 14.30.

B. 2-Amino-N-(5-chloropyridin-2-yl)-3-methylbenzamide

Using methods substantially equivalent to those described in Example 2-B, 2-amino-N-(5-chloropyridin-2-yl)-3-methylbenzamide (36 g, 95%) was prepared from N-(5-chloropyridin-2-yl)-3-methyl-2-nitrobenzamide.

$^1$H NMR

ES-MS, m/e 262.0 (m+1);

Analysis for $C_{13}H_{12}ClN_3O$: Calcd: C, 59.66; H, 4.62; N, 16.06; Found: C, 59.24; H, 4.28; N, 16.08.

C. 2-[(1-tert-Butoxycarbonylpiperidin-4-ylcarbonyl)amino]-N-(5-chloropyridin-2-yl)-3-methylbenzamide Using methods substantially equivalent to those described in Example 25-D, 2-[(1-tert-butoxycarbonylpiperidin-4-ylcarbonyl)amino]-N-(5-chloropyridin-2-yl)-3-methylbenzamide (3.82 g, 70%) was prepared from 2-amino-N-(5-chloropyridin-2-yl)-3-methylbenzamide.

$^1$H NMR

IS-MS, m/e 473.2 (m+1), 471.3 (m−1);

Analysis for $C_{24}H_{29}ClN_4O_4$: Calcd: C, 60.95; H, 6.18; N, 11.85; Found: C, 60.71; H, 6.04; N, 11.74.

D. N-(5-Chloropyridin-2-yl)-3-methyl-2-[(4-piperidinylcarbonyl)amino]benzamide Trifluoroacetate Using methods substantially equivalent to those described in Example 9-B, N-(5-chloropyridin-2-yl)-3-methyl-2-[(4-piperidinylcarbonyl)amino]benzamide trifluoroacetate (3.15 g, >100% probably due to >1 eq TFA), was prepared from 2-[(1-tert-butoxycarbonylpiperidin-4-ylcarbonyl)amino]-N-(5-chloropyridin-2-yl)-3-methylbenzamide.

$^1$H NMR

E. N-(5-Chloropyridin-2-yl)-2-[(1-isopropylpiperidin-4-ylcarbonyl)amino]-3-methylbenzamide Hydrochloride Using methods substantially equivalent to those described in Example 231-E, N-(5-chloropyridin-2-yl)-2-[(1-isopropylpiperidin-4-ylcarbonyl)amino]-3-methylbenzamide hydrochloride (0.49 g, 53%) was prepared from N-(5-chloropyridin-2-yl)-3-methyl-2-[(piperidin-4-ylcarbonyl)amino]benzamide trifluoroacetate.

$^1$H NMR

IS-MS, m/e 415.2 (m+1), 413.2 (m−1);

Analysis for $C_{22}H_{27}ClN_4O_2 \cdot 1.1HCl \cdot 0.2H_2O$: Calcd: C, 57.61; H, 6.26; N, 12.22; Cl, 16.23; Found: C, 57.42; H, 6.18; N, 12.01; Cl, 16.13.

EXAMPLE 234

Preparation of N-(5-Chloropyridin-2-yl)-2-[(1-isopropylpiperidin-4-ylcarbonyl)amino]-5-methoxybenzamide Hydrochloride

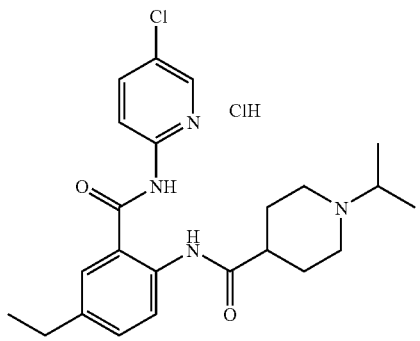

A. N-(5-Chloropyridin-2-yl)-5-methoxy-2-nitrobenzamide

Using methods substantially equivalent to those described in Example 231-A, N-(5-chloropyridin-2-yl)-5-methoxy-2-nitrobenzamide (26.5 g, 62%) was prepared from 5-methoxy-2-nitrobenzoic acid.

$^1$H NMR
ESI+MS, m/e 308.0 (m+1);
Analysis for $C_{13}H_{10}ClN_3O_4$: Calcd: C, 50.75; H, 3.28; N, 13.66; Found: C, 50.80; H, 3.15; N, 13.89.

B. 2-Amino-N-(5-chloropyridin-2-yl)-5-methoxybenzamide

Using methods substantially equivalent to those described in Example 2-B, 2-amino-N-(5-chloropyridin-2-yl)-5-methoxybenzamide (20 g, 84%) was prepared from N-(5-chloropyridin-2-yl)-5-methoxy-2-nitrobenzamide.

$^1$H NMR
ESI+MS, m/e 278.1 (m+1);
Analysis for $C_{13}H_{12}ClN_3O_2$: Calcd: C, 56.23; H, 4.36; N, 15.13; Found: C, 56.34; H, 4.32; N, 14.92.

C. 2-[(1-tert-Butoxycarbonylpiperidin-4-ylcarbonyl)amino]-N-(5-chloropyridin-2-yl)-5-methoxybenzamide Using methods substantially equivalent to those described in Example 25-D, 2-[(1-tert-butoxycarbonylpiperidin-4-ylcarbonyl)amino]-N-(5-chloropyridin-2-yl)-5-methoxybenzamide (1.59 g, 90%) was prepared from 2-amino-N-(5-chloropyridin-2-yl)-5-methoxybenzamide.

$^1$H NMR
IS-MS, m/e 489.5 (m+1), 487.5 (m−1);
Analysis for $C_{24}H_{29}ClN_4O_5$: Calcd: C, 58.95; H, 5.98; N, 11.46; Found: C, 59.10; H, 5.98; N, 11.32.

D. N-(5-Chloropyridin-2-yl)-5-methoxy-2-[(4-piperidinylcarbonyl)amino]benzamide Trifluoroacetate Using methods substantially equivalent to those described in Example 9-B, N-(5-chloropyridin-2-yl)-5-methoxy-2-[(4-piperidinylcarbonyl)amino]benzamide trifluoroacetate (1.14 g, 93%) was prepared from 2-[(1-tert-butoxycarbonylpiperidin-4-ylcarbonyl)amino]-N-(5-chloropyridin-2-yl)-5-methoxybenzamide.

$^1$H NMR
IS-MS, m/e 389.3 (m+1), 387.2 (m−1);
Analysis for $C_{19}H_{21}ClN_4O_3 \cdot 1.0 C_2HF_3O_2$: Calcd: C, 50.16; H, 4.41; N, 11.14; F, 11.33; Found: C, 49.88; H, 4.49; N, 10.86; F, 11.52.

E. N-(5-Chloropyridin-2-yl)-2-[(1-isopropylpiperidin-4-ylcarbonyl)amino]-5-methoxybenzamide Hydrochloride Using methods substantially equivalent to those described in Example 231-E, N-(5-chloropyridin-2-yl)-2-[(1-isopropylpiperidin-4-ylcarbonyl)amino]-5-methoxybenzamide hydrochloride (0.36 g, 39%) was prepared from N-(5-chloropyridin-2-yl)-5-methoxy-2-[(piperidin-4-ylcarbonyl)amino]benzamide trifluoroacetate.

$^1$H NMR
IS-MS, m/e 431.4 (m+1), 429.3 (m−1);
Analysis for $C_{22}H_{27}ClN_4O_3 \cdot 1.0 HCl$: Calcd: C, 56.54; H, 6.04; N, 11.99; Cl, 15.17; Found: C, 56.56; H, 5.77; N, 11.78; Cl, 15.46.

EXAMPLE 235

Preparation of 3-Chloro-N-(5-chloropyridin-2-yl)-2-[(1-isopropylpiperidin-4-ylcarbonyl)amino]benzamide Hydrochloride

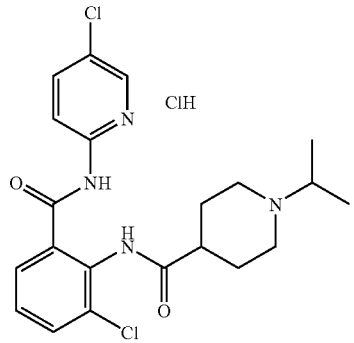

A. 3-Chloro-N-(5-chloropyridin-2-yl)-2-nitrobenzamide

Using methods substantially equivalent to those described in Example 231-A, 3-chloro-N-(5-chloropyridin-2-yl)-2-nitrobenzamide (4.11 g, 37%) was prepared from 3-chloro-2-nitrobenzoic acid.

$^1$H NMR
IS-MS, m/e 312.0 (m+1), 310.1 (m−1);
Analysis for $C_{12}H_7Cl_2N_3O_3$: Calcd: C, 46.18; H, 2.26; N, 13.46; Found: C, 46.05; H, 2.19; N, 13.54.

B. 2-Amino-3-chloro-N-(5-chloropyridin-2-yl)benzamide

Using methods substantially equivalent to those described in Example 2-B, 2-amino-3-chloro-N-(5-chloropyridin-2-yl)benzamide (2.97 g, 84%) was prepared from 3-chloro-N-(5-chloropyridin-2-yl)-2-nitrobenzamide.

$^1$H NMR
IS-MS, m/e 282.1 (m+1), 280.1 (m−1);
Analysis for $C_{12}H_9Cl_2N_3O$: Calcd: C, 51.09; H, 3.22; N, 14.89; Found: C, 50.80; H, 3.22; N, 14.66.

C. 2-[(1-tert-Butoxycarbonylpiperidin-4-ylcarbonyl)amino]-3-chloro-N-(5-chloropyridin-2-yl)benzamide Using methods substantially equivalent to those described in Example 25-D, 2-[(1-tert-butoxycarbonylpiperidin-4-ylcarbonyl)amino]-3-chloro-N-(5-chloropyridin-2-yl)benzamide (0.31 g, 18%) was prepared from 2-amino-3-chloro-N-(5-chloropyridin-2-yl)benzamide.

$^1$H NMR
IS-MS, m/e 493.0 (m+1), 491.2 (m−1);
Analysis for $C_{23}H_{26}Cl_2N_4O_4$: Calcd: C, 55.99; H, 5.31; N, 11.36; Found: C, 56.14; H, 5.58; N, 11.23.

D. 3-Chloro-N-(5-chloropyridin-2-yl)-2-[(4-piperidinylcarbonyl)amino]benzamide Trifluoroacetate Using methods substantially equivalent to those described in Example 9-B, 3-chloro-N-(5-chloropyridin-2-yl)-2-[(4-piperidinylcarbonyl)amino]benzamide trifluoroacetate (0.20 g, 100%) was prepared from 2-[(1-tert-butoxycarbonylpiperidin-4-ylcarbonyl)amino]-3-chloro-N-(5-chloropyridin-2-yl)benzamide.

$^1$H NMR

IS-MS, m/e 393.1 (m+1), 391.2 (m−1);

Analysis for $C_{18}H_{18}Cl_2N_4O_2 \cdot 1.0 C_2HF_3O_2$: Calcd: C, 47.35; H, 3.78; N, 11.04; F, 11.24; Found: C, 47.62; H, 3.87; N, 10.89; F, 11.53.

E. 3-Chloro-N-(5-chloropyridin-2-yl)-2-[(1-isopropylpiperidin-4-ylcarbonyl)amino]benzamide Hydrochloride Using methods substantially equivalent to those described in Example 231-E, 3-chloro-N-(5-chloropyridin-2-yl)-2-[(1-isopropylpiperidin-4-ylcarbonyl)amino]benzamide hydrochloride (71 mg, 50%) was prepared from 3-chloro-N-(5-chloropyridin-2-yl)-2-[(4-piperidinylcarbonyl)amino]benzamide trifluoroacetate.

$^1$H NMR

IS-MS, m/e 435.2 (m+1), 433.4 (m−1);

Analysis for $C_{21}H_{24}Cl_2N_4O_2 \cdot 1.2 HCl \cdot 0.1 H_2O$: Calcd: C, 52.45; H, 5.32; N, 11.65; Cl, 23.59; Found: C, 52.67; H, 5.11; N, 11.42; Cl, 23.81.

EXAMPLE 236

Preparation of 5-Chloro-N-(6-chloropyridazin-3-yl)-2-[(1-isopropylpiperidin-4-ylcarbonyl)amino]benzamide Hydrochloride

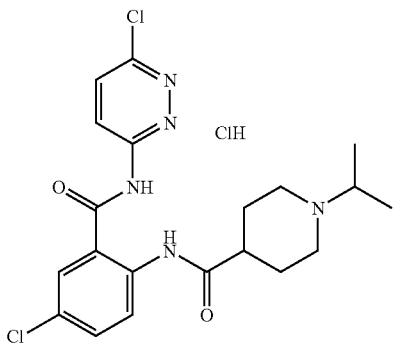

A. 2-[(1-tert-Butoxycarbonylpiperidin-4-ylcarbonyl)amino]-5-chloro-1-iodobenzene Using methods substantially equivalent to those described in Example 25-D, 2-[(1-tert-butoxycarbonylpiperidin-4-ylcarbonyl)amino]-5-chloro-1-iodobenzene (14.04 g, 94%) was prepared from 4-chloro-2-iodoaniline.

$^1$H NMR

IS-MS, m/e 465.1 (m+1), 463.2 (m−1);

Analysis for $C_{17}H_{22}ClIN_2O_3$: Calcd: C, 43.94; H, 4.77; N, 6.03; Found: C, 45.40; H, 5.14; N, 5.98.

B. 2-[(1-tert-Butoxycarbonylpiperidin-4-ylcarbonyl)amino]-5-chlorobenzoic Acid

To a stirring solution of 2-[(1-tert-butoxycarbonylpiperidin-4-ylcarbonyl)amino]-5-chloro-1-iodobenzene (10 g, 21.5 mmol) in acetonitrile (350 mL) was added potassium carbonate (14.9 g, 107.5 mmol), followed by Pd(PPh$_3$)$_4$ (1.24 g, 1.1 mmol), and copper iodide (0.21 g, 1.1 mmol). The mixture was placed under an atmosphere of carbon monoxide and heated to 80° C. After 3 h, 1 N aqueous sodium hydroxide (50 mL) was added to the hot reaction solution. The solution was stirred for 10 min and concentrated in vacuo. The residue was partitioned between ethyl acetate and water. The aqueous phase was filtered, acidified to pH 3 with citric acid, and extracted with ethyl acetate. The organic phase was washed with brine, dried over magnesium sulfate, filtered, and concentrated in vacuo to give 3.91 g (48%) of a white solid.

$^1$H NMR

C. 2-(1-tert-Butoxycarbonylpiperidin-4-yl)-6-chloro-4H-3,1-benzoxazin-4-one

Using methods substantially equivalent to those described in Example 51-C, 2-[(1-tert-butoxycarbonylpiperidin-4-yl)-6-chloro-4H-3,1-benzoxazin-4-one (2.5 g, 75%) was prepared from 2-[(1-tert-butoxycarbonylpiperidin-4-ylcarbonyl)amino]-5-chlorobenzoic acid.

$^1$H NMR

D. 2-[(1-tert-Butoxycarbonylpiperidin-4-ylcarbonyl)amino]-5-chloro-N-(6-chloropyridazin-3-yl)benzamide Using methods substantially equivalent to those described in Example 51-D, 2-[(1-tert-butoxycarbonylpiperidin-4-ylcarbonyl)amino]-5-chloro-N-(6-chloropyridazin-3-yl)benzamide (0.65 g, 26%) was prepared from 2-(1-tert-butoxycarbonylpiperidin-4-yl)-6-chloro-4H-3,1-benzoxazin-4-one (0.93 g, 2.55 mmol) and 3-amino-6-chloropyridazine. The crude product was purified by chromatography over silica gel, eluting with a step gradient of 10%–25% ethyl acetate in dichloromethane.

$^1$H NMR

IS-MS, m/e 494.2 (m+1), 492.2 (m−1);

Analysis for $C_{22}H_{25}Cl_2N_5O_4$: Calcd: C, 53.45; H, 5.10; N, 14.17; Found: C, 53.33; H, 4.95; N, 13.90.

E. 5-Chloro-N-(6-chloropyridazin-3-yl)-2-[(4-piperidinylcarbonyl)amino]benzamide Trifluoroacetate Using methods substantially equivalent to those described in Example 9-B, 5-chloro-N-(6-chloropyridazin-3-yl)-2-[(4-piperidinylcarbonyl)amino]benzamide trifluoroacetate (0.58 g, 98%) was prepared from 2-[(1-tert-butoxycarbonylpiperidin-4-ylcarbonyl)amino]-5-chloro-N-(6-chloropyridazin-3-yl)benzamide.

$^1$H NMR

IS-MS, m/e 394.1 (m+1), 392.1 (m−1);

Analysis for $C_{17}H_{17}Cl_2N_5O_2 \cdot 1.0 C_2HF_3O_2$: Calcd: C, 44.90; H, 3.57; N, 13.78; F, 11.21; Found: C, 45.17; H, 3.80; N, 13.52; F, 11.45.

F. 5-Chloro-N-(6-chloropyridazin-3-yl)-2-[(1-isopropylpiperidin-4-ylcarbonyl)amino]benzamide Hydrochloride Using methods substantially equivalent to those described in Example 231-E, 5-chloro-N-(6-chloropyridazin-3-yl)-2-[(1-isopropylpiperidin-4-ylcarbonyl)amino]benzamide hydrochloride (0.23 g, 50%) was prepared from 5-chloro-N-(6-chloropyridazin-3-yl)-2-[(4-piperidinylcarbonyl)amino]benzamide trifluoroacetate. The product was purified by RPHPLC, eluting with a gradient from 20% through 50% acetonitrile in 0.05% aqueous hydrochloric acid.

$^1$H NMR

IS-MS, m/e 436.3 (m+1), 434.3 (m−1);

Analysis for $C_{20}H_{23}Cl_2N_5O_2 \cdot 2.4HCl \cdot 0.9H_2O$: Calcd: C, 44.48; H, 5.08; N, 12.97; Cl, 28.89; Found: C, 44.21; H, 5.11; N, 12.63; Cl, 28.93.

EXAMPLE 237

Preparation of N-(5-Chloropyridin-2-yl)-2-[(1-isopropylpiperidin-4-ylcarbonyl)amino]-5-methoxycarbonylbenzamide

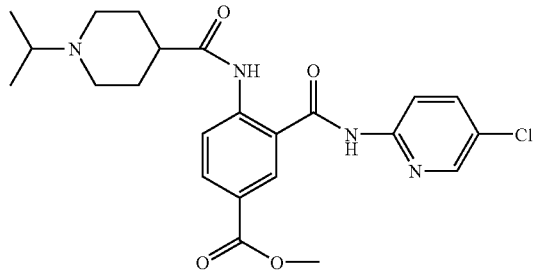

A.
2-Amino-N-(5-chloropyridin-2-yl)-5-iodobenzamide

Using methods substantially equivalent to those described in Example 173-C, 2-amino-N-(5-chloropyridin-2-yl)-5-iodobenzamide (0.49 g, 32%) was prepared from 2-amino-N-(5-chloropyridin-2-yl)benzamide. The crude product was purified by chromatography over silica gel, eluting with a step gradient of 5–10% ethyl acetate in dichloromethane. The purified by chromatography product was slurried in isopropanol and filtered.

$^1$H NMR

IS-MS, m/e 373.8 (m+1), 371.8 (m−1);

Analysis for $C_{12}H_9ClIN_3O$: Calcd: C, 38.58; H, 2.43; N, 11.25; Found: C, 38.64; H, 2.76; N, 11.22.

B. 2-[(1-tert-Butoxycarbonylpiperidin-4-ylcarbonyl)amino]-N-(5-chloropyridin-2-yl)-5-iodobenzamide Using methods substantially equivalent to those described in Example 25-D, 2-[(1-tert-butoxycarbonylpiperidin-4-ylcarbonyl)amino]-N-(5-chloropyridin-2-yl)-5-iodobenzamide (8.6 g, 62%) was prepared from 2-amino-N-(5-chloropyridin-2-yl)-5-iodobenzamide.

$^1$H NMR

IS-MS, m/e 584.8 (m+1), 582.9 (m−1);

Analysis for $C_{23}H_{26}ClIN_4O_4$: Calcd: C, 47.23; H, 4.48; N, 9.58; Found: C, 46.96; H, 4.45; N, 9.68.

C. N-(5-Chloropyridin-2-yl)-5-iodo-2-[(4-piperidinylcarbonyl)amino]benzamide Trifluoroacetate Using methods substantially equivalent to those described in Example 9-B, N-(5-chloropyridin-2-yl)-5-iodo-2-[(4-piperidinylcarbonyl)amino]benzamide trifluoroacetate (1.86 g, 90%) was prepared from 2-[(1-tert-butoxycarbonylpiperidin-4-ylcarbonyl)amino]-N-(5-chloropyridin-2-yl)-5-iodobenzamide.

$^1$H NMR

IS-MS, m/e 484.9(m+1), 482.9 (m−1);

Analysis for $C_{18}H_{18}ClIN_4O_2 \cdot 1.1C_2HF_3O_2$: Calcd: C, 39.76; H, 3.16; N, 9.18; Found: C, 39.70; H, 3.20; N, 9.35.

D. N-(5-Chloropyridin-2-yl)-5-iodo-2-[(1-isopropylpiperidin-4-ylcarbonyl)amino]benzamide Using methods substantially equivalent to those described in Example 231-E, N-(5-chloropyridin-2-yl)-5-iodo-2-[(1-isopropylpiperidin-4-ylcarbonyl)amino]benzamide (0.87 g, 65%) was prepared from N-(5-chloropyridin-2-yl)-5-iodo-2-[(4-piperidinylcarbonyl)amino]benzamide trifluoroacetate.

$^1$H NMR

IS-MS, m/e 526.9 (m+1), 525.0 (m−1);

Analysis for $C_{21}H_{24}ClIN_4O_2 \cdot 1.4H_2O$: Calcd: C, 45.69; H, 4.89; N, 10.15; Found: C, 45.37; H, 4.68; N, 10.02.

E. N-(5-Chloropyridin-2-yl)-2-[(1-isopropylpiperidin-4-ylcarbonyl)amino]-5-methoxycarbonylbenzamide To a stirring solution of N-(5-chloropyridin-2-yl)-5-iodo-2-[(1-isopropylpiperidin-4-ylcarbonyl)amino]benzamide (0.49 g, 0.92 mmol) in N,N-dimethylformamide (10 mL) was added triethylamine (0.4 mL, 2.8 mmol), followed by $PdCl_2(PPh_3)_2$, and then methanol (5 mL). The mixture was placed under a carbon monoxide atmosphere, heated to 60° C. for 18 h, and concentrated in vacuo. The crude product was purified by chromatography over silica gel, eluting with a step gradient of 10–20% 2 M solution of ammonia/methanol in dichloromethane. The chromatography product was recrystallized from methanol to give 0.16 g (38%) of a white solid.

$^1$H NMR

IS-MS, m/e 459.9 (m−1);

Analysis for $C_{23}H_{27}ClN_4O_4$: Calcd: C, 60.19; H, 5.93; N, 12.21; Found: C, 60.03; H, 5.85; N, 12.07.

EXAMPLE 238

Preparation of 6-Chloro-N-(5-chloropyridin-2-yl)-2-[(1-isopropylpiperidin-4-ylcarbonyl)amino]benzamide

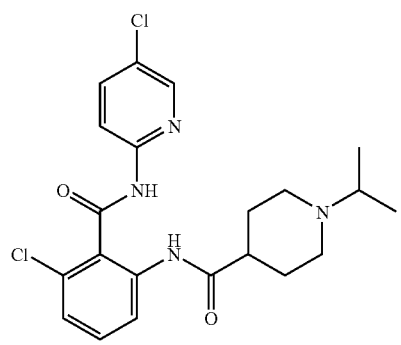

A. 2-[(1-tert-Butoxycarbonylpiperidin-4-ylcarbonyl) amino]-6-chlorobenzoic acid Using methods substantially equivalent to those described in Example 25-D, crude 2-[(1-tert-butoxycarbonylpiperidin-4-ylcarbonyl)amino]-6-chlorobenzoic acid (0.56 g, 45%) was prepared from 2-amino-6-chlorobenzoic acid.

$^1$H NMR

IS-MS, m/e 382.9 (m+1), 380.9 (m−1).

B. 2-[(1-tert-Butoxycarbonylpiperidin-4-yl)-5-chloro-4H-3,1-benzoxazin-4-one Using methods substantially equivalent to those described in Example 51-C, 2-[(1-tert-butoxycarbonylpiperidin-4-yl)-5-chloro-4H-3,1-benzoxazin-4-one (0.42 g, 76%) was prepared from crude 2-[(1-tert-butoxycarbonylpiperidin-4-ylcarbonyl)amino]-6-chlorobenzoic acid.

$^1$H NMR

FD-MS, m/e 364.1 (m+1);

Analysis for $C_{18}H_{21}ClN_2O_4$: Calcd: C, 59.26; H, 5.80; N, 7.68; Found: C, 59.30; H, 5.71; N, 7.65.

C. 2-[(1-tert-Butoxycarbonylpiperidin-4-ylcarbonyl) amino]-6-chloro-N-(5-chloropyridin-2-yl)benzamide Using methods substantially equivalent to those described in Example 51-D, 2-[(1-tert-butoxycarbonylpiperidin-4-ylcarbonyl)amino]-6-chloro-N-(5-chloropyridin-2-yl)benzamide (0.34 g, 69%) was prepared from 2-[(1-tert-butoxycarbonylpiperidin-4-yl)-5-chloro-4H-3,1-benzoxazin-4-one.

$^1$H NMR

IS-MS, m/e 493.2 (m+1), 491.2 (m−1);

Analysis for $C_{23}H_{26}Cl_2N_4O_4 \cdot 0.2H_2O$: Calcd: C, 55.58; H, 5.35; N, 11.27; Found: C, 55.35; H, 5.40; N, 11.35.

D. 6-Chloro-N-(5-chloropyridin-2-yl)-2-[(4-piperidinylcarbonyl)amino]benzamide Trifluoroacetate Using methods substantially equivalent to those described in Example 9-B, 6-chloro-N-(5-chloropyridin-2-yl)-2-[(4-piperidinylcarbonyl)amino]benzamide trifluoroacetate (0.28 g, 91%) was prepared from 2-[(1-tert-butoxycarbonylpiperidin-4-ylcarbonyl)amino]-6-chloro-N-(5-chloropyridin-2-yl)benzamide.

$^1$H NMR

IS-MS, m/e 393.1 (m+1), 391.2 (m−1);

Analysis for $C_{18}H_{18}Cl_2N_4O_2 \cdot 1.0C_2HF_3O_2$: Calcd: C, 47.35; H, 3.78; N, 11.04; F, 11.24; Found: C, 47.38; H, 3.92; N, 10.92; F, 11.47.

E. 6-Chloro-N-(5-chloropyridin-2-yl)-2-[(1-isopropylpiperidin-4-ylcarbonyl)amino]benzamide Using methods substantially equivalent to those described in Example 231-E, 6-chloro-N-(5-chloropyridin-2-yl)-2-[(1-isopropylpiperidin-4-ylcarbonyl)amino]benzamide (0.86 g, 51%) was prepared from 6-chloro-N-(5-chloropyridin-2-yl)-2-[(4-piperidinylcarbonyl)amino]benzamide trifluoroacetate.

$^1$H NMR

IS-MS, m/e 435.2 (m+1), 433.4 (m−1);

Analysis for $C_{21}H_{24}Cl_2N_4O_2 \cdot 0.1H_2O$: Calcd: C, 57.70; H, 5.58; N, 12.82; Found: C, 57.33; H, 5.50; N, 12.73.

EXAMPLE 239

Preparation of N-(5-Chloropyridin-2-yl)-6-fluoro-2-[(1-isopropylpiperidin-4-ylcarbonyl)amino]benzamide

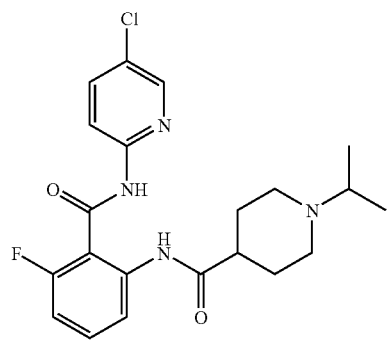

A. 2-Fluoro-6-nitrobenzoic acid

To a stirring suspension of potassium permanganate (102 g, 0.65 mol) in water (1.4 L) was added 2-fluoro-6-nitrotoluene. The reaction was heated at reflux for 4 h, cooled to room temperature, filtered, and washed with diethyl ether. The aqueous phase was acidified to pH 2 with concentrated hydrochloric acid and extracted with ethyl acetate. The organic phase was washed with brine, dried over magnesium sulfate, filtered, and concentrated in vacuo to give 11.81 g (40%).

$^1$H NMR

IS-MS, m/e 184.0 (m−1);

Analysis for $C_7H_4FNO_4$: Calcd: C, 45.42; H, 2.18; N, 7.57; Found: C, 45.22; H, 2.29; N, 7.27.

B. N-(5-Chloropyridin-2-yl)-6-fluoro-2-nitrobenzamide

Using methods substantially equivalent to those described in Example 231-A, N-(5-chloropyridin-2-yl)-6-fluoro-2-nitrobenzamide (7.83 g, 58%) was prepared from 2-amino-5-chloropyridine and 2-fluoro-6-nitrobenzoic acid. The crude product was purified by chromatography over silica gel, eluting with dichloromethane.

$^1$H NMR

IS-MS, m/e 296.2 (m+1), 294.1 (m−1);

Analysis for $C_{12}H_7ClFN_3O_3$: Calcd: C, 48.75; H, 2.39; N, 14.21; Found: C, 48.89; H, 2.42; N, 14.14.

C. 2-Amino-N-(5-chloropyridin-2-yl)-6-fluorobenzamide

Using methods substantially equivalent to those described in Example 2-B, 2-amino-N-(5-chloropyridin-2-yl)-6-fluorobenzamide (6.75 g, 97%) was prepared from N-(5-chloropyridin-2-yl)-6-fluoro-2-nitrobenzamide.

$^1$H NMR

IS-MS, m/e 264.1 (m−1);

Analysis for $C_{12}H_9ClFN_3O$: Calcd: C, 54.25; H, 3.41; N, 15.82; Found: C, 54.30; H, 3.37; N, 15.63.

D. 2-[(1-tert-Butoxycarbonylpiperidin-4-ylcarbonyl) amino]-N-(5-chloropyridin-2-yl)-6-fluorobenzamide Using methods substantially equivalent to those described in Example 25-D, 2-[(1-tert-butoxycarbonylpiperidin-4-ylcarbonyl)amino]-N-(5-chloropyridin-2-yl)-6-fluorobenzamide (1.23 g, 69%) was prepared from 2-amino-N-(5-chloropyridin-2-yl)-6-fluorobenzamide. The crude product was purified by chromatography over silica gel, eluting with a step gradient of 10–15% ethyl acetate in dichloromethane.
$^1$H NMR
IS-MS, m/e 477.2 (m+1), 475.1 (m−1);
Analysis for $C_{23}H_{26}ClFN_4O_4$: Calcd: C, 57.92; H, 5.49; N, 11.75; Found: C, 62.90; H, 6.12; N, 12.38.

E. N-(5-Chloropyridin-2-yl)-6-fluoro-2-[(4-piperidinylcarbonyl)amino]benzamide Trifluoroacetate Using methods substantially equivalent to those described in Example 9-B, N-(5-chloropyridin-2-yl)-6-fluoro-2-[(4-piperidinylcarbonyl)amino]benzamide trifluoroacetate (0.95 g, 92%) was prepared from 2-[(1-tert-butoxycarbonylpiperidin-4-ylcarbonyl)amino]-N-(5-chloropyridin-2-yl)-6-fluorobenzamide.
$^1$H NMR
IS-MS, m/e 377.3 (m+1), 375.2 (m−1);
Analysis for $C_{18}H_{18}ClFN_4O_2 \cdot 1.0C_2HF_3O_2$: Calcd: C, 48.94; H, 3.90; N, 11.41; F, 15.48; Found: C, 49.20; H, 3.87; N, 11.11; F, 16.04.

F. N-(5-Chloropyridin-2-yl)-6-fluoro-2-[(1-isopropylpiperidin-4-ylcarbonyl)amino]benzamide Using methods substantially equivalent to those described in Example 231-E, N-(5-chloropyridin-2-yl)-6-fluoro-2-[(1-isopropylpiperidin-4-ylcarbonyl)amino]benzamide hydrochloride (0.345 g, 80%) was prepared from N-(5-chloropyridin-2-yl)-6-fluoro-2-[(4-piperidinylcarbonyl)amino]benzamide trifluoroacetate.
$^1$H NMR
IS-MS, m/e 419.2 (m+1), 417.3 (m−1);
Analysis for $C_{21}H_{24}ClFN_4O_2 \cdot 0.6H_2O$: Calcd; C, 58.70; H, 5.91; N, 13.04; Found: C, 58.46; H, 5.52; N, 13.21.

EXAMPLE 240

Preparation of N-(5-Chloropyridin-2-yl)-5-ethyl-2-[(1-isopropylpiperidin-4-ylcarbonyl)amino]benzamide

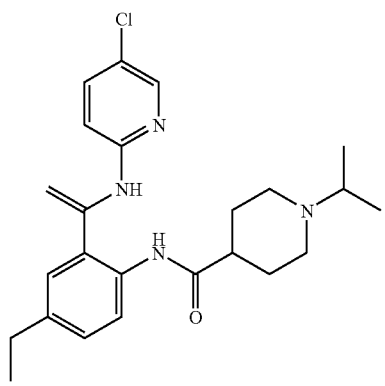

A. 4-Ethyl-2-iodoaniline

Using methods substantially equivalent to those described in Example 173-C, 4-ethyl-2-iodoaniline (22.44 g, 35%) was prepared from 4-ethylaniline.
$^1$H NMR
IS-MS, m/e 248.2 (m+1);
Analysis for $C_8H_{10}NI$: Calcd: C, 38.89; H, 4.08; N, 5.67; Found: C, 38.44; H, 3.90; N, 5.49.

B. 2-[(1-tert-Butoxycarbonylpiperidin-4-ylcarbonyl)amino]-5-ethyl-1-iodobenzene

Using methods substantially equivalent to those described in Example 25-D, 2-[(1-tert-butoxycarbonylpiperidin-4-ylcarbonyl)amino]-5-ethyl-1-iodobenzene (4.56 g, 25%) was prepared from 4-ethyl-2-iodoaniline.
$^1$H NMR
IS-MS, m/e 459.4 (m+1), 457.3 (m−1);
Analysis for $C_{19}H_{27}IN_2O_3$: Calcd: C, 49.79; H, 5.94; N, 6.11; Found: C, 50.32; H, 6.09; N, 6.07.

C. 2-[(1-tert-Butoxycarbonylpiperidin-4-yl)-6-ethyl-4H-3,1-benzoxazin-4-one

Using methods substantially equivalent to those described in Example 173-E, 2-[(1-tert-butoxycarbonylpiperidin-4-yl)-6-ethyl-4H-3,1-benzoxazin-4-one (2.34 g, 73%) was prepared from 2-[(1-tert-butoxycarbonylpiperidin-4-ylcarbonyl)amino]-5-ethyl-1-iodobenzene.
$^1$H NMR
FD-MS, m/e 390 (m+1);
Analysis for $C_{20}H_{26}N_2O_4$: Calcd: C, 67.02; H, 7.31; N, 7.82; Found: C, 66.42; H, 7.30; N, 7.64.

D. 2-[(1-tert-Butoxycarbonylpiperidin-4-ylcarbonyl)amino]-N-(5-chloropyridin-2-yl)-5-ethylbenzamide Using methods substantially equivalent to those described in Example 51-D, 2-[(1-tert-butoxycarbonylpiperidin-4-ylcarbonyl)amino]-N-(5-chloropyridin-2-yl)-5-ethylbenzamide (1.27 g, 47%) was prepared from 2-[(1-tert-butoxycarbonylpiperidin-4-yl)-6-ethyl-4H-3,1-benzoxazin-4-one.
$^1$H NMR
IS-MS, m/e 487.4 (m+1), 485.5 (m−1);
Analysis for $C_{25}H_{31}ClN_4O_4$: Calcd: C, 61.66; H, 6.42; N, 11.50; Found: C, 61.85; H, 6.08; N, 11.31.

E. N-(5-Chloropyridin-2-yl)-5-ethyl-2-[(4-piperidinylcarbonyl)amino]benzamide Trifluoroacetate Using methods substantially equivalent to those described in Example 9-B, N-(5-chloropyridin-2-yl)-5-ethyl-2-[(4-piperidinylcarbonyl)amino]benzamide trifluoroacetate (1.01 g, 89%) was prepared from 2-[(1-tert-butoxycarbonylpiperidin-4-ylcarbonyl)amino]-N-(5-chloropyridin-2-yl)-5-ethylbenzamide.
$^1$H NMR
IS-MS, m/e 387.1 (m+1), 385.2 (m−1);
Analysis for $C_{20}H_{23}ClN_4O_2 \cdot 1.0C_2HF_3O_2$: Calcd: C, 52.75; H, 4.83; N, 11.19; F, 11.38; Found: C, 52.95; H, 4.86; N, 10.83; F, 11.89.

F. N-(5-Chloropyridin-2-yl)-5-ethyl-2-[(1-isopropylpiperidin-4-ylcarbonyl)amino]benzamide Using methods substantially equivalent to those described in Example 231-E, N-(5-chloropyridin-2-yl)-5-ethyl-2-[(1-isopropylpiperidin-4-ylcarbonyl)amino]benzamide (0.38 g, 89%) was prepared from N-(5-chloropyridin-2-yl)-5-ethyl-2-[(4-piperidinylcarbonyl)amino]benzamide trifluoroacetate.

¹H NMR

IS-MS, m/e 429.2 (m+1), 427.2 (m−1);

Analysis for $C_{23}H_{29}ClN_4O_2$: Calcd: C, 64.40; H, 6.81; N, 13.06; Found: C, 64.10; H, 6.70; N, 12.85.

EXAMPLE 241

Preparation of N-(5-Chloropyridin-2-yl)-5-isopropyl-2-[(1-isopropylpiperidin-4-ylcarbonyl)amino]benzamide

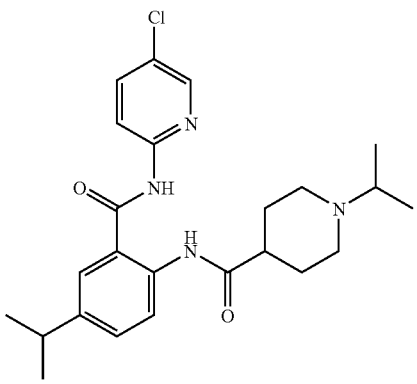

A. 2-iodo-4-isopropylaniline

Using methods substantially equivalent to those described in Example 173-C, 2-iodo-4-isopropylaniline (33.62 g, 50%) was prepared from 4-isopropylaniline.

¹H NMR

Analysis for $C_9H_{12}NI$: Calcd: C, 41.40; H, 4.63; N, 5.36; Found: C, 56.40; H, 4.73; N, 10.76.

B. 2-[(1-tert-Butoxycarbonylpiperidin-4-ylcarbonyl)amino]-1-iodo-5-isopropylbenzene Using methods substantially equivalent to those described in Example 25-D, 2-[(1-tert-butoxycarbonylpiperidin-4-ylcarbonyl)amino]-1-iodo-5-isopropylbenzene (2.05 g, 43%) was prepared from 2-iodo-4-isopropylaniline.

¹H NMR

IS-MS, m/e 473.1 (m+1), 471.2 (m−1);

Analysis for $C_{20}H_{29}IN_2O_3$: Calcd: C, 50.85; H, 6.19; N, 5.93; Found: C, 44.16; H, 5.32; N, 5.67.

C. 2-[(1-tert-Butoxycarbonylpiperidin-4-yl)-6-isopropyl-4H-3,1-benzoxazin-4-one

Using methods substantially equivalent to those described in Example 173-E, 2-[(1-tert-butoxycarbonylpiperidin-4-yl)-6-isopropyl-4H-3,1-benzoxazin-4-one (1.11 g, 94%) was prepared from 2-[(1-tert-butoxycarbonylpiperidin-4-ylcarbonyl)amino]-1-iodo-5-isopropylbenzene.

¹H NMR

IS-MS, m/e 373.2 (m+1);

Analysis for $C_{21}H_{28}N_2O_4$: Calcd: C, 67.72; H, 7.58; N, 7.52; Found: C, 68.11; H, 7.74; N, 7.62.

D. 2-[(1-tert-Butoxycarbonylpiperidin-4-ylcarbonyl)amino]-N-(5-chloropyridin-2-yl)-5-isopropylbenzamide Using methods substantially equivalent to those described in Example 51-D, 2-[(1-tert-butoxycarbonylpiperidin-4-ylcarbonyl)amino]-N-(5-chloropyridin-2-yl)-5-isopropylbenzamide (0.55 g, 41%) was prepared from 2-[(1-tert-butoxycarbonylpiperidin-4-yl)-6-isopropyl-4H-3,1-benzoxazin-4-one.

¹H NMR

IS-MS, m/e 501.1 (m+1), 499.2 (m−1);

Analysis for $C_{26}H_{33}ClN_4O_4$: Calcd: C, 62.33; H, 6.64; N, 11.18; Found: C, 60.69; H, 6.34; N, 11.15.

E. N-(5-Chloropyridin-2-yl)-5-isopropyl-2-[(4-piperidinylcarbonyl)amino]benzamide Trifluoroacetate Using methods substantially equivalent to those described in Example 9-B, N-(5-chloropyridin-2-yl)-5-isopropyl-2-[(4-piperidinylcarbonyl)amino]benzamide trifluoroacetate (0.45 g, 98%) was prepared from 2-[(1-tert-butoxycarbonylpiperidin-4-ylcarbonyl)amino]-N-(5-chloropyridin-2-yl)-5-isopropylbenzamide.

¹H NMR

IS-MS, m/e 401.2 (m+1), 399.2 (m−1);

Analysis for $C_{21}H_{25}ClN_4O_2 \cdot 1.0C_2HF_3O_2 \cdot 0.1H_2O$: Calcd: C, 53.46; H, 5.11; N, 10.84; F, 11.03; Found: C, 53.22; H, 5.04; N, 10.98; F, 11.50.

F. N-(5-Chloropyridin-2-yl)-5-isopropyl-2-[(1-isopropylpiperidin-4-ylcarbonyl)amino]benzamide Using methods substantially equivalent to those described in Example 231-E, N-(5-chloropyridin-2-yl)-5-isopropyl-2-[(1-isopropylpiperidin-4-ylcarbonyl)amino]benzamide (0.38 g, 89%) was prepared from N-(5-chloropyridin-2-yl)-5-isopropyl-2-[(4-piperidinylcarbonyl)amino]benzamide trifluoroacetate.

¹H NMR

IS-MS, m/e 443.2 (m+1), 441.3 (m−1);

Analysis for $C_{24}H_{31}ClN_4O_2 \cdot 0.3H_2O$: Calcd: C, 64.29; H, 7.10; N, 12.50; Found: C, 64.10; H, 6.97; N, 12.23.

EXAMPLE 242

Preparation of 4-Chloro-N-(5-chloropyridin-2-yl)-2-[(1-isopropylpiperidin-4-ylcarbonyl)amino]benzamide

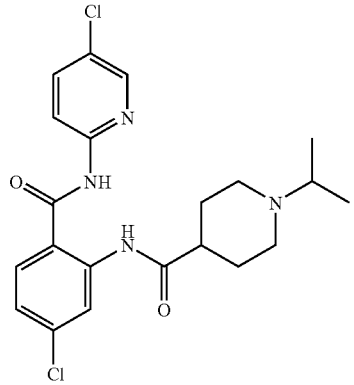

A. 2-[(1-tert-Butoxycarbonylpiperidin-4-ylcarbonyl)amino]-4-chloro-N-(5-chloropyridin-2-yl)benzamide Using methods substantially equivalent to those described in Example 25-D, 2-[(1-tert-butoxycarbonylpiperidin-4-ylcarbonyl)amino]-4-chloro-N-(5-chloropyridin-2-yl)benzamide (3.83 g, 97%) was prepared from 2-amino-4-chloro-N-(5-chloropyridin-2-yl)benzamide.
$^1$H NMR
IS-MS, m/e 493.0 (m+1), 491.0 (m−1);

B. 4-Chloro-N-(5-chloropyridin-2-yl)-2-[(4-piperidinylcarbonyl)amino]benzamide Trifluoroacetate Using methods substantially equivalent to those described in Example 9-B, 4-chloro-N-(5-chloropyridin-2-yl)-2-[(4-piperidinylcarbonyl)amino]benzamide trifluoroacetate (3.66 g, 93%) was prepared from 2-[(1-tert-butoxycarbonylpiperidin-4-ylcarbonyl)amino]-4-chloro-N-(5-chloropyridin-2-yl)benzamide.
$^1$H NMR

C. 4-Chloro-N-(5-chloropyridin-2-yl)-2-[(1-isopropylpiperidin-4-ylcarbonyl)amino]benzamide Using methods substantially equivalent to those described in Example 231-E, 4-chloro-N-(5-chloropyridin-2-yl)-2-[(1-isopropylpiperidin-4-ylcarbonyl)amino]benzamide (0.22 g, 51%) was prepared from 4-chloro-N-(5-chloropyridin-2-yl)-2-[(4-piperidinylcarbonyl)amino]benzamide trifluoroacetate.
$^1$H NMR
IS-MS, m/e 435.2 (m+1), 433.4 (m−1);
Analysis for $C_{21}H_{24}Cl_2N_4O_2 \cdot 0.3H_2O$: Calcd: C, 57.22; H, 5.63; N, 12.71; Found: C, 56.93; H, 5.48; N, 12.64.

EXAMPLE 243

Preparation of N-(5-chloropyridin-2-yl)-4-fluoro-2-[(1-isopropylpiperidin-4-ylcarbonyl)amino]benzamide

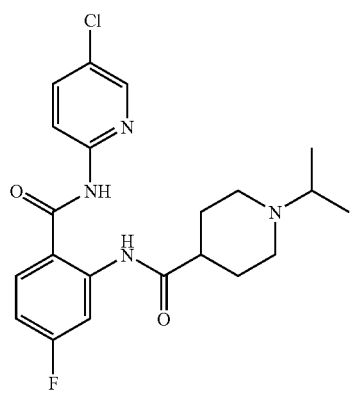

A. 2-[(1-tert-Butoxycarbonylpiperidin-4-ylcarbonyl)amino]-N-(5-chloropyridin-2-yl)-4-fluorobenzamide Using methods substantially equivalent to those described in Example 25-D, 2-[(1-tert-butoxycarbonylpiperidin-4-ylcarbonyl)amino]-N-(5-chloropyridin-2-yl)-4-fluorobenzamide (2.08 g, 55%) was prepared from 2-amino-N-(5-chloropyridin-2-yl)-4-fluorobenzamide.
$^1$H NMR
IS-MS, m/e 477.0 (m+1), 475.0 (m−1).

B. N-(5-Chloropyridin-2-yl)-4-fluoro-2-[(4-piperidinylcarbonyl)amino]benzamide Trifluoroacetate Using methods substantially equivalent to those described in Example 9-B, N-(5-chloropyridin-2-yl)-4-fluoro-2-[(4-piperidinylcarbonyl)amino]benzamide trifluoroacetate (1.68 g, 100%) was prepared from 2-[(1-tert-butoxycarbonylpiperidin-4-ylcarbonyl)amino]-N-(5-chloropyridin-2-yl)-4-fluorobenzamide.
$^1$H NMR
IS-MS, m/e 377.0 (m+1), 375.0 (m−1).

C. N-(5-Chloropyridin-2-yl)-4-fluoro-2-[(1-isopropylpiperidin-4-ylcarbonyl)amino]benzamide Using methods substantially equivalent to those described in Example 231-E, N-(5-chloropyridin-2-yl)-4-fluoro-2-[(1-isopropylpiperidin-4-ylcarbonyl)amino]benzamide (0.32 g, 74%) was prepared from N-(5-chloropyridin-2-yl)-4-fluoro-2-[(4-piperidinylcarbonyl)amino]benzamide trifluoroacetate.
$^1$H NMR
IS-MS, m/e 419.2 (m+1), 417.2 (m−1);
Analysis for $C_{21}H_{24}ClFN_4O_2 \cdot 0.3H_2O$: Calcd: C, 59.44; H, 5.84; N, 13.21; Found: C, 59.22; H, 5.60; N, 13.14.

EXAMPLE 244

Preparation of N-(5-Chloropyridin-2-yl)-5-iodo-2-[(1-isopropylpiperidin-4-ylcarbonyl)amino]benzamide

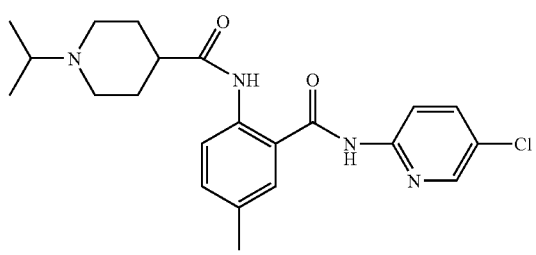

A. N-(5-Chloropyridin-2-yl)-2-nitrobenzamide

To a stirring solution of 2-amino-5-chloropyridine (3.7 g, 29 mmol) and pyridine (7.3 mL, 90 mmol) in dichloromethane was added 2-nitrobenzoyl chloride (5.7 g, 30 mmol). After stirring for 4 h, the solvents were removed in vacuo and the residue partitioned between ethyl acetate and water. The organic phase was washed with brine, dried over magnesium sulfate, filtered, and concentrated in vacuo. After standing at room temperature overnight, the mixture was filtered to give 6.4 g (79%) of a white solid.
$^1$H NMR
FD-MS, m/e 276.9 (m);
Analysis for $C_{12}H_8ClN_3O_3$: Calcd: C, 51.91; H, 2.90; N, 15.13; Found: C, 52.61; H, 2.89; N, 15.29.

B. N-(5-Chloropyridin-2-yl)-2-aminobenzamide

To a solution of N-(5-chloropyridin-2-yl)-2-nitrobenzamide (2 g, 7.2 mmol) in tetrahydrofuran (50 mL) and ethyl acetate (50 mL) was added Raney nickel (0.2 g) and the mixture was placed under hydrogen (4.1 bar) in a high pressure apparatus. After shaking overnight, the mixture was filtered and concentrated in vacuo and purified by flash chromatography to give 1.5 g (83%) of an off-white solid.
$^1$H NMR

C. 2-Amino-N-(5-chloropyridin-2-yl)-5-iodobenzamide

To an ice cold stirring suspension of N-(5-chloropyridin-2-yl)-2-aminobenzamide (1.01 g, 4.09 mmol) in ethanol (80 mL) was added a mixture of iodine (1.04 g, 4.10 mmol) and silver sulfate (1.29 g, 4.09 mmol). The mixture was stirred at room temperature for 3 d and filtered. The filtrate was concentrated, partitioned between dichloromethane and saturated aqueous sodium bicarbonate. The organic phase was dried over magnesium sulfate, filtered, and concentrated in vacuo. The crude product was purified by chromatography over silica gel, eluting with a step gradient of 5–10% ethyl acetate in dichloromethane. The chromatography product was slurried in isopropanol and filtered to give 0.49 g (32%) of an orange solid.
$^1$H NMR
IS-MS, m/e 373.8 (m+1), 371.8 (m−1);
Analysis for $C_{12}H_9ClIN_3O$: Calcd: C, 38.58; H, 2.43; N, 11.25; Found: C, 38.64; H, 2.76; N, 11.22.

D. 2-[(1-tert-Butoxycarbonylpiperidin-4-ylcarbonyl)amino]-N-(5-chloropyridin-2-yl)-5-iodobenzamide To a stirring solution of 1-Boc-isonipecotic acid (15.26 g, 66.55 mmol) in methanol (135 mL) was added sodium methoxide (3.8 g, 66.8 mmol). After stirring for 1 h, the solvent was removed in vacuo. A portion of the residue (8.92 g, 35.5 mmol) was suspended in dichloromethane (95 mL) and oxalyl chloride (4 mL, 45 mmol) was added, followed by a couple of drops of N,N-dimethylformamide. After stirring for 1 h, the solvent was removed in vacuo. The residue was suspended in dichloromethane (45 mL) and added to a solution of 2-amino-N-(5-chloropyridin-2-yl)-5-iodobenzamide (8.86 g, 23.7 mmol), N,N-diisopropylethylamine (5 mL, 28 mmol), and 4-(N,N-dimethylamino)pyridine (0.33 g, 2.7 mmol) in dichloromethane (50 mL). After stirring 19 h, the reaction mixture was partitioned between dichloromethane and saturated aqueous sodium bicarbonate. The organic phase was dried over magnesium sulfate, filtered, and concentrated in vacuo. The residue was slurried in diethyl ether and filtered to give 8.6 g (62%) of a pink solid.
$^1$H NMR
IS-MS, m/e 584.8 (m+1), 582.9 (m−1);
Analysis for $C_{23}H_{26}ClIN_4O_4$: Calcd: C, 47.23; H, 4.48; N, 9.58; Found: C, 46.96; H, 4.45; N, 9.68.

E. N-(5-Chloropyridin-2-yl)-5-iodo-2-[(4-piperidinylcarbonyl)amino]benzamide Trifluoroacetate To a stirring solution of 2-[(1-tert-butoxycarbonylpiperidin-4-ylcarbonyl)amino]-N-(5-chloropyridin-2-yl)-5-iodobenzamide (2.0 g, 3.45 mmol) in dichloromethane (65 mL) and anisole (2 mL, 18 mmol) was added trifluoroacetic acid (6.7 mL, 87 mmol). The reaction solution was stirred at room temperature for 4 h, concentrated in vacuo, treated with diethyl ether and concentrated (3×), treated with diethyl ether, sonicated, and filtered to give 1.86 g (90%) of a gray solid.
$^1$H NMR
IS-MS, m/e 484.9(m+1), 482.9 (m−1);
Analysis for $C_{18}H_{18}ClIN_4O_2 \cdot 1.1 C_2HF_3O_2$: Calcd: C, 39.76; H, 3.16; N, 9.18; Found: C, 39.70; H, 3.20; N, 9.35.

F. N-(5-Chloropyridin-2-yl)-5-iodo-2-[(1-isopropylpiperidin-4-ylcarbonyl)amino]benzamide To a stirring suspension of N-(5-chloropyridin-2-yl)-5-iodo-2-[(4-piperidinylcarbonyl)amino]benzamide trifluoroacetate (1.5 g, 2.52 mmol) in methanol (25 mL) was added acetone (25 mL), followed by acetic acid (0.6 mL, 10 mmol), and then sodium cyanoborohydride (0.67 g, 10 mmol). After stirring overnight, the solution was treated with saturated aqueous ammonium acetate solution, concentrated, and partitioned between dichloromethane and saturated aqueous sodium bicarbonate. The organic phase was washed with brine, dried over magnesium sulfate, filtered, and concentrated. The crude product was purified by chromatography over silica gel, eluting with a step gradient of 5–15% 2 M solution of ammonia/methanol in dichloromethane. The chromatography product was slurried in diethyl ether and filtered to give 0.87 g (65%) of a white solid.
$^1$H NMR
IS-MS, m/e 526.9 (m+1), 525.0 (m−1);
Analysis for $C_{21}H_{24}ClIN_4O_2 \cdot 1.4H_2O$: Calcd: C, 45.69; H, 4.89; N, 10.15; Found: C, 45.37; H, 4.68; N, 10.02.

EXAMPLE 245

Preparation of N-(5-Chloropyridin-2-yl)-2-[(1-isopropylpiperidin-4-ylcarbonyl)amino]-5-phenylbenzamide Hydrochloride

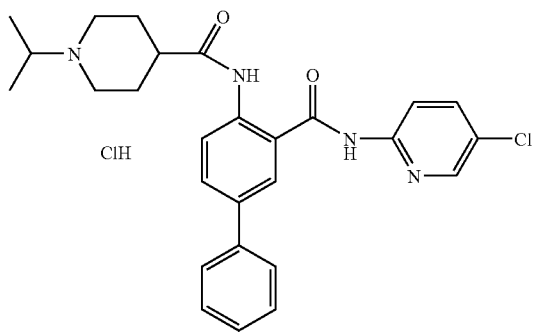

To a stirring solution of N-(5-chloropyridin-2-yl)-5-iodo-2-[(1-isopropylpiperidin-4-ylcarbonyl)amino]benzamide (0.29 g, 0.54 mmol), tetrakis(triphenylphosphine)palladium (0) (35 mg, 0.03 mmol), and phenylboronic acid (81 mg, 0.66 mmol) in toluene (5 mL) was added water (0.55 mL) and a 2 M aqueous sodium carbonate solution (0.55 mL, 1.1 mmol). The mixture was heated to 85–95° C. for 1 h, cooled to room temperature, partitioned between ethyl acetate and saturated aqueous sodium bicarbonate. The organic phase was treated with 0.002 N aqueous hydrochloric acid. To the aqueous phase was added dichloromethane followed by saturated aqueous sodium bicarbonate until pH 8–9. The phases were separated and the organic phase was concentrated. The crude product was purified by RPHPLC, eluting with a gradient from 25% through 65% acetonitrile in 0.05% aqueous hydrochloric acid, to give 0.16 g (57%) of a yellow solid.

¹H NMR

IS-MS, m/e 477.0 (m+1), 475.0 (m−1);

Analysis for $C_{27}H_{29}ClN_4O_2 \cdot 1.8HCl \cdot 0.9H_2O$: Calcd: C, 58.03; H, 5.88; N, 10.03; Cl, 17.76; Found: C, 58.08; H, 5.65; N, 9.79; Cl, 17.58.

EXAMPLE 246

Preparation of N-(5-Chloropyridin-2-yl)-2-[(1-isopropylpiperidin-4-ylcarbonyl)amino]-5-(3-thienyl)benzamide Hydrochloride

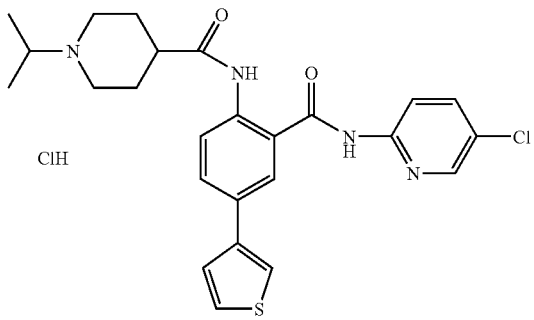

Using methods substantially equivalent to those described in Example 245, N-(5-chloropyridin-2-yl)-2-[(1-isopropylpiperidin-4-ylcarbonyl)amino]-5-(3-thienyl)benzamide hydrochloride (0.25 g, 50%) was prepared from N-(5-chloropyridin-2-yl)-5-iodo-2-[(1-isopropylpiperidin-4-ylcarbonyl)amino]benzamide.

¹H NMR

IS-MS, m/e 482.9 (m+1), 481.0 (m−1);

Analysis for $C_{25}H_{27}ClN_4O_2S \cdot 1.7HCl \cdot 0.7H_2O$: Calcd: C, 53.85; H, 5.44; N, 10.05; Cl, 17.17; Found: C, 53.82; H, 5.53; N, 9.86; Cl, 17.01.

EXAMPLE 247

Preparation of N-(5-Chloropyridin-2-yl)-2-[(1-isopropylpiperidin-4-ylcarbonyl)amino]-3-methoxybenzamide Hydrochloride

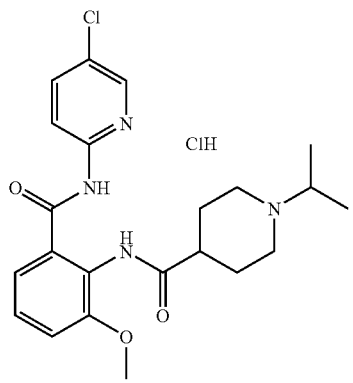

A. N-(5-Chloropyridin-2-yl)-3-methoxy-2-nitrobenzamide

To a stirring suspension of 3-methoxy-2-nitrobenzoic acid (14.5 g, 73.5 mmol) in dichloromethane (100 mL) was added a couple of drops of N,N-dimethylformamide followed by oxalyl chloride (6.7 mL, 77.1 mmol). The reaction was stirred at room temperature overnight and the residue transferred slowly to antic cold solution of 2-amino-5-chloropyridine (9 g, 70 mmol) and pyridine (20 mL) in dichloromethane (200 mL). The reaction was stirred overnight, treated with water, and concentrated. The resulting mixture was treated with ethyl acetate, washed consecutively with aqueous citric acid, saturated aqueous sodium bicarbonate, dried over magnesium sulfate, filtered, and concentrated in vacuo. The crude product was purified by recrystallization from toluene to give 17 g (79%) of a white solid.

¹H NMR

ESI+MS, m/e 308.0 (m+1);

Analysis for $C_{13}H_{10}ClN_3O_4$: Calcd: C, 50.75; H, 3.28; N, 13.66; Found: C, 51.60; H, 2.75; N, 13.44.

B. 2-Amino-N-(5-chloropyridin-2-yl)-3-methoxybenzamide

Using methods substantially equivalent to those described in Example 244-B, 2-amino-N-(5-chloropyridin-2-yl)-3-methoxybenzamide (11.5 g, 75%) was prepared from N-(5-chloropyridin-2-yl)-3-methoxy-2-nitrobenzamide.

¹H NMR

ES-MS, m/e 278.1 (m+1);

Analysis for $C_{13}H_{12}ClN_3O_2$: Calcd: C, 56.23; H, 4.36; N, 15.13; Found: C, 55.95; H, 4.48; N, 14.86.

C. 2-[(1-tert-Butoxycarbonylpiperidin-4-ylcarbonyl)amino]-N-(5-chloropyridin-2-yl)-3-methoxybenzamide Using methods substantially equivalent to those described in Example 244-D, 2-[(1-tert-butoxycarbonylpiperidin-4-ylcarbonyl)amino]-N-(5-chloropyridin-2-yl)-3-methoxybenzamide (1.50 g, 85%) was prepared from 2-amino-N-(5-chloropyridin-2-yl)-3-methoxybenzamide.

¹H NMR

IS-MS, m/e 489.3 (m+1), 487.5 (m−1);

Analysis for $C_{24}H_{29}ClN_4O_5$: Calcd: C, 58.95; H, 5.98; N, 11.46; Found: C, 58.73; H, 5.92; N, 11.23.

D. N-(5-Chloropyridin-2-yl)-3-methoxy-2-[(4-piperidinylcarbonyl)amino]benzamide Trifluoroacetate Using methods substantially equivalent to those described in Example 244-E, N-(5-chloropyridin-2-yl)-3-methoxy-2-[(4-piperidinylcarbonyl)amino]benzamide trifluoroacetate (1.22 g, 99%) was prepared from 2-[(1-tert-butoxycarbonylpiperidin-4-ylcarbonyl)amino]-N-(5-chloropyridin-2-yl)-3-methoxybenzamide.

¹H NMR

IS-MS, m/e 389.2 (m+1), 387.2 (m−1);

Analysis for $C_{19}H_{21}ClN_4O_3 \cdot 1.0C_2HF_3O_2$: Calcd: C, 50.16; H, 4.41; N, 11.14; F, 11.33; Found: C, 50.09; H, 4.16; N, 10.87; F, 11.46.

E. N-(5-Chloropyridin-2-yl)-2-[(1-isopropylpiperidin-4-ylcarbonyl)amino]-3-methoxybenzamide Hydrochloride Using methods substantially equivalent to those described in Example 244-F, N-(5-chloropyridin-2-yl)-2-[(1-isopropylpiperidin-4-ylcarbonyl)amino]-3-methoxybenzamide hydrochloride (0.34 g, 37%) was prepared from N-(5-chloropyridin-2-yl)-3-methoxy-2-[(4-piperidinylcarbonyl)amino]benzamide trifluoroacetate. To a stirring solution of the purified product in dichloromethane was added 1.0 N hydrochloric acid in diethyl ether until precipitate formed. The mixture was filtered to give the title compound.

$^1$H NMR

IS-MS, m/e 431.3 (m+1), 429.3 (m−1);

Analysis for $C_{22}H_{27}ClN_4O_3 \cdot 1.1HCl \cdot 0.4H_2O$: Calcd: C, 55.25; H, 6.09; N, 11.72; Cl, 15.57; Found: C, 55.03; H, 5.90; N, 11.54; Cl, 15.30.

EXAMPLE 248

Preparation of 5-Acetyl-N-(5-chloropyridin-2-yl)-2-[(1-isopropylpiperidin-4-ylcarbonyl)amino]benzamide Hydrochloride

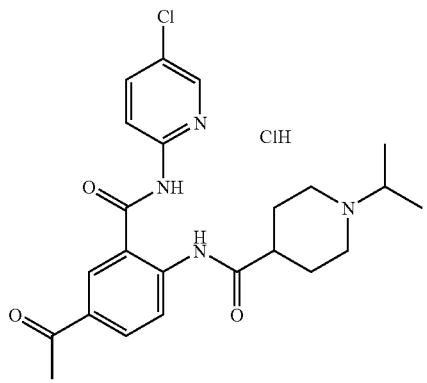

A. 4-Amino-3-iodoacetophenone

Using methods substantially equivalent to those described in Example 244-C, 4-amino-3-iodoacetophenone (3.9 g, 40%) was prepared from 4-aminoacetophenone.

$^1$H NMR

IS-MS, m/e 261.8 (m+1), 259.9 (m−1);

Analysis for $C_8H_8INO \cdot 0.2C_4H_8O_2$: Calcd: C, 37.93; H, 3.47; N, 5.03; Found: C, 37.82; H, 3.22; N, 5.26.

B. 5-Acetyl-2-[(1-tert-butoxycarbonylpiperidin-4-ylcarbonyl)amino]-1-iodobenzene Using methods substantially equivalent to those described in Example 244-D, 5-acetyl-2-[(1-tert-butoxycarbonylpiperidin-4-ylcarbonyl)amino]-1-iodobenzene (7.80 g, 48%) was prepared from 4-amino-3-iodoacetophenone.

$^1$H NMR

IS-MS, m/e 473.0 (m+1), 471.2 (m−1);

Analysis for $C_{19}H_{25}IN_2O_4$: Calcd: C, 48.32; H, 5.34; N, 5.93; Found: C, 48.45; H, 5.49; N, 5.83.

C. 5-Acetyl-2-[(1-tert-butoxycarbonylpiperidin-4-ylcarbonyl)amino]benzoic Acid To a stirring solution of 5-acetyl-2-[(1-tert-butoxycarbonylpiperidin-4-ylcarbonyl)amino]-1-iodobenzene (4.5 g, 9.53 mmol) in acetonitrile (150 mL) was added potassium carbonate (6.6 g, 47.7 mmol), followed by tetrakis(triphenylphosphine)palladium(0) (0.55 g, 0.48 mmol), and copper iodide (91 mg, 0.48 mmol). The mixture was placed under an atmosphere of carbon monoxide and heated to 80° C. After 3 h, 1 N aqueous sodium hydroxide (50 mL) was added to the hot reaction solution. The solution was stirred for 10 min and concentrated in vacuo. The residue was partitioned between ethyl acetate and water. The aqueous phase was filtered, acidified to pH 3 with citric acid, and extracted with ethyl acetate. The organic phase was washed with brine, dried over magnesium sulfate, filtered, and concentrated in vacuo to give 1.4 g (38%) of a white solid.

$^1$H NMR

IS-MS, m/e 389.2 (m−1);

Analysis for $C_{20}H_{26}N_2O_6 \cdot 0.4H_2O$: Calcd: C, 60.41; H, 6.79; N, 7.05; Found: C, 60.27; H, 6.55; N, 6.92.

D. 6-Acetyl-2-[(1-tert-butoxycarbonylpiperidin-4-yl)-4H-3,1-benzoxazin-4-one To a stirring solution of 5-acetyl-2-[(1-tert-butoxycarbonylpiperidin-4-ylcarbonyl)amino]benzoic acid (0.22 g, 0.57 mmol) in N,N-dimethylformamide (3 mL) was added 1-(3-dimethylaminopropyl)-3-ethylcarbodiimide hydrochloride (0.14 g, 0.74 mmol). The reaction solution was stirred for 30 min, treated with cold water and the resulting mixture stirred for 10 min and filtered to give 0.20 g (92%) of a tan solid.

$^1$H NMR

FD-MS, m/e 372.3 (m+1);

Analysis for $C_{20}H_{24}N_2O_5$: Calcd: C, 64.50; H, 6.50; N, 7.52; Found: C, 64.20; H, 6.40; N, 7.45.

E. 5-Acetyl-2-[(1-tert-butoxycarbonylpiperidin-4-ylcarbonyl)amino]-N-(5-chloropyridin-2-yl)benzamide To an ice cold stirring solution of 2-amino-5-chloropyridine (0.11 g, 0.86 mmol) in tetrahydrofuran (20 mL) was added dropwise a 1.0 M solution of allylmagnesium bromide in diethyl ether (0.9 mL, 0.9 mmol). After stirring for 10 min, 6-acetyl-2-[(1-tert-butoxycarbonylpiperidin-4-yl)-4H-3,1-benzoxazin-4-one (0.16 g, 0.43 mmol) was added. After stirring overnight at room temperature, the solvent was removed in vacuo. The residue was partitioned between ethyl acetate and saturated aqueous sodium chloride, and layers were separated. The organic phase was washed with water dried over magnesium sulfate, filtered, and concentrated in vacuo. The crude product was purified by chromatography, eluting with a step gradient of 25–28% ethyl acetate in dichloromethane to give 155 mg (72%) of a white solid.

$^1$H NMR

IS-MS, m/e 501.3 (m+1), 499.2 (m−1);

Analysis for $C_{25}H_{29}ClN_4O_5$: Calcd: C, 59.94; H, 5.83; N, 11.18; Found: C, 59.69; H, 6.03; N, 11.17.

F. 5-Acetyl-N-(5-chloropyridin-2-yl)-2-[(4-piperidi-nylcarbonyl)amino]benzamide Trifluoroacetate Using methods substantially equivalent to those described in Example 244-E, 5-acetyl-N-(5-chloropyridin-2-yl)-2-[(piperidin-4-ylcarbonyl)amino]benzamide trifluoroacetate (101 mg, 98%) was prepared from 5-acetyl-2-[(1-tert-butoxycarbonylpiperidin-4-ylcarbonyl)amino]-N-(5-chloropyridin-2-yl)benzamide.

$^1$H NMR

IS-MS, m/e 401.2 (m+1), 399.2 (m−1);

Analysis for $C_{20}H_{21}Cl_2N_4O_3 \cdot 1.2C_2HF_3O_2 \cdot 0.1H_2O$: Calcd: C, 49.87; H, 4.31; N, 10.39; F, 12.68; Found: C, 49.89; H, 4.31; N, 10.48; F, 12.44.

G. 5-Acetyl-N-(5-chloropyridin-2-yl)-2-[(1-isopropylpiperidin-4-ylcarbonyl)amino]benzamide Hydrochloride Using methods substantially equivalent to those described in Example 244-F, 5-acetyl-N-(5-chloropyridin-2-yl)-2-[(1-isopropylpiperidin-4-ylcarbonyl)amino]benzamide hydrochloride (48 mg, 67%) was prepared from 5-acetyl-N-(5-chloropyridin-2-yl)-2-[(4-piperidinylcarbonyl)amino]benzamide trifluoroacetate. To a stirring solution of the purified product in dichloromethane was added 1.0 N hydrochloric acid in diethyl ether until precipitate formed. The mixture was filtered to give the title compound.

$^1$H NMR

IS-MS, m/e 443.2 (m+1), 441.2 (m−1);

Analysis for $C_{23}H_{27}ClN_4O_3 \cdot 1.3HCl \cdot 0.6H_2O$: Calcd: C, 55.12; H, 5.93; N, 11.18; Cl, 16.27; Found: C, 54.79; H, 6.32; N, 11.13; Cl, 16.30.

EXAMPLE 249

Preparation of N-(5-Chloropyridin-2-yl)-2-[(1-isopropylpiperidin-4-ylcarbonyl)amino]-5-(2-thienyl)benzamide Hydrochloride

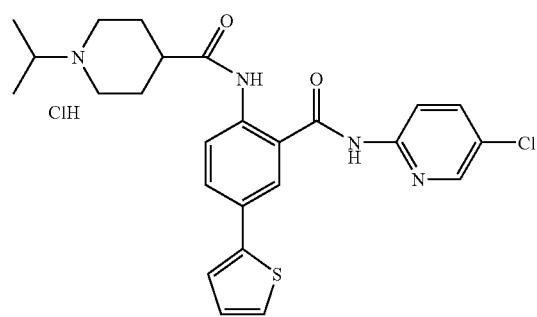

Using methods substantially equivalent to those described in Example 245, N-(5-chloropyridin-2-yl)-2-[(1-isopropylpiperidin-4-ylcarbonyl)amino]-5-(2-thienyl)benzamide hydrochloride (0.21 g, 42%) was prepared from N-(5-chloropyridin-2-yl)-5-iodo-2-[(1-isopropylpiperidin-4-ylcarbonyl)amino]benzamide.

$^1$H NMR

IS-MS, m/e 482.9 (m+1), 480.9 (m−1);

Analysis for $C_{25}H_{27}ClN_4O_2S \cdot 2.0HCl \cdot 2.1H_2O$: Calcd: C, 50.57; H, 5.64; N, 9.44; Cl, 17.91; Found: C, 50.59; H, 5.46; N, 9.43; Cl, 17.85.

EXAMPLE 250

Preparation of N-(5-chloropyridin-2-yl)-2-[(1-isopropylpiperidin-4-ylcarbonyl)amino]-5-(2-thiazolyl)benzamide

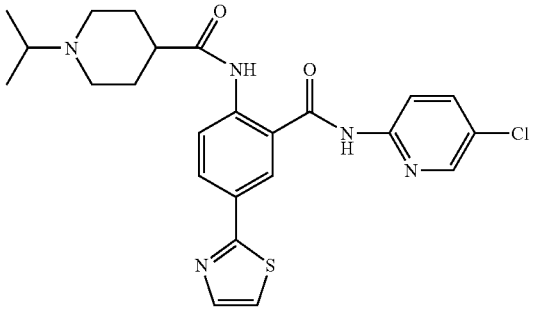

To a stirring solution of N-(5-chloropyridin-2-yl)-5-iodo-2-[(1-isopropylpiperidin-4-ylcarbonyl)amino]benzamide (0.52 g, 0.99 mmol) and tetrakis(triphenylphosphine)palladium(0) (59 mg, 0.05 mmol) in tetrahydrofuran (7 mL) was added a solution of 0.5 M 2-thiazolezinc bromide (2.4 mL, 1.2 mmol) in tetrahydrofuran. The reaction mixture was stirred overnight at room temperature and then diluted with 3:1 chloroform:isopropanol. The resulting solution was washed with saturated aqueous ammonium chloride and the phases separated. The aqueous phase was treated with saturated aqueous sodium bicarbonate to pH 8 and extracted with 3:1 chloroform:isopropanol. The organic phase was dried over magnesium sulfate, filtered, and concentrated in vacuo. The crude product was resubmitted to reaction conditions [tetrakis(triphenylphosphine)palladium(0) (38 mg, 0.03 mmol), tetrahydrofuran (7 mL), and a solution of 0.5 M 2-thiazolezinc bromide (9.6 mL, 4.8 mmol)], stirred overnight, and worked up as above. The crude product was purified by chromatography over silica gel, eluting with a step gradient of 5–20% 2 M ammonia/methanol solution in dichloromethane. The chromatography product was slurried in diethyl ether and filtered to give 0.27 g (57%) of a white solid.

$^1$H NMR

IS-MS, m/e 483.8 (m+1), 481.9 (m−1);

Analysis for $C_{24}H_{26}ClN_5O_2S \cdot 0.5H_2O$: Calcd: C, 58.47; H, 5.52; N, 14.21; Found: C, 58.16; H, 5.21; N, 14.04.

EXAMPLE 251

Preparation of N-(5-Chloropyridin-2-yl)-2-[(1-isopropylpiperidin-4-ylcarbonyl)amino]-5-(3-pyridinyl)benzamide

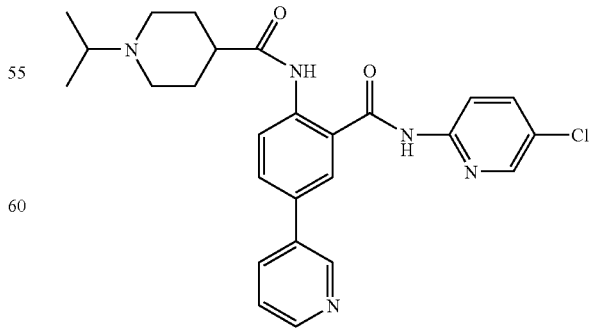

Using methods substantially equivalent to those described in Example 245, N-(5-chloropyridin-2-yl)-2-[(1-isopropylpiperidin-4-ylcarbonyl)amino]-5-(3-pyridinyl)benzamide (0.11 g, 24%) was prepared from N-(5-chloropyridin-2-yl)-5-iodo-2-[(1-isopropylpiperidin-4-ylcarbonyl)amino]benzamide and 3-pyridyldiethylborate in tetrahydrofuran. The crude product was purified by chromatography over silica gel, eluting with a step gradient of 10–15% 2 M ammonia/methanol solution in dichloromethane. The chromatography product was slurried in diethyl ether and filtered to give the title compound.

$^1$H NMR

IS-MS, m/e 477.9 (m+1), 475.9 (m−1);

Analysis for $C_{26}H_{28}ClN_5O_2 \cdot 0.7H_2O$: Calcd: C, 63.65; H, 6.04; N, 14.28; Found: C, 63.32; H, 5.87; N, 14.29.

EXAMPLE 252

Preparation of N-(5-Chloropyridin-2-yl)-2-[(1-isopropylpiperidin-4-ylcarbonyl)amino]-5-(4-pyridinyl)benzamide

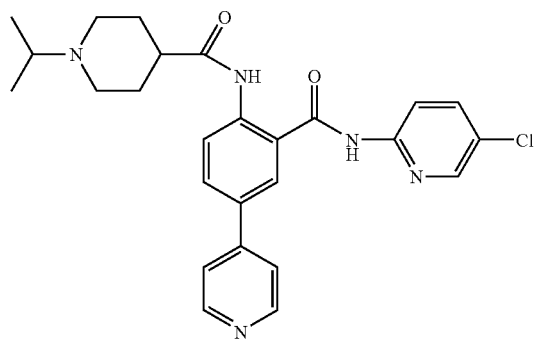

To a stirring solution of N-(5-chloropyridin-2-yl)-5-iodo-2-[(1-isopropylpiperidin-4-ylcarbonyl)amino]benzamide (0.52 g, 0.98 mmol), dichlorobis(triphenylphosphine)palladium(II) (34 mg, 0.05 mmol), and lithium chloride (0.15 g, 3.56 mmol) in 1,4-dioxane (5 mL) was added 4-(tributylstannyl)pyridine (1.16 g, 3.14 mmol) and dioxane (5 mL). The reaction mixture was heated to reflux, stirred overnight, and then filtered through diatomaceous earth. The filtrate was partitioned between 3:1 chloroform:isopropanol and saturated aqueous sodium bicarbonate, and the layers separated. The organic phase was dried over magnesium sulfate, filtered, and concentrated in vacuo. The crude product was purified by chromatography over silica gel, eluting with a step gradient of 10–25% 2 M ammonia/methanol solution in dichloromethane. The chromatography product was recrystallized from methanol and ethyl acetate to give 47 mg (20%) of a white solid.

$^1$H NMR

IS-MS, m/e 478.0 (m+1), 476.0 (m−1);

Analysis for $C_{26}H_{28}ClN_5O_2 \cdot 1.6H_2O$: Calcd: C, 61.62; H, 6.21; N, 13.82; Found: C, 61.29; H, 5.87; N, 13.76.

EXAMPLE 253

Preparation of N-(5-Chloropyridin-2-yl)-5-cyano-2-[(1-isopropylpiperidin-4-ylcarbonyl)amino]benzamide

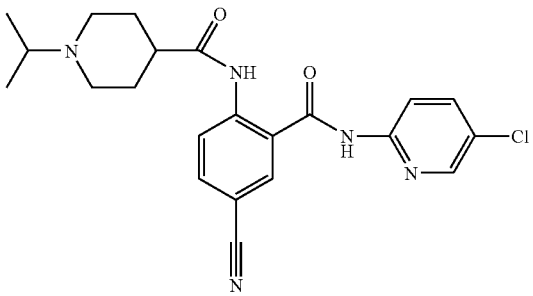

To a stirring solution of N-(5-chloropyridin-2-yl)-5-iodo-2-[(1-isopropylpiperidin-4-ylcarbonyl)amino]benzamide (0.50 g, 0.94 mmol) in N,N-dimethylformamide (6 mL) was added zinc cyanide (70 mg, 0.58 mmol) followed by tetrakis(triphenylphosphine)palladium(0) (49 mg, 0.04 mmol). The reaction mixture was stirred at 83° C. for 6 h and then at room temperature overnight. It was then partitioned between 3:1 chloroform:isopropanol and ammonium hydroxide and the layers separated. The organic phase was dried over magnesium sulfate, filtered, and concentrated in vacuo. The crude product was suspended in methanol and filtered. The filtered solid was then slurried in diethyl ether and filtered to give 70 mg (18%) of the title compound as white solid. The methanolic filtrate was concentrated in vacuo and purified by chromatography over silica gel, eluting with 5–20% 2 M ammonia/methanol solution in dichloromethane. The chromatography product was slurried in methanol and filtered to give an additional 0.14 g (35%) of the title compound.

$^1$H NMR

IS-MS, m/e 426.0 (m+1), 424.0 (m−1);

Analysis for $C_{22}H_{24}ClN_5O_2 \cdot 1.1H_2O$: Calcd: C, 59.28; H, 5.92; N, 15.71; Found: C, 58.91; H, 5.55; N, 15.72.

EXAMPLE 254

Preparation of N-(5-Chloropyridin-2-yl)-5-(2-furanyl)-2-[(1-isopropylpiperidin-4-ylcarbonyl)amino]benzamide

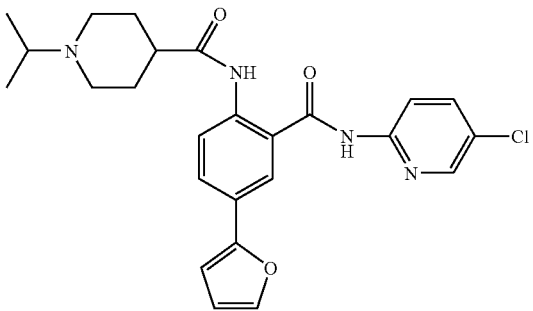

Using methods substantially equivalent to those described in Example 245, N-(5-chloropyridin-2-yl)-5-(2-furanyl)-2-

[(1-isopropylpiperidin-4-ylcarbonyl)amino]benzamide (0.15 g, 34%) was prepared from N-(5-chloropyridin-2-yl)-5-iodo-2-[(1-isopropylpiperidin-4-ylcarbonyl)amino]benzamide, 2-(tributylstannyl)furan, and dichlorobis-(triphenylphosphine)palladium(II) in tetrahydrofuran.

¹H NMR

IS-MS, m/e 466.9 (m+1), 464.9 (m−1);

Analysis for $C_{25}H_{27}ClN_4O_3 \cdot 0.1H_2O$: Calcd: C, 64.05; H, 5.85; N, 11.95; Found: C, 63.83; H, 5.83; N, 11.93.

EXAMPLE 255

Preparation of N-(5-Chloropyridin-2-yl)-2-[(1-isopropylpiperidin-4-ylcarbonyl)amino]-5-(2-pyridinyl)benzamide

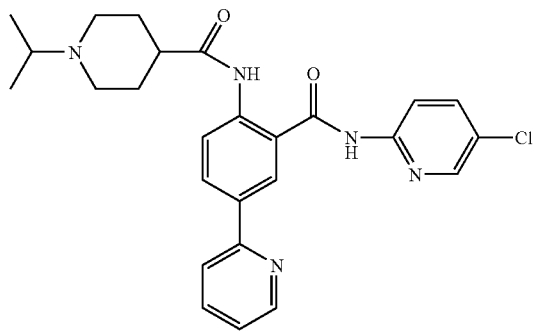

Using methods substantially equivalent to those described in Example 245, N-(5-chloropyridin-2-yl)-2-[(1-isopropylpiperidin-4-ylcarbonyl)amino]-5-(2-pyridinyl)benzamide (0.30 g, 65%) was prepared from N-(5-chloropyridin-2-yl)-5-iodo-2-[(1-isopropylpiperidin-4-ylcarbonyl)amino]benzamide and 2-pyridylzinc bromide.

¹H NMR

IS-MS, m/e 477.9 (m+1), 475.9 (m−1);

Analysis for $C_{26}H_{28}ClN_5O_2 \cdot 0.2H_2O$: Calcd: C, 64.84; H, 5.94; N, 14.54; Found: C, 64.67; H, 5.94; N, 14.22.

EXAMPLE 256

Preparation of N-(5-Chloropyridin-2-yl)-2-[(1-isopropylpiperidin-4-ylcarbonyl)amino]-5-vinylbenzamide

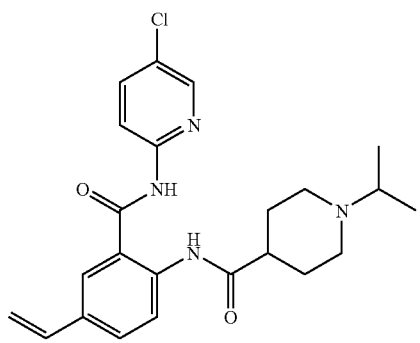

To a stirring solution of N-(5-chloropyridin-2-yl)-5-iodo-2-[(1-isopropylpiperidin-4-ylcarbonyl)amino]benzamide (1.0 g, 1.90 mmol) in N-methyl-2-pyrrolidinone (25 mL) was added tetrakis(triphenylphosphine)palladium(0) (0.12 g, 0.1 mmol), triphenylarsine (60 mg, 0.2 mmol) and copper iodide (10 mg, 0.05 mmol) followed by tributyl(vinyl)tin (0.63 mL, 2.09 mmol). The reaction solution was heated to 105° C., stirred for 8 h, partitioned between dichloromethane and saturated aqueous sodium bicarbonate, and the layers separated. The organic phase was washed with brine, dried over magnesium sulfate, filtered, and concentrated in vacuo. The crude product was purified by chromatography over silica gel, eluting with 10% 2 M ammonia/methanol solution in dichloromethane. The chromatography product was slurried in methanol and filtered to give 131 mg (16%) of a white solid.

¹H NMR

IS-MS, m/e 427.1 (m+1), 425.1 (m−1);

Analysis for $C_{23}H_{27}ClN_4O_2$: Calcd: C, 64.70; H, 6.37; N, 13.12; Found: C, 64.72; H, 6.51; N, 13.06.

EXAMPLE 257

Preparation of N-(5-Chloropyridin-2-yl)-5-formyl-2-[(1-isopropylpiperidin-4-ylcarbonyl)amino]benzamide Hydrochloride

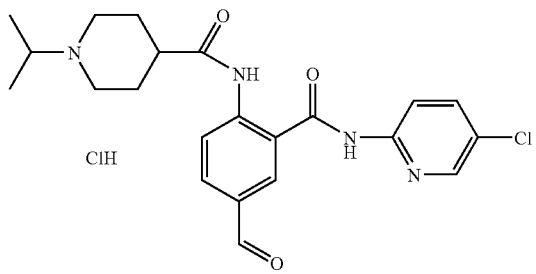

To a stirring solution of N-(5-chloropyridin-2-yl)-5-iodo-2-[(1-isopropylpiperidin-4-ylcarbonyl)amino]benzamide (0.51 g, 0.97 mmol) in N,N-dimethylformamide (10 mL) was added sodium formate (0.11 g, 1.6 mmol), calcium sulfate (0.39 g, 2.9 mmol), triphenylphosphine (6 mg, 0.02 mmol) and dichlorobis(triphenylphosphine)palladium(II) (15 mg, 0.02 mmol). The reaction mixture was heated to 80° C., stirred overnight, cooled to room temperature, partitioned between dichloromethane and saturated aqueous sodium bicarbonate, and the layers separated. The organic phase was filtered to remove solids, dried over magnesium sulfate, filtered, and concentrated in vacuo. The crude product was purified by RPHPLC, eluting with a gradient of 10% through 50% acetonitrile in 0.05% aqueous hydrochloric acid, to give 0.14 g (31%) of a yellow solid.

¹H NMR

IS-MS, m/e 428.9 (m+1), 426.9 (m−1);

Analysis for $C_{22}H_{25}ClN_4O_3 \cdot 1.9HCl \cdot 2.0H_2O$: Calcd. C, 49.46; H, 5.83; N, 10.49; Cl, 19.25; Found: C, 49.51; H, 5.51; N, 10.39; Cl, 19.30.

EXAMPLE 258

Preparation of N-(5-Chloropyridin-2-yl)-5-(1-hydroxyethyl)-2-[(1-isopropylpiperidin-4-ylcarbonyl)amino]benzamide

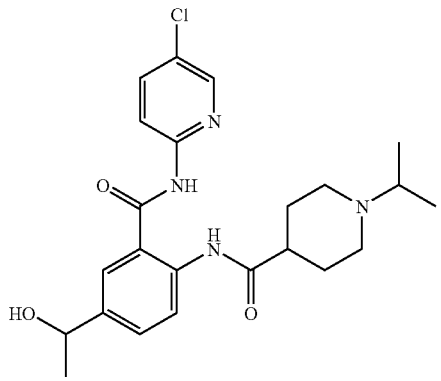

A. 2-[(1-tert-Butoxycarbonylpiperidin-4-ylcarbonyl)amino]-N-(5-chloropyridin-2-yl)-5-(1-hydroxyethyl)benzamide To a stirring solution of 5-acetyl-2-[(1-tert-butoxycarbonylpiperidin-4-ylcarbonyl)amino]-N-(5-chloropyridin-2-yl)benzamide (0.48 g, 0.96 mmol) in methanol (20 mL), was added sodium borohydride (36 mg, 0.96 mmol). The reaction was stirred at room temperature for 5 min, treated with water, and concentrated in vacuo. The residual mixture was partitioned between ethyl acetate and water and the layers separated. The organic phase was washed with brine, dried over magnesium sulfate, filtered, and concentrated in vacuo to give 0.47 g (98%) of a white foam.

$^1$H NMR

IS-MS, m/e 502.9 (m+1), 500.9 (m−1);

Analysis for $C_{25}H_{31}ClN_4O_5$: Calcd: C, 59.70; H, 6.21; N, 11.14; Found: C, 53.77; H, 5.18; N, 10.77.

B. N-(5-Chloropyridin-2-yl)-5-(1-hydroxyethyl)-2-[(4-piperidinylcarbonyl)amino]benzamide Trifluoroacetate Using methods substantially equivalent to those described in Example 244-E, N-(5-chloropyridin-2-yl)-5-(1-hydroxyethyl)]-2-[(4-piperidinylcarbonyl)amino]benzamide trifluoroacetate (0.35 g, 86%) was prepared from 2-[(1-tert-butoxycarbonylpiperidin-4-ylcarbonyl)amino]-N-(5-chloropyridin-2-yl)-5-(1-hydroxyethyl)benzamide.

$^1$H NMR

IS-MS, m/e 403.3 (m+1), 401.1 (m−1);

Analysis for $C_{20}H_{23}ClN_4O_3 \cdot 1.6C_2HF_3O_2$: Calcd: C, 47.61; H, 4.24; N, 9.57; F, 15.58; Found: C, 47.64; H, 3.96; N, 9.19; F, 16.91.

C. N-(5-Chloropyridin-2-yl)-5-(1-hydroxyethyl)-2-[(1-isopropylpiperidin-4-ylcarbonyl)amino]benzamide Using methods substantially equivalent to those described in Example 244-F, N-(5-chloropyridin-2-yl)-5-(1-hydroxyethyl)-2-[(1-isopropylpiperidin-4-ylcarbonyl)amino]benzamide (0.15 g, 58%) was prepared from N-(5-chloropyridin-2-yl)-5-(1-hydroxyethyl)-2-[(4-piperidinylcarbonyl)amino]benzamide trifluoroacetate.

$^1$H NMR

IS-MS, m/e 445.2 (m+1), 443.3 (m−1);

Analysis for $C_{23}H_{29}ClN_4O_3$: Calcd: C, 62.08; H, 6.57; N, 12.59; Found: C, 61.54; H, 5.42; N, 12.29.

EXAMPLE 260

Preparation of (E)-1-(5-chloropyridin-2-yl)-2-[(1-isopropylpiperidin-4-ylcarbonyl)amino]-5-(2-methoxycarbonylvinyl)benzamide

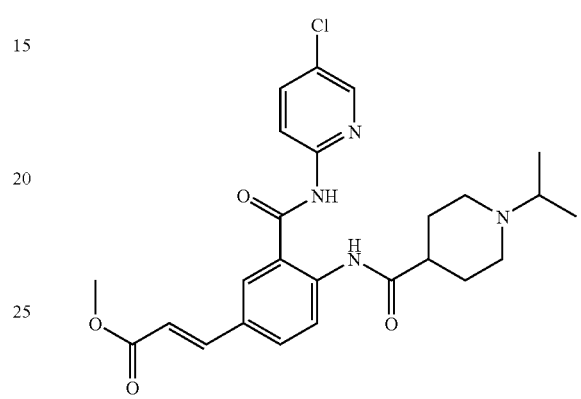

A. (E)-2-[(1-tert-Butoxycarbonylpiperidin-4-ylcarbonyl)amino]-N-(5-chloropyridin-2-yl)-5-(2-methoxycarbonylvinyl)benzamide To a stirring solution of 2-[(1-tert-butoxycarbonylpiperidin-4-ylcarbonyl)amino]-N-(5-chloropyridin-2-yl)-5-iodobenzamide (1.17 g, 2 mmol) in acetonitrile (4 mL) was added triethylamine (2 mL, 14.3 mmol) followed by palladium(II) acetate (22 mg, 0.1 mmol) and then methyl acrylate (0.36 mL, 4 mmol). The mixture was heated to 100° C. in a sealed tube. After 15 h, the reaction mixture was cooled to room temperature and concentrated in vacuo. The crude product was purified by chromatography on silica gel, eluting with 20% ethyl acetate in dichloromethane, to give 0.96 g (88%) of a white solid.

$^1$H NMR

IS-MS, m/e 543.2 (m+1), 541.4 (m−1);

Analysis for $C_{27}H_{31}ClN_4O_6$: Calcd: C, 59.72; H, 5.75; N, 10.32; Found: C, 61.46; H, 5.97; N, 10.42.

B. (E)-N-(5-Chloropyridin-2-yl)-5-(2-methoxycarbonylvinyl)-2-[(4-piperidinylcarbonyl)amino]benzamide Trifluoroacetate Using methods substantially equivalent to those described in Example 244-E, E-N-(5-chloropyridin-2-yl)-5-(2-methoxycarbonylvinyl)-2-[(4-piperidinylcarbonyl)amino]benzamide trifluoroacetate (0.30 g, 98%) was prepared from (E)-2-[(1-tert-butoxycarbonylpiperidin-4-ylcarbonyl)amino]-N-(5-chloropyridin-2-yl)-5-(2-methoxycarbonylvinyl)benzamide.

$^1$H NMR

IS-MS, m/e 443.2 (m+1), 441.2 (m−1);

Analysis for $C_{22}H_{23}ClN_4O_4 \cdot 1.0C_2HF_3O_2$: Calcd: C, 51.76; H, 4.34; N, 10.06; F, 10.23; Found: C, 51.90; H, 4.17; N, 9.73; F, 10.93.

C. (E)-N-(5-Chloropyridin-2-yl)-2-[(1-isopropylpiperidin-4-ylcarbonyl)amino]-5-(2-methoxycarbonylvinyl)benzamide Using methods substantially equivalent to those described in Example 244-F, (E)-N-(5-chloropyridin-2-yl)-2-[(1-isopropylpiperidin-4-ylcarbonyl)amino]-5-(2-methoxycarbonylvinyl)benzamide (92 mg, 42%) was prepared from (E)-N-(5-chloropyridin-2-yl)-5-(2-methoxycarbonylvinyl)]-2-[(4-piperidinylcarbonyl)amino]benzamide trifluoroacetate.
¹H NMR
IS-MS, m/e 485.5 (m+1), 483.4 (m−1);
Analysis for $C_{25}H_{29}ClN_4O_4 \cdot 0.1H_2O$: Calcd: C, 61.68; H, 6.05; N, 11.51; Found: C, 61.39; H, 6.13; N, 11.63.

EXAMPLE 260

Preparation of (E)-N-(5-Chloropyridin-2-yl)-5-(2-cyanovinyl)-2-[(1-isopropylpiperidin-4-ylcarbonyl)amino]benzamide

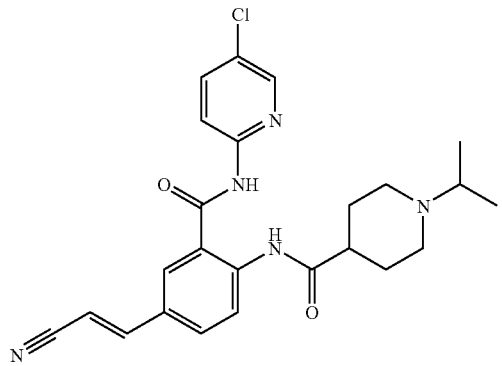

A. (E)-2-[(1-tert-Butoxycarbonylpiperidin-4-ylcarbonyl)amino]-N-(5-chloropyridin-2-yl)-5-(2-cyanovinyl)benzamide Using methods substantially equivalent to those described in Example 259-A, 2-[(1-tert-butoxycarbonylpiperidin-4-ylcarbonyl)amino]-N-(5-chloropyridin-2-yl)-5-iodobenzamide was condensed with acrylonitrile. From the reaction mixture was isolated (E)-2-[(1-tert-butoxycarbonylpiperidin-4-ylcarbonyl)amino]-N-(5-chloropyridin-2-yl)-5-(2-cyanovinyl)benzamide (0.49 g, 48%), as well as the (Z)-isomer (see next example).
¹H NMR
IS-MS, m/e 510.2 (m+1), 508.2 (m−1);
Analysis for $C_{26}H_{28}ClN_5O_4$: Calcd: C, 61.23; H, 5.53; N, 13.73; Found: C, 61.12; H, 5.79; N, 12.84.

B. (E)-N-(5-Chloropyridin-2-yl)-5-(2-cyanovinyl)]-2-[(4-piperidinylcarbonyl)amino]benzamide Trifluoroacetate Using methods substantially equivalent to those described in Example 244-E, (E)-N-(5-chloropyridin-2-yl)-5-(2-cyanovinyl)-2-[(4-piperidinylcarbonyl)amino]benzamide trifluoroacetate (0.20 g, 95%) was prepared from (E)-2-[(1-tert-butoxycarbonylpiperidin-4-ylcarbonyl)amino]-N-(5-chloropyridin-2-yl)-5-(2-cyanovinyl)benzamide.

¹H NMR
IS-MS, m/e 408.3 (m−1);
Analysis for $C_{21}H_{20}ClN_5O_2 \cdot 1.1C_2HF_3O_2$: Calcd: C, 52.05; H, 3.97; N, 13.08; F, 11.71; Found: C, 52.20; H, 4.13; N, 12.72; F, 11.47.

C. (E)-N-(5-Chloropyridin-2-yl)-5-(2-cyanovinyl)-2-[(1-isopropylpiperidin-4-ylcarbonyl)amino]benzamide Using methods substantially equivalent to those described in Example 244-F, (E)-N-(5-chloropyridin-2-yl)-5-(2-cyanovinyl)-2-[(1-isopropylpiperidin-4-ylcarbonyl)amino]benzamide (48 mg, 36%) was prepared from (E)-N-(5-chloropyridin-2-yl)-5-(2-cyanoethenyl)-2-[(4-piperidinylcarbonyl)amino]benzamide trifluoroacetate.
¹H NMR
IS-MS, m/e 452.2 (m+1), 450.1 (m−1);
Analysis for $C_{24}H_{26}ClN_5O_2$: Calcd: C, 63.78; H, 5.80; N, 15.50; Found: C, 63.39; H, 5.84; N, 15.75.

EXAMPLE 261

Preparation of (Z)-N-(5-Chloropyridin-2-yl)-5-(2-cyanovinyl)-2-[(1-isopropylpiperidin-4-ylcarbonyl)amino]benzamide

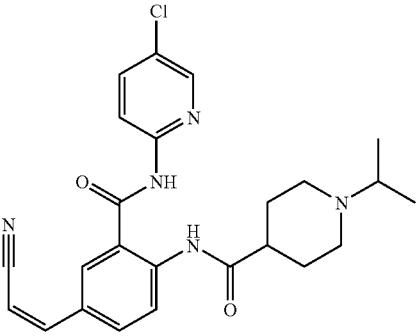

A. (Z)-2-[(1-tert-Butoxycarbonylpiperidin-4-ylcarbonyl)amino]-N-(5-chloropyridin-2-yl)-5-(2-cyanovinyl)]benzamide Using methods substantially equivalent to those described in Example 259-A, 2-[(1-tert-butoxycarbonylpiperidin-4-ylcarbonyl)amino]-N-(5-chloropyridin-2-yl)-5-iodobenzamide was condensed with acrylonitrile. From the reaction mixture was isolated (Z)-2-[(1-tert-butoxycarbonylpiperidin-4-ylcarbonyl)amino]-N-(5-chloropyridin-2-yl)-5-(2-cyanovinyl)benzamide (0.19 g, 19%), as well as the (E)-isomer (see prior example).
¹H NMR
IS-MS, m/e 510.3 (m+1), 508.2 (m−1);
Analysis for $C_{26}H_{28}ClN_5O_4$: Calcd: C, 61.23; H, 5.53; N, 13.73; Found: C, 44.22; H, 4.08; N, 9.55.

B. (Z)-N-(5-Chloropyridin-2-yl)-5-(2-cyanovinyl)-2-[(4-piperidinylcarbonyl)amino]benzamide Trifluoroacetate Using methods substantially equivalent to those described in Example 244-E, (Z)-N-(5-chloropyridin-2-yl)-5-(2-cyanovinyl)]-2-[(4-piperidinylcarbonyl)amino]benzamide trifluoroacetate (0.13 g, 84%) was prepared from (Z)-2-[(1-tertbutoxycarbonylpiperidin-4-ylcarbonyl)amino]-N-(5-chloropyridin-2-yl)-5-(2-cyanovinyl)benzamide.

$^1$H NMR

C. (Z)-N-(5-Chloropyridin-2-yl)-5-(2-cyanovinyl)-2-[(1-isopropylpiperidin-4-ylcarbonyl)amino]benzamide Using methods substantially equivalent to those described in Example 244-F, (Z)-N-(5-chloropyridin-2-yl)-5-(2-cyanovinyl)-2-[(1-isopropylpiperidin-4-ylcarbonyl)amino]benzamide (41 mg, 46%) was prepared from (Z)-N-(5-chloropyridin-2-yl)-5-(2-cyanovinyl)-2-[(4-piperidinylcarbonyl)amino]benzamide trifluoroacetate.

$^1$H NMR

IS-MS, m/e 452.2 (m+1), 450.1 (m−1);

EXAMPLE 262

Preparation of N-(5-Chloropyridin-2-yl)-2-[(1-isopropylpiperidin-4-ylcarbonyl)amino]-5-methylthiobenzamide

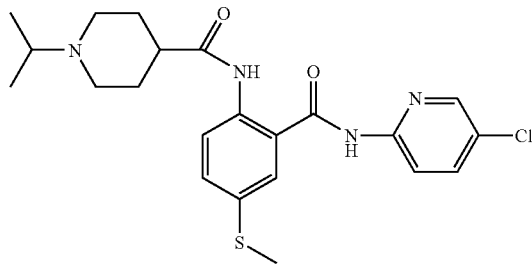

A. N-(5-Chloropyridin-2-yl)-5-fluoro-2-nitrobenzamide

Using methods substantially equivalent to those described in Example 247-A, N-(5-chloropyridin-2-yl)-5-fluoro-2-nitrobenzamide (8.7 g, 70%) was prepared from 5-fluoro-2-nitrobenzoic acid and 2-amino-5-chloropyridine.

$^1$H NMR

IS-MS, m/e 296.2 (m+1);

Analysis for $C_{12}H_7ClFN_3O_3$: Calcd: C, 48.75; H, 2.39; N, 14.21; Found: C, 48.96; H, 2.59; N, 14.02.

B. N-(5-Chloropyridin-2-yl)-5-methylthio-2-nitrobenzamide

To a stirring solution of sodium methylsulfide (0.13 g, 2 mmol) in N,N-dimethylformamide (20 mL) was added N-(5-chloropyridin-2-yl)-5-fluoro-2-nitrobenzamide (0.48 g, 1.6 mmol) and additional N,N-dimethylformamide (5 mL). The reaction solution was stirred overnight at room temperature and concentrated in vacuo. The resulting residue was partitioned between dichloromethane and water and the layers separated. The organic phase was washed with saturated aqueous sodium bicarbonate, dried over magnesium sulfate, filtered, and concentrated in vacuo. The crude product was slurried in diethyl ether and filtered to give 0.33 g (63%) of a yellow solid.

$^1$H NMR

IS-MS, m/e 323.8 (m+1), 321.8 (m−1);

Analysis for $C_{13}H_{10}ClN_3O_3S$: Calcd: C, 48.23; H, 3.11; N, 12.98; Found: C, 48.21; H, 3.01; N, 12.64.

C. 2-Amino-N-(5-chloropyridin-2-yl)-5-methylthiobenzamide

To an argon-purged slurry of N-(5-chloropyridin-2-yl)-5-methylthio-2-nitrobenzamide (0.78 g, 2.4 mmol) in ethanol (30 mL) was added graphite (0.73 g) and hydrazine monohydrate (0.5 mL, 10.3 mmol). The reaction mixture was heated to reflux, stirred overnight, cooled to room temperature, and filtered through diatomaceous earth. The filtrate was concentrated in vacuo to give 0.71 g (100%) of a yellow solid.

$^1$H NMR

IS-MS, m/e 294 (m+1), 291.9 (m−1);

Analysis for $C_{13}H_{12}ClN_3OS$: Calcd: C, 53.15; H, 4.12; N, 14.30; Found: C, 52.34; H, 4.19; N, 13.87; and C, 52.36; H, 4.12; N, 13.44.

D. 2-[(1-tert-Butoxycarbonylpiperidin-4-ylcarbonyl)amino]-N-(5-chloropyridin-2-yl)-5-methylthiobenzamide Using methods substantially equivalent to those described in Example 244-D, 2-[(1-tert-butoxycarbonylpiperidin-4-ylcarbonyl)amino]-N-(5-chloropyridin-2-yl)-5-methylthiobenzamide (0.96 g, 67%) was prepared from 2-amino-N-(5-chloropyridin-2-yl)-5-methylthiobenzamide and Boc-isonipecotic acid.

$^1$H NMR

IS-MS, m/e 504.8 (m+1), 502.9 (m−1);

Analysis for $C_{24}H_{29}ClN_4O_4S$: Calcd: C, 57.08; H, 5.79; N, 11.09; Found: C, 56.27; H, 4.82; N, 10.59; and C, 56.46; H, 4.80; N, 10.30.

E. N-(5-Chloropyridin-2-yl)-5-methylthio-2-[(4-piperidinylcarbonyl)amino]benzamide Trifluoroacetate Using methods substantially equivalent to those described in Example 244-E, N-(5-chloropyridin-2-yl)-5-methylthio-2-[(4-piperidinylcarbonyl)amino]benzamide trifluoroacetate (0.51 g, 96%) was prepared from 2-[(1-tert-butoxycarbonylpiperidin-4-ylcarbonyl)amino]-N-(5-chloropyridin-2-yl)-5-methylthiobenzamide.

$^1$H NMR

IS-MS, m/e 404.9 (m+1), 402.9 (m−1);

Analysis for $C_{19}H_{21}ClN_4O_2S.1.0C_2HF_3O_2$: Calcd: C, 48.60; H, 4.30; N, 10.76; Found: C, 48.97; H, 4.40; N, 10.26.

F. N-(5-Chloropyridin-2-yl)-2-[(1-isopropylpiperidin-4-ylcarbonyl)amino]-5-methylthiobenzamide Using methods substantially equivalent to those described in Example 244-F, N-(5-chloropyridin-2-yl)-2-[(1-isopropylpiperidin-4-ylcarbonyl)amino]-5-methylthiobenzamide (0.25 g, 74%) was prepared from N-(5-chloropyridin-2-yl)-5-methylthio-2-[(piperidin-4-ylcarbonyl)amino]benzamide trifluoroacetate.

$^1$H NMR

IS-MS, m/e 447.1 (m+1), 445.2 (m−1);

Analysis for $C_{22}H_{27}ClN_4O_2S.0.5H_2O$: Calcd: C, 57.95; H, 6.19; N, 12.29; Found: C, 57.76; H, 6.08; N, 12.20.

EXAMPLE 263

Preparation of N-(5-Chloropyridin-2-yl)-2-[(1-isopropylpiperidin-4-ylcarbonyl)amino]-5-[1-(hydroxyimino)ethyl]benzamide

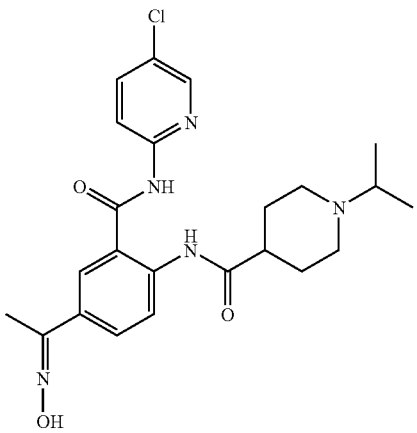

To a stirring solution of 5-acetyl-N-(5-chloropyridin-2-yl)-2-[(1-isopropylpiperidin-4-ylcarbonyl)amino]benzamide (0.25 g, 0.56 mmol) in methanol (2 mL) was added sodium acetate (0.1 g, 1.2 mmol) followed by hydroxylamine hydrochloride (46 mg, 0.67 mmol). The mixture was stirred overnight at room temperature and concentrated in vacuo. The resulting residue was partitioned between dichloromethane and saturated aqueous sodium bicarbonate, and the layers separated. The organic phase was dried over magnesium sulfate, filtered, and concentrated in vacuo. The crude product was purified by chromatography over silica gel, eluting with 3% 2 M ammonia/methanol solution in dichloromethane to give 0.22 g (85%) of a white solid.

$^1$H NMR

IS-MS, m/e 458.4 (m+1), 456.3 (m−1);

Analysis for $C_{23}H_{28}ClN_5O_3$: Calcd: C, 60.32; H, 6.16; N, 15.29; Found: C, 54.52; H, 6.35; N, 16.62.

EXAMPLE 264

Preparation of N-(5-Chloropyridin-2-yl)-5-hydroxymethyl-2-[(1-isopropylpiperidin-4-ylcarbonyl)amino]benzamide

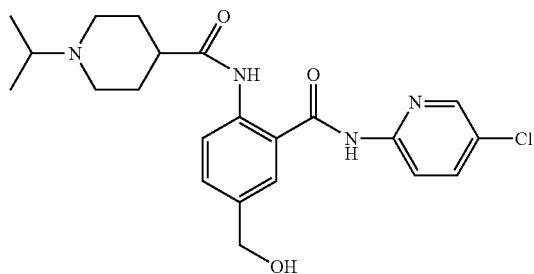

A. 2-[(1-tert-Butoxycarbonylpiperidin-4-ylcarbonyl)amino]-5-carboxy-N-(5-chloropyridin-2-yl)benzamide To a stirring solution of 2-[(1-tert-butoxycarbonylpiperidin-4-ylcarbonyl)amino]-N-(5-chloropyridin-2-yl)-5-iodobenzamide (0.51 g, 0.88 mmol) in N,N-dimethylformamide (13 mL) under argon was added dichlorobis(triphenylphosphine)palladium(II) (28 mg, 0.04 mmol) and triethylamine (0.5 mL, 3.5 mmol) followed by water (3 mL). The reaction mixture was evacuated and placed under an atmosphere of carbon monoxide, heated at 60° C. for 3 h., and concentrated in vacuo. The resulting residue was partitioned between aqueous sodium bicarbonate and ethyl acetate and the layers separated. The aqueous phase was treated with a small amount of dichloromethane and then solid citric acid to pH 3. The resulting mixture was extracted with 3:1 chloroform:isopropanol. The organic phase was dried over magnesium sulfate, filtered, and concentrated in vacuo. The crude product was purified by chromatography over silica gel, eluting with 2:4:0.5 ethyl acetate:toluene:acetic acid. The chromatography product was slurried in diethyl ether and filtered to give 0.31 g (69%) of a yellow solid.

$^1$H NMR

IS-MS, m/e 502.8 (m+1), 500.9 (m−1);

Analysis for $C_{24}H_{27}ClN_4O_6$: Calcd: C, 57.31; H, 5.41; N, 11.14; Found: C, 55.96; H, 5.23; N, 10.64; and C, 56.84; H, 5.34; N, 10.91.

B. 2-[(1-tert-Butoxycarbonylpiperidin-4-ylcarbonyl)amino]-N-(5-chloropyridin-2-yl)-5-hydroxymethylbenzamide To a stirring slurry of 2-[(1-tert-butoxycarbonylpiperidin-4-ylcarbonyl)amino]-5-carboxy-N-(5-chloropyridin-2-yl)benzamide (0.25 g, 0.49 mmol) in tetrahydrofuran (5 mL) under argon was added N-methylmorpholine (0.055 mL, 0.5 mmol) followed by ethyl chloroformate (0.05 mL, 0.5 mmol) After 20 min. the reaction slurry was cooled in an ice bath and treated with sodium borohydride (61 mg, 1.6 mmol) followed by dropwise addition of methanol (10 mL). After 30 min the resulting reaction solution was treated with saturated aqueous ammonium chloride. The mixture was partitioned between dichloromethane and saturated aqueous ammonium chloride. The organic phase was dried over magnesium sulfate, filtered, and concentrated in vacuo. The crude product was purified by chromatography over silica gel, eluting with 20–50% ethyl acetate in hexane and then 5% methanol in ethyl acetate, to give 0.15 g (63%) of a white solid.

$^1$H NMR

IS-MS, m/e 488.9 (m+1), 486.9 (m−1);

Analysis for $C_{24}H_{29}ClN_4O_5$: Calcd: C, 58.95; H, 5.98; N, 11.46; Found: C, 57.31; H, 5.86; N, 11.05; and C, 58.37; H, 5.86; N, 11.30.

C. N-(5-Chloropyridin-2-yl)-5-hydroxymethyl-2-[(4-piperidinylcarbonyl)amino]benzamide Trifluoroacetate Using methods substantially equivalent to those described in Example 244-E, N-(5-chloropyridin-2-yl)-5-hydroxymethyl-2-[(4-piperidinylcarbonyl)amino]benzamide trifluoroacetate (0.21 g, 96%) was prepared from 2-[(1-tert-butoxycarbonylpiperidin-4-ylcarbonyl)amino]-N-(5-chloropyridin-2-yl)-5-hydroxymethylbenzamide.

¹H NMR

IS-MS, m/e 388.9 (m+1), 387.0 (m−1);

Analysis for $C_{19}H_{21}ClN_4O_3 \cdot 1.2C_2HF_3O_2 \cdot 0.5H_2O$: Calcd: C, 48.07; H, 4.37; N, 10.48; F, 12.79; Found: C, 47.69; H, 4.05; N, 10.35; F, 12.71.

D. N-(5-Chloropyridin-2-yl)-5-hydroxymethyl-2-[(1-isopropylpiperidin-4-ylcarbonyl)amino]benzamide Using methods substantially equivalent to those described in Example 244-F, N-(5-chloropyridin-2-yl)-5-hydroxymethyl-2-[(1-isopropylpiperidin-4-ylcarbonyl)amino]benzamide (0.11 g, 85%) was prepared from N-(5-chloropyridin-2-yl)-5-hydroxymethyl-2-[(piperidin-4-ylcarbonyl)amino]benzamide trifluoroacetate.

¹H NMR

IS-MS, m/e 431.0 (m+1), 429.0 (m−1);

Analysis for $C_{22}H_{27}ClN_4O_3$: Calcd: C, 61.32; H, 6.32; N, 13.00; Found: C, 61.53; H, 6.61; N, 12.83.

EXAMPLE 265

Preparation of N-(5-Chloropyridin-2-yl)-2-[(1-isopropylpiperidin-4-ylcarbonyl)amino]-5-[2-(methoxycarbonyl)ethyl]benzamide

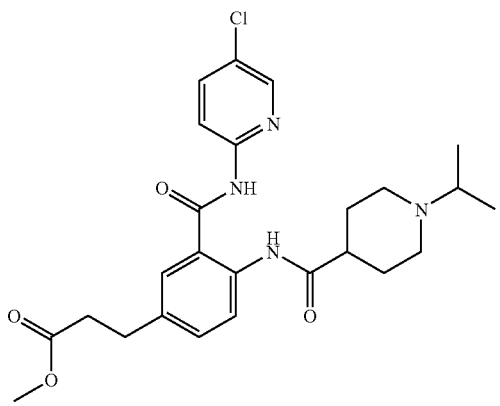

A. 2-[(1-tert-Butoxycarbonylpiperidin-4-ylcarbonyl)amino]-N-(5-chloropyridin-2-yl)-5-[2-(methoxycarbonyl)ethyl]benzamide Using methods substantially equivalent to those described in Example 244-B, 2-[(1-tert-butoxycarbonylpiperidin-4-ylcarbonyl)amino]-N-(5-chloropyridin-2-yl)-5-[2-(methoxycarbonyl)ethyl]benzamide (44 mg, 45%) was prepared from (E)-2-[(1-tert-butoxycarbonylpiperidin-4-ylcarbonyl)amino]-N-(5-chloropyridin-2-yl)-5-[2-(methoxycarbonyl)vinyl]benzamide and Raney nickel in 1:1 ethanol:ethyl acetate. The crude product was purified by chromatography over silica gel, eluting with 50% ethyl acetate in hexane.

¹H NMR

IS-MS, m/e 545.3 (m+1), 543.3 (m−1);

Analysis for $C_{27}H_{33}ClN_4O_6$: Calcd: C, 59.50; H, 6.10; N, 10.28; Found: C, 59.05; H, 5.61; N, 10.07.

B. N-(5-Chloropyridin-2-yl)-5-[2-(methoxycarbonyl)ethyl]-2-[(4-piperidinylcarbonyl)amino]benzamide Trifluoroacetate Using methods substantially equivalent to those described in Example 244-E, N-(5-chloropyridin-2-yl)-5-[2-(methoxycarbonyl)ethyl]-2-[(4-piperidinylcarbonyl)amino]benzamide trifluoroacetate (30 mg, 100%) was prepared from 2-[(1-tert-butoxycarbonylpiperidin-4-ylcarbonyl)amino]-N-(5-chloropyridin-2-yl)-5-[2-(methoxycarbonyl)ethyl]benzamide.

C. N-(5-Chloropyridin-2-yl)-2-[(1-isopropylpiperidin-4-ylcarbonyl)amino]-5-[2-(methoxycarbonyl)ethyl]benzamide Using methods substantially equivalent to those described in Example 244-F, N-(5-chloropyridin-2-yl)-2-[(1-isopropylpiperidin-4-ylcarbonyl)amino]-5-[1-(2-methoxycarbonylethyl)benzamide (20 mg, 77%) was prepared from N-(5-chloropyridin-2-yl)-5-[1-(2-methoxycarbonylethyl)-2-[(4-piperidinylcarbonyl)amino]benzamide trifluoroacetate.

HPLC/MS, m/e 459.2 (m+1).

EXAMPLE 266

Preparation of N-(5-Chloropyridin-2-yl)-2-[(1-isopropylpiperidin-4-ylcarbonyl)amino]-5-[1-(methoxyimino)ethyl]benzamide

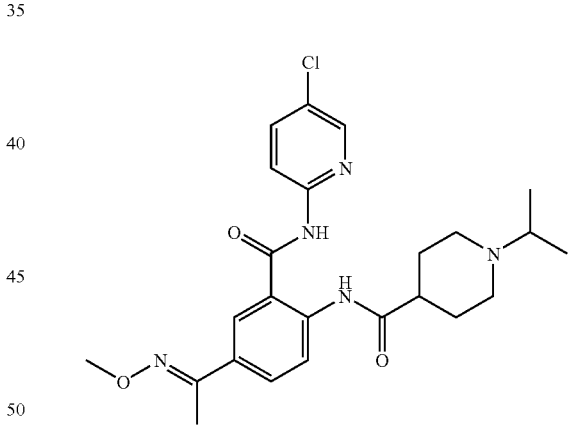

Using methods substantially equivalent to those described in Example 263, N-(5-chloropyridin-2-yl)-2-[(1-isopropylpiperidin-4-ylcarbonyl)amino]-5-[1-(methoxyimino)ethyl]benzamide (0.10 g, 67%) was prepared from 5-acetyl-N-(5-chloropyridin-2-yl)-2-[(1-isopropylpiperidin-4-ylcarbonyl)amino]benzamide, methoxylamine hydrochloride and sodium acetate in methanol. The crude product was purified by chromatography over silica gel, eluting with 5% 2 M solution of ammonia/methanol in dichloromethane.

¹H NMR

IS-MS, m/e 472.3 (m+1), 470.3 (m−1);

Analysis for $C_{24}H_{30}ClN_5O_3$: Calcd: C, 61.07; H, 6.41; N, 14.84; Found: C, 56.07; H, 6.45; N, 14.46.

EXAMPLE 267

Preparation of N-(5-Chloropyridin-2-yl)-2-[(methyl)-[1-(4-pyridinyl)piperidin-4-ylmethyl]amino]benzamide

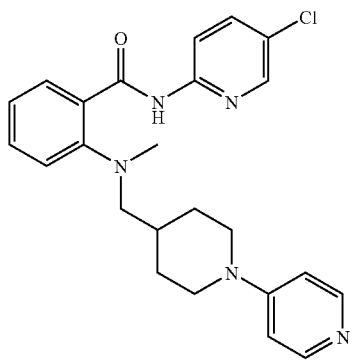

Using a similar procedure to that described in Example 27, N-(5-chloropyridin-2-yl)-2-[1-(4-pyridinyl)piperidin-4-ylmethyl]aminobenzamide (100 mg, 0.237 mmol) and paraformaldehyde (20 mg, 0.238 mmol) afforded, after purification by column chromatography (SiO$_2$: 2 to 4% [2 N ammonia in methanol]:chloroform), 25 mg (24%) of the title compound.

$^1$NMR

IS-MS, m/e 436 (m)

EXAMPLE 268

Preparation of N-(5-Chloropyridin-2-yl)-2-[[1-(1-isopropylpiperidin-4-yl)ethyl]amino]-4-methoxycarbonylbenzamide Trihydrochloride

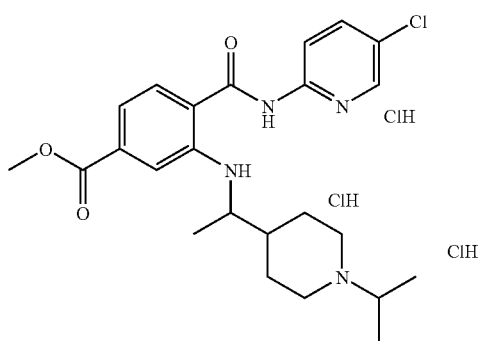

A. 1-(tert-Butoxycarbonyl)piperidine-4-ethanol

A solution of 1-(tert-butoxycarbonyl)piperidine-4-carboxaldehyde (14.9 g, 69.8 mmol) in THF at −78° C. was treated with methylmagnesium bromide (25.6 mL, 3.0 M in THF, 76.8 mmol). After 16 h, the mixture was treated with additional methylmagnesium bromide (15.0 mL, 3.0 M in THF). After 1 h, the mixture was treated with saturated aqueous ammonium chloride and partitioned between EtOAc and water. The aqueous phase was washed with EtOAc, the organic extracts were combined and washed with brine, dried (MgSO$_4$), and concentrated. The residue was purified by column chromatography (SiO$_2$: 30 to 40% EtOAc:hexanes) affording 5.0 g (31%) of the title compound.

$^1$NMR

IS-MS, m/e 230 (m+1)

B. 1-(tert-Butoxycarbonyl)piperidine-4-acetaldehyde

A solution of 1-(tert-butoxycarbonyl)piperidine-4-ethanol (5.0 g, 22 mmol) in methylene chloride (100 mL) was treated with pyridinium chlorochromate (5.2 g, 24 mmol), and diatomaceous earth (5 g). After 3 days, the mixture was filtered through diatomaceous earth, concentrated, and the residue purified by column chromatography (SiO$_2$: 20 to 30% EtOAc:hexanes) affording 4.0 g (81%) of the title compound.

$^1$NMR

IS-MS, m/e 228 (m+1)

C. N-(5-Chloropyridin-2-yl)-2-[[1-(1-Boc-piperidin-4-yl)ethyl]amino]-4-methoxycarbonylbenzamide Using a similar procedure to that described in Example 47-C, 2-amino-N-(5-chloropyridin-2-yl)-4-methoxycarbonylbenzamide (2.7 g, 8.8 mmol) and 1-(tert-butoxycarbonyl)piperidine-4-acetaldehyde (3.0 g, 13 mmol) afforded, after trituration with EtOAc:methylene chloride, 2.8 g (61%) of the title compound.

$^1$NMR

IS-MS, m/e 513 (m−1)

Analysis for $C_{26}H_{31}ClN_4O_5$: Calcd: C, 60.64; H, 6.07; N, 10.88; Found: C, 60.30; H, 6.26; N, 10.74.

D. N-(5-Chloropyridin-2-yl)-4-methoxycarbonyl-2-[[1-(4-piperidinyl)ethyl]amino]benzamide Using a similar procedure to that described in Example 47-D, N-(5-chloropyridin-2-yl)-2-[[1-(1-Boc-piperidin-4-yl)ethyl]amino]-4-methoxycarbonylbenzamide (0.35 g, 0.68 mmol) and borane trimethylamine complex (0.15 g, 2.0 mmol) afforded 70 mg of the title compound.

IS-MS, m/e 417 (m+1)

Analysis for $C_{21}H_{25}ClN_4O_3$.2 HCl: Calcd: C, 51.50; H, 5.56; N, 11.44; Found: C, 51.51; H, 5.73; N, 11.26.

E. N-(5-Chloropyridin-2-yl)-2-[[1-(1-isopropylpiperidin-4-yl)ethyl]amino]-4-methoxycarbonylbenzamide Trihydrochloride Using a similar procedure to that described in Example 27, N-(5-chloropyridin-2-yl)-4-methoxycarbonyl-2-[[1-(4-piperidinyl)ethyl]amino]benzamide (0.35 g, 0.77 mmol) afforded, after purification by RPHPLC, 100 mg (26%) of the title compound as a hydrochloride salt.

$^1$NMR

IS-MS, m/e 459 (m+1)

Analysis for $C_{24}H_{30}ClN_4O_3$.3 HCl.1.5 H$_2$O: Calcd: C, 48.42; H, 6.26; N, 9.41; Found: C, 48.49; H, 6.21; N, 9.55.

EXAMPLE 269

Preparation of N-(5-Chloropyridin-2-yl)-4-hydroxymethyl-2-[(1-isopropylpiperidin-4-ylmethyl)amino]benzamide Dihydrochloride

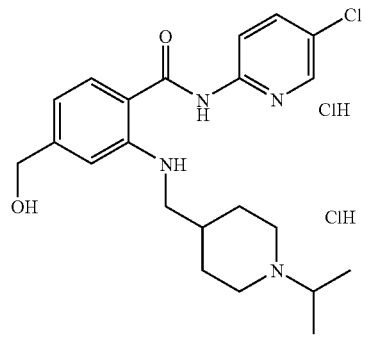

A. N-(5-Chloropyridin-2-yl)-4-hydroxymethyl-2-[(1-Boc-piperidin-4-ylmethyl)amino]benzamide Using a similar procedure to that described in Example 47-A, 4-carboxy-N-(5-chloropyridin-2-yl)-2-[(1-Boc-piperidin-4-ylmethyl)amino]benzamide (2.0 g, 4.1 mmol), ethyl chloroformate (0.40 mL, 4.1 mmol), N-methylmorpholine (0.46 mL, 4.1 mmol), and sodium borohydride (466 mg, 12.3 mmol) afforded 1.45 g (75%) of the title compound, which was used without further purification.

$^1$NMR

IS-MS, m/e 473 (m+1)

Analysis for $C_{22}H_{28}ClN_5O_2$: Calcd: C, 60.95; H, 6.18; N, 11.85; Found: C, 60.56; H, 6.25; N, 11.40.

B. N-(5-Chloropyridin-2-yl)-4-hydroxymethyl-2-[(4-piperidinylmethyl)amino]benzamide Using a similar procedure to that described in Example 47-D, N-(5-chloropyridin-2-yl)-4-hydroxymethyl-2-[(1-Boc-piperidin-4-ylmethyl)amino]benzamide (1.45 g, 3.07 mmol) and borane trimethylamine complex (672 mg, 9.22 mmol) afforded 900 mg (79%) of the title compound; which was used without, further purification.

$^1$NMR

IS-MS, m/e 375 (m+1)

C. N-(5-Chloropyridin-2-yl)-4-hydroxymethyl-2-[(1-isopropylpiperidin-4-ylmethyl)amino]benzamide dihydrochloride Using a similar procedure to that described in Example 27, N-(5-chloropyridin-2-yl)-4-hydroxymethyl-2-[(4-piperidinylmethyl)amino]benzamide (0.90 g, 2.4 mmol) afforded, after purification by RPHPLC, 630 mg (54%) of the title compound as a hydrochloride salt.

$^1$NMR

IS-MS, m/e 417 (m+1)

Analysis for $C_{23}H_{30}ClN_5O_2 \cdot 2 \, HCl \cdot 0.4 \, H_2O$: Calcd: C, 53.16; H, 6.45; N, 11.27; Found: C, 53.43; H, 6.23; N, 11.10.

EXAMPLE 270

Preparation of N-(5-Chloropyridin-2-yl)-2-[(1-isopropylpiperidin-4-ylcarbonyl)amino]-4-methoxycarbonylbenzamide

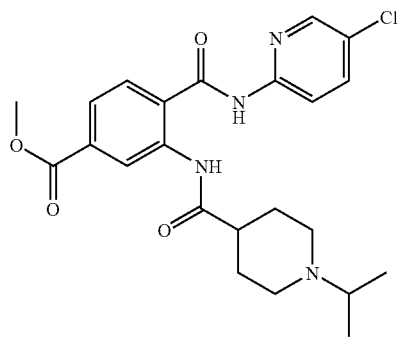

A solution of 1-isopropylpiperidine-4-carboxylic acid (2.0 g, 9.6 mol) in methylene chloride (70 mL) was treated dropwise with thionyl chloride (0.70 mL, 9.6 mmol). After heating to reflux for 1 h, 2-amino-N-(5-chloropyridin-2-yl)-4-methoxycarbonylbenzamide (1.5 g, 4.8 mmol) was added. After 0.5 h, pyridine (0.80 mL) was added and the resulting mixture heated at reflux. After 12 h, the mixture was cooled, treated with water, 1 N NaOH (20 mL), and concentrated. The residue was purified by column chromatography ($SiO_2$: 5% methanol:methylene chloride) affording 1.14 g (52%) of the title compound.

$^1$NMR

FIA-MS, m/e 459 (m+)

Analysis for $C_{24}H_{27}ClN_4O_4 \cdot 0.5 \, H_2O$: Calcd: C, 59.03; H, 6.03; N, 11.97; Found: C, 59.31; H, 5.78; N, 11.91.

EXAMPLE 271

Preparation of N-(5-Chloropyridin-2-yl)-2-[(1-isopropylpiperidin-4-ylcarbonyl)amino]-4-methoxycarbonylbenzamide

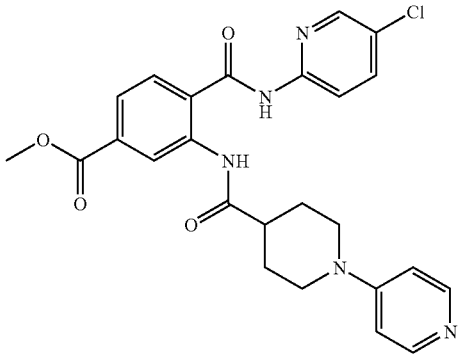

Using a similar procedure to that described in Example 275, 1-(4-pyridinyl)piperidin-4-ylcarboxylic acid (2.0 g, 9.7 mmol), thionyl chloride (1.4 mL, 19 mmol), and 2-amino-N-(5-chloropyridin-2-yl)-4-methoxycarbonylbenzamide (2.8 g, 9.2 mmol) afforded, after purification by column chromatography (SiO$_2$: 5 to 10% [2.0 N ammonia in methanol]:methylene chloride), 0.40 g (9%) of the title compound.
$^1$NMR
FIA-MS, m/e 494 (m+)
Analysis for C$_{25}$H$_{24}$ClN$_5$O$_4$: Calcd: C, 60.79; H, 4.90; N, 14.18; Found: C, 60.88; H, 4.90; N, 13.90.

EXAMPLE 272

Preparation of N-(5-Chloropyridin-2-yl)-2-[(1-isopropylpiperidin-4-ylmethyl)amino]-5-methoxycarbonylbenzamide

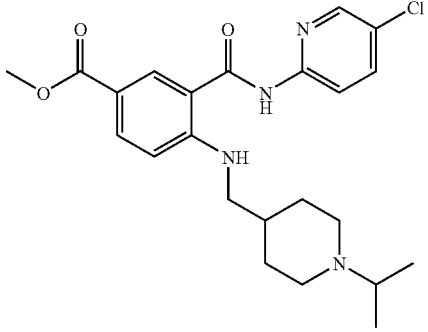

A. N-(5-Chloropyridin-2-yl)-5-(methoxycarbonyl)-2-nitrobenzamide

Using a similar procedure to that described in Example 8-A, 5-methoxycarbonyl-2-nitrobenzoic acid (20 g, 89 mmol) and 2-amino-5-chloropyridine (11 g, 85 mmol) afforded, after recrystallization from toluene, 23.6 g (83%) of the title compound.
$^1$NMR
FIA-MS, m/e 336 (m+)
Analysis for C$_{14}$H$_{10}$ClN$_3$O$_5$: Calcd: C, 50.09; H, 3.00; N, 12.52; Found: C, 50.37; H, 3.08; N, 12.52.

B. 2-Amino-N-(5-chloropyridin-2-yl)-5-methoxycarbonylbenzamide

Using a similar procedure to that described in Example 2-B, N-(5-chloropyridin-2-yl)-5-(methoxycarbonyl)-2-nitrobenzamide (23.5 g, 70.0 mmol) afforded, after purification by column chromatography (1 to 2% methanol:methylene chloride), 13.1 g (61%) of the title compound.
$^1$NMR
FIA-MS, m/e 306 (m+)

C. 1-Isopropylpiperidine-4-methanol

A solution of ethyl 1-isopropylpiperidine-4-carboxylate (10.0 g, 50.2 mmol) in THF (250 mL) at 0° C. was treated with lithium aluminum hydride (2.1 g, 55 mmol). After 1 h, the mixture was treated with a saturated aqueous solution of sodium potassium tartrate, partitioned with EtOAc, and the aqueous layer washed with EtOAc (2×). The combined extracts, were dried (Na$_2$SO$_4$), concentrated, and the residue purified by column chromatography (SiO2: 10% methanol:methylene chloride) affording 4.30 g (54%) of the title compound.
$^1$NMR
FIA-MS, m/e 158 (m+)

D. 1-Isopropylpiperidine-4-carboxaldehyde

A solution of 1-isopropylpiperidine-4-methanol (0.40 g, 2.5 mmol) and N-methylmorpholine (0.46 g, 3.8 mmol) in methylene chloride (20 mL) was treated with tetrapropylammonium perruthenate (0.089 g, 0.25 mmol). After 3 h, the mixture was concentrated and the residue purified by column chromatography (SiO$_2$: 10% to 20% methanol:methylene chloride) affording 0.20 g (50%) of the title compound.
$^1$NMR
FIA-MS, m/e 156 (m+)

E. N-(5-Chloropyridin-2-yl)-2-[(1-isopropylpiperidin-4-ylmethyl)amino]-5-methoxycarbonylbenzamide Using a similar procedure to that described in Example 47-C, 2-amino-N-(5-chloropyridin-2-yl)-5-methoxycarbonylbenzamide (0.35 g, 1.2 mmol) and 1-isopropylpiperidinecarboxaldehyde (0.20 g, 1.3 mmol) afforded, after purification by column chromatography (SiO$_2$: 10% methanol:methylene chloride), 150 mg (28%) of the title compound.
$^1$NMR
FIA-MS, m/e 443 (m+)

F. N-(5-Chloropyridin-2-yl)-2-[(1-isopropylpiperidin-4-ylmethyl)amino]-5-methoxycarbonylbenzamide Using a similar procedure to that described in Example 47-D, N-(5-chloropyridin-2-yl)-2-[(1-isopropylpiperidin-4-ylmethyl)amino]-5-methoxycarbonylbenzamide (0.14 g, 0.32 mmol) and borane trimethylamine complex (0.70 g, 0.96 mmol) afforded, after purification by column chromatography (SiO$_2$: 5 to 10% methanol:methylene chloride), 110 mg (77%) of the title compound.
$^1$NMR
FIA-MS, m/e 445 (m+)
Analysis for C$_{23}$H$_{27}$ClN$_4$O$_4$·0.5 H$_2$O: Calcd: C, 60.86; H, 6.66; N, 12.34; Found: C, 61.20; H, 6.31; N, 11.94.

EXAMPLE 273

Preparation of 5-Carboxy-N-(5-chloropyridin-2-yl)-2-[(1-isopropylpiperidin-4-ylmethyl)amino]benzamide Trihydrochloride

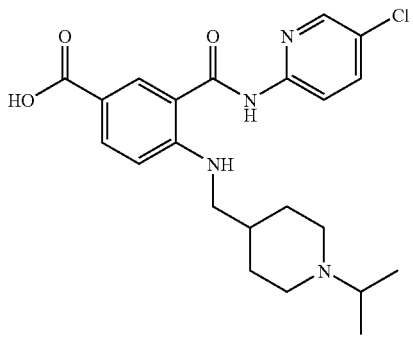

A solution of N-(5-chloropyridin-2-yl)-2-[(1-isopropylpiperidin-4-ylmethyl)amino]-5-methoxycarbonylbenzamide (0.50 g, 1.1 mmol) in 1:1:1 methanol:THF:water was treated with barium hydroxide octahydrate (3.6 g, 11 mmol). After 3 days, the mixture was treated with 5 N HCl and concentrated under reduced pressure until precipitation resulted. The mixture was filtered affording 250 mg (52%) of the title compound as a hydrochloride salt.

$^1$NMR

FIA-MS, m/e 431 (m+)

Analysis for $C_{22}H_{25}ClN_4O_4 \cdot 3.25$ HCl: Calcd: C, 48.09; H, 5.55; N, 10.20; Found: C, 47.76; H, 5.59; N, 10.05.

EXAMPLE 274

Preparation of N-(5-Chloropyridin-2-yl)-5-methoxycarbonyl-2-[[1-(4-pyridinyl)piperidin-4-ylmethyl]amino]benzamide

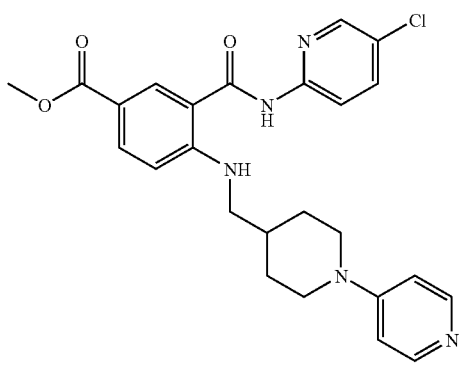

A. N-(5-Chloropyridin-2-yl)-5-methoxycarbonyl-2-[(4-piperidinylmethyl)amino]benzamide Using a similar procedure to that described in Example 47-C&D, 2-amino-N-(5-chloropyridin-2-yl)-5-methoxycarbonylbenzamide (3.23 g, 10.6 mmol), 1-tert-butoxycarbonylpiperidine-4-carboxaldehyde (2.50 g, 11.7 mmol), and borane trimethylamine complex (2.31 g, 31.7 mmol) afforded, after purification by column chromatography (SiO$_2$: 10 to 25% methanol:methylene chloride), 3.10 g (73%) of the title compound.

$^1$NMR

FIA-MS, m/e 403 (m+)

B. N-(5-Chloropyridin-2-yl)-5-methoxycarbonyl-2-[[1-(4-pyridinyl)piperidin-4-ylmethyl]amino]benzamide Using a similar procedure to that described in Example 52, N-(5-chloropyridin-2-yl)-5-methoxycarbonyl-2-[(4-piperidinylmethyl)amino]benzamide (0.30 g, 0.74 mmol) and 4-chloropyridine hydrochloride (0.22 g, 1.5 mmol) afforded, after purification by ion-exchange chromatography (SCX), 260 mg (73%) of the title compound.

$^1$NMR

FIA-MS, m/e 480 (m+)

Analysis for $C_{25}H_{26}ClN_5O_3 \cdot 0.45$ MeOH: Calcd: C, 61.83; H, 5.67; N, 14.17; Found: C, 62.19; H, 5.37; N, 13.76.

EXAMPLE 275

Preparation of 5-Carboxy-N-(5-chloropyridin-2-yl)-2-[[1-(4-pyridinyl)piperidin-4-ylmethyl]amino]benzamide

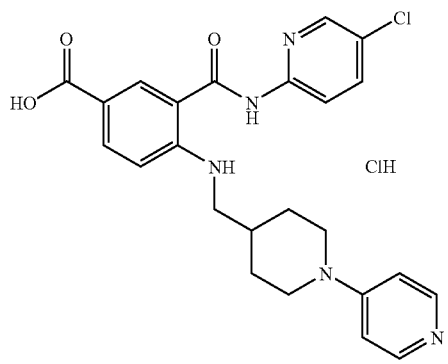

Using a similar procedure to that described in Example 278, N-(5-chloropyridin-2-yl)-5-methoxycarbonyl-2-[[1-(4-pyridinyl)piperidin-4-ylmethyl]amino]benzamide (0.13 g, 0.26 mmol) afforded 105 mg (87%) of the title compound.

$^1$NMR

FIA-MS, m/e 466 (m+)

Analysis for $C_{24}H_{24}ClN_5O_3 \cdot 0.75$ H$_2$O: Calcd: C, 55.87; H, 5.18; N, 13.17; Found: C, 55.96; H, 5.10; N, 12.75.

EXAMPLE 276

Preparation of N-(5-Chloropyridin-2-yl)-5-methoxycarbonyl-2-[[1-(2-carboxypyridin-4-yl)piperidin-4-ylmethyl]amino]benzamide

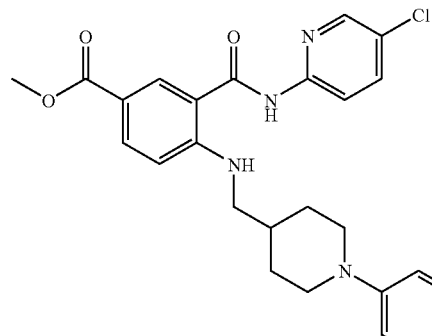

Using a similar procedure to that described in Example 52, N-(5-chloropyridin-2-yl)-5-methoxycarbonyl-2-[(4-piperidinylmethyl)amino]benzamide (0.30 g, 0.74 mmol) and 4-chloropicolinic acid (0.23 g, 1.5 mmol) afforded 320 mg (82%) of the title compound.

$^1$NMR

FIA-MS, m/e 524 (m+)

Analysis for $C_{26}H_{26}ClN_5O_5 \cdot 1.85$ H$_2$O: Calcd: C, 56.04; H, 5.37; N, 12.57; Found: C, 55.80; H, 4.98; N, 12.32.

EXAMPLE 277

Preparation of N-(5-Chloropyridin-2-yl)-2-[[1-(2-cyanopyridin-4-yl)piperidin-4-ylmethyl]amino]-5-methoxycarbonylbenzamide

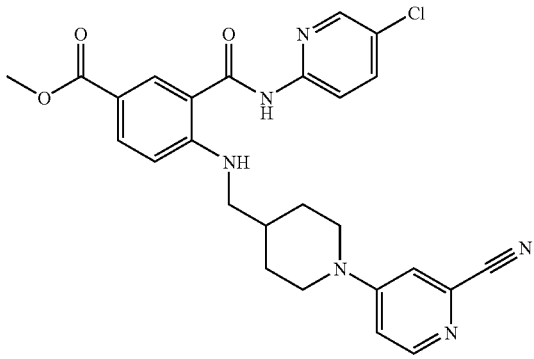

Using a similar procedure to that described in Example 52, N-(5-chloropyridin-2-yl)-5-methoxycarbonyl-2-[(4-piperidinylmethyl)amino]benzamide (0.30 g, 0.74 mmol) and 4-chloro-2-cyanopyridine (0.21 g, 1.5 mmol) afforded 360 mg (96%) of the title compound.

$^1$NMR
FIA-MS, m/e 505 (m+)

EXAMPLE 278

Preparation of 2-(4-tert-Butylbenzoylamino)-N-(5-chloropyridin-2-yl)-4-methoxycarbonylbenzamide

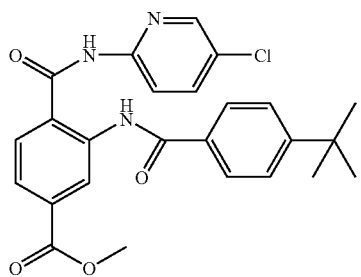

A. 2-(4-tert-Butylbenzoyl)aminoterephthalic acid dimethyl ester

Into 200 mL methylene chloride was dissolved 10.45 g (50 mmol) 2-aminoterephthalic acid dimethyl ester. The solution was cooled in an ice bath, and 7.73 mL (55 mmol) triethylamine was added, followed by 10.76 mL 4-tert-butylbenzoyl chloride in 50 mL methylene chloride dropwise. The mixture was allowed to come slowly to room temperature, and after 16 h the mixture was shaken with 200 mL cold dilute HCl and 200 mL satd NaHCO$_3$. The organic layer was dried (MgSO$_4$) and evaporated. The residue was redissolved in a minimum ether, giving 13.5 g (73%) of crystalline desired intermediate.

$^1$NMR, MS

B. 2-(4-tert-Butylbenzoylamino)terephthalic acid

Into 100 mL MeOH was dissolved 5.0 g (13.6 mmol) of the above dimethyl ester, followed by 13.6 mL (68 mmol) 5 N NaOH. The mixture was stirred 4 h at room temperature, concentrated under vacuum, acidified with dilute HCl and extracted with 200 mL EtOAc. Organic layer was dried (MgSO$_4$), concentrated under vacuum, and diluted with hexane, giving 2.59 g (56%) crystalline desired intermediate.

$^1$NMR, MS

C. 2-(4-tert-Butylphenyl)-7-methoxycarbonyl-4H-3,1-benzoxazin-4-one

Into 50 mL methylene chloride was dissolved 0.682 g (2 mmol) of the above intermediate terephthalic acid, followed by 5 drops DMF and 3.88 mL (48 mmol) triethylamine. The mixture was cooled in an ice bath, and 0.42 mL (4.8 mmol) oxayl chloride was added in one portion. After 30 min 10 mL MeOH was added and ice bath was removed. After stirring an additional 30 min, the mixture was shaken between EtOAc (100 mL) and cold dilute HCl (100 mL). The organic layer was washed with satd NaHCO$_3$ (100 mL), dried (MgSO$_4$), and evaporated. Crystalline desired benzoxazinone (456 g, 66%) was obtained from a concentrated methylene chloride-hexane solution.

$^1$NMR, MS

D. 2-(4-tert-Butylbenzoylamino)-N-(5-chloropyridin-2-yl)-4-methoxycarbonylbenzamide Into 25 mL THF was dissolved 0.174 g (0.5 mmol) of the above intermediate benzoxazinone. The solution was cooled in an ice bath, and 1.25 mL (0.5 mmol) of a 0.5 M THF solution of the magnesium salt of 2-amino-5-chloropyridine [prepared by treating 1.29 g (10 mmol) 2-amino-5-chloropyridine in 22 mL THF at ice bath temperature under nitrogen with 3.3 mL (10 mmol) 3 M methylmagnesium bromide, allowing the mixture to slowly come to room temperature]. After 30 min, 0.42 mL (0.17 mmol) of additional magnesium salt was added, and the mixture was stirred an additional 15 min. The mixture was quenched with 30 mL cold dilute HCl and extracted with 100 mL EtOAc. The organic layer was dried (MgSO$_4$) and evaporated. The crystalline title compound was obtained (107 mg, 46%) from CH$_2$Cl$_2$-hexane.

NMR, MS

EXAMPLE 279

Preparation of 2-(4-tert-Butylbenzoylamino)-4-carbonoxy-N-(5-chloropyridin-2-yl)benzamide

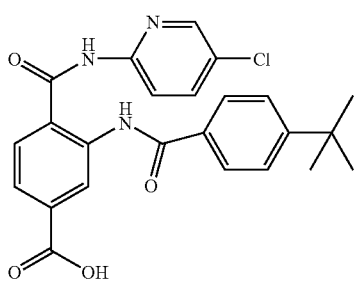

Into 2 mL MeOH was dissolved 103 mg (0.22 mmol) 2-(4-tert-butylbenzoylamino)-N-(5-chloropyridin-2-yl)-4-methoxycarbonylbenzamide. To the solution was added 0.53 mL (0.27 mmol) of 0.5 N NaOH. The mixture was stirred 16 h at room temperature, diluted with 25 mL water and extracted with 50 mL EtOAc. The aquous layer was acidified with dilute HCl and extracted with 50 mL EtOAc. Organic layer was dried (MgSO$_4$), and evacuated, giving 32 mg (32%) of the title compound.

$^1$NMR, MS

EXAMPLE 280

Preparation of 2-(4-tert-Butylbenzoylamino)-N-(5-chloropyridin-2-yl)-5-methoxycarbonylbenzamide

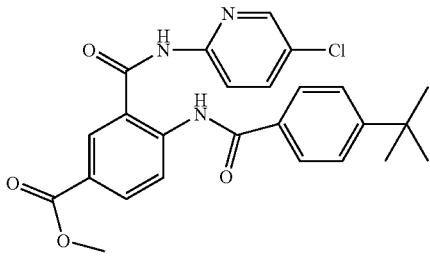

A. 4-Aminoisophthalic acid

Into 20 mL EtOH and 20 mL HOAc was dissolved 2 g (9.48 mmol) 4-nitroisophthalic acid, and the solution was subjected to hydrogenation at atmospheric conditions over 1 g of 5% Pd on carbon. After 16 h, mixture was filtered, and filtrate was evaporated. The residue crystallized from methylene chloride-hexane, giving 1.29 g (75%) crystalline desired intermediate.

$^1$NMR, MS

B. 4-(4-tert-Butylbenzoylamino)isophthalic acid

Into 60 mL acetone was dissolved 0.905 g (5 mmol) 4-aminoisophthalic acid. To the solution was added 30 mL water. The mixture was cooled in an ice bath, and 1.08 mL (5.5 mmol) 4-tert-butylbenzoyl chloride in 10 mL acetone was added dropwise. The mixture was allowed to warm slowlyly to room temperature and after 24 h was concentrated under vacuum and shaken between EtOAc (150 mL) and cold dilute HCl (150 mL). The organic layer was dried (MgSO$_4$) and evaporated. The desired crystalline product (0.489 g, 29%) was obtained from methylene chloride-hexane.

$^1$NMR, MS

C. 2-(4-tert-Butylphenyl)-6-methoxycarbonyl-4H-3,1-benzoxazin-4-one

Into 25 mL methylene chloride was dissolved 0.341 g (1 mmol) of the above intermediate isophthalic acid, followed by 2 drops DMF and 1.94 mL (24 mmol) pyridine. The mixture was cooled in an ice bath, and 0.21 mL (2.4 mmol) oxayl chloride was added. The mixture was stirred 30 min, 5 mL MeOH added, and the ice bath was removed. The mixture was stirred an additional 30 min, shaken between CH$_2$Cl$_2$ (100 mL) and cold dilute HCl (100 mL). The organic layer was washed with satd NaHCO$_3$ (100 mL), dried (MgSO$_4$), and concentrated under vacuum. Crystalline desired product (184 mg, 53%) was obtained from CH$_2$Cl$_2$-hexane.

$^1$NMR, MS

D. 2-(4-tert-Butylbenzoylamino)-N-(5-chloropyridin-2-yl)-5-methoxycarbonylbenzamide Into 25 mL THF was dissolved 0.174 g (0.5 mmol) of the above benzoxazinone intermediate. The solution was cooled in an ice bath and placed under nitrogen atmosphere. To the mixture was added 1.5 mL (0.6 mmol) of a 0.4 M solution of the magnesium salt of 2-amino-5-chloropyridine (See Prep. D, Example 278). After 30 min, an additional 1.5 mL (0.6 mmol) of the magnesium salt was added. Stirring was continued for 15 min, and the reaction mixture was quinched with 100 mL cold dilute HCl. The mixture was extracted with 100 mL EtOAc, and the organic layer was washed with 100 mL cold dilute HCl, dried (MgSO$_4$), and concentrated under vacuum. The crude product was chromatographed over silica (0 to 30% EtOAc in hexane gradient), giving 91 mg (39%) of title compound as a crystalline solid.

$^1$NMR, MS

EXAMPLE 281

Preparation of 4-(4-tert-Butylbenzoylamino)-N-(5-chloropyridin-2-yl)isophthalamic acid

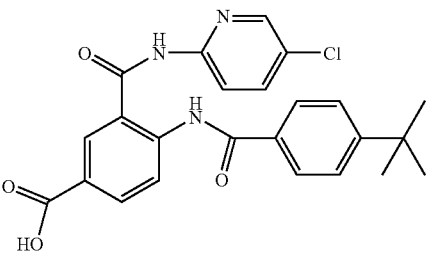

Into 5 mL MeOH was dissolved 91 mg (0.195 mmol) 2-(4-tert-butylbenzoylamino)-N-(5-chloropyridin-2-yl)-5-methoxycarbonylbenzamide, followed by 0.47 mL of 0.5 N (0.23 mmol) NaOH. The mixture was stirred 16 h, evaporated, diluted with 39.0 mL water, and extracted with 15 mL EtOAc-15 mL hexane mixture. The aquous layer was acidified with dilute HCl and extracted with 30 mL EtOH. The organic layer was dried (MgSO$_4$) and evaporated, giving 43 mg (49%) title compound.

$^1$NMR, MS

What is claimed is:

1. A compound of formula I

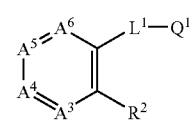

(or a pharmaceutically acceptable salt thereof) wherein:
A$^3$, A$^4$, A$^5$ and A$^6$, together with the two carbons to which they are attached, complete a substituted benzene in which A$^3$ is CR$^3$, A$^4$ is CR$^4$, A$^5$ is CR$^5$, and A$^6$ is CR$^6$; wherein
R$^3$ is hydrogen, methyl, methoxy, fluoro, chloro or carboxy;
one of R$^4$ and R$^5$ is hydrogen, (1–4C)alkyl, halo, trifluoromethyl, trifluoromethoxy, R$'$O—, R$'$O$_2$CCH$_2$O—, HO(CH$_2$)$_a$O— (in which a is 2, 3 or 4), R$^f$O$_2$C—, R$^f$O$_2$CCH$_2$—, R$^g$NH—, R$^h$SO$_2$—, hydroxymethyl, formyl, cyano, acetyl, 1-hydroxyethyl, 1-(hydroxyimino)ethyl, 1-(methoxyimino)ethyl, methylthio or R$^f$O$_2$C(CH$_2$)$_2$—;

the other of R$^4$ and R$^5$ is hydrogen; and

R$^6$ is hydrogen, methyl, fluoro, chloro or methoxy;

in which R$^f$ is hydrogen, (1–4C)alkyl or benzyl; R$^g$ is hydrogen or R$^h$SO$_2$—; and R$^h$ is (1–4C)alkyl or dimethylamino;

or each of R$^3$, R$^4$ and R$^6$ is hydrogen; and R$^5$ is vinyl, 2-cyanovinyl, 2-({(1–2C)alkoxy}carbonyl)vinyl or R$^a$ in which R$^a$ is phenyl (which is unsubstituted or bears one or more substituents independently selected from halo, methyl, methoxy and hydroxy) or heteroaryl (which heteroaryl is a 5-membered aromatic ring which has one to four heteroatoms selected from sulfur, oxygen and nitrogen or is a 6-membered aromatic ring which has one to three nitrogen atoms, wherein the heteroaryl is attached at carbon and may bear one or more methyl substituents on carbon or nitrogen);

L$^1$ is —CO—NH— such that -L$^1$-Q$^1$ is —CO—NH-Q$^1$;

Q$^1$ is 2-pyrimidinyl (which may bear a methyl, fluoro or chloro substituent at the 5-position);

R$^2$ is -L$^2$-Q$^2$ in which -L$^2$- is —NH—CO—, —NH—CO—X—, —NH—CO—O—X—, —NH—CO—NH—X—, —NH—CH$_2$—, —NH—C(CH$_3$)H—, —N(CH$_3$)—CH$_2$— or —O—CH$_2$—; and Q$^2$ is Q$^{2A}$, Q$^{2B}$, Q$^{2C}$, Q$^{2D}$, Q$^{2E}$ or Q$^{2F}$ wherein X is a single bond or methylene and the values of L$^2$ and Q$^2$ are together selected from —NH—CO—X-Q$^{2A}$, —NH—CO—O—X-Q$^{2A}$, —NH—CO—NH—X-Q$^{2A}$, —NH—CH$_2$-Q$^{2A}$, —NH—C(CH$_3$)H-Q$^{2A}$, —N(CH$_3$)—CH$_2$-Q$^{2A}$, —O—CH$_2$-Q$^{2A}$, —NH—CO—X-Q$^{2B}$, —NH—CO-Q$^{2C}$, —NH—CO-Q$^{2D}$, —NH—CO-Q$^{2E}$ and —NH—CO-Q$^{2F}$ in which:

Q$^{2A}$ (showing the L$^2$ to which it is attached) is

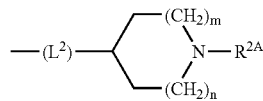

in which each of m and n independently is 0 or 1, or m is 2 and n is 1, and

R$^{2A}$ is hydrogen, t-butyl, methylsulfonyl, —CHR$^y$R$^z$, —CHR$^w$R$^x$, or 4-pyridinyl (which is unsubstituted or bears a substituent R$^v$ at the 2- or 3-position) wherein R$^v$ is methyl, hydroxymethyl, {(1–2C)alkoxy}carbonyl; cyano, carbamoyl, thiocarbamoyl, or N-hydroxyamidino;

each of R$^w$ and R$^x$ independently is hydrogen or (1–3C) normal alkyl; or —CHR$^w$R$^x$ is 2-indanyl or (showing the nitrogen to which it is attached) is

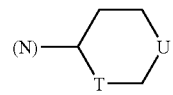

in which T is a single bond or methylene and U is methylene, ethylene, oxy, —S(O)$_q$— (wherein q is 0, 1 or 2) or imino (which may bear a methyl substituent), or T is ethan-1,1-diyl and U is a single bond or methylene;

R$^y$ is hydrogen or methyl; and

R$^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which has one to four heteroatoms selected from sulfur, oxygen and nitrogen or is a 6-membered aromatic ring which has one to three nitrogen atoms, wherein the heteroaryl is attached at carbon and may bear one or more methyl substituents on carbon or nitrogen);

or R$^{2A}$ is -L$^b$-CH$_2$-R$^b$ in which -L$^b$- is a direct bond, —CH$_2$—, —C(CH$_3$)H— or —CH$_2$—CH$_2$—; and R$^b$ is carboxy, {(1–2C)alkoxy}carbonyl, cyano, carbamoyl or trifluoromethyl;

or R$^{2A}$ is —CO—R$^c$ in which R$^c$ is hydrogen, (1–3C) alkyl, {(1–2C)alkoxy}carbonyl-(CH$_2$)$_c$— (in which c is 1 or 2), phenyl (which is unsubstituted or bears one or more substituents independently selected from halo, methyl, methoxy and hydroxy), heteroaryl (which heteroaryl is a 5-membered aromatic ring which has one to four heteroatoms selected from sulfur, oxygen and nitrogen or is a 6-membered aromatic ring which has one to three nitrogen atoms, wherein the heteroaryl is attached at carbon and may bear one or more methyl substituents on carbon or nitrogen) or —NR$^d$R$^e$ in which each of R$^d$ and R$^e$ is independently hydrogen, methyl or ethyl, or —NR$^d$R$^e$ is pyrrolidino, piperidino, morpholino or thiomorpholino;

Q$^{2B}$ is 1-piperazinyl which bears at the 4-position the group R$^{2A}$ (defined as above);

Q$^{2C}$ is 3,4-didehydropiperidin-4-yl which bears at the 1-position the group R$^{2A}$ (defined as above);

Q$^{2D}$ is cyclohexyl which bears at the 4-position the group —NR$^s$R$^t$ in which each of R$^s$ and R$^t$ independently is hydrogen or methyl or R$^s$ and R$^t$ together are trimethylene or tetramethylene;

Q$^{2E}$ is 1-piperidinyl which bears at the 4-position the group —NR$^s$R$^t$ (defined as above); and Q$^{2F}$ (showing the L$^2$ to which it is attached) is

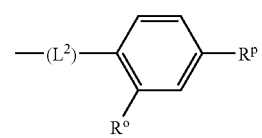

in which R$^o$ is hydrogen, halo, (1–6C)alkyl, hydroxy, (1–4C)alkoxy, benzyloxy or (1–4C)alkylthio; and R$^p$ is acetylamino, 1-hydroxyethyl, 1-hydroxy-1-methylethyl, 1-methoxy-1-methylethyl, 4-piperidinyl, 4-pyridinyl, dimethylaminosulfonyl or -J-R$^q$ in which J is a single bond, methylene, carbonyl, oxy, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl; or —NR$^q$R$^r$ is pyrrolidino.

2. The compound of formula I as claimed in claim 1

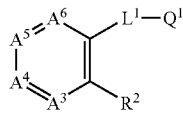

(or a pharmaceutically acceptable salt thereof) wherein:

$A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein $R^3$ is hydrogen, methyl, fluoro, chloro or carboxy;

one of $R^4$ and $R^5$ is hydrogen, (1–4C)alkyl, halo, trifluoromethyl, trifluoromethoxy, $R^fO$—, $R^fO_2CCH_2O$—, $HO(CH_2)_aO$— (in which a is 2, 3 or 4), $R^fO_2C$—, $R^fO_2CCH_2$—, $R^gNH$— or $R^hSO_2$—;

the other of $R^4$ and $R^5$ is hydrogen; and $R^6$ is hydrogen, methyl, fluoro, chloro or methoxy;

in which $R^f$ is hydrogen, (1–4C)alkyl or benzyl; $R^g$ is hydrogen or $R^hSO_2$—; and $R^h$ is (1–4C)alkyl or dimethylamino;

$L^1$ is —CO—NH— such that -$L^1$-$Q^1$ is —CO—NH-$Q^1$;

$Q^1$ is 2-pyrimidinyl (which may bear a methyl, fluoro or chloro substituent at the 5-position);

$R^2$ is -$L^2$-$Q^2$ in which -$L^2$- is —NH—CO—, —NH—CO—X—, —NH—CO—O—X—, —NH—CO—NH—X—, —NH—CH$_2$— or —O—CH$_2$—; and $Q^2$ is $Q^{2A}$, $Q^{2B}$, $Q^{2C}$, $Q^{2D}$, $Q^{2E}$ or $Q^{2F}$ wherein X is a single bond or methylene and the values of $L^2$ and $Q^2$ are together selected from —NH—CO—X-$Q^{2A}$, —NH—CO—O—X-$Q^{2A}$, —NH—CO—NH—X-$Q^{2A}$, —NH—CH$_2$-$Q^{2A}$, —O—CH$_2$-$Q^{2A}$, —NH—CO—X-$Q^{2B}$, —NH—CO-$Q^{2C}$, —NH—CO-$Q^{2D}$, —NH—CO-$Q^{2E}$ and —NH—CO-$Q^{2F}$ in which:

$Q^{2A}$ (showing the $L^2$ to which it is attached) is

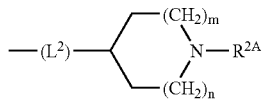

in which each of m and n independently is 0 or 1, and $R^{2A}$ is hydrogen, t-butyl, methylsulfonyl, —CHR$^y$R$^z$, —CHR$^w$R$^x$, or 4-pyridinyl (which is unsubstituted or bears a substituent R$^v$ at the 2- or 3-position) wherein R$^v$ is methyl, hydroxymethyl, {(1–2C)alkoxy}carbonyl; cyano, carbamoyl, thiocarbamoyl, or N-hydroxyamidino;

each of R$^w$ and R$^x$ independently is hydrogen or (1–3C) normal alkyl; or —CHR$^w$R$^x$ is 2-indanyl or (showing the nitrogen to which it is attached) is

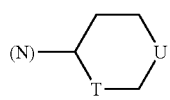

in which T is a single bond or methylene and U is methylene, ethylene, oxy, —S(O)$_q$— (wherein q is 0, 1 or 2) or imino (which may bear a methyl substituent), or T is ethan-1,1-diyl and U is a single bond or methylene;

R$^y$ is hydrogen or methyl; and

R$^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which has one to four heteroatoms selected from sulfur, oxygen and nitrogen or is a 6-membered aromatic ring which has one to three nitrogen atoms, wherein the heteroaryl is attached at carbon and may bear one or more methyl substituents on carbon or nitrogen);

$Q^{2B}$ is 1-piperazinyl which bears at the 4-position the group $R^{2A}$ (defined as above);

$Q^{2C}$ is 3,4-didehydropiperidin-4-yl which bears at the 1-position the group $R^{2A}$ (defined as above);

$Q^{2D}$ is cyclohexyl which bears at the 4-position the group —NR$^s$R$^t$ in which each of R$^s$ and R$^t$ independently is hydrogen or methyl or R$^s$ and R$^t$ together are trimethylene or tetramethylene;

$Q^{2E}$ is 1-piperidinyl which bears at the 4-position the group —NR$^s$R$^t$ (defined as above); and $Q^{2F}$ (showing the $L^2$ to which it is attached) is

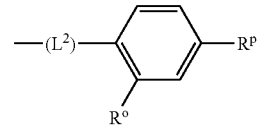

in which R$^o$ is hydrogen, halo, (1–6C)alkyl, hydroxy, (1–4C)alkoxy, benzyloxy or (1–4C)alkylthio; and R$^p$ is acetylamino, 1-hydroxyethyl, 1-hydroxy-1-methylethyl, 1-methoxy-1-methylethyl, 4-piperidinyl, 4-pyridinyl, dimethylaminosulfonyl or -J-R$^q$ in which J is a single bond, methylene, carbonyl, oxy, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl.

3. A compound of formula I (or a pharmaceutically acceptable salt thereof) as claimed in claim 2 wherein:

$A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein $R^3$ is hydrogen;

one of $R^4$ and $R^5$ is hydrogen, methyl, fluoro, chloro, trifluoromethyl, trifluoromethoxy, $R^fO_2C$— or $R^gNH$—;

the other of $R^4$ and $R^5$ is hydrogen; and $R^6$ is hydrogen;

in which $R^f$ is hydrogen, (1–4C)alkyl or benzyl; $R^g$ is hydrogen or $R^hSO_2$—; and $R^h$ is (1–4C)alkyl or dimethylamino;

$L^1$ is —CO—NH— such that -$L^1$-$Q^1$ is —CO—NH-$Q^1$;

$Q^1$ is 2-pyrimidinyl (which may bear a methyl, fluoro or chloro substituent at the 5-position);

$R^2$ is -$L^2$-$Q^2$ in which -$L^2$- is —NH—CO—, —NH—CO—X—, —NH—CO—O—X—, —NH—CO—NH—X—, —NH—CH$_2$— or —O—CH$_2$—; and $Q^2$ is $Q^{2A}$, $Q^{2B}$, $Q^{2C}$, $Q^{2D}$, $Q^{2E}$ or $Q^{2F}$ wherein X is a single bond or methylene and the values of $L^2$ and $Q^2$ are together selected from —NH—CO—X-$Q^{2A}$, —NH—

CO—O—X-$Q^{2A}$, —NH—CO—NH—X-$Q^{2A}$, —NH—$CH_2$-$Q^{2A}$, —O—$CH_2$-$Q^{2A}$, —NH—CO—X-$Q^{2B}$, —NH—CO-$Q^{2C}$, —NH—CO-$Q^{2D}$, —NH—CO-$Q^{2E}$ and —NH—CO-$Q^{2F}$ in which:

$Q^{2A}$ (showing the $L^2$ to which it is attached) is

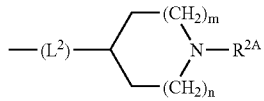

in which
each of m and n independently is 0 or 1, and
$R^{2A}$ is hydrogen, —$CHR^yR^z$, —$CHR^wR^x$, or 4-pyridinyl (which is unsubstituted or bears a substituent $R^v$ at the 2- or 3-position) wherein
$R^v$ is methyl, hydroxymethyl, {(1–2C)alkoxy}carbonyl; cyano, carbamoyl, thiocarbamoyl, or N-hydroxyamidino;
each of $R^w$ and $R^x$ independently is hydrogen or (1–3C) normal alkyl; or —$CHR^wR^x$ is 2-indanyl or (showing the nitrogen to which it is attached) is

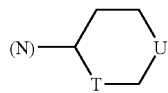

in which T is a single bond or methylene and U is methylene, oxy, thioxy or imino (which may bear a methyl substituent), or T is ethan-1,1-diyl and U is a single bond or methylene;
$R^y$ is hydrogen or methyl; and
$R^z$ is isopropyl, t-butyl, (3–6C)cyclopropyl, phenyl (which is unsubstituted or bears one or more substituents independently selected from halo, methyl, methoxy and hydroxy), 4-quinolinyl or heteroaryl (which heteroaryl is a 5-membered aromatic ring which has one to four heteroatoms selected from sulfur, oxygen and nitrogen or is a 6-membered aromatic ring which has one to three nitrogen atoms, wherein the heteroaryl is attached at carbon and may bear one or more methyl substituents on carbon or nitrogen);
$Q^{2B}$ is 1-piperazinyl which bears at the 4-position the group $R^{2A}$ (defined as above);
$Q^{2C}$ is 3,4-didehydropiperidin-4-yl which bears at the 1-position the group $R^{2A}$ (defined as above);
$Q^{2D}$ is cyclohexyl which bears at the 4-position the group —$NR^sR^t$ in which each of $R^s$ and $R^t$ independently is hydrogen or methyl or $R^s$ and $R^t$ together are trimethylene or tetramethylene;
$Q^{2E}$ is 1-piperidinyl which bears at the 4-position the group —$NR^sR^t$ (defined as above); and
$Q^{2F}$ (showing the $L^2$ to which it is attached) is

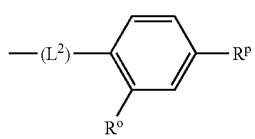

in which $R^o$ is hydrogen and $R^p$ is acetylamino, 1-hydroxyethyl, 1-hydroxy-1-methylethyl, 1-methoxy-1-methylethyl, 4-piperidinyl, 4-pyridinyl, dimethylaminosulfonyl or -J-$R^q$ in which J is a single bond, methylene, carbonyl, oxy, —$S(O)_q$— (wherein q is 0, 1 or 2), or —$NR^r$— (wherein $R^r$ is hydrogen or methyl); and $R^q$ is (1–6C)alkyl, phenyl, 3-pyridyl or 4-pyridyl.

4. The compound of claim 1, 2 or 3 wherein halo is fluoro, chloro, bromo or iodo; (1–2C)alkyl is methyl or ethyl; (1–3C)normal alkyl is methyl, ethyl or propyl; (1–4C)alkyl is methyl, ethyl, propyl, isopropyl, butyl, isobutyl, or t-butyl; (1–6C)alkyl is methyl, ethyl, propyl, butyl, pentyl or hexyl; (3–6C)cycloalkyl is cyclopropyl, cyclobutyl, cyclopenytyl or cyclohexyl.

5. The compound of claim 4 wherein $Q^1$ is 5-chloropyrimidin-2-yl.

6. The compound of claim 4 wherein $R^2$ is (1-isopropylpiperidin-4-ylcarbonyl)amino, (1-cyclohexylpiperidin-4-ylcarbonyl)amino, (4-isopropylpiperazin-1-ylcarbonyl)amino, [1-(tetrahydropyran-4-yl)piperidin-4-ylcarbonyl]amino, [4-(1-pyrrolidinyl)piperidin-1-ylcarbonyl]amino, [1-(4-pyridinyl)piperidin-4-ylmethyl]amino, [1-(2-carboxypyridin-4-yl)piperidin-4-ylmethyl]amino, or [1-(2-methoxycarbonylpyridin-4-yl)piperidin-4-ylmethyl]amino.

7. The compound as claimed in claim 4 wherein each of $R^3$–$R^6$ is hydrogen.

8. The compound as claimed in claim 4 wherein each of $R^3$, $R^4$ and $R^6$ is hydrogen and $R^5$ is chloro or fluoro.

9. The compound as claimed in claim 1 wherein each of $R^3$, $R^4$ and $R^6$ is hydrogen and $R^5$ is $R^a$ wherein $R^a$ is phenyl, furanyl, thienyl, 2-isothiazolyl or pyridyl; and wherein halo is fluoro, chloro, bromo or iodo; (1–2C)alkyl is methyl or ethyl; (1–3C)normal alkyl is methyl, ethyl or propyl; (1–4C) alkyl is methyl, ethyl, propyl, isopropyl, butyl, isobutyl, or t-butyl; (1–6C)alkyl is methyl, ethyl, propyl, butyl, pentyl or hexyl; (3–6C)cycloalkyl is cyclopropyl, cyclobutyl, cyclopenytyl or cyclohexyl.

10. The pharmaceutically acceptable salt of a compound of formula I as claimed in any of claims 1–3 which is an acid-addition salt made from a basic compound of formula I and an acid which provides a pharmaceutically acceptable anion or a salt which is made from an acidic compound of formula I and a base which provides a pharmaceutically acceptable cation.

11. The compound of claim 5 wherein $R^2$ is (1-isopropylpiperidin-4-ylcarbonyl)amino, (1-cyclohexylpiperidin-4-ylcarbonyl)amino, (4-isopropylpiperazin-1-ylcarbonyl)amino, [1-(tetrahydropyran-4-yl)piperidin-4-ylcarbonyl]amino, [4-(1-pyrrolidinyl)piperidin-1-ylcarbonyl]amino, [1-(4-pyridinyl)piperidin-4-ylmethyl]amino, [1-(2-carboxypyridin-4-yl)piperidin-4-ylmethyl]amino, or [1-(2-methoxycarbonylpyridin-4-yl)piperidin-4-ylmethyl]amino.

12. The compound as claimed in claim 5 wherein each of $R^3$–$R^6$ is hydrogen.

13. The compound as claimed in claim 6 wherein each of $R^3$–$R^6$ is hydrogen.

14. The compound as claimed in claim 11 wherein each of $R^3$–$R^6$ is hydrogen.

15. The compound as claimed in claim 5 wherein each of $R^3$, $R^4$ and $R^6$ is hydrogen and $R^5$ is chloro or fluoro.

16. The compound as claimed in claim 6 wherein each of $R^3$, $R^4$ and $R^6$ is hydrogen and $R^5$ is chloro or fluoro.

17. The compound as claimed in claim 11 wherein each of $R^3$, $R^4$ and $R^6$ is hydrogen and $R^5$ is chloro or fluoro.

18. The compound of claim 9 wherein $Q^1$ is 5-chloropyrimidin-2-yl.

19. The compound of claim 9 wherein $R^2$ is (1-isopropylpiperidin-4-ylcarbonyl)amino, (1-cyclohexylpiperidin-4-ylcarbonyl)amino, (4-isopropylpiperazin-1-ylcarbonyl)

amino, [1-(tetrahydropyran-4-yl)piperidin-4-ylcarbonyl]amino, [4-(1-pyrrolidinyl)piperidin-1-ylcarbonyl]amino, [1-(4-pyridinyl)piperidin-4-ylmethyl]amino, [1-(2-carboxypyridin-4-yl)piperidin-4-ylmethyl]amino, or [1-(2-methoxycarbonylpyridin-4-yl)piperidin-4-ylmethyl]amino.

20. The compound of claim 18 wherein $R^2$ is (1-isopropylpiperidin-4-ylcarbonyl)amino, (1-cyclohexylpiperidin-4-ylcarbonyl)amino, (4-isopropylpiperazin-1-ylcarbonyl) amino, [1-(tetrahydropyran-4-yl)piperidin-4-ylcarbonyl]amino, [4-(1-pyrrolidinyl)piperidin-1-ylcarbonyl]amino, [1-(4-pyridinyl)piperidin-4-ylmethyl]amino, [1-(2-carboxypyridin-4-yl)piperidin-4-ylmethyl]amino, or [1-(2-methoxycarbonylpyridin-4-yl)piperidin-4-ylmethyl]amino.

21. N-(5-Chloropyrimidin-2-yl)-2-[[1-(4-pyridinyl)piperidin-4-ylcarbonyl]amino]benzamide, or
a pharmaceutically acceptable salt thereof.

22. A pharmaceutical formulation comprising in association with a pharmaceutically acceptable carrier, diluent or excipient, a novel compound of formula I (or a pharmaceutically acceptable salt thereof) as provided in any of claims 1–3.

23. A process for preparing a compound of formula I (or a pharmaceutically acceptable salt thereof) as provided in claim 1 or 2 which is selected from (A) for a compound of formula I in which $-L^2-Q^2$, is $-NH-CO-Q^2$, $-NH-CO-X-Q^2$, $-NH-CO-O-X-Q^2$ or $-NH-CO-NH-X-Q^2$, acylating an amine of formula II,

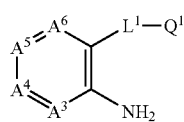

II using a corresponding acid of formula $HO-CO-Q^2$, $HO-CO-X-Q^2$, $HO-CO-O-X-Q^2$, or $HO-CO-NH-X-Q^2$, or an activated derivative thereof;

(B) for a compound of formula I in which $-L^2-Q^2$ is $-O-CH_2-Q^{2A}$, akylating a phenol of formula III

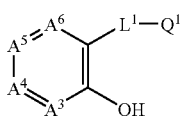

III using a reagent of formula $Y-CH_2-Q^{2A}$ in which Y is a conventional leaving group;

(C) acylating an amine of formula $H_2N-Q^1$, or a deprotonated derivative thereof, using an acid of formula IV, or an activated derivative thereof;

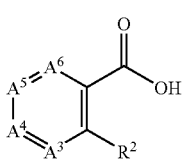

IV (D) for a compound of formula I in which $R^2$ is $-NH-CH_2-Q^{2A}$, alkylating an amine of formula II directly, using a compound of formula $Y-CH_2-Q^{2A}$, or indirectly by reductive alkylation using an aldehyde of formula $Q^{2A}$-CHO;

(E) for a compound of formula I in which $R^2$ is $-NH-CO-O-X-Q^{2A}$, or $-NH-CO-NH-X-Q^{2A}$, acylating an alcohol of formula $HO-X-Q^{2A}$ or an amine of formula $NH_2-X-Q^{2A}$, using an activated derivative of an acid of formula VI;

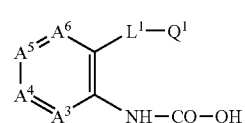

VI (F) for a compound of formula I in which $R^2$ is $-NH-CO-X-Q^{2B}$ in which X is a single bond, acylating at the 1-position a piperazine of formula $H-Q^{2B}$, using an activated derivative of an acid of formula VI;

(G) for a compound of formula I in which $R^2$ is $-NH-CO-X-Q^{2B}$ in which X is methylene, alkylating at the 1-position a piperazine of formula $H-Q^{2B}$, using an alkylating agent of formula VII

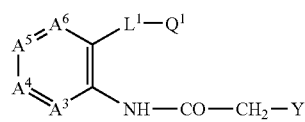

VII in which Y is a leaving group;

(H) for a compound of formula I in which $R^{2A}$ is methylsulfonyl, substituting the amino nitrogen of a corresponding compound of formula I in which $R^{2A}$ is hydrogen using an activated derivative of methanesulfonic acid;

(I) for a compound of formula I in which $R^{2A}$ is $-CHR^yR^z$ or $-CHR^wR^x$, alkylating the amino nitrogen of a corresponding compound of formula I in which $R^{2A}$ is hydrogen using an alkylating agent of formula $Y-CHR^yR^z$ or $Y-CHR^wR^x$ or reductively alkylating the amine using a compound of formula $R^y-CO-R^z$ or $R^w-CO-R^x$;

(J) for a compound of formula I in which $R^{2A}$ is 4-pyridinyl (which is unsubstituted or bears a substituent $R^v$ at the 2- or 3-position), substituting the amino nitrogen of a corresponding compound of formula I in which $R^{2A}$ is hydrogen using a corresponding pyridine reagent bearing a leaving group Y at the 4-position;

(K) for a compound of formula I in which $R^{2A}$ is 4-pyridinyl in which $R^v$ is alkoxycarbonyl, esterifying a corresponding compound of formula I in which $R^v$ is carboxy;

(L) for a compound of formula I in which $R^{2A}$ is 4-pyridinyl in which $R^v$ is hydroxymethyl, reducing the ester of a corresponding compound of formula I in which $R^v$ is alkoxycarbonyl;

(M) for a compound of formula I in which $R^{2A}$ is 4-pyridinyl in which $R^v$ is carbamoyl, amidating the ester of a corresponding compound of formula I in which $R^v$ is alkoxycarbonyl;

(N) for a compound of formula I in which $R^{2A}$ is 4-pyridinyl in which $R^v$ is thiocarbamoyl, adding $H_2S$ to the nitrile of a corresponding compound of formula I in which $R^v$ is cyano;

(O) for a compound of formula I in which $R^{2A}$ is 4-pyridinyl in which $R^v$ is N-hydroxyamidino, adding $H_2NOH$ to the nitrile of a corresponding compound of formula I in which $R^v$ is cyano;

(P) for a compound of formula I in which $R^{2A}$ is 4-pyridinyl in which $R^v$ is carboxy, decomposing the ester of a corresponding compound of formula I in which $R^v$ is alkoxycarbonyl;

(Q) for a compound of formula I in which —$NR^sR^t$ is other than amino, alkylating a corresponding compound of formula I in which —$NR^sR^t$ is amino using a conventional method;

(R) for a compound of formula I which bears —$NR^sR^t$, reductively alkylating H—$NR^sR^t$ using a corresponding compound but in which the carbon to bear the —$NR^sR^t$ group bears an oxo group;

(S) for a compound of formula I in which $R^p$ is 1-hydroxy-1-methylethyl, adding a methyl group to the carbonyl group of a corresponding compound of formula I in which $R^p$ is acetyl using an organometallic reagent;

(T) for a compound of formula I in which $R^p$ is 1-methoxy-1-methylethyl, treating a corresponding compound of formula I in which $R^p$ is 1-hydroxy-1-methylethyl with methanol and an acid catalyst;

(U) for a compound of formula I in which $R^4$ or $R^5$ is amino, reducing the nitro group of a compound corresponding to a compound of formula I but in which $R^4$ or $R^5$ is nitro;

(V) for a compound of formula I in which $R^4$ or $R^5$ is $R^gNH$— and $R^g$ is $R^hSO_2$—, substituting the amino group of a corresponding compound of formula I in which $R^4$ or $R^5$ is amino using an activated derivative of the sulfonic acid $R^hSO_2$—OH;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure;

and wherein, unless otherwise specified, $A^3$–$A^6$, $L^1$, $Q^1$ and $R^2$ have any of the values defined in claim 1 or 2.

24. A method of inhibiting factor Xa in a mammal comprising administering to the mammal in need thereof, and effective amount of a compound of formula I as provided in any of claims 1–3.

* * * * *